US010287601B2

(12) United States Patent
Anterola

(10) Patent No.: US 10,287,601 B2
(45) Date of Patent: May 14, 2019

(54) INDOLE-DERIVED COMPOUND PRODUCTION

(71) Applicant: Board of Trustees of Southern Illinois University, Carbondale, IL (US)

(72) Inventor: Aldwin Anterola, Carbondale, IL (US)

(73) Assignee: BOARD OF TRUSTEES OF SOUTHERN ILLINOIS UNIVERSITY, Carbondale, IL (US)

( * ) Notice: Subject to any disclaimer, the term of this patent is extended or adjusted under 35 U.S.C. 154(b) by 31 days.

(21) Appl. No.: 15/323,996

(22) PCT Filed: Jul. 7, 2015

(86) PCT No.: PCT/US2015/039392
§ 371 (c)(1),
(2) Date: Jan. 5, 2017

(87) PCT Pub. No.: WO2016/007521
PCT Pub. Date: Jan. 14, 2016

(65) Prior Publication Data

US 2017/0204424 A1 Jul. 20, 2017

Related U.S. Application Data

(60) Provisional application No. 62/021,512, filed on Jul. 7, 2014.

(51) Int. Cl.

| | |
|---|---|
| ***C12N 15/82*** | (2006.01) |
| ***C07K 14/80*** | (2006.01) |
| ***C12N 9/88*** | (2006.01) |
| ***C12P 17/12*** | (2006.01) |
| ***C07D 209/34*** | (2006.01) |
| ***C07D 209/36*** | (2006.01) |
| ***C12N 9/02*** | (2006.01) |

(52) U.S. Cl.
CPC ......... *C12N 15/825* (2013.01); *C07D 209/34* (2013.01); *C07D 209/36* (2013.01); *C07K 14/80* (2013.01); *C12N 9/0042* (2013.01); *C12N 9/0071* (2013.01); *C12N 9/88* (2013.01); *C12P 17/12* (2013.01); *C12Y 106/02004* (2013.01); *C12Y 114/00* (2013.01); *C12Y 402/0102* (2013.01)

(58) Field of Classification Search
CPC .................................................... C12N 15/825
See application file for complete search history.

(56) References Cited

U.S. PATENT DOCUMENTS 5,494,816 A 2/1996 Murdock

FOREIGN PATENT DOCUMENTS

WO WO1996040924 12/1996
WO WO 2001/14565 A1 3/2001

OTHER PUBLICATIONS

Salvini, M. et al. Plant Physiology and Biochemistry; May 2008, vol. 46, pp. 715-723.*

Daykin, T., Jun. 2011; PhD dissertation, Disecting the Indigo Pathway; Department of Biotechnology and Environmental Biology: RMIT University; Melbourne, Victoria, AUstrailia, 1-186 pp.*

International Search Report dated Jan. 12, 2016 corresponding to PCT/US15/39392.

Salvini, M., et al., Alpha-Tryptophan Synthase of isatis tinctoria: Gene Cloning and Expression, Plant Physiology and Biochemistry. 2008, vol. 46; pp. 715-723. DOI: 10.1016/j.plaphy.2008.04.002.

Salvini, M. et al., Isatis tinctoria mRNA for tryptophan synthase, alpha Subunit (TSA1) (tsa1 gene)[1] [online database] GenBank Accession AJ841704, version AJ841704.1; GI:52673239, submitted Sep. 22, 2004 [retrieved on Oct. 23, 2015] retrieved from: NCBI, GenBank Accession AJ841704.

Kim, J. Y., et al., Multicomponent phenol hydroxylase-catalysed formation of hydroxydindoles and dyestuffs from indole and its derivatives. Letters in Applied Microbiology, 2005, Vo. 41, pp. 163-168. DOI:10.1111/j.1472-765X.2005.01734.x.

Berry, A. et al., Application of Metabolic Engineering to Improve Both the Production and Use of Biotech Indigo; Journal of Industrial Microbiology & Biotechnology, vol. 28, 2002, pp. 127-133.

Burd, V., et al., Oxidation of Indole and Indole Derivatives Catalyzed by Nonheme Chloroperoxidases; Applied Biochemistry and Microbiology; vol. 37(3), 2001, pp. 248-250, Available at http://link.springer.com/article/10.10234/A: 1010220916145 [Accessed Feb. 10, 2014].

Choi, H.S. et al., A Novel Flavin-containing Monooxygenase from Methylophage sp Strain SK1 and its Indigo Synthesis in *Escherichia coli*, Biochemical and Biophysical Research Communications, 2003, vol. 306, pp. 930-936.

Edwards, H. G. M. et al., Nondestructive Analysis of Ancient Egyptian Funerary Relics by Raman Spectroscopic Techniques, Analytical Chemica Acta, 2004, vol. 503, pp. 223-233.

Ensley, B. D., et al., Expression of Naphthalene Oxidation Genes in *Escherichia coli* Results in the Biosynthesis of Indigo, Science (New York, NY), 1983, vol. 222, pp. 167-169.

Frey, M., et al., Analysis of a Chemical Plant Defense Mechanism in Grasses, Science, Aug. 1, 1997, (New York, NY, vol. 227(5326), pp. 696-699, Available at http://www.ncbi.nlm.nih.gov/pubmed/9235894 [Accessed Jun. 24, 2014].

(Continued)

*Primary Examiner* — Russell Kallis
(74) *Attorney, Agent, or Firm* — Dentons US LLP

(57) ABSTRACT

Among the various aspects of the present disclosure is the provision of a transgenic organism, an artificial DNA construct, and methods for producing a transgenic organism for indigo, indirubin, and other indole-derived compound production. Another aspect of the present disclosure is the provision of a transgenic organism wherein the indole-derived compound imparts color to the transgenic organism or to a portion of the transgenic organism.

19 Claims, 38 Drawing Sheets

Specification includes a Sequence Listing.

(56) References Cited

OTHER PUBLICATIONS

Fukui, Y. et al., A Rationale for the Shift in Colour Towards Blue in Transgenic Carnation Flowers Expressing the Flavonoid 3'5'-hydroxylase gene, Phytochemicstry, 2003, vol. 63(1), pp. 15-23, Available at http://www.sciencedirect.com/science/article/pii/S0031942202006842 [Accessed Feb. 12, 2014].
Gilliam, E. M et al., Oxidation of Indole by Cytochrome P450 Enzymes, Biochemistry, 2000, vol. 39(45), pp. 13817-13824, Available at http://www.ncbi.nlm, nih.gov/pubmed/11076521.
Gilliam, E. M. J. et al., Formation of Indigo by Recombinant Mammalian, Biochemical and Biophysical Research Communications, 1999, vol. 265(2), pp. 469-472.
Hart, S. et al., Identification of Indigo-related Pigments Produced by *Escherichia coli* Containing a Cloned Rhodococcus Gene, Journal of General Microbiology, vol. 138,1992, pp. 211-216.
Hoessel, R., et al., Indirubin, the Active Constituent of a Chinese Antileukaemia Medicine, Inhibits Cyclin-dependent Kinsases, Nature Cell Biology, May 1999, vol. 1(1), pp. 60-67, Available at http://www.ncbi.nim.nih.gov/pubmed/10559866.
Kim, J/ Y., et al., Multicomponent Phenol Hydroxylase-catalyzed Formation of Hydroxyindoles and Dyestuffs from Indole and its Derivatives, 2005, Letters in Applied Microbiol, vol. 41, pp. 163-168.
Kim J. Y., et al, Produciton of Dyestuffs from Indole Derivaties by Naphthalene Dioxygenase and Toluene Dioxygenese, 2003, Letters in Applied. Microbiol , vol. 36, pp. 343-348.
Kuo, H. H. et al., Indole Peroxygenase Activity of Indoleaine 2,3-dioxygenase, Proceedings of the National Academy of Sciences, Aug. 28, 2012, vol. 109, pp. 13966-13971.
Li, Q. S., et al., Directed Evolution of the Fatty-acid Hydroxylase P450 BM-3 into an Indole-Hydroxylating Catalyst, Chemistry (weinheim an der Bergstrasse, Germany, 2000, vol. 6, pp. 1531-1536.
Manna, S. K. et.al., Tuning the Substrase specificity by Engineering the Active Site of Cytochrome P450cam: a Rational Approach, Datlon Transactions (Cambridge, England, 2010, vol. 39, pp. 3115-3123.
Marcinek, H. et al., Indoxyl-UDPG-Glucosyltransferase from Baphicacanthus Cusia, Phytochemicstry, vol. 53, 2000, pp. 201-207, Available at: http://linkinghub.elsevier.com/retrieve/pii, S0031942299004306.
Maugard, T., et al., Identification of an Indigo Precursor from Leaves of *Isatis tinctoria* (Woad), Phytochemicstry, vol. 58(6), 2001, pp. 897-904, Available at : http://www.ncbi.nim.nih.gov/pubmed/17191785.
McClay, K. et al., Mutations of Toluene-40-monooxygenase That After Reiospecificity of Indole Oxidation and Lead to Production of Novel Indigold Pigments, 2005, Applied and Environmental Microbiology, vol. 71(9), pp. 5476-5484, Sep. 2005; Available at http://www.pubmedcentral.nih.gov/articlerenderlfcgi?artid=1214665&tool=pmcentrez&rendertype=abstract [Accessed Feb. 12, 2014.
Melanson, A., et al., A Deletion in an Indole Synthase Gene is Responsible for the DIMBOA Deficient Phenotype of bxb Maise, Proceedings of the National Academy of Sciences, vol. 94(24), Nov. 1997, pp. 13345-13350, Available at: http://www.pnas.org/content/94/24/13345.long [Accessed Jun. 24, 2014.
Mermod, N., et al., New Route to Bacterial Production of Indigo, Nature Biotechnology, 4(4), Apr. 1986, pp. 321-324, available at: http://dx.doi.org/10.1038/nbt0486-321 [Accessed Feb. 12, 2014].
Meyer, A., et al., Hydroxylation of Indole by Laboratory-Evolved 2-hydroxybiphenyl 3-Monooxygenase, 2002, The Journal of Biological Chemistry, vol. 277, pp. 34161-34167.
Minami, Y. et al., 1999, Cloning, Sequencing, Characterization, and Expression of a Beta-glucosidase cDNA from the Indigo Plant, Plant Science, 142, 1999, pp. 219-226.
Minami, Y., et al., Tissue and Intracellular Localization of Indican and the Purification and.Characterization of Indican Synthase for Indogo Plants, Plant Cell Physiology, vol. 41(2), 2000, pp. 215-218, Available at http://www.ncbi.nlm.nih. Gov/pubmed/10794317.
Moreno-Ruiz, E., et al., Identification and Functional Characterization of Sphingomonas Macrogolitabida Strain, TFA Genes Involved in the First Two Steps of the Tetralin Catabolic Pathway, Journal of Bacteriology, Mar. 2003, vol. 185, pp. 2026-2030.
O'Connor, K. E., et al., Indigo Formation by Microorganism Expressing Styrene Monooxygenase Activity, Applied and Environmental Microbiology, Nov. 1997, vol. 63, pp. 4287-4291.
Russell. G. A., et al., Oxidation of Carbanions, IV. Oxidation of Indoxyl to Indigo in Basic Solution, Journal of the American Chemical Society, Jul. 1969, vol. 228(2), pp. 3851-3859.
Stephens, G. M. et al., Cloning and Expression in *Escherichia coli* of the Toluene Dioxygenase Gene from Pseudomonas Putida NCIB11767, FEMS Microbiology Letters, 1989, vol. 48, pp. 295-300.
Xia, Z, et al., Biosynthesis of Indigo Precursors in Higher Plants, Phytochemistry, 1992, vol. 31(8), pages 2695-2697, Available at: http://www.sciencedirect.com/science/article/pii/0031942292836134 [Accessed Feb. 14, 2014].
Zhang, R., et al., *Arabidopsis* Indole Synthase, a Homolog of Tryptophan Synthase Alpha, is an Enzyme Involved in the Trp-Independent Indole-containing Metabolite Biosynthesis, Journal of Integrative Plant Biology, 2008, vol. 50(9), pp. 1070-1077.
Barnes. H. J., Maximizing Expression of Eukaryotic Cyctochrome P450s in *Escherichia coli*, Methods in Enzymology, 1996, vol. 272, pp. 3-14, Available at: http://www.ncbi.nlm.nih.Gov/pubmed/8791757 [Accessed Jun. 21, 2014].
Belnap, W. et al.., pBINPLUS/ARS: An Improved Plant Transformation Vector Based on PBINPLUS, BioTechniques, 2008, vol. 44(6), pp. 753-755, Available at http://www.Ncbi.nlm.nih.gov/pubmed/18476828 [Accessed Jun. 23, 2014].
Bent, A., *Arabidopsis thaliana* Floral Dip Transformation Method, Methods in Molecular Biology (Clifton, NJ), 2006, vol. 343, pp. 87-103, Available at http://ncbi.nlm.nih. Gov/pubmed/16988336. [Accessed Jun. 11, 2014].
Borissova, A., et al., Agrobacterium—Mediated transformation of Secondary Somatic Embryos from *Rosa hybrida* L. and Recovery of transgenic Plants, Biotechnology & Biotechnological Equipment, 2005, vol. 19(1), pp. 70-74, Available at : http://www.tandfonline.com/doi/abs/10.1080/13102818.2005.10817156 [Accessed Jun. 24, 2014].
Clough, S. J. et al., Floral Dip: A Simplified Method for Agrobacterium-Mediated Transformation of *Arabidopsis thaliana*, The Plant Journal, 1998, vol. 16(6) pp. 735-743, Available at: http://doi.wiley.com/10.1046/j.1365-313x.1998.00343.x [Accessed Jun. 4, 2014].
Davis, A. M. et al., Protocol: Streamlined Sub-Protocols for Floral-dip Transformation and Selection of Transformants in *Arabidopsis thaliana*, Plant Methods, 2009, vol. 5(3), p. 1-7, Available at: http://www.plantmethods.com/content/5/1/3, [Accessed May 29, 2014].
Donnelly, M. L. L. et al., Analysis of the Aphthovirus 2A/2B Polyprotein "cleavage" Mechanism Indicates not a Proteolytic Reaction but a Novel Translational Effect: a Putative Ribosomal "skip", Journal Gen. Virol, 2001, vol. 82(5), pp. 1013-1025, Available at: http://vir.sgmjournals.org/content/82/5/1013.long, [Accessed Jun. 23, 2014].
Engelen, F. A. et al., pBINPLUS: An Improved Plant Transformation Vector Based on PBIN19, Transgenic Research, 1995, vol. 4(4), pp. 288-290, Available at: http://link.springer.com/10.1007/BFO1969123 [Accessed Jun. 23, 2014].
Finer, J. J. et al., Transformation of Cotton (*Gossypium hirsutum* L) Via Particle Bombardment, Plant Cell Reports, 1990, vol. 8(10), pp. 586-589, Available at: http: www.ncbi.nlm.nkh.gov/pubmed/24232677, [Accessed Jun. 24, 2014].
Firoozabady, E., et al., Regeneration of transgenic Rose (*Rosa hybrida*) Plants from Embryogenic Tissue, Bio/Technology, Jan. 1994, vol. 12(6), pp. 609-613, Available at: http://dx.doi.org/10.1038/nbt0694-609, [Accessed Jun. 24, 2014].
Fisher, C. W. et al., High-level Expression in *Escherichia coli* of Enzymatically Active Fusion Proteins Containing the Domains of Mammalian Cytochromes P450 and NADPH-P450 Reductase Flavoprotein, Proceedings of the National Academy of Sciences of the United States of America, Nov. 1992, vol. 89(22), pp. 10817-

(56) References Cited

OTHER PUBLICATIONS

10821, Available at: http://www.pubmedcentral.nih.gov/articlerenderlfcgi?artid=50433&tool=pmcentrez&rendertype=abstract [Accessed Jun. 21, 2014].
Harada, H. et al., Efficient Functional Analysis System for Cyanobacterial or Plant Cytochromes P450 Involved in Sesquiterpene Biosynthesis, Applied Microbiology and Biotechnology, 2011, vol. 90(2). pp. 467-476, Available at: http://www.ncbi.nim.nih.gov/pubmed/21229242 [Accessed Sep. 3, 2011.
Hull, A., et al., Bacterial Expression and Purification of the *Arabidopsis* NADPH-cytochrome P450 Reductase ATR2, Protein Expression and Purification, 2002, vol. 18(3), pp. 310-315, Available at: https://www.ncbi.nim.hih.gov/pubmed/10733884, [Accessed Nov. 3, 2011].
Katsumoto, Y., et al., Engineering of the Rose Flavonoid Biosynthetic Pathway Successfully Generated Blue-hued Flowers Accumulating Delphinidin, Plant Cell Physiology, 2007, vol. 48(11), pp. 1589-1600, Available at: http://pc.oxfordjournals.org/content/48/11/1589.full [Accessed May 28, 2014].
Korban, S. S. et al., Rose (*Rosa hybrida* L.), Methods in Molecular Biology (Clifton, NJ), 2006, vol. 344, pp. 351-358, Available at: http://www.ncbi.nlm.nih.gov/pubmed/17033077 [Accessed Jun. 8, 2014].
Liu, H.C., et al., Cloning and Promoter Analysis of the Cotton Lipid Transfer Protein Gene Ltp311, The Nucleotide Sequence Data Reported Will Appear in the GenBank Nucleotide Sequence Database Under the Accession No. AF228333, Biochmical et Biophysica Acata (BBA), Molecular and Cell Biology of Lipds, 2000, vol. 1487(1), pp. 105-111, Available at: http://www.sciencedirect.com/science/article/pii/S138819810000072X [Accessed Jun. 24, 2014].
Logemann, E. et al., An Improved Method for Preparing Agrobacterium Cells that Simplifies the *Arabidopsis* Transformation Protocol, Plant Methods, 2006, vol. 2(1), pp. 1-5, Available at: http://www.plantmethods.com/content/2/1/16 [Accessed May 25, 2014].
Marchant, R., Biolistic Transformation of Rose (*Rosa hybrida* L.), Annals of Botany, 1998, vol. 81(1), pp. 109-114, Available at: http://aob.xofordjournals.org/content/81/1/109 [Accessed Jun. 23, 2014].
Mitsuhara, I., et al., Efficient Promotor Cassettes for Enhanced Expression of Foreign Genes in Dicotytledonous and Monocotyledonous Plants, Plant and Cell Physiology, 1996, vol. 37(1), pp. 49-59, Available At: http:/www.pcp.oxfordjournals.org/content/37/1/49.abstract?ijkey=35dfa8fbf87d4a4cbb11cc05ba53cc206654bbcc&keytype2=tf_ipsecsha [Accessed Jun. 23, 2014].
Pritchard, M. P. et al., A General Strategy for the Expression of Recombinant Human Cytochrome P450s in *Escherichia coli* Using Bacterial Signal Peptides: Expression of CYP3A4, CYP2A6, and CYP2E1, Archives of Biochemistry and Biophysics, Sep. 1997, vol. 345, pp. 342-354, Available at: http://www.sciencedirect.com/science/article/pii.S0003986197902654, [Accessed Jun. 21, 2014].
Umbeck, P. et al., Genetically Transformed Cotton (*Gossypium hirsutum* L.,) Plants, Bio/Technology, Mar. 1987, vol. 5(3), pp. 263-266, Available at: http://dx.doi.org/10,1038/nbt0387-263 [Accessed Jun. 24, 2014].
Xiao, Y. et al., Transgenic Tetraploid Isastic Indigotica Expressing Bt Cry1Ac and Pinellia Ternanta Agglutinin Showed Enhanced Resistance to Moths and Aphids, Molecular Biology Reports, 2012, vol. 39(1), pp. 485-491,Available at: http://www.ncbi.nlm.nkh.gov/pubmed/21559837 Accessed Nov. 15, 2011.
Xu, X. et al., Designing and Transgenic Expression of Melanin Gene in Tobacco Trichome and Cotton Fiber, Plant Biology (Stuttgart, Germany), 2007, vol. 9(1), pp. 41-48, Available at: http://www.ncbi.nlm.nih.gov/ubmed/17006798 [Accessed Jun. 24, 2014.
Zakizadeh, H. et al., Transformation of Miniature Potted Rose (*Rosa hybrida* cv Linda), with P(SAG12)-ipt Gene Delays Leaf Senescence and Enhanced Resistance to Exogenous Ethylene, Plant Cell Reports, 2013, vol. 32(2), pp. 195-205, Available at: http:/www.ncbi.nlm.nih.gov/pubmed/23207761 [Accessed Jun. 24, 2014].
Zhang, X. et al., Agrobacterium-Mediated Transformation of *Arabidopsis thaliana* Using the Floral Dip Method, Nature Protocols, Jun. 2006, vol. 1(2), pp. 641-646, Available at: http://dx.doi.org/10.1038/nprot/2006.97 [Accessed May 30, 2014].
Zhou, G. et al., Introduction of Exogenous DNA into Cotton Embryos, Methods in Enzymology, 1983, vol. 101, pp. 433-481, Available at: http://www.ncbi.nlm.nih.gov/pubmed/6577258 [Accessed Jun. 24, 2014].

* cited by examiner

Indirubin

Indigo

PRIOR ART (Hossel et al, 1999)

ItB24_AtR2 in modified TB
1.25 g of TB in 50 ml of water

Indigo: 4.13μg/ml
Indirubin: 0.36μg/ml

ItB24_AtR2 in TB
2.38 g of TB in 50 ml of water

Indigo: 0.1μg/ml
Indirubin: 0.97μg/ml

ItB24_AtR2 in LB
1.25 g of LB in 50 ml of water

Indigo: < LOD
Indirubin: < LOD ltB24_AtR2 in modified TB
supplemented with ALA amino levulinic acid ltB24_AtR2 in modified TB
supplemented with no ALA Indigo: 4.1μg/ml
Indirubin: 0.64μg/ml Indigo: < LOD
Indirubin: <LOD Blue fraction Pink Fraction ItB24_IsH_AtR2 in TB Indigo: 4.41μg/ml
Indirubin: 0.15μg/ml Indigo: 0.1 μg/ml
Indirubin: 0.91μg/ml 1H-indol-3-yl-ribohex-3-ulopyranoside Isatan B indoxyl Indican Indigo

A

B indole 2-oxindole 2-hydroxyindole 3-hydroxyindole 3-oxindole indigo isatin isatic acid indirubin

INDOLE-DERIVED COMPOUND PRODUCTION

CROSS-REFERENCE TO RELATED APPLICATIONS

The present application claims the benefit of PCT International Application No. PCT/US15/39392, filed 7 Jul. 2015; which claims the benefit of U.S. Provisional Application No. 62/021,512, filed 7 Jul. 2014; each of which is incorporated herein by reference in its entirety.

STATEMENT REGARDING FEDERALLY SPONSORED RESEARCH OR DEVELOPMENT

Not Applicable.

MATERIAL INCORPORATED-BY-REFERENCE

The Sequence Listing, which is a part of the present disclosure, includes a computer readable form comprising nucleotide and/or amino acid sequences of the present invention. The subject matter of the Sequence Listing is incorporated herein by reference in its entirety.

FIELD OF THE INVENTION

The present disclosure generally relates to a transgenic organism producing an indole-derived compound. Aspects of the present disclosure provide transgenic organisms, artificial DNA constructs, and methods for producing transgenic organisms for indigo, indirubin, and other indole-derived compound production.

BACKGROUND OF THE INVENTION

Indigo is a chemical compound that can be used as a blue dye in the food and textile industry, for example, as a blue dye for jeans. Natural indigo was originally obtained from various unrelated plants, most notably *Indigofera tinctoria, Isatis tinctoria*, and *Polygonum tinctorium*, which were the principal sources of the blue dye since ancient times (perhaps as early as 2000 B.C.) until chemical methods were developed in the 19th century to make indigo.

Synthetic indigo has largely replaced natural indigo in the dye and pigment industry. Microorganisms having enzymes capable of producing indigo (from indole) have been reported.

The role of indole in tryptophan biosynthesis in plants is conventionally understood. In plants, indole is a transient intermediate of tryptophan biosynthesis where it is produced by the alpha subunit of a bifunctional tryptophan synthase enzyme (TSA) by cleaving indole-3-glycerol phosphate (I3GP) into indole and D-glyceraldehyde-3-phosphate (G3P). Indole is subsequently channeled to the active site of the tryptophan synthase beta subunit (TSB), where it is condensed with the amino acid serine to produce tryptophan and water. TSA-like genes associated with tryptophan biosynthesis have been reported in various plant species including maize, *Arabidopsis*, and *Isatis tinctoria* (also known as woad).

Indigo can be made from indole. Conversion of indole to indigo requires a hydroxylation of indole at position 3 that gives rise to indoxyl (i.e., 3-hydroxyindole), which spontaneously dimerizes in the presence of oxygen to form indigo. To date, neither a plant gene nor a plant enzyme that can convert indole to indoxyl has been identified.

In indigo-producing plants, indoxyl molecules can be prevented from spontaneously dimerizing into indigo by immediately converting indoxyl into indoxyl glycosides, such as indican (in the case of *Indigofera tinctoria*) and isatin B (in the case of *Isatis tinctoria*). To extract indigo (e.g., by vat fermentation), indoxyl glycosides can be hydrolyzed by beta-glucosidases (either from microorganisms or the plant) to release indoxyl, which then spontaneously forms indigo under aerobic conditions. Glucosyltransferases that convert indoxyl to indican have been purified and characterized in *Polygonum tinctorium* and *Baphicacanthus cusia*, while a beta-glucosidase gene that converts indican into indoxyl can be cloned from *Polygonum tinctorium* (Minami et al. 1999).

Different types of non-plant enzymes (e.g., from microorganisms or human liver) have been found to catalyze the oxidation of indole to indoxyl. But none have ever been identified in plants prior to the following disclosure. In microorganisms, these enzymes mainly oxidize other substrates, with indole being a fortuitous substrate. Such is the case for naphthalene (Ensley et al. 1983), toluene (Stephens et al. 1989) and tetralin (Moreno-Ruiz et al. 2003) dioxygenases, as well as for styrene (O'Connor et al. 1997), xylene (Mermod et al. 1986), and flavin-containing (Choi et al. 2003) monooxygenases, among other bacterial indole oxidases. In humans, certain P450 enzymes in the liver can oxidize indole (Gillam et al. 1999) besides other substrates, as a first step in detoxification of xenobiotics. Another human enzyme, indoleamine-2,3-dioxygenase, can also oxidize indole to form indigo, but only in the presence of hydrogen peroxide (Kuo & Mauk 2012), similar to the reaction catalyzed by chloroperoxidases in *Streptomyces lividans* that converts indole to indoxyl (Burd et al. 2001). Various enzymes have also been modified by mutation to enable indole oxidation into indigo and other related pigments, examples of which include toluene-4-monooxygenase (McClay et al. 2005), flavin-containing monooxygenase (Meyer et al. 2002), and at least two bacterial P450s (Li et al. 2000; Manna & Mazumdar 2010).

Indirubin (an anticancer compound useful for the treatment of chronic myeloid leukemia) can be produced by the dimerization of 3-hydroxyindole and isatin, an oxidation product of 3-hydroxyindole. No plant genes for producing free indole or indole hydroxylation have been identified.

Formation of indigo from indoxyl, either during vat fermentation of indigo-producing plants (Maugard et al. 2001) or during catalysis by microbial (Hart et al. 1992) and human enzymes (Gillam et al. 2000), can be often accompanied by formation of the red pigment indirubin. This pigment is an isomer of indigo, and formed by the coupling of indoxyl and isatin, a double oxidation product of indole. Indirubin is considered an impurity in indigo dye preparations, but is also the active constituent of an herbal remedy for leukemia containing *Isatis tinctoria* (Hoessel et al. 1999).

SUMMARY OF THE INVENTION

Among the various aspects of the present disclosure is the provision of a transgenic organism engineered to accumulate an indole-derived compound. In some embodiments, the organism can be transformed with an artificial DNA construct including, as operably associated components in the 5' to 3' direction of transcription: (i) a promoter that functions in the organism; (ii) a first transcribable nucleic acid sequence or a second transcribable nucleic acid sequence, (a) the first transcribable nucleic acid sequence encoding a tryptophan synthase alpha subunit (TSA) selected from the group consisting of (1) SEQ ID NO: 1 (TSA1), or a nucleotide sequence at least 90% identical thereto and encoding a polypeptide catalyzing cleavage of indole-3-glycerol phosphate (I3GP) into indole and D-glyceraldehyde-3-phosphate (G3P); and (2) SEQ ID NO: 2 (TSA2), or a nucleotide sequence at least 90% identical thereto and encoding a polypeptide catalyzing cleavage of indole-3-glycerol phosphate (I3GP) into indole and D-glyceraldehyde-3-phosphate (G3P); and (b) the second transcribable nucleic acid sequence encoding a cytochrome P450 polypeptide selected from the group consisting of (1) SEQ ID NO 3 (ItB4), or a nucleotide sequence at least 90% identical thereto and encoding a polypeptide catalyzing formation of 2-hydroxyindole from indole; or (2) SEQ ID NO: 4 (ItB24), or a nucleotide sequence at least 90% identical thereto and encoding a polypeptide catalyzing formation of 3-hydroxyindole from indole; and (iii) a transcriptional termination sequence; wherein the organism produces increased levels of indole-derived compounds, or precursors thereof, compared to an organism without the artificial DNA construct.

In some embodiments, the artificial DNA construct further includes a transcribable nucleic acid sequence selected from the group consisting of: (a) SEQ ID NO: 61 (indole hydroxylase), or a nucleotide sequence at least 90% identical thereto and encoding a polypeptide having indole hydroxylase activity; (b) SEQ ID NO: 59 (isatin hydrolase, IsH), or a nucleotide sequence at least 90% identical thereto and encoding a polypeptide having IsH activity; (c) SEQ ID NO: 60 (PtBG), or a nucleotide sequence at least 90% identical thereto and encoding a polypeptide having PtBG activity; (d) SEQ ID NO: 56 (AtR2), or a nucleotide sequence at least 90% identical thereto and encoding a polypeptide having AtR2 activity or P450 reductase activity; and (e) SEQ ID NO: 62 (AtR1), or a nucleotide sequence at least 90% identical thereto and encoding a polypeptide having AtR1 activity or P450 reductase activity.

Another aspect provides a method of producing a transgenic organism including: transforming an organism with an artificial DNA construct, the artificial construct includes, as operably associated components in the 5' to 3' direction of transcription, (i) a promoter that functions in the organism; (ii) a first transcribable nucleic acid sequence or a second transcribable nucleic acid sequence, (a) the first transcribable nucleic acid sequence encoding a tryptophan synthase alpha subunit (TSA) selected from the group consisting of (1) SEQ ID NO: 1 (TSA1), or a nucleotide sequence at least 90% identical thereto and encoding a polypeptide catalyzing cleavage of indole-3-glycerol phosphate (I3GP) into indole and D-glyceraldehyde-3-phosphate (G3P); and (2) SEQ ID NO: 2 (TSA2), or a nucleotide sequence at least 90% identical thereto and encoding a polypeptide catalyzing cleavage of indole-3-glycerol phosphate (I3GP) into indole and D-glyceraldehyde-3-phosphate (G3P); and (b) the second transcribable nucleic acid sequence encoding a cytochrome P450 polypeptide selected from the group consisting of (1) SEQ ID NO 3 (ItB4), or a nucleotide sequence at least 90% identical thereto and encoding a polypeptide catalyzing formation of 2-hydroxyindole from indole; or (2) SEQ ID NO: 4 (ItB24), or a nucleotide sequence at least 90% identical thereto and encoding a polypeptide catalyzing formation of 3-hydroxyindole from indole; and (iii) a transcriptional termination sequence; wherein the organism produces increased levels of indole-derived compounds, or precursors thereof, compared to an organism without the artificial DNA construct.

In some embodiments, the artificial DNA construct further includes a transcribable nucleic acid sequence selected from the group consisting of: (a) SEQ ID NO: 61 (indole hydroxylase), or a nucleotide sequence at least 90% identical thereto and encoding a polypeptide having indole hydroxylase activity; and (b) SEQ ID NO: 59 (isatin hydrolase, IsH), or a nucleotide sequence at least 90% identical thereto and encoding a polypeptide having IsH activity; (c) SEQ ID NO: 60 (PtBG), or a nucleotide sequence at least 90% identical thereto and encoding a polypeptide having PtBG activity.

In some embodiments, the method further includes the growth medium including amino levulinic acid (ALA).

In some embodiments, the transgenic organism or method includes a bacteria or plant.

In some embodiments, the transgenic organism or method includes *E. coli* or *Agrobacterium tumefaciens.*

In some embodiments, the transgenic organism or method includes *Indigofera tinctoria* (Fabaceae); *Indigofera suffruticosa* (Fabaceae); *Indigofera micheliana; Indigofera arrecta; Inidgofera coerulea; Baptisia leucantha* (Fabaceae); *Isatis tinctoria* (Brassicacea); *Polygonum tinctorium* (Polygonaceae) aka *Persicaria tinctoria; Calanthe* discolor (Orchidaceae); *Strobilanthes cusia* (Acanthaceae) aka *Baphicacanthus cusia; Justicia spicegera* (Acanthaceae) aka *Jacobinia mohintli; Justicia colorifera* (Acanthaceae) aka *Jacobinia tinctoria; Couroupita guaianensis* (Lecythidaceae); *Wrightia tinctoria* (Apocyanceae); *Marsdenia tinctoria* (Apocynaceae); *Lonchocarpus cyanescence* (Fabaceae) syn *Philenoptera cyanescens; Isatis indigotica* (Brassicaceae); *Isatis candoleana; Isatis buschiana; Isatis tinctoria* subsp. *Corymbosa; Koaophyllon tinctorium* (Compositae, Eupatorieae) syn *Eupatorium indigofera; Cybistax antisyphilitica* (Bignoniacea) aka *Yangua tinctoria, Isatis tinctoria; Arabidopsis thaliana; Indigofera tinctoria; Polygonum tinctorium; Baphicacanthus cusia*; rose; onion; carnation; or cotton.

In some embodiments, the transgenic organism or method includes an artificial DNA construct further including beta-glucosidase or P450 reductase.

In some embodiments, the transgenic organism or method includes a transgenic organism, or a portion thereof, which includes a colored phenotype.

In some embodiments, the transgenic organism or method includes colored phenotype which includes a visible color selected from the group consisting of magenta, violet, blue, pink, green, yellow, red, yellow, orange, or purple.

In some embodiments, the transgenic organism or method includes an accumulation of an indole derived compound which can impart a visible color to the transgenic organism or a portion of the transgenic organism.

In some embodiments, the transgenic organism or method includes an accumulation of an indole derived compound which can impart a magenta, violet, blue, pink, green, yellow, red, yellow, orange, or purple color to the transgenic organism or a portion of the transgenic organism.

Another aspect provides a method for increasing indole-derived compound production in an organism that includes P450 reductase including: isolating the RNA from an indigo producing plant; obtaining the sequences of the genes by RNA sequencing and assembly; identifying P450 genes based on comparison to sequences similar to known P450 genes; cloning the coding regions of P450 genes into an expression vector; transforming the vector containing the P450 gene and the P450 reductase into the organism; and inducing the expression of the P450 gene and P450 reductase.

Another aspect provides an artificial DNA construct includes: (i) a promoter that functions in the organism; (ii) a first transcribable nucleic acid sequence or a second transcribable nucleic acid sequence, (a) the first transcribable nucleic acid sequence encoding a tryptophan synthase alpha subunit (TSA) selected from the group consisting of (1) SEQ ID NO: 1 (TSA1), or a nucleotide sequence at least 90% identical thereto and encoding a polypeptide catalyzing cleavage of indole-3-glycerol phosphate (I3GP) into indole and D-glyceraldehyde-3-phosphate (G3P); and (2) SEQ ID NO: 2 (TSA2), or a nucleotide sequence at least 90% identical thereto and encoding a polypeptide catalyzing cleavage of indole-3-glycerol phosphate (I3GP) into indole and D-glyceraldehyde-3-phosphate (G3P); and (b) the second transcribable nucleic acid sequence encoding a cytochrome P450 polypeptide selected from the group consisting of (1) SEQ ID NO 3 (ItB4), or a nucleotide sequence at least 90% identical thereto and encoding a polypeptide catalyzing formation of 2-hydroxyindole from indole; or (2) SEQ ID NO: 4 (ItB24), or a nucleotide sequence at least 90% identical thereto and encoding a polypeptide catalyzing formation of 3-hydroxyindole from indole; and (iii) a transcriptional termination sequence.

In some embodiments, the artificial DNA construct further includes a transcribable nucleic acid sequence selected from the group consisting of: (a) SEQ ID NO: 61 (indole hydroxylase), or a nucleotide sequence at least 90% identical thereto and encoding a polypeptide having indole hydroxylase activity; (b) SEQ ID NO: 59 (isatin hydrolase, IsH), or a nucleotide sequence at least 90% identical thereto and encoding a polypeptide having IsH activity; (c) SEQ ID NO: 60 (PtBG), or a nucleotide sequence at least 90% identical thereto and encoding a polypeptide having PtBG activity; (d) SEQ ID NO: 56 (AtR2), or a nucleotide sequence at least 90% identical thereto and encoding a polypeptide having AtR2 activity or P450 reductase activity; and (e) SEQ ID NO: 62 (AtR1), or a nucleotide sequence at least 90% identical thereto and encoding a polypeptide having AtR1 activity or P450 reductase activity.

In some embodiments, the artificial DNA construct further includes beta-glucosidase or P450 reductase.

Other objects and features will be in part apparent and in part pointed out hereinafter.

DESCRIPTION OF THE DRAWINGS

Those of skill in the art will understand that the drawings, described below, are for illustrative purposes only. The drawings are not intended to limit the scope of the present teachings in any way.

FIG. 1A shows the chemical structure of indirubin.

FIG. 1B shows the chemical structure of indigo.

Solvent B— Methanol. Mtd-50% for 10 min. 50-100% for 30 min. Flow rate-0.5 mL/min. Injection volume-5 μL. Detector—540 nm for indirubin. 615 nm for indigo.

Figure 22:
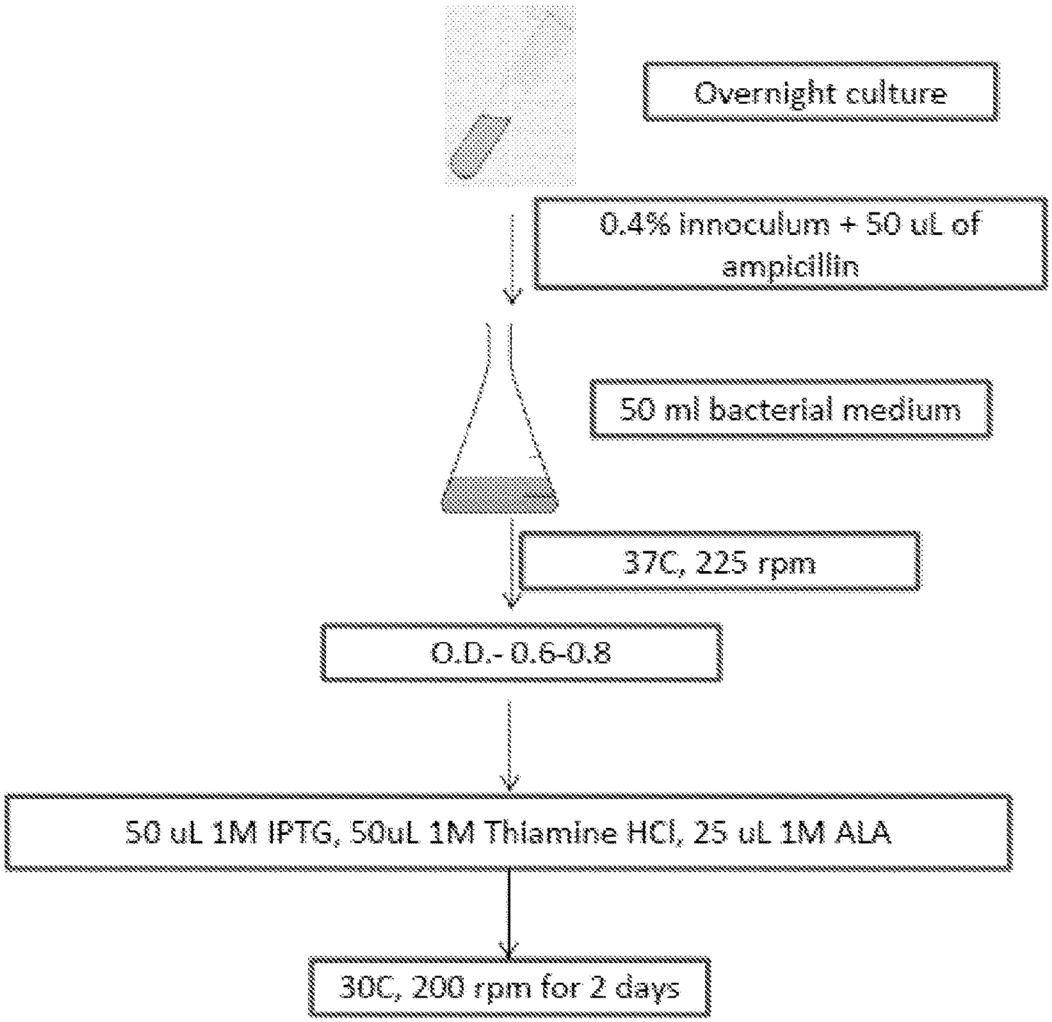

FIG. 22 is a scheme showing the experimental method for bacteria culture.

Figure 23:
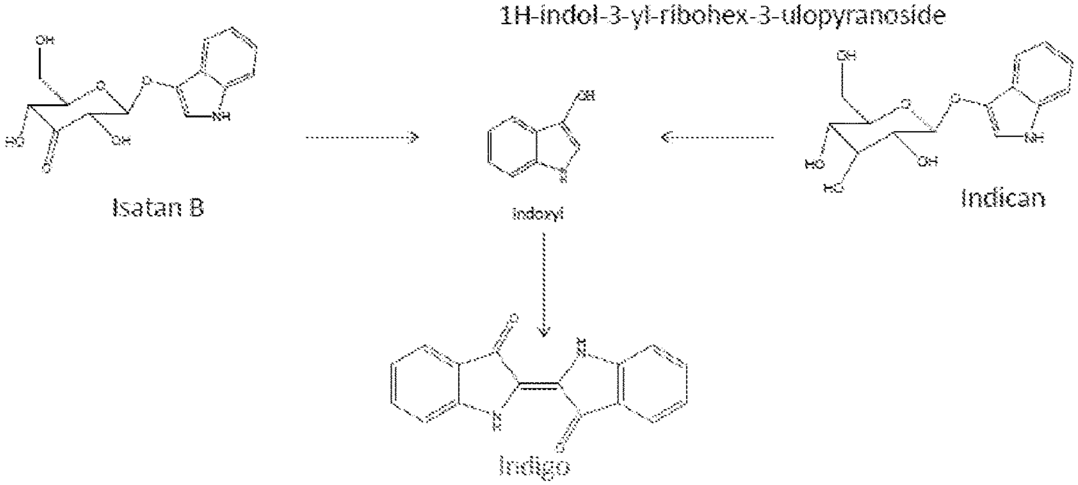

FIG. 23 is a scheme showing the indigo precursors: Isatan B (indoxyl-β-ketogluconate), indoxyl, and Indican (indoxyl-β-D-glucoside).

Figure 24:
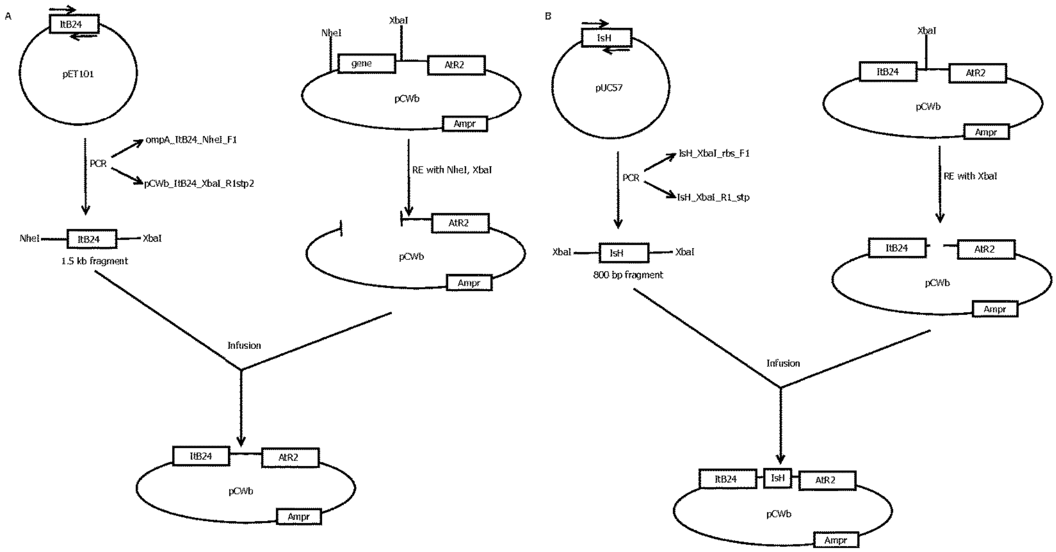

FIG. 24 is a scheme showing the construction of plasmids (i) ItB24_AtR2 and (ii) ItB24_IsH_AtR2.

Figures 25A, 25B:
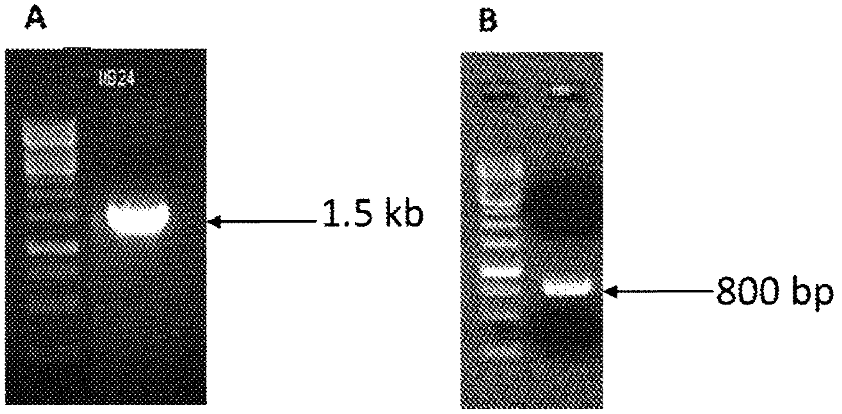

FIG. 25A-FIG. 25B shows Agarose gel electrophoresis. FIG. 25A shows ItB24 amplification from pCWb_ItB24_AtR2 plasmid showing 1.5 kb band. FIG. 25B shows IsH amplification from pCWb_ItB24_IsH_AtR2 plasmid showing 800 bp band.

Figures 26A, 26B:
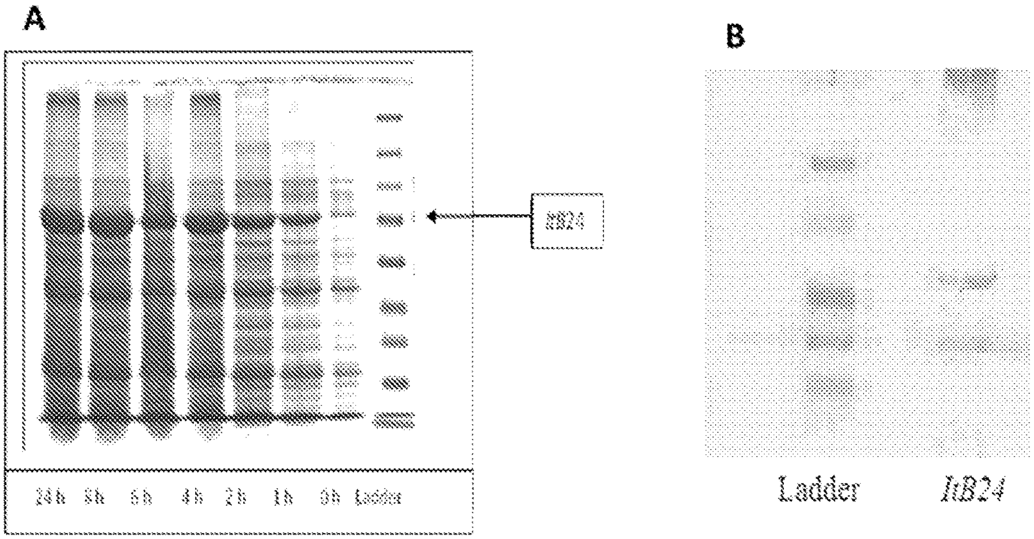

FIG. 26A shows protein expression by SDS-PAGE gel electrophoresis of bacterial cell lysates expressing ItB24_AtR2 at different time points.

FIG. 26B shows protein expression by Western blot analysis of bacterial cell lysates expressing His-tagged ItB24_AtR2.

Figure 27A:
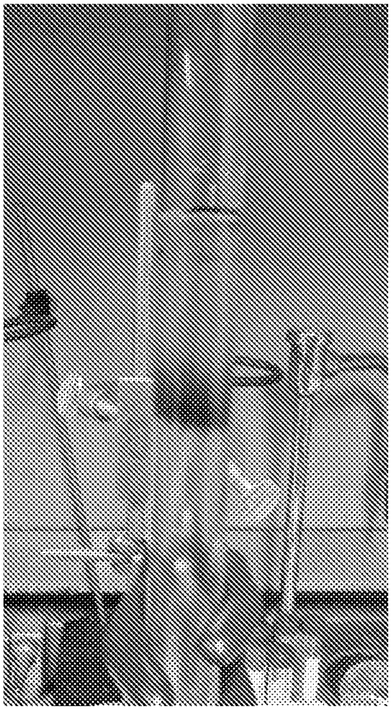

FIG. 27A is an image of column chromatography showing of indigo and indirubin fractions.

Figure 27B:
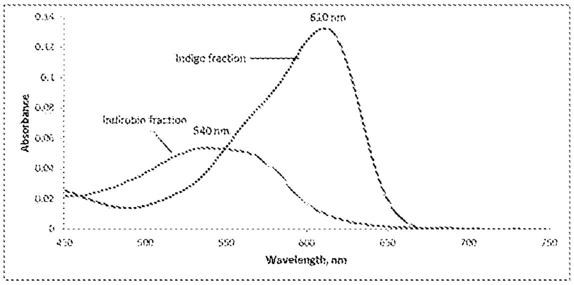

FIG. 27B shows a UV scan of indigo and indirubin fractions from column chromatography.

Figures 28A, 28B, 28C, 28D, 28E:
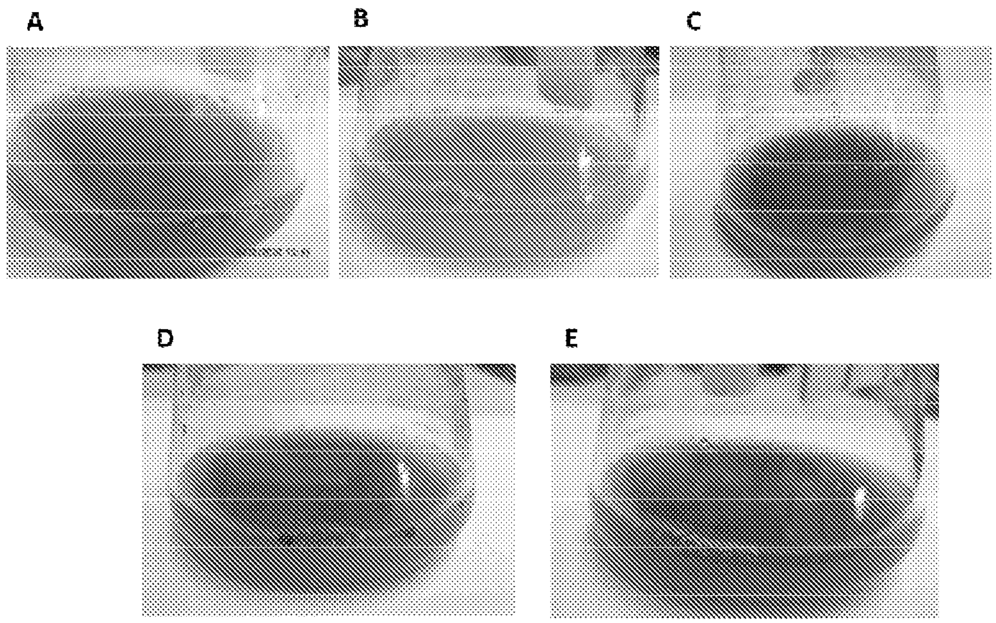

FIG. 28A-FIG. 28E is a series of images of heterologous expression in *E. coli*. FIG. 28A shows expression of ItB24_AtR2 in mod.TB. FIG. 28B shows expression of ItB24_AtR2 with no ALA in mod. TB. FIG. 28C shows expression of ItB24_AtR2 in regular TB. FIG. 28D shows expression of ItB24_IsH_AtR2 in mod. TB. FIG. 28E shows expression of ItB24_IsH_AtR2 in regular TB.

Figures 29A, 29B, 29C, 29D:
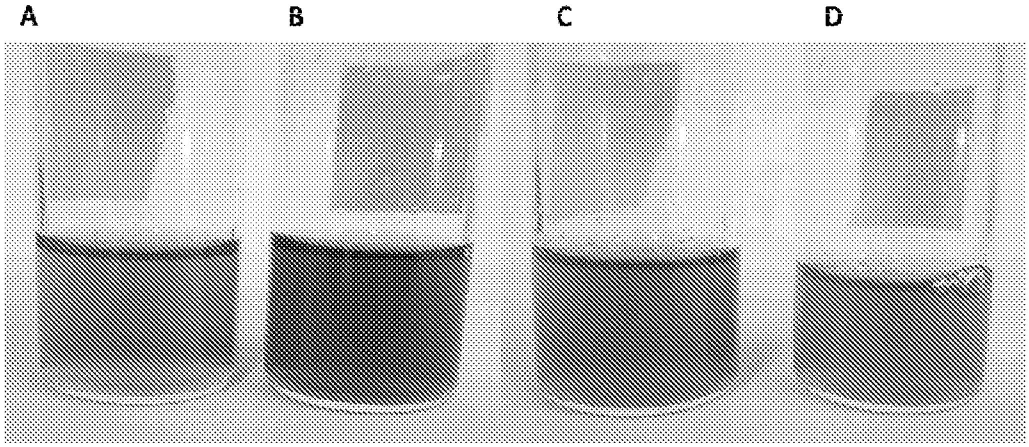

FIG. 29A-FIG. 29D is a series of images showing pigment formation in DMF extracts. FIG. 29A is an image showing pigment formation in DMF extract from ItB24_AtR2 in mod. TB (blue). FIG. 29B is an image showing pigment formation in DMF extract from ItB24_IsH_AtR2 in mod. TB (blue). FIG. 29C is an image showing pigment formation in DMF extract from ItB24_IsH_AtR2 in reg TB (green). FIG. 29D is an image showing pigment formation in DMF extract from ItB24_IsH_AtR2 in reg TB (yellow).

Figure 30A:
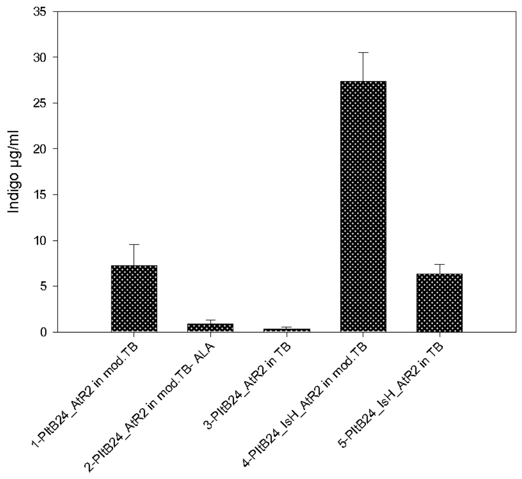

FIG. 30A is a comparison of Indigo in-1-ItB24_AtR2 in modified TB medium, 2-ItB24AtR2 in modified TB medium lacking 5-ALA, 3-ItB24_AtR2 in regular TB, 4-ItB24_IsH_AtR2 in modified TB medium, and 5-ItB24_IsH_AtR2 in regular TB medium.

Figure 30B:
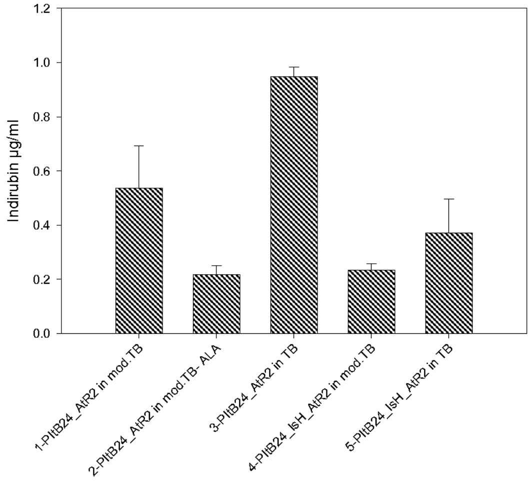

FIG. 30B is a comparison of indirubin in-1-ItB24_AtR2 in modified TB medium, 2-ItB24_AtR2 in modified TB medium lacking 5-ALA, 3-ItB24_AtR2 in regular TB, 4-ItB24_IsH_AtR2 in modified TB medium, and 5-ItB24_IsH_AtR2 in regular TB medium.

Figures 31A, 31B:
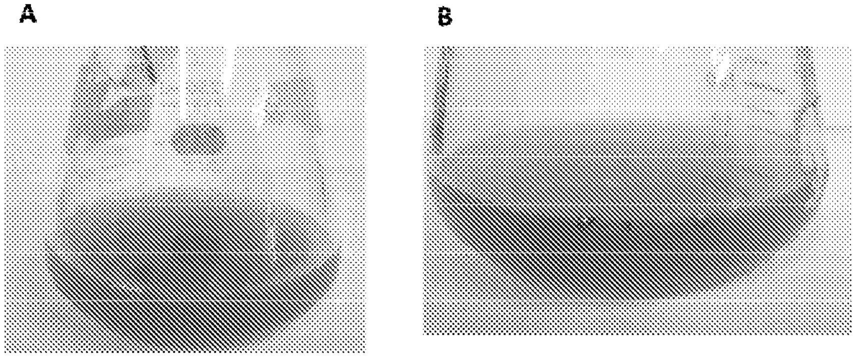

FIG. 31A shows the heterologous expression of ItB24_AtR2 in 100 mg/L isatin concentration.

FIG. 31B shows the heterologous expression of ItB24_AtR2 in 500 mg/L 2-oxindole concentration.

Figure 32:
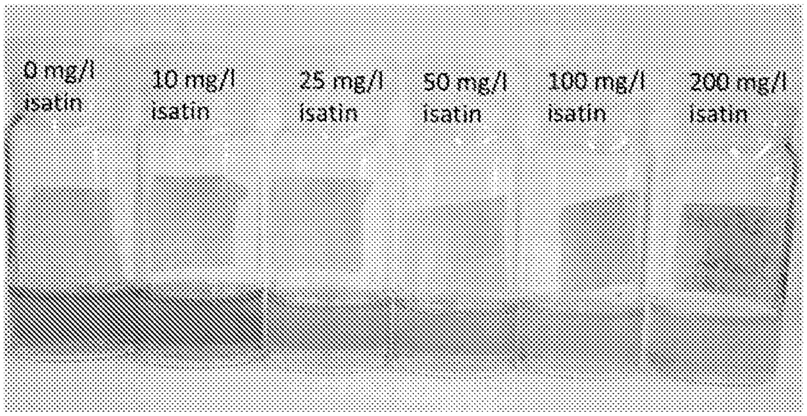

FIG. 32 is an image of vials showing pigment formation in different concentration of isatin (blue, blue, unkn, pink, pink, pink/orange).

Figure 33A:
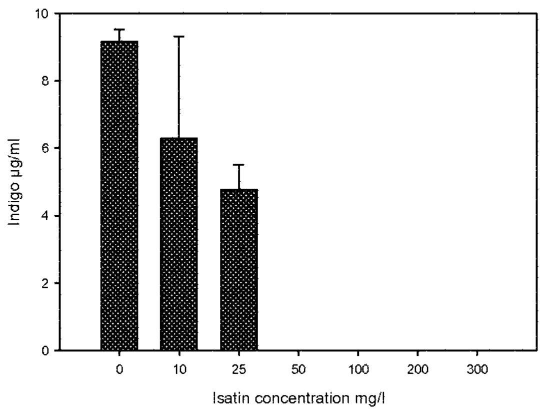

FIG. 33A is a bar graph showing the effect of different concentrations of isatin (mg/L) on indigo production (μg/ml).

Figure 33B:
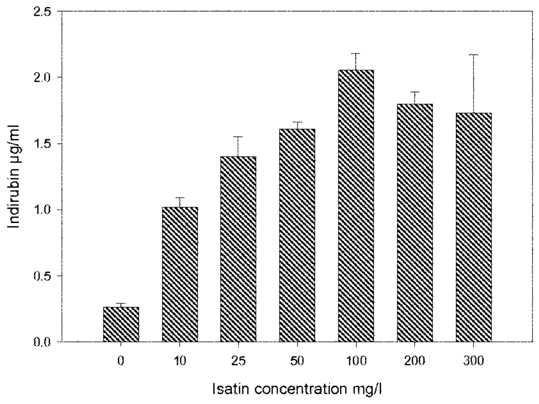

FIG. 33B is a bar graph showing the effect of different concentrations of isatin (mg/L) on indirubin production (μg/ml).

Figure 34:
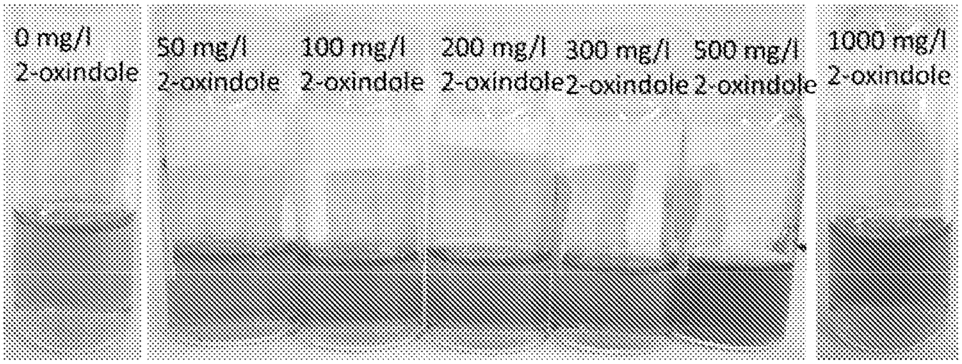

FIG. 34 is an image showing pigment formation in different concentrations of 2-oxindole (green, pink/magenta/orange).

Figure 35A:
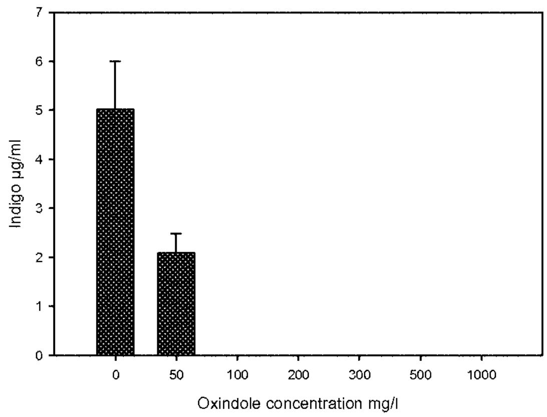

FIG. 35A is a bar graph showing the effect of different concentration of 2-oxindole (mg/L) on indigo production (μg/ml).

Figure 35B:
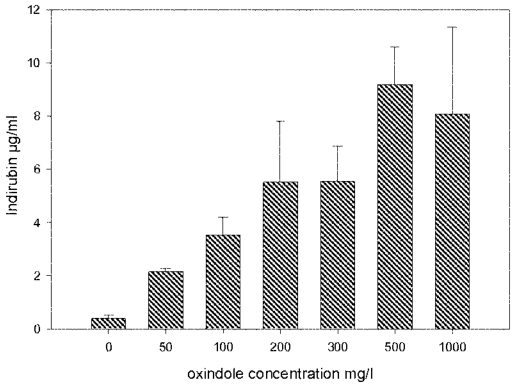

FIG. 35B is a bar graph showing the effect of different concentration of 2-oxindole (mg/L) on indirubin production (μg/ml).

Figure 36:
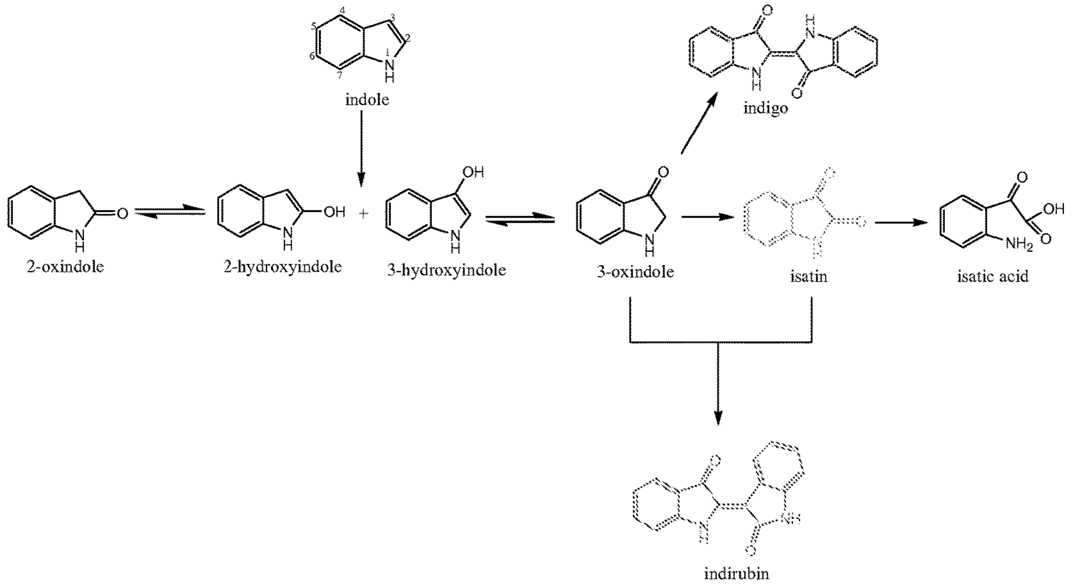

FIG. 36 is a scheme showing the proposed pathway of ItB24 in *E. coli.*

Figure 37A:
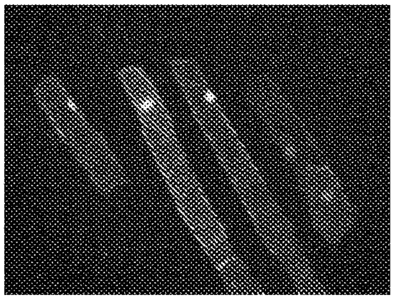
Figure 37B:
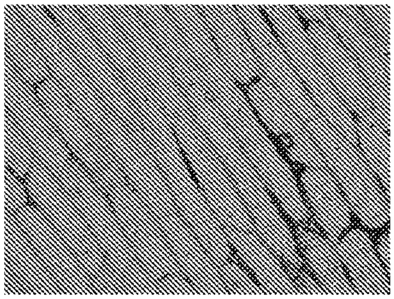
Figure 37C:
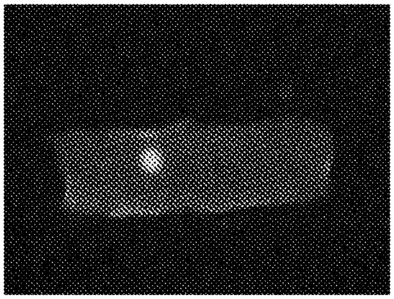
Figure 37D:
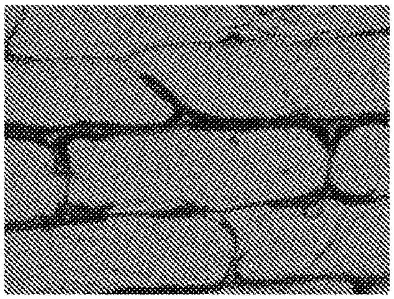

FIG. 37A-FIG. 37D is a series of images showing successful expression of GFP in onion. Blue was observed in between cells in the cell wall. FIG. 37A is a fluoroscopy image of GFP expression in onion. FIG. 37B is a corresponding bright field image to FIG. 37A. FIG. 37C is a higher magnification fluoroscopy image of GFP expression in onion. FIG. 37D is a corresponding bright field image to FIG. 37C.

DETAILED DESCRIPTION OF THE INVENTION

The present disclosure is based, at least in part, on the discovery that a gene isolated from woad (*Isatis tinctoria*) (e.g., TSA2) produces the precursor indole for indigo and indirubin production. Further, the present disclosure is based, at least in part, on the discovery that further genes (e.g., ItB4, ItB24) isolated from woad can synthesize intermediate precursors for indigo and indirubin production.

To date, despite the wide variety of genes that can produce indigo (and indirubin) from indole, none so far have been successfully used to enhance the production of indigo (or indirubin) in plants.

Described herein are genes (e.g., TSA1, TSA2) isolated from the woad plant (*Isatis tinctoria* L.), which can provide the precursor, indole, and convert indole into indoxyl (a precursor of indigo and indirubin) and a method to enhance production of indigo, indirubin, and other indole-derived compounds in plants by overexpression of the gene. The present disclosure further describes plant nucleotide sequences and their encoding proteins (e.g., cytochrome P450 genes from *Isatis tinctoria*) that enable an organism to produce blue and red pigments. Cytochrome P450 genes (e.g., ItB4, ItB24) in woad encode cytochrome P450 enzymes that oxidize indole to yield indigo and indirubin.

It can be advantageous to increase levels of indigo precursors in plants for markets such as the dye industry. It can be advantageous to increase levels of indirubin for markets such as the medical therapeutics industry. In some embodiments, indirubin production can be reduced (e.g., by genetic modification) to improve quality or quantity of extractable indigo.

Thus is provided compositions and methods for producing exogenous, or increasing production of endogenous, indigo or related compounds in plants. Indigo or related compounds derived from a plant (i.e., a natural indigo) can provide a more environment-friendly (e.g., less polluting) or non-petroleum based (e.g., more sustainable in the long-term) alternative over synthetic compounds.

Combining an endogenous ability of plants to make indigo with the biotechnological enhancement provided by indigo-producing genes can lead to large-scale production of "biotech plant indigo" by transgenic plants. Such enzymes can be transferred to plants to produce increased levels of indigo precursors in transgenic plants, or produce genetically modified plants or plant parts having a colored phenotype (e.g., blue cotton fibers and blue flowers).

Compositions and methods of the present disclosure can provide advantages over bacterial production of indole or related compounds. Bacteria can require input of carbon and other nutrients for growth, which can add to the cost of production. Because plants use sunlight as a carbon source and can be grown as a crop, the use of plants can be more economical than using bacteria. Further, expression of bacterial genes in plants can be lethal because the bacterial enzyme can act on other metabolites besides indole.

Indigo-producing genes from bacteria or humans transferred into plants have been reported, but results showed that plants were stunted and sickly. Such problems with bacterial or human enzymes may be associated with non-specific activity, such as oxidation of other substrates besides indole. It is presently thought that these undesirable results can be likely due to the fact that indole-oxidizing enzymes from bacteria and humans are mainly used in xenobiotic metabolism, which generally requires broad substrate specificities to detoxify a wide range of compounds.

Prior to the present disclosure, transgenic plants with enhanced levels of indigo or its precursors have not been reported, at least partly because genes for producing indigo in plants were not known.

Thus, as disclosed herein, an indole-oxidizing enzyme with narrower specificity or naturally-occurring in plants can be used.

Indole-Derived Compound

A host organism can be transformed so as to produce an indole-derived compound. As described herein, constructs that modulate production of indole or indole derived compounds in plants have been identified. For example, an enzyme that converts indole to indoxyl in plants has been identified.

An indole or indole-derived compound can be any compound that can be synthesized from indole. For example, an indole derived compound can be indole, indoxyl, indigo, indirubin, isatin, hydroxyindole (e.g., 2-hydroxyindole and 3-hydroxyindole), isatan B, indican, 2-oxindole, 3-oxindole, or isatic acid.

As another example, an indole or indole-derived compound can be one or more of the following:

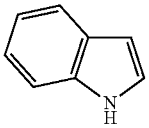

indole;

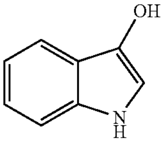

indoxyl;

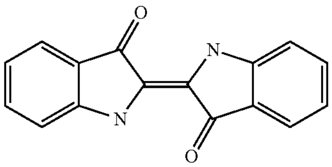 [SMILES: O=C1/C(=C2\Nc3ccccc3C2=O)Nc2ccccc21]

indigo;

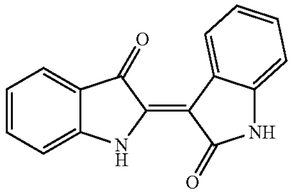 [SMILES: O=C1Nc2ccccc2/C1=C1/Nc2ccccc2C1=O]

indirubin;

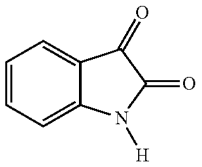 [SMILES: O=C1Nc2ccccc2C1=O]

isatin;

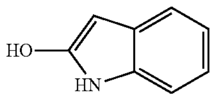

2-hydroxyindole;

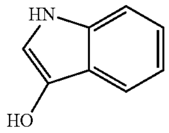

3-hydroxyindole;

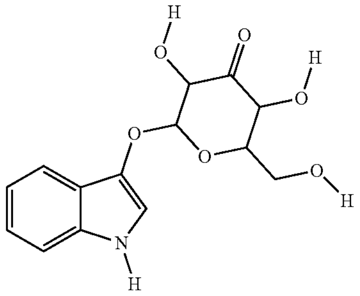 [SMILES: O=C1C(O)C(CO)OC(Oc2c[nH]c3ccccc23)C1O]

isatan B;

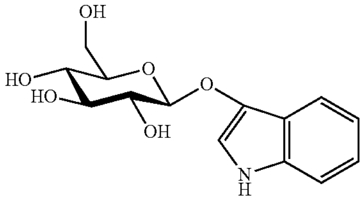

indican;

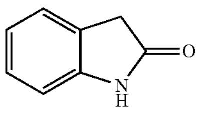

2-oxindole;

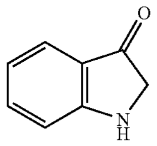

3-oxindole; or

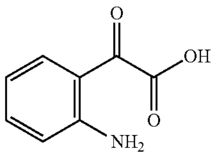 [SMILES: Nc1ccccc1C(=O)C(=O)O]

isatic acid.

An indole-derived compound can exhibit a visible color. For example, modulation of an indole-derived compound can produce a compound having a visible color. As another example, an indole derived compound color can have any color in the visible spectrum (e.g., between about 390-700 nm). As another example, an indole derived compound color can have one of the following colors: violet (e.g., about 380-450 nm), blue (e.g., about 450-495 nm), green (e.g., about 495-570 nm), yellow (e.g., about 570-590 nm), orange (e.g., about 590-620 nm), or red (e.g., about 620-750 nm).

An indole-derived compound can be endogenous or exogenous to the host organism. Where an indole-derived compound is endogenous, the host organism can be engineered to produce increased levels of such indole-derived compound. Where an indole-derived compound is exogenous, the host organism can be engineered to produce such indole-derived compound.

The host organism can be engineered to synthesize an indole-derived compound, after some developmental state, or upon being induced to do so. Induction of an indole-derived compound synthesis can be according to the actions of an inducible promoter associated with the transcribable polynucleic acid sequence, as discussed in further detail herein.

A transformed host organism or a host cell can be analyzed for the presence of an indole-derived compound conferred by the expression system of the present disclosure. Those of skill in the art are aware of the numerous methods available for the analysis of such compounds. For example, methods for analysis include, but are not limited to TLC, HPLC, NMR, or GC-MS.

Transcribable Nucleic Acid Sequences

Provided herein are transcribable nucleic acid sequences that can be expressed or overexpressed in a host organism so as to produce or increase production of an indole-derived compound.

Various transcribable nucleic acid sequences described herein encode polypeptides that can convert (i) indole-3-glycerol phosphate (I3GP) into indole or (ii) indole to indoxyl. Such acid sequences can ultimately facilitate production of indigo or indirubin.

Formation of indole requires cleavage of indole-3-glycerol phosphate (I3GP) into indole and D-glyceraldehyde-3-phosphate (G3P).

Conversion of indole to indigo can require hydroxylation of indole at position 3 that gives rise to indoxyl (i.e., 3-hydroxyindole), which can spontaneously dimerize with another 3-hydroxyindole in the presence of oxygen to form indigo.

Conversion of indoxyl to indirubin can require hydroxylation of indole at position 2 that gives rise to isatin, which can spontaneously couples with indoxyl (i.e., 3-hydroxyindole) in the presence of oxygen to form indirubin. Indirubin can conceivably be formed by coupling indoxyl (i.e., 3-hydroxyindole) and 2-hydroxyindole.

Exemplary transcribable nucleic acid sequences that can be expressed or overexpressed in a host organism so as to produce or increase production of an indole-derived compound include, but are not limited to, TSA (e.g., TSA1, TSA2), P450 (e.g., ItB4, ItB24), indole hydroxylase, isatin hydrolase, and PtBG. Such transcribable nucleic acid sequences can be used alone or in various combinations to transform a plant.

A transcribable nucleic acid sequence (or multiple transcribable nucleic acid sequence) can be inserted into a cloning vector.

A transcribable nucleic acid sequence (or multiple transcribable nucleic acid sequences) can form indole when expressed in *E. coli.*

TSA.

A transcribable nucleic acid sequence encoding a polypeptide having a tryptophan synthase alpha subunit (TSA) activity can be expressed or overexpressed in a host organism.

As described herein, TSA has been identified in plants and shown to form indole by cleaving indole-3-glycerol phosphate (I3GP) into indole and D-glyceraldehyde-3-phosphate (G3P) (e.g., TSA activity as used herein). A gene isolated from a plant, such as woad (*Isatis tinctoria*), can be advantageous over a bacteria gene because (i) the gene is specific for indole or (ii) the gene is a plant gene for indigo production.

A host organism can be transformed so as to have TSA activity. A plant-derived TSA gene (e.g., isolated from the woad plant) can provide for the precursor, indole, and convert indole into indoxyl (a precursor of indigo and indirubin). As disclosed herein, overexpression of a transcribable nucleic acid sequence encoding a polypeptide having TSA activity can provide a method to enhance production of indigo, indirubin, or other indole-derived compounds. The alpha subunit (TSA) of a bifunctional tryptophan synthase enzyme can produce indole by cleaving indole-3-glycerol phosphate (I3GP) into indole and D-glyceraldehyde-3-phosphate (G3P). TSA-like genes can be found in various plant species including maize, *Arabidopsis*, and *Isatis tinctoria* (also known as woad).

TSA1.

A transcribable nucleic acid sequence can be TSA1. A TSA1 transcribable nucleic acid sequence can include SEQ ID NO: 1. A TSA1 transcribable nucleic acid sequence can include a nucleic acid sequence having at least about 80% sequence identity to SEQ ID NO: 1 and encoding a polypeptide having TSA activity. For example, a TSA1 transcribable nucleic acid sequence can include a nucleic acid sequence having at least about 80%, at least about 85%, at least about 90%, at least about 91%, at least about 92%, at least about 93%, at least about 94%, at least about 95%, at least about 96%, at least about 97%, at least about 98%, or at least about 99% sequence identity to SEQ ID NO: 1 and encoding a polypeptide having a TSA or TSA1 activity.

TSA2.

A transcribable nucleic acid sequence can be TSA2. A TSA2 transcribable nucleic acid sequence can include SEQ ID NO: 2. A TSA2 transcribable nucleic acid sequence can include a nucleic acid sequence having at least about 80% sequence identity to SEQ ID NO: 2 and encoding a polypeptide having TSA activity. For example, A TSA2 transcribable nucleic acid sequence can include a nucleic acid sequence having at least about 80%, at least about 85%, at least about 90%, at least about 91%, at least about 92%, at least about 93%, at least about 94%, at least about 95%, at least about 96%, at least about 97%, at least about 98%, or at least about 99% sequence identity to SEQ ID NO: 2 and encoding a polypeptide having a TSA or TSA2 activity.

TSA2 can be inserted into a cloning vector. For example, TSA2 can be inserted into pUC18 with ampicillin resistance marker.

As described herein, this plasmid can be used to complement a trpA-mutant known as JW1252-1. Thus TSA2 can also make indole when expressed in *E. coli.*

P450.

A transcribable nucleic acid sequence encoding a polypeptide having a P450 activity (i.e., P450 transcribable nucleic acid sequence) can be expressed or overexpressed in a host organism. A P450 transcribable nucleic acid sequence can encode a cytochrome P450 enzyme that can oxidize indole to yield indigo or indirubin.

Conversion of indole to indirubin can require hydroxylation of indole at position 2 that gives rise to 2-hydroxyindole, which can spontaneously dimerize with indoxyl (i.e., 3-hydroxyindole) in the presence of oxygen to form indigo. Indirubin can be formed by coupling indoxyl (i.e., 3-hydroxyindole) and isatin.

As described herein, plant P450 genes were identified that encode proteins that oxidize indole to indoxyl or isatin (e.g., P450 activity as used herein), which spontaneously lead to the formation of indigo or indirubin. These nucleotide sequences can be used to modify or increase indigo or indirubin production in plants and microorganisms. A gene isolated from a plant, such as woad (*Isatis tinctoria*), can be advantageous over a bacteria gene because (i) the gene is specific for indole or (ii) the gene is a plant gene for indigo production. Because the disclosed P450 transcribable nucleic acid sequences are from plants, expression of such sequences in plants are shown to have no or substantially no detrimental effects, contrary to what was observed in the expression of bacterial and human P450s in plants.

A P450 transcribable nucleic acid sequence can be used to enhance production of indigo, indirubin, or other indigoids in a host organism, such as a woad plant. A P450 transcribable nucleic acid sequence can provide for production of pigments (e.g., blue or red) in a host organism. For example, a P450 transcribable nucleic acid sequence can be used to make colored cotton (e.g., blue cotton) by expressing the P450 transcribable nucleic acid sequence in a cotton plants. Such methods or compositions can provide a textile (e.g., jeans) that does not have to be dyed (e.g., blue). As another example, a P450 transcribable nucleic acid sequence can also be expressed in a flower petal (e.g., roses) to make them colored (e.g., blue). Such a colored rose can have a worldwide market. Production of a plant or plant part having a colored phenotype is further described herein.

One aspect of the present disclosure provides for isolated P450 nucleic acid or amino acid sequences associated with the biosynthesis of indigo precursors or indirubin in plants. Using indole as substrate, one P450 transcribable nucleic acid sequence (e.g., ItB24) can make more indigo than indirubin, while the other (e.g., ItB4) can make more indirubin than indigo (sequences further discussed below). A ratio of indigo to indirubin can affect the resulting color of the enzyme-catalyzed indole oxidation, ranging from dark blue to different shades of purple to light red. Thus, the ratio of expressed P450 sequences (e.g., ItB24 and ItB4), can provide different colors for plants and plant parts (e.g., flowers or fibers, such as cotton fibers).

A plant P450 gene can fuse to a P450 reductase, so that the P450 gene may no longer require the endogenous P450 reductase of a host organism. A P450 reductase of a plant can be found in the endoplasmic reticulum, where plant P450 enzymes are also targeted. P450/P450 reductase fusion proteins may be targeted to another compartment, such as the chloroplast, where there are no glycosyltransferases that can convert indoxyl to indican. Such an approach can allow indoxyl to spontaneously form indigo. To verify that the chloroplast has indole precursors that the fusion protein can use to make indoxyl, a chloroplast can also be co-transformed with indole synthase gene from maize (Melanson et al. 1997; Frey et al. 1997), *Arabidopsis* (Zhang et al. 2008), or *Isatis tinctoria*, the sequence of which is also provided herein (TSA2 (SEQ ID NO: 2)).

Nucleotide sequences can also be used to design DNA probes and oligonucleotide primers to isolate other P450 genes that encode proteins having indole oxidation capability for the production of indigo and indirubin.

Also provided is a method to isolate other P450s from other plants having indole oxidation activity that can lead to indigo and indirubin formation. The method can include (1) isolating RNA from indigo-producing plants, (2) obtaining the sequences of the genes by RNA sequencing and assembly, (3) looking for P450 genes based on sequence similar to known P450 genes using nucleotide comparison algorithms such as BLAST and ClustalW, (4) PCR cloning the coding regions of P450 genes into a bacterial expression plasmid that already has a plant P450 reductase, (5) transforming the plasmid containing the P450 gene and the P450 reductase into bacteria, (6) inducing the expression of the P450 gene and P450 reductase, and (7) monitoring for the formation of blue and/or red pigments by TLC, HPLC or GC-MS.

Exemplary P450 transcribable nucleic acid sequences include ItB4 or ItB24.

ItB4.

A transcribable nucleic acid sequence can be ItB4. An ItB4 polypeptide can catalyze formation of 2-hydroxyindole along with indoxyl from indole (e.g., ItB4 activity as used herein). Expression of an ItB4 transcribable nucleic acid sequence can result in increased production of indirubin compared to indigo given increased production of 2-hydroxyindole.

An ItB4 transcribable nucleic acid sequence can include SEQ ID NO: 3. An ItB4 transcribable nucleic acid sequence can include a nucleic acid sequence having at least about 80% sequence identity to SEQ ID NO: 3 and encoding a polypeptide having a P450 activity or ItB4 activity. For example, A, ItB4 transcribable nucleic acid sequence can include a nucleic acid sequence having at least about 80%, at least about 85%, at least about 90%, at least about 91%, at least about 92%, at least about 93%, at least about 94%, at least about 95%, at least about 96%, at least about 97%, at least about 98%, or at least about 99% sequence identity to SEQ ID NO: 3 and encoding a polypeptide having a P450 activity or ItB4 activity.

ItB24.

A transcribable nucleic acid sequence can be ItB24. An ItB24 polypeptide can catalyze formation of 3-hydroxyindole from indole (e.g., ItB24 activity as used herein). Expression of an ItB24 transcribable nucleic acid sequence can result in increased production of indigo compared to indirubin given increased production of 3-hydroxyindole.

An ItB24 transcribable nucleic acid sequence can include SEQ ID NO: 4. An ItB24 transcribable nucleic acid sequence can include a nucleic acid sequence having at least about 80% sequence identity to SEQ ID NO: 4 and encoding a polypeptide having a P450 activity or ItB24 activity. For example, an ItB24 transcribable nucleic acid sequence can include a nucleic acid sequence having at least about 80%, at least about 85%, at least about 90%, at least about 91%, at least about 92%, at least about 93%, at least about 94%, at least about 95%, at least about 96%, at least about 97%, at least about 98%, or at least about 99% sequence identity to SEQ ID NO: 4 and encoding a polypeptide having a P450 activity or ItB24 activity.

P450 Reductase.

Because wild type *E. coli* does not have a P450 reductase, P450 reductase (e.g., AtR1, AtR2) can be coexpressed with one or more genes (e.g., ItB24).

As shown herein, AtR2 (SEQ ID NO: 56) is a P450 reductase from *Arabidopsis*. For example, an AtR2 transcribable nucleic acid sequence can include SEQ ID NO: 56. An AtR2 transcribable nucleic acid sequence can include a nucleic acid sequence having at least about 80% sequence identity to SEQ ID NO: 56 and encoding a polypeptide having a P450 or AtR2 activity. For example, an AtR2 transcribable nucleic acid sequence can include a nucleic acid sequence having at least about 80%, at least about 85%, at least about 90%, at least about 91%, at least about 92%, at least about 93%, at least about 94%, at least about 95%, at least about 96%, at least about 97%, at least about 98%, or at least about 99% sequence identity to SEQ ID NO: 56 and encoding a polypeptide having a P450 reductase or AtR2 activity.

As another example, an AtR1 transcribable nucleic acid sequence can include SEQ ID NO: 62. An AtR1 transcribable nucleic acid sequence can include a nucleic acid sequence having at least about 80% sequence identity to SEQ ID NO: 62 and encoding a polypeptide having a P450 or AtR1 activity. For example, an AtR2 transcribable nucleic acid sequence can include a nucleic acid sequence having at least about 80%, at least about 85%, at least about 90%, at least about 91%, at least about 92%, at least about 93%, at least about 94%, at least about 95%, at least about 96%, at least about 97%, at least about 98%, or at least about 99% sequence identity to SEQ ID NO: 62 and encoding a polypeptide having a P450 reductase or AtR1 activity.

Two genes (e.g., ItB24 and AtR2, or variants thereof) can be inserted into a cloning vector. For example, ItB24 and AtR2 can be inserted in a pCWb cloning vector (e.g., pCWb_ItB24_AtR2). As another example, pCWb can be derived from the pCWori+ vector.

Coexpression of two genes (e.g., ItB24 and AtR2) can be achieved using a Tac promoter. The Tac promoter can direct the production of a bicistronic transcript, where each gene can have its own ribosome binding site.

As shown herein, transformation of this plasmid into DH5alpha can enable the *E. coli* to produce indigo.

Indole Hydroxylase.

Figure 9:
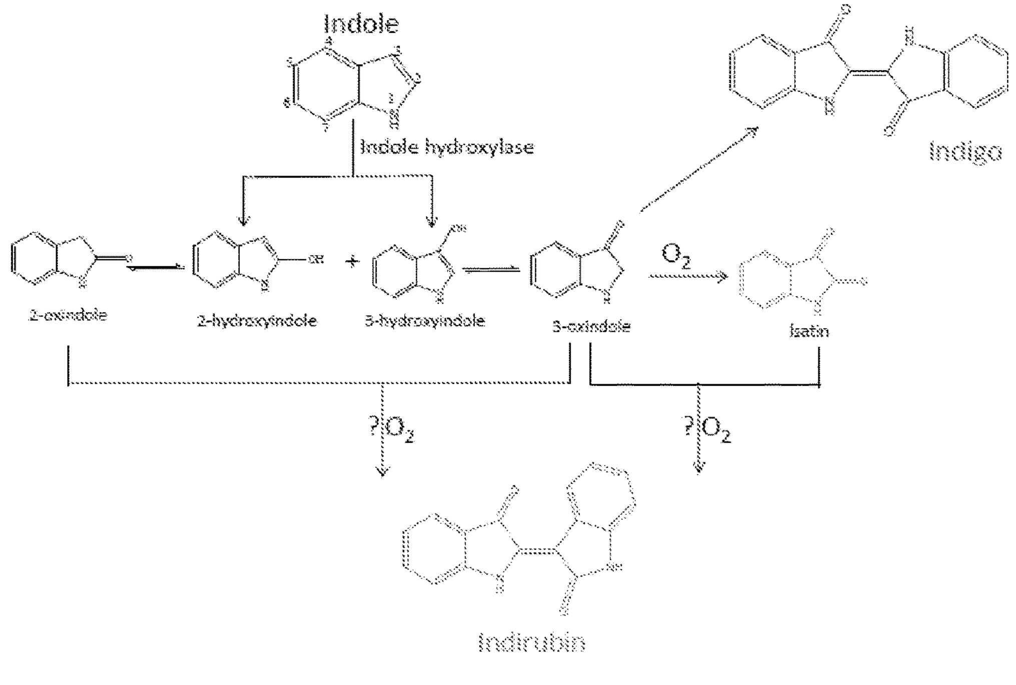
FIG. 9 is a scheme showing the formation of indigo and indirubin.
Figure 10:
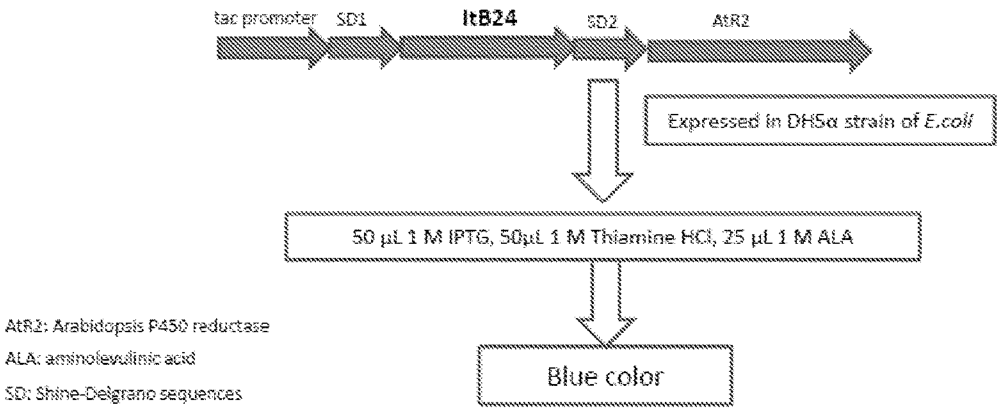
FIG. 10 is a scheme showing the identification of indole hydroxylase. The mRNA was extracted from woad leaves. The cDNA was constructed. P450 genes were cloned into a pCW plasmid.

A transcribable nucleic acid sequence can be indole hydroxylase. Indole hydroxylase can produce indigo and indirubin when expressed in bacteria (Kim et al. 2005, Kim et al. 2003; Ensley et al. 1983). Expression of indole hydroxylase can oxidize indole to increase production indigo and indirubin (see e.g., FIG. 9, FIG. 10, Example 15).

As described herein, indole hydroxylase has been identified in plants (e.g., woad) and shown to form hydroxyindole by hydroxylation of indole (e.g., indole hydroxylase activity as used herein).

An indole hydroxylase transcribable nucleic acid sequence can include SEQ ID NO: 61. An indole hydroxylase transcribable nucleic acid sequence can include a nucleic acid sequence having at least about 80% sequence identity to SEQ ID NO: 61 and encoding a polypeptide having indole hydroxylase activity. For example, an indole hydroxylase transcribable nucleic acid sequence can include a nucleic acid sequence having at least about 80%, at least about 85%, at least about 90%, at least about 91%, at least about 92%, at least about 93%, at least about 94%, at least about 95%, at least about 96%, at least about 97%, at least about 98%, or at least about 99% sequence identity to SEQ ID NO: 61 and encoding a polypeptide having indole hydroxylase activity.

Isatin Hydrolase (IsH).

Figure 16:
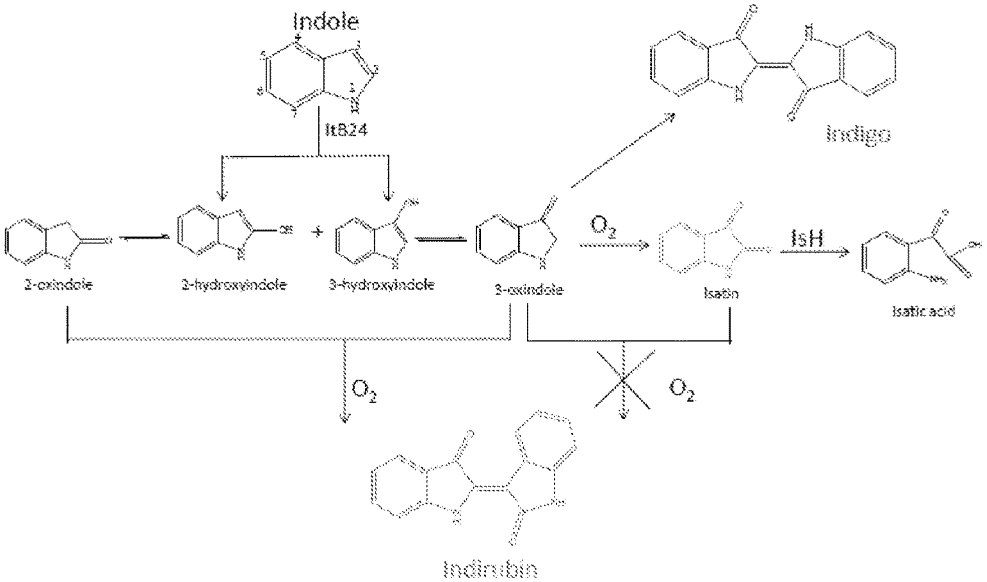
FIG. 16 is a scheme showing how isatin hydroxylase decreases the formation of indirubin.

A transcribable nucleic acid sequence can be isatin hydrolase (IsH). An IsH polypeptide can inhibit formation of indirubin by hydrolyzing the precursor, isatin, to form isatic acid (e.g., IsH activity as used herein) (see e.g., FIG. 16). Expression of an IsH transcribable nucleic acid sequence can result in increased production of indigo production compared with indirubin given decreased production of indirubin.

An IsH transcribable nucleic acid sequence can include SEQ ID NO: 59. An IsH transcribable nucleic acid sequence can include a nucleic acid sequence having at least about 80% sequence identity to SEQ ID NO: 59 and encoding a polypeptide having IsH activity. For example, an IsH transcribable nucleic acid sequence can include a nucleic acid sequence having at least about 80%, at least about 85%, at least about 90%, at least about 91%, at least about 92%, at least about 93%, at least about 94%, at least about 95%, at least about 96%, at least about 97%, at least about 98%, or at least about 99% sequence identity to SEQ ID NO: 59 and encoding a polypeptide having IsH activity.

IsH is an artificially synthesized gene based on a published sequence (AAE030703.1).

IsH can be a bacterial gene. IsH can be expressed in a bacterium. IsH can be expressed in a plant. IsH can be recoded so it is codon optimized for a host organism. IsH can be recoded so it is codon optimized for plants. IsH can be recoded so it is codon optimized for a rose.

IsH can be inserted in a cloning vector. For example, IsH can be inserted in a pUC 57 cloning vector (e.g., IsH in pUC 57).

PtBG.

A transcribable nucleic acid sequence can be PtBG.

A PtBG polypeptide can hydrolyze indican to form indoxyl (e.g., PtBG activity as used herein). Expression of a PtBG transcribable nucleic acid sequence can result in increased production of indigo by increasing production of indoxyl (see e.g., Example 11, Example 12, Example 13).

A PtBG transcribable nucleic acid sequence can include SEQ ID NO: 53. An PtBG transcribable nucleic acid sequence can include a nucleic acid sequence having at least about 80% sequence identity to SEQ ID NO: 53 and encoding a polypeptide having PtBG activity. For example, an PtBG transcribable nucleic acid sequence can include a nucleic acid sequence having at least about 80%, at least about 85%, at least about 90%, at least about 91%, at least about 92%, at least about 93%, at least about 94%, at least about 95%, at least about 96%, at least about 97%, at least about 98%, or at least about 99% sequence identity to SEQ ID NO: 53 and encoding a polypeptide having PtBG activity.

PtBG is an artificially synthesized gene based on the published sequence (GenBank AB003089.1).

PtBG can be inserted into a cloning vector. For example, PtBG can be inserted into a pUC57 cloning vector (e.g., BG_Hh in pUC57).

PtBG can also include a flower-specific promoter, His-tag and terminator (see e.g., SEQ ID NO: 60).

Host Organism

Provided herein is a host organism or cell genetically engineered to produce one or more indole-derived compounds. A host organism or cell can be transformed with a construct described herein, such that the organism or cell can produce indole-derived compounds.

A host organism can be a eukaryotic or a prokaryotic organism.

A host organism can be a photosynthetic organism. A host organism can be, for example, a naturally photosynthetic microorganism, such as a cyanobacterium, or an engineered photosynthetic microorganism, such as an artificially photosynthetic bacterium. Exemplary microorganisms that are either naturally photosynthetic or can be engineered to be photosynthetic include, but are not limited to, bacteria; fungi; archaea; protists; microscopic plants, such as a green algae; and animals such as plankton, planarian, and amoeba. Examples of naturally occurring photosynthetic microorganisms include, but are not limited to, *Spirulina maximum, Spirulina platensis, Dunaliella salina, Botrycoccus braunii, Chlorella vulgaris, Chlorella pyrenoidosa, Serenastrum capricomutum, Scenedesmus auadricauda, Porphyridium cruentum, Scenedesmus acutus, Dunaliella* sp., *Scenedesmus obliquus, Anabaenopsis, Aulosira, Cylindrospermum, Synechoccus* sp., *Synechocystis* sp., or *Tolypothrix.*

For example, a host photosynthetic microorganism can be a cyanobacterium. Cyanobacteria, also known as blue-green algae, are a broad range of oxygenic photoautotrophs. The host cyanobacterium can be any photosynthetic microorganism from the phylum Cyanophyta. The cyanobacterium can have a unicellular or colonial (e.g., filaments, sheets, or balls) morphology. Preferably, the host cyanobacterium is a unicellular cyanobacterium. Examples of cyanobacteria that can be engineered to accumulate a disaccharide sugar include, but are not limited to, the genus *Synechocystis, Synechococcus, Thermosynechococcus, Nostoc, Prochlorococcu, Microcystis, Anabaena, Spirulina*, and *Gloeobacter*. Preferably the host cyanobacterium is a *Synechocystis* spp. or *Synechococcus* spp. More preferably, the host cyanobacterium is *Synechococcus elongatus* PCC 7942 (ATCC 33912) and/or *Synechocystis* spp. PCC 6803 (ATCC 27184).

A host organism can be a plant. As used herein, the term “plant” can include plant cells, plant protoplasts, plant cells of tissue culture from which a plant can be regenerated, plant calli, plant clumps and plant cells that are intact in plants or parts of plants such as pollen, flowers, seeds, leaves, stems, and the like.

A host plant can be any plant in which it is desirable to increase production of an indole-derived compound. A plant can be a flowering plant, conifer, fern, or moss. A host plant can be an angiosperm or a gymnosperm. A plant can be a monocot or a dicot.

A host plant can be a plant capable of producing textiles and fabric, such as cotton, flax, ramie, hemp, and jute.

A host plant can be an industrially important plant, such as woad (*Isatis tinctoria*), *Arabidopsis thaliana, Indigofera tinctoria, Polygonum tinctorium, Baphicacanthus*, roses, cotton, flax, algae, or hemp.

A host plant can be a plant capable of producing dye, such as Alder (*Alnus rubra*), Barberry (*mahonia* sp.), Bloodroot (*Sanguinaria canadensis*), Butternut Tree (*Juglans cinerea*), Carrot (*Daucus carota*), *Eucalyptus*, Giant *Coreopsis* (*Coreopsis gigantea*), Lichen (orchella weed) (Roccellaceae), Lilac (*Syringa vulgaris*), Onion (*Allium cepa*), Pomegranate, Sassafras, Turmeric, Acorns, Amur Maple (*Acer Ginnala*), Beetroot, Birch, Broom, Broom Sedge, Butternut Tree (*Juglans cinerea*), Colorado Fir, Coneflower, Dandelion, Fennel, Goldenrod, Hollyhock, Ivy, Juniper Berries, Maple Trees, Oregano, Pine Tree Bark, St John’s Wort, Sumac, Wild plum root, Strawberries, Avocado, Cherries, Raspberries, Roses, Lavender, Lichens, Camilla, Grand Fir, Dogwood, Red cabbage, Woad (*Isatis tinctoria*), Mulberries, Elderberries, Saffron, Grapes, Blueberries, Cornflower, Cherry, Blackberry, Hyacinth, Japanese indigo, Indigo (leaves), Red Cedar Root, Raspberry, Red Maple Tree, Nearly Black Iris, Dogwood, Oregon Grape, Purple Iris, Sweetgum, Queen Anne’s Lace, Bloodroot (*Sanguinaria canadensis*), Elderberry, pomegranates, Sumac, Sycamore, Dandelion, Beets, Bamboo, Crab Apple, Chokecherries, Madder, Hibiscus Flowers, Canadian Hemlock, Japanese Yew, Wild ripe Blackberries, Brazilwood, St. John’s Wort, Bedstraw (*Galium triflorum*), Iris, Sumac, Meadowsweet, Blackberry, Butternut, Carob, Oak galls, Sawthorn Oak, Walnut, Pokeweed, Hibiscus, Daylilies, Safflower, Logwood, Huckleberry, *Portulaca*, Beluga Black Lentils, Dark Hollyhock, Basil, *Artemisia*, Artichokes, Tea Tree, Spinach, Sorrel, Foxglove, Lilac, *Camellia*, Snapdragon, Black-Eyed Susans, Grass, Pigsweed, Red Pine, Nettle, Broom, Larkspur, Plantain Roots, White Ash, Purple Milkweed, Lily-of-the-valley, Barberry root, Red onion, Yarrow, Mulga Acacia, Coneflower, Peppermint, Peony, Black-Eyed Susans, *Hydrangea*, Broom Flower, Peach, Plum tree, Weeping Willow, Virgina Creeper, Balm, Jewelweed, Broom Flower, Virginia Creeper, Achiote, Plum tree, Weeping Willow, Alfalfa, Bay leaves, Barberry, Beetroot, Burdock, Cameleon plant, Celery, *Crocus*, Daffodil, Dahlia, Dandelion, Dyer’s Greenwood, Fustic, Golden Rod, Heather, Hickory, Marigold, *Mimosa*, Mulga Acacia, Mullein (*verbascum thapsus*), Old man’s beard lichen, Onion, Oregon-grape, Osage Orange also known as Bois d’arc or hedgeapple, Oxallis, Queen Anne’s Lace, Peach, Red Clover, Saffron, Safflower, Sassafras, St. John’s Wort, Sumac, Sunflowers, Syrian Rue, Tansy, Turmeric, Weld, White mulberry tree, Willow, Yellow cone flower, Yellow, Curly, Bitter, or Butter Dock, Virgina Creeper, or Balm-Chamomile.

A host plant can be a plant capable of producing indigo, such as *Indigofera tinctoria* (Fabaceae); *Indigofera suffruticosa* (Fabaceae); *Indigofera micheliana; Indigofera arrecta; Inidgofera coerulea; Baptisia leucantha* (Fabaceae); *Isatis tinctoria* (Brassicacea); *Polygonum tinctorium* (Polygonaceae) aka *Persicaria tinctoria; Calanthe discolor* (Orchidaceae); *Strobilanthes cusia* (Acanthaceae) aka *Baphicacanthus cusia; Justicia spicegera* (Acanthaceae) aka *Jacobinia mohintli; Justicia colorifera* (Acanthaceae) aka *Jacobinia tinctoria; Couroupita guaianensis* (Lecythidaceae); *Wrightia tinctoria* (Apocyanceae); *Marsdenia tinctoria* (Apocynaceae); *Lonchocarpus cyanescence* (Fabaceae) syn *Philenoptera cyanescens; Isatis indigotica* (Brassicaceae); *Isatis candoleana; Isatis buschiana; Isatis tinctoria* subsp. *Corymbosa; Koaophyllon tinctorium* (Compositae, Eupatorieae) syn *Eupatorium indigofera*; or *Cybistax antisyphilitica* (Bignoniacea) aka *Yangua tinctoria.*

A host plant can be a flowering plant, such as alstroemeria (peruvian lilies), *amaranthus*, amaryllis, anemone anthurium, aster, baby’s breath, bells of ireland bird of paradise, bupleurum, calla, carnation, *chrysanthemum*, daisy, coxcomb, daffodil, dahlia, delphinium, eremurus, freesia, *gardenia, gerbera*, ginger, *gladiolus*, heather, *heliconia*, hyacinth *hydrangea, hypericum*, iris, kangaroo paw, larkspur, *leptospermum*, liatris, lily, *limonium*, lisianthus, monte cassino aster, *narcissus*, orchid, omithoalum, pear blossom, peony, poinsettia, protea, queen anne's lace, quince, *ranunculus*, rose, snapdragon, soldaster, statice, stephanotis, stock, sunflower tulip, *viburnum*, or waxflower.

A host plant can be an agronomically important plant, such as maize (corn), bean, soybean, wheat, barley, hay (e.g., alfalfa and legume and grass mixtures), rice, peanut, cotton, tomato, cucurbit (e.g., squash, pumpkin, gourd, cucumber, melon, watermelon, zucchini), okra, eggplant, pepper, sugar beet, sugarcane, cassava, potatoes, palm, rapeseed (canola), sunflower, coconut, olive, flax, safflower, sesame, apple, pear, grape, strawberry, blackcurrant, redcurrant, gooseberry, guava, lucuma, chili pepper, pomegranate, kiwifruit, cranberry, blueberry, blackberry, raspberry, boysenberry, banana, plum, cherry, peach, apricot, mango, orange, lime, lemon, grapefruit, pineapple, fig, mulberry, hedge apple, osage-orange, or breadfruit.

A host organism can be a cell with or without a nucleus.

A host cell can be a cell without a nucleus, such as bacteria. For example, a bacteria host cell can be *E. coli*. A bacteria host cell can be a strain of *E. coli* such as DH5alpha, TOP10, JW1252-1, HME5, or JW1251.

As another example, a bacteria host can be *Agrobacterium tumefaciens*. A bacteria host cell can be a strain on *Agrobacterium tumefaciens*, such as AGL0, AGL1, EHA101, EHA105, GV3101, GV3850 or LBA4404.

A host cell can be a cell with a nucleus, such as a yeast, fungi, or animal cell.

A transformed host organism or a host cell can be analyzed for the presence of a gene of interest or the expression level or profile conferred by the expression system of the present disclosure. Those of skill in the art are aware of the numerous methods available for the analysis of transformed hosts. For example, methods for host analysis include, but are not limited to Southern blots or northern blots, PCR-based approaches, biochemical analyses, phenotypic screening methods, and immunodiagnostic assays.

Colored Host Organism

Provided herein is a host organism that is genetically engineered to produce one or more indole-derived compound which imparts a colored phenotype, e.g., a visible color to the host organism or a part or portion of the host organism. A host organism or cell can be transformed with a construct described herein, such that the organism or cell can produce one or more indole-derived compounds, which can result in a colored phenotype (e.g., a visible color) to the host organism or cell, or extract thereof.

As shown herein, a visible color can be obtained by genetically engineering a host organism to increase or decrease formation of an indole-derived compound. For example, an indole derived compound can be indole, indoxyl, indigo, indirubin, isatin, hydroxyindole (e.g., 2-hydroxyindole, 3-hydroxyindole), isatan B, indican, 2-oxindole, 3-oxindole, or isatic acid.

The visible color of the host organism (e.g., plant) or a portion of the host organism (e.g., fiber, flower), or an extract thereof, can be any color in which an indole-derived compound can be observed in the visible spectrum. As described herein, an indole-derived compound can impart any color in the visible spectrum to the host organism or a portion of the host organism, or an extract thereof. For example, indole-derived compounds can impart colors on the visible spectrum (e.g., between 390 nm to 700 nm) to the host organism.

A colored phenotype of a host organism or a portion of the host organism can have a visible color having a wavelength of about 380 nm to about 750 nm. For example, a colored phenotype of a host organism or a portion of the host organism can have a visible color having a wavelength of about 380 nm, 390 nm, 400 nm, 410 nm, 420 nm, 430 nm, 440 nm, 450 nm, 460 nm, 470 nm, 480 nm, 490 nm, 500 nm, 510 nm, 520 nm, 530 nm, 540 nm, 550 nm, 560 nm, 570 nm, 580 nm, 590 nm, 600 nm, 610 nm, 620 nm, 630 nm, 640 nm, 650 nm, 660 nm, 670 nm, 680 nm, 690 nm, 700 nm, 710 nm. 720 nm, 730 nm, 740 nm, or 750 nm. Recitation of the above discrete values is understood to described ranges between each individual value. Unless otherwise indicated herein, ranges between each individual value recited above are incorporated into the specification.

A colored phenotype of a host organism or a portion of the host organism can include one or more of the following colors (e.g., wavelengths): violet (e.g., about 380-450 nm), blue (e.g., about 450-495 nm), green (e.g., about 495-570 nm), yellow (e.g., about 570-590 nm), orange (e.g., about 590-620 nm), or red (e.g., about 620-750 nm).

As shown herein, a colored phenotype of the host organism or a portion of the host organism can be an unsaturated color. For example, a colored phenotype of the host organism or a portion of the host organism can include a visible color selected from magenta, pink, or purple.

Promoter

One or more of the nucleotide sequences discussed herein can be operably linked to a promoter that can function in the host organism. Promoter selection can allow expression of a desired gene product under a variety of conditions.

Promoters can be selected for optimal function in a host organism into which the vector/construct will be inserted. Promoters can also be selected on the basis of their regulatory features. Examples of such features include enhancement of transcriptional activity and inducibility.

The promoter can be an inducible promoter. For example, the promoter can be induced according to temperature, pH, a hormone, a metabolite (e.g., lactose, mannitol, an amino acid), light (e.g., wavelength specific), osmotic potential (e.g., salt induced), a heavy metal, or an antibiotic. Numerous standard inducible promoters will be known to one of skill in the art.

The term "chimeric" is understood to refer to the product of the fusion of portions of two or more different polynucleotide molecules. "Chimeric promoter" is understood to refer to a promoter produced through the manipulation of known promoters or other polynucleotide molecules. Such chimeric promoters can combine enhancer domains that can confer or modulate gene expression from one or more promoters or regulatory elements, for example, by fusing a heterologous enhancer domain from a first promoter to a second promoter with its own partial or complete regulatory elements. Thus, the design, construction, and use of chimeric promoters according to the methods disclosed herein for modulating the expression of operably linked polynucleotide sequences are encompassed by the present disclosure.

Novel chimeric promoters can be designed or engineered by a number of methods. For example, a chimeric promoter may be produced by fusing an enhancer domain from a first promoter to a second promoter. The resultant chimeric promoter may have novel expression properties relative to the first or second promoters. Novel chimeric promoters can be constructed such that the enhancer domain from a first promoter is fused at the 5' end, at the 3' end, or at any position internal to the second promoter.

A P450 transcribable nucleic acid sequence can be linked to a regulatory sequence, such as a promoter, that can allow for constitutive expression of the sequence in a host organism. Modifications to the transcribable nucleic acid sequence can be made according to desired host organism. For example, expression of plant P450 genes in bacteria can be enhanced by removal of the N-terminal portion of the gene encoding a signal peptide, and replacing it with the leader sequence of a periplasmic protein such as ompA.

A plant P450 transcribable nucleic acid sequence can be linked to a promoter that can control expression of the gene in specific tissues of a host organism, such as seed trichomes (e.g., cotton fibers) or flower petals, that can allow for the production of indigo and indirubin in these tissues.

Construct

Any of the transcribable nucleic acid sequences described herein can be provided in one or more constructs. For example, multiple transcribable nucleic acid sequences can be included in one construct. As another example, a single transcribable nucleic acid sequence can be included in a construct. A plurality of constructs (containing multiple or single transcribable nucleic acid sequences) can be used in conjunction (e.g., to transform a host organism).

Constructs of the present disclosure generally include a promoter functional in the host organism operably linked to a transcribable polynucleotide molecule.

Exemplary promoters are discussed above. One or more additional promoters may also be provided in the recombinant construct. These promoters can be operably linked to any of the transcribable polynucleotide molecule sequences described above.

The term "construct" is understood to refer to any recombinant polynucleotide molecule such as a plasmid, cosmid, virus, autonomously replicating polynucleotide molecule, phage, or linear or circular single-stranded or double-stranded DNA or RNA polynucleotide molecule, derived from any source, capable of genomic integration or autonomous replication, comprising a polynucleotide molecule where one or more polynucleotide molecule has been linked in a functionally operative manner, i.e. operably linked. The term "vector" or "vector construct" is understood to refer to any recombinant polynucleotide construct that may be used for the purpose of transformation, i.e., the introduction of heterologous DNA into a host organism.

In addition, a construct can include additional polynucleotide molecules from an untranslated region of the gene of interest. These additional polynucleotide molecules can be derived from a source that is native or heterologous with respect to the other elements present in the construct.

A construct described herein can be plasmid-based or integrated into the host genome. For example, a construct described herein can be present in the host as a plasmid. As another example, a construct described herein can be integrated into the genome of the host. In some embodiments, integration into the genome of the host can increase inducible expression of the target nucleotide.

Host strains developed according to the approaches described herein can be evaluated by a number of means known in the art (see e.g., Studier (2005) Protein Expr Purif. 41(1), 207-234; Gellissen, ed. (2005) Production of Recombinant Proteins: Novel Microbial and Eukaryotic Expression Systems, Wiley-VCH, ISBN-10: 3527310363; Baneyx (2004) Protein Expression Technologies, Taylor & Francis, ISBN-10: 0954523253).

Molecular Engineering

The following definitions and methods are provided to better define the present invention and to guide those of ordinary skill in the art in the practice of the present invention. Unless otherwise noted, terms are to be understood according to conventional usage by those of ordinary skill in the relevant art.

The terms "heterologous DNA sequence", "exogenous DNA segment" or "heterologous nucleic acid," as used herein, each refer to a sequence that originates from a source foreign to the particular host cell or, if from the same source, is modified from its original form. Thus, a heterologous gene in a host cell includes a gene that is endogenous to the particular host cell but has been modified through, for example, the use of DNA shuffling. The terms also include non-naturally occurring multiple copies of a naturally occurring DNA sequence. Thus, the terms refer to a DNA segment that is foreign or heterologous to the cell, or homologous to the cell but in a position within the host cell nucleic acid in which the element is not ordinarily found. Exogenous DNA segments are expressed to yield exogenous polypeptides. A "homologous" DNA sequence is a DNA sequence that is naturally associated with a host cell into which it is introduced.

Expression vector, expression construct, plasmid, or recombinant DNA construct is generally understood to refer to a nucleic acid that has been generated via human intervention, including by recombinant means or direct chemical synthesis, with a series of specified nucleic acid elements that permit transcription or translation of a particular nucleic acid in, for example, a host cell. The expression vector can be part of a plasmid, virus, or nucleic acid fragment. Typically, the expression vector can include a nucleic acid to be transcribed operably linked to a promoter.

A "promoter" is generally understood as a nucleic acid control sequence that directs transcription of a nucleic acid. An inducible promoter is generally understood as a promoter that mediates transcription of an operably linked gene in response to a particular stimulus. A promoter can include necessary nucleic acid sequences near the start site of transcription, such as, in the case of a polymerase II type promoter, a TATA element. A promoter can optionally include distal enhancer or repressor elements, which can be located as much as several thousand base pairs from the start site of transcription.

A "transcribable nucleic acid molecule" as used herein refers to any nucleic acid molecule capable of being transcribed into a RNA molecule. Methods are known for introducing constructs into a cell in such a manner that the transcribable nucleic acid molecule is transcribed into a functional mRNA molecule that is translated and therefore expressed as a protein product. Constructs may also be constructed to be capable of expressing antisense RNA molecules, in order to inhibit translation of a specific RNA molecule of interest. For the practice of the present disclosure, conventional compositions and methods for preparing and using constructs and host cells are well known to one skilled in the art (see e.g., Sambrook and Russel (2006) Condensed Protocols from Molecular Cloning: A Laboratory Manual, Cold Spring Harbor Laboratory Press, ISBN-10: 0879697717; Ausubel et al. (2002) Short Protocols in Molecular Biology, 5th ed., Current Protocols, ISBN-10: 0471250929; Sambrook and Russel (2001) Molecular Cloning: A Laboratory Manual, 3d ed., Cold Spring Harbor Laboratory Press, ISBN-10: 0879695773; Elhai, J. and Wolk, C. P. 1988. Methods in Enzymology 167, 747-754).

The "transcription start site" or "initiation site" is the position surrounding the first nucleotide that is part of the transcribed sequence, which is also defined as position +1. With respect to this site all other sequences of the gene and its controlling regions can be numbered. Downstream sequences (i.e., further protein encoding sequences in the 3' direction) can be denominated positive, while upstream sequences (mostly of the controlling regions in the 5' direction) are denominated negative.

"Operably-linked" or "functionally linked" refers preferably to the association of nucleic acid sequences on a single nucleic acid fragment so that the function of one is affected by the other. For example, a regulatory DNA sequence is said to be "operably linked to" or "associated with" a DNA sequence that codes for an RNA or a polypeptide if the two sequences are situated such that the regulatory DNA sequence affects expression of the coding DNA sequence (i.e., that the coding sequence or functional RNA is under the transcriptional control of the promoter). Coding sequences can be operably-linked to regulatory sequences in sense or antisense orientation. The two nucleic acid molecules may be part of a single contiguous nucleic acid molecule and may be adjacent. For example, a promoter is operably linked to a gene of interest if the promoter regulates or mediates transcription of the gene of interest in a cell.

A "construct" is generally understood as any recombinant nucleic acid molecule such as a plasmid, cosmid, virus, autonomously replicating nucleic acid molecule, phage, or linear or circular single-stranded or double-stranded DNA or RNA nucleic acid molecule, derived from any source, capable of genomic integration or autonomous replication, comprising a nucleic acid molecule where one or more nucleic acid molecule has been operably linked.

A constructs of the present disclosure can contain a promoter operably linked to a transcribable nucleic acid molecule operably linked to a 3' transcription termination nucleic acid molecule. In addition, constructs can include but are not limited to additional regulatory nucleic acid molecules from, e.g., the 3'-untranslated region (3' UTR). Constructs can include but are not limited to the 5' untranslated regions (5' UTR) of an mRNA nucleic acid molecule which can play an important role in translation initiation and can also be a genetic component in an expression construct. These additional upstream and downstream regulatory nucleic acid molecules may be derived from a source that is native or heterologous with respect to the other elements present on the promoter construct.

The term "transformation" refers to the transfer of a nucleic acid fragment into the genome of a host cell, resulting in genetically stable inheritance. Host cells containing the transformed nucleic acid fragments are referred to as "transgenic" cells, and organisms comprising transgenic cells are referred to as "transgenic organisms".

"Transformed," "transgenic," and "recombinant" refer to a host cell or organism such as a bacterium, cyanobacterium, animal or a plant into which a heterologous nucleic acid molecule has been introduced. The nucleic acid molecule can be stably integrated into the genome as generally known in the art and disclosed (Sambrook 1989; Innis 1995; Gelfand 1995; Innis & Gelfand 1999). The term "untransformed" refers to normal cells that have not been through the transformation process.

"Wild-type" refers to a virus or organism found in nature without any known mutation.

Known methods of PCR include, but are not limited to, methods using paired primers, nested primers, single specific primers, degenerate primers, gene-specific primers, vector-specific primers, partially mismatched primers, and the like.

Design, generation, and testing of the variant nucleotides, and their encoded polypeptides, having the above required percent identities and retaining a required activity of the expressed protein is within the skill of the art. For example, directed evolution and rapid isolation of mutants can be according to methods described in references including, but not limited to, Link et al. (2007) Nature Reviews 5(9), 680-688; Sanger et al. (1991) Gene 97(1), 119-123; Ghadessy et al. (2001) Proc Natl Acad Sci USA 98(8) 4552-4557. Thus, one skilled in the art could generate a large number of nucleotide and/or polypeptide variants having, for example, at least 95-99% identity to the reference sequence described herein and screen such for desired phenotypes according to methods routine in the art.

Nucleotide and/or amino acid sequence identity percent (%) is understood as the percentage of nucleotide or amino acid residues that are identical with nucleotide or amino acid residues in a candidate sequence in comparison to a reference sequence when the two sequences are aligned. To determine percent identity, sequences are aligned and if necessary, gaps are introduced to achieve the maximum percent sequence identity. Sequence alignment procedures to determine percent identity are well known to those of skill in the art. Often publicly available computer software such as BLAST, BLAST2, ALIGN2 or Megalign (DNASTAR) software is used to align sequences. Those skilled in the art can determine appropriate parameters for measuring alignment, including any algorithms needed to achieve maximal alignment over the full-length of the sequences being compared. When sequences are aligned, the percent sequence identity of a given sequence A to, with, or against a given sequence B (which can alternatively be phrased as a given sequence A that has or comprises a certain percent sequence identity to, with, or against a given sequence B) can be calculated as: percent sequence identity=X/Y100, where X is the number of residues scored as identical matches by the sequence alignment program's or algorithm's alignment of A and B and Y is the total number of residues in B. If the length of sequence A is not equal to the length of sequence B, the percent sequence identity of A to B will not equal the percent sequence identity of B to A.

Generally, conservative substitutions can be made at any position so long as the required activity is retained. So-called conservative exchanges can be carried out in which the amino acid which is replaced has a similar property as the original amino acid, for example the exchange of Glu by Asp, Gln by Asn, Val by Ile, Leu by Ile, and Ser by Thr. Deletion is the replacement of an amino acid by a direct bond. Positions for deletions include the termini of a polypeptide and linkages between individual protein domains. Insertions are introductions of amino acids into the polypeptide chain, a direct bond formally being replaced by one or more amino acids. Amino acid sequence can be modulated with the help of art-known computer simulation programs that can produce a polypeptide with, for example, improved activity or altered regulation. On the basis of this artificially generated polypeptide sequences, a corresponding nucleic acid molecule coding for such a modulated polypeptide can be synthesized in-vitro using the specific codon-usage of the desired host cell.

"Highly stringent hybridization conditions" are defined as hybridization at 65° C. in a 6×SSC buffer (i.e., 0.9 M sodium chloride and 0.09 M sodium citrate). Given these conditions, a determination can be made as to whether a given set of sequences will hybridize by calculating the melting temperature ($T_m$) of a DNA duplex between the two sequences. If a particular duplex has a melting temperature lower than 65° C. in the salt conditions of a 6×SSC, then the two sequences will not hybridize. On the other hand, if the melting temperature is above 65° C. in the same salt conditions, then the sequences will hybridize. In general, the melting temperature for any hybridized DNA:DNA sequence can be determined using the following formula: $T_m$=81.5° C.+16.6($\log_{10}$[$Na^+$])+0.41(fraction G/C content)−0.63(% formamide)−(600/l). Furthermore, the $T_m$ of a DNA:DNA hybrid is decreased by 1-1.5° C. for every 1% decrease in nucleotide identity (see e.g., Sambrook and Russel, 2006).

Host cells can be transformed using a variety of standard techniques known to the art (see, e.g., Sambrook and Russel (2006) Condensed Protocols from Molecular Cloning: A Laboratory Manual, Cold Spring Harbor Laboratory Press, ISBN-10: 0879697717; Ausubel et al. (2002) Short Protocols in Molecular Biology, 5th ed., Current Protocols, ISBN-10: 0471250929; Sambrook and Russel (2001) Molecular Cloning: A Laboratory Manual, 3d ed., Cold Spring Harbor Laboratory Press, ISBN-10: 0879695773; Elhai, J. and Wolk, C. P. 1988. Methods in Enzymology 167, 747-754). Such techniques include, but are not limited to, viral infection, calcium phosphate transfection, liposome-mediated transfection, microprojectile-mediated delivery, receptor-mediated uptake, cell fusion, electroporation, and the like. The transfected cells can be selected and propagated to provide recombinant host cells that comprise the expression vector stably integrated in the host cell genome.

Exemplary nucleic acids which may be introduced to a host cell include, for example, DNA sequences or genes from another species, or even genes or sequences which originate with or are present in the same species, but are incorporated into recipient cells by genetic engineering methods. The term "exogenous" is also intended to refer to genes that are not normally present in the cell being transformed, or perhaps simply not present in the form, structure, etc., as found in the transforming DNA segment or gene, or genes which are normally present and that one desires to express in a manner that differs from the natural expression pattern, e.g., to over-express. Thus, the term "exogenous" gene or DNA is intended to refer to any gene or DNA segment that is introduced into a recipient cell, regardless of whether a similar gene may already be present in such a cell. The type of DNA included in the exogenous DNA can include DNA which is already present in the cell, DNA from another individual of the same type of organism, DNA from a different organism, or a DNA generated externally, such as a DNA sequence containing an antisense message of a gene, or a DNA sequence encoding a synthetic or modified version of a gene.

Host strains developed according to the approaches described herein can be evaluated by a number of means known in the art (see e.g., Studier (2005) Protein Expr Purif. 41(1), 207-234; Gellissen, ed. (2005) Production of Recombinant Proteins: Novel Microbial and Eukaryotic Expression Systems, Wiley-VCH, ISBN-10: 3527310363; Baneyx (2004) Protein Expression Technologies, Taylor & Francis, ISBN-10: 0954523253).

Methods of down-regulation or silencing genes are known in the art. For example, expressed protein activity can be down-regulated or eliminated using antisense oligonucleotides, protein aptamers, nucleotide aptamers, and RNA interference (RNAi) (e.g., small interfering RNAs (siRNA), short hairpin RNA (shRNA), and micro RNAs (miRNA) (see e.g., Fanning and Symonds (2006) Handb Exp Pharmacol. 173, 289-303G, describing hammerhead ribozymes and small hairpin RNA; Helene, C., et al. (1992) Ann. N.Y. Acad. Sci. 660, 27-36; Maher (1992) Bioassays 14(12): 807-15, describing targeting deoxyribonucleotide sequences; Lee et al. (2006) Curr Opin Chem Biol. 10, 1-8, describing aptamers; Reynolds et al. (2004) Nature Biotechnology 22(3), 326-330, describing RNAi; Pushparaj and Melendez (2006) Clinical and Experimental Pharmacology and Physiology 33(5-6), 504-510, describing RNAi; Dillon et al. (2005) Annual Review of Physiology 67, 147-173, describing RNAi; Dykxhoorn and Lieberman (2005) Annual Review of Medicine 56, 401-423, describing RNAi). RNAi molecules are commercially available from a variety of sources (e.g., Ambion, Tex.; Sigma Aldrich, Mo.; Invitrogen). Several siRNA molecule design programs using a variety of algorithms are known to the art (see e.g., Cenix algorithm, Ambion; BLOCK-iT™ RNAi Designer, Invitrogen; siRNA Whitehead Institute Design Tools, Bioinformatics & Research Computing). Traits influential in defining optimal siRNA sequences include G/C content at the termini of the siRNAs, Tm of specific internal domains of the siRNA, siRNA length, position of the target sequence within the CDS (coding region), and nucleotide content of the 3' overhangs.

Kits

Also provided are kits. Such kits can include an agent or composition described herein and, in certain embodiments, instructions for administration. Such kits can facilitate performance of the methods described herein. When supplied as a kit, the different components of the composition can be packaged in separate containers and admixed immediately before use. Components include, but are not limited to a construct, expression system, expression cassette described herein, or components or sequences thereof. Such packaging of the components separately can, if desired, be presented in a pack or dispenser device which may contain one or more unit dosage forms containing the composition. The pack may, for example, comprise metal or plastic foil such as a blister pack. Such packaging of the components separately can also, in certain instances, permit long-term storage without losing activity of the components.

Kits may also include reagents in separate containers such as, for example, sterile water or saline to be added to a lyophilized active component packaged separately. For example, sealed glass ampules may contain a lyophilized component and in a separate ampule, sterile water, sterile saline or sterile each of which has been packaged under a neutral non-reacting gas, such as nitrogen. Ampules may consist of any suitable material, such as glass, organic polymers, such as polycarbonate, polystyrene, ceramic, metal or any other material typically employed to hold reagents. Other examples of suitable containers include bottles that may be fabricated from similar substances as ampules, and envelopes that may consist of foil-lined interiors, such as aluminum or an alloy. Other containers include test tubes, vials, flasks, bottles, syringes, and the like. Containers may have a sterile access port, such as a bottle having a stopper that can be pierced by a hypodermic injection needle. Other containers may have two compartments that are separated by a readily removable membrane that upon removal permits the components to mix. Removable membranes may be glass, plastic, rubber, and the like.

In certain embodiments, kits can be supplied with instructional materials. Instructions may be printed on paper or other substrate, and/or may be supplied as an electronic-readable medium, such as a floppy disc, mini-CD-ROM, CD-ROM, DVD-ROM, Zip disc, videotape, audio tape, and the like. Detailed instructions may not be physically associated with the kit; instead, a user may be directed to an Internet web site specified by the manufacturer or distributor of the kit.

Compositions and methods described herein utilizing molecular biology protocols can be according to a variety of standard techniques known to the art (see, e.g., Sambrook and Russel (2006) Condensed Protocols from Molecular Cloning: A Laboratory Manual, Cold Spring Harbor Laboratory Press, ISBN-10: 0879697717; Ausubel et al. (2002) Short Protocols in Molecular Biology, 5th ed., Current Protocols, ISBN-10: 0471250929; Sambrook and Russel (2001) Molecular Cloning: A Laboratory Manual, 3d ed., Cold Spring Harbor Laboratory Press, ISBN-10: 0879695773; Elhai, J. and Wolk, C. P. 1988. Methods in Enzymology 167, 747-754; Studier (2005) Protein Expr Purif. 41(1), 207-234; Gellissen, ed. (2005) Production of Recombinant Proteins: Novel Microbial and Eukaryotic Expression Systems, Wiley-VCH, ISBN-10: 3527310363; Baneyx (2004) Protein Expression Technologies, Taylor & Francis, ISBN-10: 0954523253).

Definitions and methods described herein are provided to better define the present disclosure and to guide those of ordinary skill in the art in the practice of the present disclosure. Unless otherwise noted, terms are to be understood according to conventional usage by those of ordinary skill in the relevant art.

In some embodiments, numbers expressing quantities of ingredients, properties such as molecular weight, reaction conditions, and so forth, used to describe and claim certain embodiments of the present disclosure are to be understood as being modified in some instances by the term "about." In some embodiments, the term "about" is used to indicate that a value includes the standard deviation of the mean for the device or method being employed to determine the value. In some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the present disclosure are approximations, the numerical values set forth in the specific examples are reported as precisely as practicable. The numerical values presented in some embodiments of the present disclosure may contain certain errors necessarily resulting from the standard deviation found in their respective testing measurements. The recitation of ranges of values herein is merely intended to serve as a shorthand method of referring individually to each separate value falling within the range. Unless otherwise indicated herein, each individual value is incorporated into the specification as if it were individually recited herein. Unless otherwise indicated herein, ranges between each individual value are incorporated into the specification as if separately recited herein.

In some embodiments, the terms "a" and "an" and "the" and similar references used in the context of describing a particular embodiment (especially in the context of certain of the following claims) can be construed to cover both the singular and the plural, unless specifically noted otherwise. In some embodiments, the term "or" as used herein, including the claims, is used to mean "and/or" unless explicitly indicated to refer to alternatives only or the alternatives are mutually exclusive.

The terms "comprise," "have" and "include" are open-ended linking verbs. Any forms or tenses of one or more of these verbs, such as "comprises," "comprising," "has," "having," "includes" and "including," are also open-ended. For example, any method that "comprises," "has" or "includes" one or more steps is not limited to possessing only those one or more steps and can also cover other unlisted steps. Similarly, any composition or device that "comprises," "has" or "includes" one or more features is not limited to possessing only those one or more features and can cover other unlisted features.

All methods described herein can be performed in any suitable order unless otherwise indicated herein or otherwise clearly contradicted by context. The use of any and all examples, or exemplary language (e.g. "such as") provided with respect to certain embodiments herein is intended merely to better illuminate the present disclosure and does not pose a limitation on the scope of the present disclosure otherwise claimed. No language in the specification should be construed as indicating any non-claimed element essential to the practice of the present disclosure.

Groupings of alternative elements or embodiments of the present disclosure disclosed herein are not to be construed as limitations. Each group member can be referred to and claimed individually or in any combination with other members of the group or other elements found herein. One or more members of a group can be included in, or deleted from, a group for reasons of convenience or patentability. When any such inclusion or deletion occurs, the specification is herein deemed to contain the group as modified thus fulfilling the written description of all Markush groups used in the appended claims.

Citation of a reference herein shall not be construed as an admission that such is prior art to the present disclosure.

Having described the present disclosure in detail, it will be apparent that modifications, variations, and equivalent embodiments are possible without departing the scope of the present disclosure defined in the appended claims. Furthermore, it should be appreciated that all examples in the present disclosure are provided as non-limiting examples.

EXAMPLES

The following non-limiting examples are provided to further illustrate the present disclosure. It should be appreciated by those of skill in the art that the techniques disclosed in the examples that follow represent approaches the inventors have found function well in the practice of the present disclosure, and thus can be considered to constitute examples of modes for its practice. However, those of skill in the art should, in light of the present disclosure, appreciate that many changes can be made in the specific embodiments that are disclosed and still obtain a like or similar result without departing from the spirit and scope of the present disclosure.

Example 1: Biosynthetic Pathway

The following Example describes the studies supporting the proposed biosynthetic pathway for indirubin and indigo.

Figure 1A:
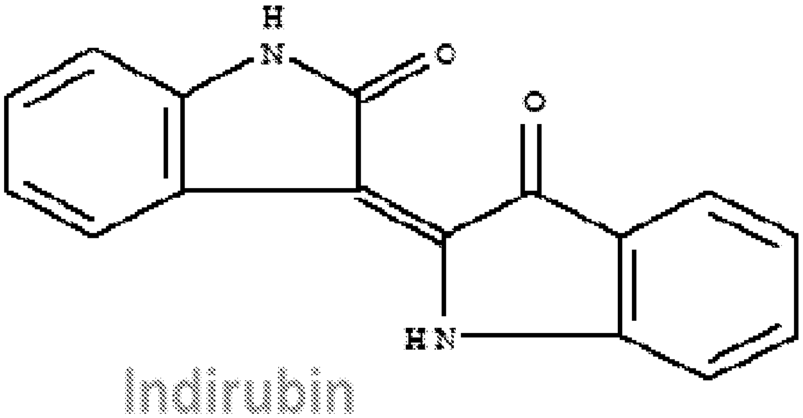
FIG. 1A-B are a series of chemical structures depicting products of the oxidation of indole and subsequent dimerization of hydroxylated intermediates.
Figure 1B:
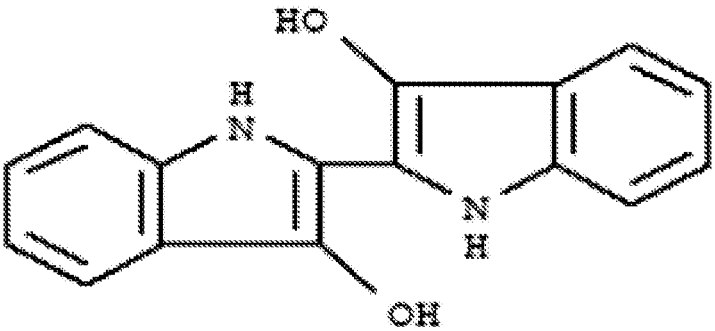
Figure 2:
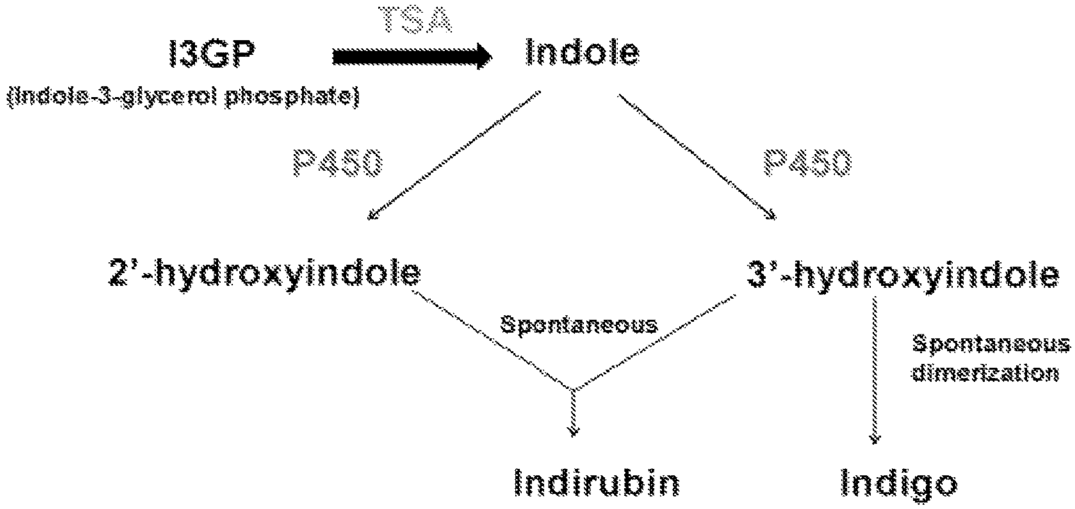
FIG. 2 is a schematic of the proposed pathway of the biosynthesis of indirubin and indigo. Formation is 2-hydroxyindole from indole can be catalyzed by ItB4. Formation is 3-hydroxyindole from indole can be catalyzed by ItB24.

The blue dye indigo (see e.g., FIG. 1A) and the anticancer compound indirubin (see e.g., FIG. 1B) found in *Isatis tinctoria* is presently thought to be derived biosynthetically from the oxidation of indole and subsequent dimerization of hydroxylated intermediates (see e.g., FIG. 2).

Subcloning of TSA and P450 (ItBs) Genes into Expression Vectors

Figure 5:
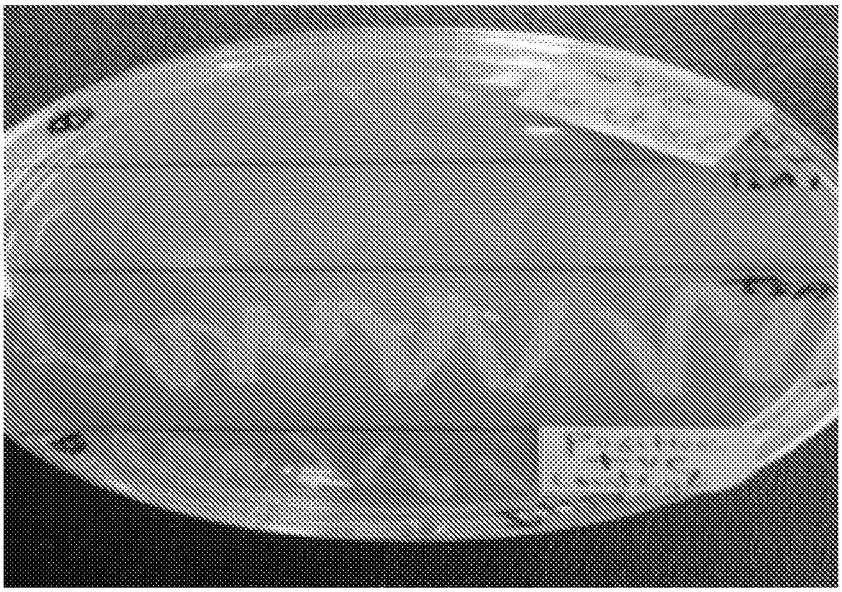
FIG. 5 is an image of TSA1 (SEQ ID NO: 1) and TSA2 (SEQ ID NO: 2) genes which complimented tryptophan biosynthesis and enabled growth of TSA mutant *E. coli* on minimal media.
Figure 6A:
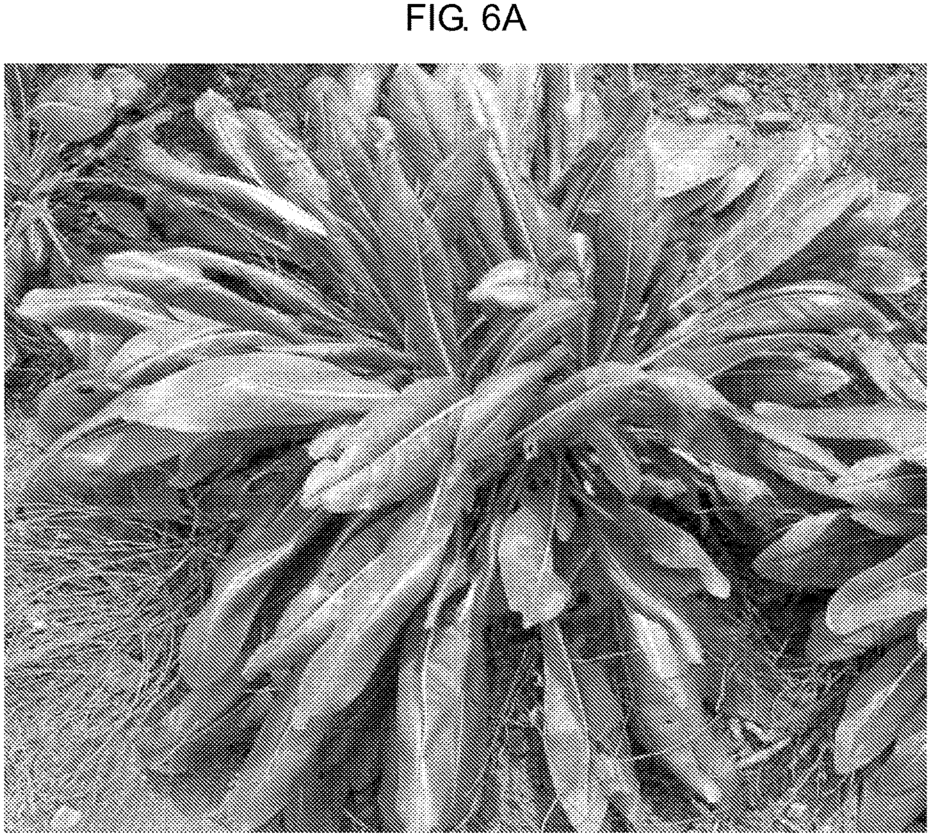
FIG. 6A is an image of the woad plant (*Isatis tinctoria*), a biennial herb of the family Brassicaceae found in Europe, North America and Asia. Woad can be found in traditional Chinese herbal remedies and can be a source of natural indigo dye.
Figure 6B:
FIG. 6B is an image of the woad plant (*Isatis tinctoria*) flower (yellow flower).
Figure 7:
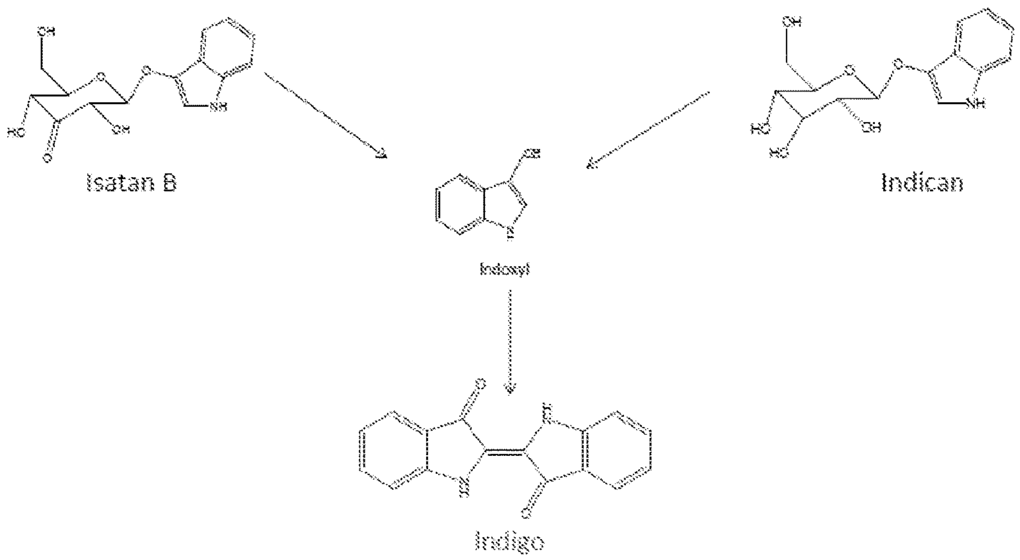
FIG. 7 is a scheme showing indigo precursors in woad.
Figure 8A:
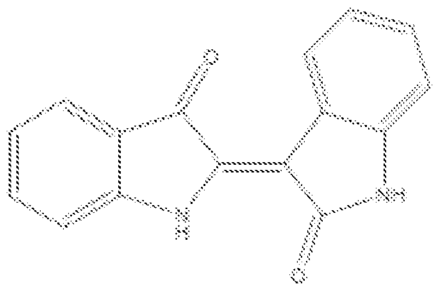
FIG. 8A is a chemical structure of indirubin, an isomer of indigo.
Figure 8B:
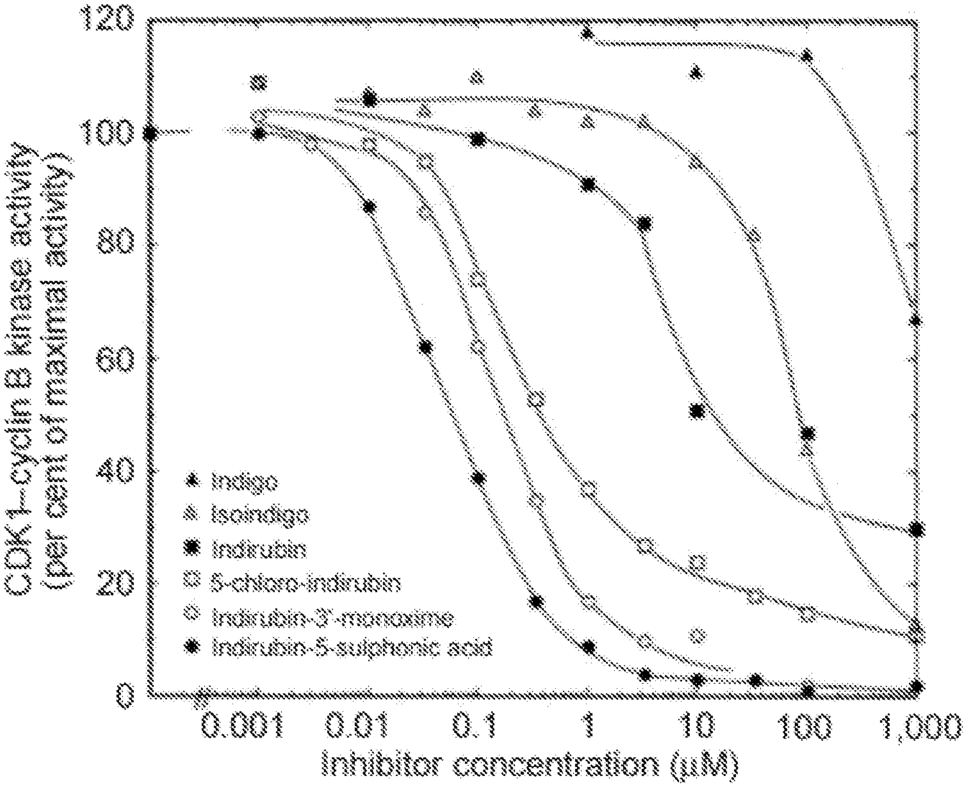
FIG. 8B is a graph showing potent inhibitors of cyclin dependent kinases.

Two TSA genes (TSA1 (SEQ ID NO: 1) and TSA2 (SEQ ID NO: 2)) from *I. tinctoria* were subcloned into pUC18 plasmid and transformed into a mutant *E. coli* strain lacking a functional TSA gene ($trpA^-$). Both TSA genes were able to complement tryptophan auxotrophy in $trpA^-$ *E. coli* cells grown on minimal media lacking tryptophan (see e.g., FIG. 5).

Candidate P450 genes (ItB4, SEQ ID NO: 3 and ItB24, SEQ ID NO: 4) from *I. tinctoria* were sub-cloned into a bicistronic pCWori expression vector together with a P450 reductase gene from *Arabidopsis* (SEQ ID NO: 56), and transformed into DH5alpha *E. coli* cells.

Optimization of Protein Expression

Protein expression was optimized and confirmed by SDS-PAGE and western blot. Upon expression in *E. coli* cells, two P450 proteins produced indigo and indirubin, which were identified based on Rf values by thin layer chromatography (TLC) (see e.g., FIG. 4).

Coexpression of TSA and P450 Genes

Bicistronic vector constructs were prepared to co-express *Isatis tinctoria* (woad) P450 genes (ItB4, SEQ ID NO: 3 and ItB24, SEQ ID NO: 4) with a P450-reductase gene from *Arabidopsis* (AtR2) (SEQ ID NO: 56). A bicistronic plasmid (pCWb) containing human cytochrome P450 gene (CYP2A6) (SEQ ID NO: 38) with a human P450-reductase gene (hNPR) (SEQ ID NO: 39) (previously shown to produce indigo in *E. coli* cells) was used as a positive control. *E. coli* bacterial cells (DH5alpha) were transformed with bicistronic plasmid constructs and grown to an optical density (600 nm) of 0.6 before induction of protein expression with IPTG.

Induction of Protein Expression

Figure 3:
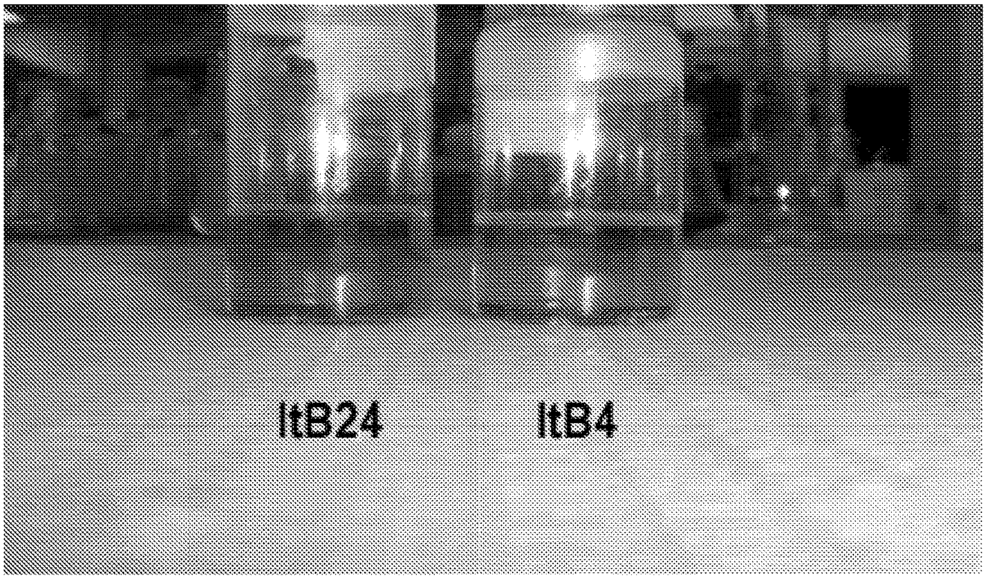
FIG. 3 is an image of chloroform extractions of *E. coli* cultures expressing *Isatis tinctoria* P450 proteins ItB4 (SEQ ID NO: 3) and ItB24 (SEQ ID NO: 4).

Protein expression in IPTG-induced samples was detected and confirmed by SDS-PAGE and western blot using anti-His antibodies. Bacterial (*E. coli*) cultures expressing candidate P450 genes (SEQ ID NO: 3 and SEQ ID NO: 4) from *Isatis tinctoria* were extracted with two different solvents, chloroform (see e.g., FIG. 3) and ethyl acetate (not shown). The extracts were analyzed by thin layer chromatography on a silica gel plate. Two woad (*Isatis tinctoria*) P450 proteins (ItB4 (SEQ ID NO: 3), ItB24 (SEQ ID NO: 4)) produced indigo and indirubin.

Indole-Derived Compound Analysis

Figure 4:
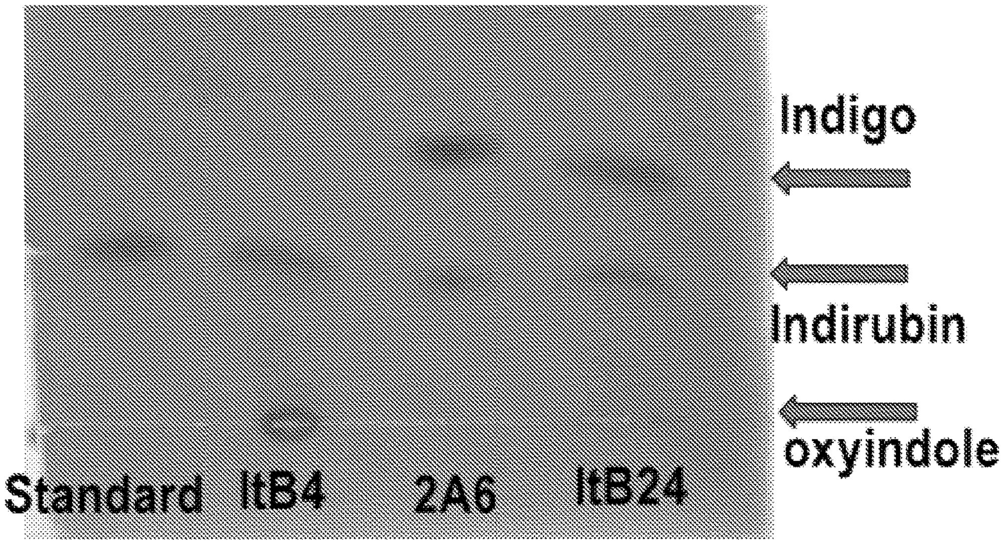
FIG. 4 is an image of a TLC separation of chemical products of *Isatis tinctoria* P450 (ItB4 (SEQ ID NO: 3), ItB24 (SEQ ID NO: 4)) expression in *E. coli.*

Different compounds were identified based on Rf values compared to CYP2A6 (SEQ ID NO: 38) products and indirubin standard (see e.g., FIG. 4). A yellow compound seen on silica gel plate was 2-hydroxyindole, a pink compound was identified as indirubin, and a blue compound found in some extractions has an Rf value similar to indigo. The 2-hydroxyindole due to its high polarity did not move upward when chloroform or ethyl acetate was used as mobile phase solvent, so an ethanol/ethyl acetate mixture (3:1) was used to elute it from the origin.

TSA2 Complementation of Tryptophan Auxotrophy

A previously characterized woad (*Isatis tinctoria*) TSA gene (TSA1 (SEQ ID NO: 1)), a new woad TSA-like gene (TSA2 (SEQ ID NO: 2)), and a woad TSB gene were sub-cloned into pUC18 plasmid vector. Plasmid constructs containing TSA1 (SEQ ID NO: 1) and TSA2 (SEQ ID NO: 2) genes were transformed into competent JW1251 cells. JW1251 cells lack the ability to synthesize tryptophan in minimal media and thus fail to grow in minimal media lacking tryptophan. Empty pUC18 plasmid DNA containing no TSA genes was also transformed into JW1251 cells as control. No colonies were observed on control plates indicating inability of JW1251 cells to grow in absence of tryptophan and inability to synthesize tryptophan from C and N sources available in minimal media. Colonies were produced by JW1251 cells transformed with pUC18 constructs containing TSA2 gene (SEQ ID NO: 2) indicating the ability of TSA2 gene (SEQ ID NO: 2) to complement the tryptophan auxotrophy of JW1251 cells on minimal media (see e.g., FIG. 5).

Coexpression of TSA and ItB in Bacteria Lacking Tryptophanase Gene

Woad P450 genes (SEQ ID NO: 3 and SEQ ID NO: 4) were also coexpressed with woad TSA genes (SEQ ID NO: 1 and SEQ ID NO: 2) in a mutant *E. coli* strain lacking tryptophanase gene and ability to produce indole (see e.g., TABLE 1).

TABLE 1

Chemical products of coexpression of woad P450 (SEQ ID NO: 3 and SEQ ID NO: 4) and TSA (SEQ ID NO: 1 and SEQ ID NO: 2) genes in a mutant *E. coli* strain lacking tryptophanase (indole producing enzyme) activity.

| Expected Products | TSA1 (SEQ ID NO: 1) + ItB4 (SEQ ID NO: 3) | TSA2 (SEQ ID NO: 2) + ItB4 (SEQ ID NO: 3) | TSA1 (SEQ ID NO: 1) + ItB24 (SEQ ID NO: 4) | TSA2 (SEQ ID NO: 2) + ItB24 (SEQ ID NO: 4) |
|---|---|---|---|---|
| Isatin | Present | No growth of cells | Present | Present |
| Oxyindole | Present | No growth of cells | Present | Present |
| Indigo | x | No growth of cells | x | x |
| Indirubin | Present | No growth of cells | Present | x |

In summary, this Example showed TSA (SEQ ID NO: 1 and SEQ ID NO: 2) and P450 (SEQ ID NO: 3 and SEQ ID NO: 4) genes have been expressed in bacteria to produce indoxyl derived compounds including indigo and indole. This Example also showed that tryptophansynthase alpha (TSA) in *I. tinctoria* can be responsible for the production of free indole molecules from indole-3-glycerol phosphate, and that P450 proteins catalyze the oxidation of free indole molecules to produce 2-hydroxyindole and 3-hydroxyindole.

Example 2: Isolation of P450s (ItBs) from Plants

This Example describe methods to isolate P450s from plants having indole oxidation activity that can lead to indigo and indirubin formation. The methods include (1) isolating RNA from indigo-producing plants, (2) obtaining the sequences of the genes by RNA sequencing and assembly, (3) looking for P450 genes based on sequence similar to known P450 genes using nucleotide comparison algorithms such as BLAST and ClustalW, (4) PCR cloning the coding regions of P450 genes into a bacterial expression plasmid that already has a plant P450 reductase (see e.g., Example 4), (5) transforming the plasmid containing the P450 gene and the P450 reductase into bacteria (see e.g., Example 5), (6) inducing the expression of the P450 gene and P450 reductase (see e.g., Example 5), and (7) monitoring for the formation of blue and/or red pigments by TLC, HPLC, or GC-MS (see e.g., Example 6).

Example 3: TSA and P450 (ItB) Gene Cloning

The following example describes TSA (SEQ ID NO: 1 and SEQ ID NO: 2) and P450 gene (SEQ ID NO: 3 and SEQ ID NO: 4) cloning from *Isatis tinctoria.*

Four young leaves from a one-year old *Isatis tinctoria* plant (purchased from Companion Plants, Athens, Ohio) was ground to a fine powder in liquid nitrogen using a mortar and pestle. The powder was transferred to a 1.5 mL microfuge tube and resuspended in 0.55 mL RNA extraction buffer (0.2 M Tris-HCl pH 9.0, 0.4 M LiCl, 25 mM EDTA and 1% SDS) by mixing with a vortex mixer. An equal volume of water-saturated phenol was added and then mixed. After centrifugation at 16,000 g for 2 minutes, the top layer was transferred to a new microfuge tube, which was again extracted with water-saturated phenol, and then with 0.55 mL chloroform. After transferring the top layer to a new tube, 55 μL of sodium acetate (3 M, pH 5.3) and 500 μL of 95% ethanol were added to the solution, mixed and chilled at −80° C. for 20 minutes.

The tube was centrifuged at 16,000 g for 5 minutes, and the supernatant was discarded while the pellet was resuspended in 300 μL of 2 M LiCl by pipetting up and down. The tube was placed on ice for 30 minutes and centrifuged 16,000 g for 2 minutes. The supernatant was discarded and the pellet was resuspended in 300 μL water. After adding 30 μL sodium acetate (3 M, pH 5.3) and 700 μL 95% ethanol, the mixture was chilled at −80° C. for 15 minutes. The tube was centrifuged at 16,000 g for 2 minutes and the supernatant was discarded. The pellet was rinsed with 75% ethanol and the tube was centrifuged at 16,000 g for 2 minutes. The supernatant was carefully removed using a pipet and the pellet was air dried for 10 minutes. The pellet was resuspended in 50 μL nuclease-free water, and the resulting solution was used as the RNA for cDNA synthesis, which was done with a SuperScript® II enzyme kit (Invitrogen) following the manufacturer's protocol, using Oligo_dT24 (SEQ ID NO: 8) as a primer.

The cDNA was used as a template for the PCR amplification of two P450 genes named ItB4 (SEQ ID NO: 3) and ItB24 (SEQ ID NO: 4), which required two amplification reactions. The first PCR used ItB4_5 utr_F1 (SEQ ID NO: 10) or ItB24_5 utr_F1 (SEQ ID NO: 11) as forward primers, and GR_3'-primer (SEQ ID NO: 9) as the reverse primer. The second PCR used ItB4_F1cacc (SEQ ID NO: 12) or ItB24_F1cacc (SEQ ID NO: 13) as forward primers, and ItB4_R1stp (SEQ ID NO: 14) or ItB24_R1stp (SEQ ID NO: 15) as reverse primers, respectively. The PCR mixture consisted of 36 μL water, 1 μL 40 mM dNTP, 1 μL 10 μM forward primer, 1 μL of 10 μM forward primer, 0.5 μL template (cDNA for the first PCR and a 1/100 dilution of the first PCR product for the second PCR), 0.5 μL Advantage® HD Polymerase Mix (Clontech) and 10 μL of the accompanying 5× buffer. The cycling conditions for the first PCR included a 98° C. hot start for 10 sec, followed by 30 cycles of 98° C. for 10 sec, 55° C. for 10 sec, and 72° C. for 2 min, ending with 72° C. for 5 minutes. The cycling conditions for the second PCR also included a 98° C. hot start for 10 sec, followed by 30 cycles of 98° C. for 10 sec, 58° C. for 5 sec, and 72° C. for 1 min, with 72° C. incubation for 5 minutes at the end. The second PCR products were cloned into pET101 TOPO-vector (Invitrogen) according to the manufacturer's protocol, and transformed into either OneShot® TOP10 (Invitrogen) or Stellar™ (Clontech) chemically competent *E. coli* cells.

Transformed cells were grown in LB Broth, Miller (Fisher) containing 100 μg/mL ampicillin at 37° C. for 16 hours, from which plasmids were prepared using the Wizard® Plus SV Minipreps DNA Purification System (Promega), to yield the plasmids pET101-ItB4 and pET101-ItB24.

The same steps were performed for the cloning of TSA1 (SEQ ID NO: 1) and TSA2 (SEQ ID NO: 2), except using a different set of primers. The first PCR used TSA1_5 utr_F1 (SEQ ID NO: 26) or TSA2_5 utr_F1 (SEQ ID NO: 29) as forward primers, and GR_3'-primer (SEQ ID NO: 9) as the reverse primer. The second PCR used TSA1_cacc_F1 (SEQ ID NO: 27) or TSA2_cacc_F1 (SEQ ID NO: 30) as forward primers, and TSA1_stp_R1 (SEQ ID NO: 28) or TSA2_stp_R1 (SEQ ID NO: 31) as reverse primers, respectively. Cloning of the PCR products into pET101, transformation of TOP10 cells, and overnight culture of transformed cells from plasmids were prepared, as was done for ItB4 (SEQ ID NO: 3) and ItB24 (SEQ ID NO: 4), yielded two additional plasmids designated pET101-TSA1 and pET101-TSA2.

Example 4: P450 (ItB) Gene Subcloning into Expression Vector

The following example describes the subcloning of P450 genes (SEQ ID NO: 3 and SEQ ID NO: 4) into a suitable expression vector for bacterial expression.

An effective expression vector for the expression of P450 (SEQ ID NO: 3 and SEQ ID NO: 4) genes in bacteria can be the pCWori+ vector (Barnes, 1996), which has been used to express the human P450 gene CYP2A6 (SEQ ID NO: 38) and its native P450 reductase partner in a bicistronic fashion, in a plasmid construct designated as pCWb-2A6-hNPR (Gillam et al. 1999). The human P450 reductase (SEQ ID NO: 39) was replaced with a truncated (missing the first 72 amino acids in the N-terminal) plant P450 reductase gene (AtR2) (SEQ ID NO: 56) from *Arabidopsis thaliana* (Hull & Celenza 2000), and the human P450 (CYP2A6) (SEQ ID NO: 38) along with a modified amino-terminal leader sequence derived from bovine CYP17A gene (SEQ ID NO: 43) (Fisher et al. 1992) was replaced with either one of the *Isatis tinctoria* P450 genes (SEQ ID NO: 3 or SEQ ID NO: 4) preceded by the OmpA leader sequence (SEQ ID NO: 42) (Pritchard et al. 1997).

To replace the human P450 reductase (SEQ ID NO: 39) with a P450 reductase of *A. thaliana* (SEQ ID NO: 56) (Hull & Celenza 2000), the pCWb-2A6-hNPR was used as template for a PCR using pCWb_vector_F1 (SEQ ID NO: 24) and pCWb_vector_R1 (SEQ ID NO: 25) as forward and reverse primers, respectively. The PCR mixture consisted of 35.5 μL water, 1 μL 40 mM dNTP, 1 μL of 10 μM forward primer, 1 μL of 10 μM forward primer, 1 μL template, 0.5 μL Advantage® HD Polymerase Mix (Clontech), and 10 μL of the accompanying 5× buffer. The cycling conditions included a 98° C. hot start for 10 sec, followed by 30 cycles of 98° C. for 10 sec, 55° C. for 10 sec, and 72° C. for 3 min, ending with 72° C. for 5 minutes. After amplification, the mixture was treated with DpnI at 37° C. for 1 hour, and the PCR product was purified by passing the mixture through a Nucleospin® column (Macherey-Nagel) to yield a linearized pCWori+ vector without the human P450 reductase (SEQ ID NO: 39), although still harboring CYP2A6 (SEQ ID NO: 38), which is designated as pCWb-2A6.

A truncated (missing the first 72 amino acids in the N-terminal) *A. thaliana* P450 reductase (SEQ ID NO: 56) was amplified from the pSTV28-ATR2 plasmid (Harada et al. 2011) using pCWb_AtR2_F1coR (SEQ ID NO: 20) and pCWb_AtR2_R1stp (SEQ ID NO: 21) as forward and reverse primers, respectively. The PCR mixture consisted of 35.5 μL water, 1 μL of 40 mM dNTP, 1 μL of 10 μM forward primer, 1 μL of 10 μM forward primer, 1 μL template, 0.5 μL Advantage® HD Polymerase Mix (Clontech), and 10 μL of the accompanying 5× buffer. The cycling conditions included a 98° C. hot start for 10 sec, followed by 30 cycles of 98° C. for 10 sec, 55° C. for 10 sec, and 72° C. for 2 min, ending with 72° C. for 5 minutes. The PCR product was purified by passing the mixture through a Nucleospin® column (Macherey-Nagel) to yield ATR2mod (Hull and Celenza 2000) flanked by 15 nucleotides on either side that overlap with the terminal regions of the linearized pCWB-2A6, thus allowing for the insertion of ATR2mod into pCWb-2A6 using the In-Fusion® HD cloning kit (Clontech). PCR-amplified ATR2mod was cloned into PCR-amplified linearized pCWb-2A6 using the In-Fusion® HD cloning kit (Clontech) according to the manufacturer's instructions, to yield the plasmid pCWb-2A6-ATR2mod.

pCWb-2A6-ATR2mod was digested with FastDigest® NdeI and XbaI (Thermo Scientific) at 37° C. for 15 minutes, separated by agarose gel electrophoresis and recovered from the gel using a scalpel and a Nucleospin® Gel and PCR Clean-up kit (Macherey-Nagel) to yield a linearized pCWb-ATR2mod (i.e., without CYP2A6 (SEQ ID NO: 38)). To replace CYP2A6 (SEQ ID NO: 38) with *Isatis tinctoria* P450 genes (SEQ ID NO: 3 and SEQ ID NO: 4) preceded by OmpA leader sequence (SEQ ID NO: 42), CYP2A6 (SEQ ID NO: 38) was first replaced by a P450 gene construct that already had OmpA. This gene construct designated OmpA:T13H:His (SEQ ID NO: 7) had been manufactured and sequence-verified by BioBasic, Inc. OmpA-T13H-His (SEQ ID NO: 7) was PCR amplified from the manufactured gene contained in a pUC57 vector provided by BioBasic, Inc. using pCWb_OmpA_Nde_F1 (SEQ ID NO: 22) and pCWb_His_XbaI_R1 (SEQ ID NO: 23) as forward and reverse primers, respectively. The PCR mixture consisted of 36 μL water, 1 μL of 40 mM dNTP, 1 μL of 10 μM forward primer, 1 μL of 10 μM forward primer, 0.5 μL template (1 ng pUC57 plasmid containing OmpA:T13H:His (SEQ ID NO: 7) synthesized by BioBasic, Inc.), 0.5 μL Phusion® High Fidelity DNA Polymerase Mix (Thermo Scientific), and 10 μL of the accompanying 5× buffer. The cycling conditions included a 98° C. hot start for 30 sec, followed by 30 cycles of 98° C. for 10 sec, 55° C. for 20 sec, and 72° C. for 1 min, ending with 72° C. for 5 minutes. After amplification, the mixture was treated with DpnI at 37° C. for 1 hour, and the PCR product was purified by passing the mixture through a Nucleospin® column (Macherey-Nagel) to yield OmpA:T13H:His (SEQ ID NO: 7) flanked by 15 nucleotides on either side that overlap with the terminal regions of the linearized pCWB-ATR2mod, thus allowing for the insertion of OmpA:T13H:His (SEQ ID NO: 7) into pCWb-ATR2mod using the In-Fusion® HD cloning kit (Clontech). PCR-amplified OmpA:T13H:His (SEQ ID NO: 7) was cloned into PCR-amplified linearized pCWb-ATR2mod using the In-Fusion® HD cloning kit (Clontech) according to the manufacturer's instructions, to yield the plasmid pCWb-OmpA:T13H:His-ATR2mod.

To replace OmpA:T13H:His (SEQ ID NO: 7) with *Isatis tinctoria* P450 genes (SEQ ID NO: 3 and SEQ ID NO: 4) preceded by the OmpA leader sequence (SEQ ID NO: 42) (i.e., OmpA:ItB4 and OmpA:ItB24), pCWb-OmpA:T13H:His-ATR2mod was digested with FastDigest® NheI and XbaI (Thermo Scientific) at 37° C. for 15 minutes, separated by agarose gel electrophoresis and the linearized plasmid recovered from the gel using a scalpel and a Nucleospin® Gel and PCR Clean-up kit (Macherey-Nagel) to yield pCWb-OmpA-ATR2mod. ItB4 (SEQ ID NO: 3) and ItB24 (SEQ ID NO: 4) were each amplified by PCR using OmpA_ItB4_NheI_F1 (SEQ ID NO: 16) and OmpA_ItB24_NheI_F1 (SEQ ID NO: 18) as forward primers, and pCWB_ItB4_XbaI_R1stp (SEQ ID NO: 17) and pCWB_ItB24_XbaI_R1stp (SEQ ID NO: 19) as reverse primers, respectively. The PCR mixture consisted of 35.5 μL water, 1 μL of 40 mM dNTP, 1 μL of 10 μM forward primer, 1 μL of 10 μM forward primer, 1 μL template (pET101-ItB4 or pET101-ItB24), 0.5 μL Phusion® High Fidelity DNA Polymerase Mix (Thermo Scientific) and 10 μL of the accompanying 5× buffer. The cycling conditions included a 98° C. hot start for 1 min, followed by 30 cycles of 98° C. for 10 sec, 60° C. for 15 sec, and 72° C. for 2.5 min, ending with 72° C. for 5 minutes. After amplification, the mixture was treated with DpnI at 37° C. for 1 hour, and the PCR product was purified by passing the mixture through a Nucleospin® column (Macherey-Nagel) to yield either pET101-ItB4 or pET101-ItB24 with 15 extra nucleotides on both sides of each gene that overlap with the terminal regions of the linearized pCWb-OmpA-ATR2mod, thus allowing for the insertion of either ItB4 (SEQ ID NO: 3) or ItB24 (SEQ ID NO: 4) into pCWb-OmpA-ATR2mod using the In-Fusion® HD cloning kit (Clontech). PCR-amplified ItB4 (SEQ ID NO: 3) and ItB24 (SEQ ID NO: 4) were each cloned into PCR-amplified linearized pCWb-OmpA-ATR2mod using the In-Fusion® HD cloning kit (Clontech) according to the manufacturer's instructions, to yield the plasmids pCWb-OmpA: ItB4-ATR2mod and pCWb-OmpA: ItB24-ATR2mod, respectively.

Example 5: P450 (ItB) Gene Expression and Induction in Bacteria

The following example describes the heterologous expression of *Isatis tinctoria* P450 genes (SEQ ID NO: 3 and SEQ ID NO: 4) in bacteria.

The plasmids pCWb-OmpA: ItB4-ATR2mod and pCWb-OmpA: ItB24-ATR2mod were each transformed into chemically competent DH5alpha cells. Transformed cells were grown overnight at 37° C. with shaking (250 rpm) in LB broth containing 100 μg/mL ampicillin. Overnight, grown culture (50 μL) was inoculated into 50 mL Terrific Broth (TB) media (Invitrogen) containing 100 μg/mL ampicillin and 100 μL 80% glycerol. After growing at 37° C. with shaking (250 rpm) and reaching an optical density at 600 nm of 0.6 to 0.8, the bacteria were induced with 0.5 mM isopropyl β-D-1-thiogalactopyranoside (IPTG) and supplemented with 1.0 mM thiamine and 0.5 mM δ-aminolevulenic acid. The bacteria were then incubated at 29° C. with shaking (250 rpm) for two days.

Example 6: Indigo and Indirubin Analysis

The following example describes the analysis of Indigo and Indirubin.

Bacterial cultures were extracted with equal amounts of chloroform. The combined chloroform extract was evaporated to minimal volume under reduced pressure and applied onto a silica TLC plate developed with chloroform/acetone (97:3). Two colored bands were observed: a pink band with the same Rf value as indirubin, and a blue band with the same Rf value as indigo.

Example 7: Codon-Optimized P450 (ItB) Gene Subcloning for Bacterial Expression The following example describes the subcloning of codon-optimized plant P450 genes for bacterial expression.

Codon optimization software was used to generate ItB4 (SEQ ID NO: 3) and ItB24 (SEQ ID NO: 4) nucleotide sequences (coItB4 and coItB24) that were codon-optimized for bacteria. These nucleotide sequences were synthesized with a His-tag at the C-terminal and cloned into pUC57 vector by BioBasic Inc. to yield the plasmids pUC57-coItB4:His and pUC57-coItB24:His. These plasmids were used as template for PCR amplification of coItB4 and coItB24 using OmpA_coItB4_NheI_F1 (SEQ ID NO: 32) and OmpA_coItB24_NheI_F1 (SEQ ID NO: 33) as forward primers, respectively, and pCWb_His_XbaI_R1 (SEQ ID NO: 23) as a reverse primer. The PCR mixture consisted of 35.5 μL water, 1 μL of 40 mM dNTP, 1 μL of 10 μM forward primer, 1 μL of 10 μM forward primer, 1 μL template, 0.5 μL Phusion® High Fidelity DNA Polymerase Mix (Thermo Scientific) and 10 μL of the accompanying 5× buffer. The cycling conditions included a 98° C. hot start for 30 sec, followed by 30 cycles of 98° C. for 10 sec, 55° C. for 15 sec, and 72° C. for 1 min, ending with 72° C. for 5 minutes. After amplification, the PCR products were each purified by agarose gel electrophoresis and passing the excised bands through a Nucleospin® column (Macherey-Nagel), yielding PCR-amplified coItB4-His (SEQ ID NO: 5) and coItB24:His (SEQ ID NO: 6) each flanked by 15 nucleotides that overlap with the terminal regions of the linearized pCWb-OmpA-ATR2mod. PCR-amplified coItB4:His (SEQ ID NO: 5) and coItB24:His (SEQ ID NO: 6) were each cloned into PCR-amplified linearized pCWb-OmpA-ATR2mod using the In-Fusion® HD cloning kit (Clontech) according to the manufacturer's instructions, to yield the plasmids pCWb-OmpA: ItB4:His-ATR2mod and pCWb-OmpA: ItB24:His-ATR2mod, respectively.

Example 8: TSA2 Complementation of TSA Mutation in Bacteria

The following example describes the complementation of TSA mutation in bacteria by TSA2 gene (SEQ ID NO: 2) from *Isatis tinctoria.*

The plasmids pET101-TSA1 and pET101-TSA2 were used as a template for a PCR amplification of TSA1 (SEQ ID NO: 1) and TSA2 (SEQ ID NO: 2), using pUC18_TSA1_EcoRI_F1 (SEQ ID NO: 34) and pUC18_TSA2_EcoRI_F1 (SEQ ID NO: 36) as forward primers, and pUC18_TSA1_HindIII_R1stp (SEQ ID NO: 35) and pUC18_TSA2_HindIII_R1stp (SEQ ID NO: 37) as reverse primers. The PCR mixture consisted of 22 μL water, 1 μL of 40 mM dNTP, 1 μL of 10 μM forward primer, 1 μL of 10 μM forward primer, 1 μL template, and 25 μL CloneAmp™ HiFi PCR Mix (Clontech). The cycling conditions included 30 cycles of 98° C. for 10 sec, 55° C. for 10 sec, and 72° C. for 8 sec, followed by 72° C. incubation for 5 minutes. After amplification, PCR products were purified by agarose gel electrophoresis, using the Wizard® SV Gel and PCR Clean-Up System (Promega) to recover TSA1 (SEQ ID NO: 1) and TSA2 (SEQ ID NO: 2) which are both flanked by 15 nucleotide sequences on either side that overlap the EcoRI and HindIII sites of pUC18. TSA1 (SEQ ID NO: 1) and TSA2 (SEQ ID NO: 2) were each cloned into EcoRI/HindIII digested pUC18 using In-Fusion® HD Eco-Dry™ Cloning kit (Clontech) according to the manufacturer's instructions. The resulting pUC18-TSA1 and pUC18-TSA2 plasmids were transformed into chemically competent *E. coli* strain JW1252-1 (a trpA deletion mutant obtained from *Coli* Genetic Stock Center) and single colony transformants were grown overnight at 37° C. in LB containing 100 μg/mL ampicillin. Overnight grown cultures were used to prepare glycerol stocks, which were stored in −80° C. until use.

Glycerol stocks of JW1252-1 transformed with either pUC18-TSA1 or pUC18-TSA2 grew on M9 minimal media, while glycerol stocks of untransformed JW1252-1 did not. Untransformed JW1252-1 would grow on M9 minimal media supplemented with tryptophan, as did the JW1252-1 transformed with either pUC18-TSA1 or pUC18-TSA2.

Example 9: TSA and P450 (ItB) Coexpression in Bacteria

The following example describes the heterologous coexpression of woad (*Isatis tinctoria*) TSA genes and ItB genes in bacteria.

TSA1 (SEQ ID NO: 1) and TSA2 (SEQ ID NO: 2) were cloned into EcoRI/HindIII digested pK184 using In-Fusion® HD EcoDry™ Cloning kit (Clontech) and transformed into alpha-select gold efficiency chemically competent *E. coli* cells (Bioline), from which plasmids were prepared to obtain pK184-TSA1 and pK184-TSA2 cells. Each of these plasmids were cotransformed with pCWb-OmpA: ItB4:His-ATR2mod and pCWb-OmpA: ItB24:His-ATR2mod into trnA$^-$ *E. coli* HME5 strain (Wu et al. 2005) to obtain four double transformants (TSA1 (SEQ ID NO: 1)/coItB4:His (SEQ ID NO: 5), TSA1 (SEQ ID NO: 1)/coItB24:His (SEQ ID NO: 6), TSA2 (SEQ ID NO: 2)/coItB4:His (SEQ ID NO: 5), and TSA2 (SEQ ID NO: 2)/coItB24:His (SEQ ID NO: 6)) which were grown in LB containing 100 μg/mL ampicillin and 100 μg/mL kanamycin.

Example 10: TSA2 and P450 (ItB) Expression in *Arabidopsis*

The following example describes the transgenic expression of woad (*Isatis tinctoria*) TSA2 (SEQ ID NO: 2) and ItB genes in *arabidopsis* flowers.

Apetala3 (AP3) is a gene that is specifically expressed in petals of *arabidopsis*, thus its promoter (SEQ ID NO: 46) can be used to drive the expression of TSA and ItB genes in *arabidopsis* flowers. Other petal-specific promoters that can be used include the promoters of PISTILLATA (P1) (SEQ ID NO: 47), chalcone synthase (CHS) (SEQ ID NO: 48), and *Chrsyanthemum morifolium* carotenoid cleavage dioxygenase 4a-5 (CmCCD4a-5) (SEQ ID NO: 49) genes. To express TSA2 (SEQ ID NO: 2) and ItB4 (SEQ ID NO: 3) in *Arabidopsis* petals, TSA2 (SEQ ID NO: 2) preceded by a portion of the AP3 promoter (SEQ ID NO: 46), pAP3 (SEQ ID NO: 50), and ItB4 genes (SEQ ID NO: 3) preceded pAP3 (SEQ ID NO: 50) is artificially synthesized and cloned into pUC57 vector (by BioBasic Inc.) to generate the plasmids pUC57-pAP3:TSA2 and pUC57-pAP3:ItB4 (SEQ ID NO: 40), respectively. The synthetic constructs pAP3:TSA2 (SEQ ID NO: 41) and pAP3:ItB4 (SEQ ID NO: 40) are each subcloned into pCAMBIA1300 and pCAMBIA3300, respectively, by first amplifying them by PCR and inserting them into the linearized vectors (digested with the appropriate restriction enzymes) using In-Fusion® Cloning kit (Clontech), to generate the plasmids pCAMBIA1300-pAP3:TSA2 and pCAMBIA3300-pAP3:ItB4. After transformation into *E. coli*, these plasmids are isolated using a Wizard® Plus SV Minipreps DNA Purification System (Promega), and sent to the Plant Transformation Research Center at the University California Riverside for *Agrobacterium*-mediated transformation into *Arabidopsis.*

There are several protocols for *Agrobacterium*-mediated transformation of *Arabidopsis*, especially for the floral dip method (Clough & Bent 1998; Zhang et al. 2006; Bent 2006; Davis et al. 2009; Logemann et al. 2006). As an example of such a procedure (Bent 2006), the plasmids pCAMBIA1300-pAP3:TSA2 and pCAMBIA3300-pAP3:ItB4 are transformed into *Agrobacterium tumefaciens* strain GV3101

(strain LBA4404 can also be used) by electroporation. A single colony of transformed *A. tumefaciens* is inoculated into 2.5 mL LB broth overnight at 28° C. with shaking at 200 rpm to yield a starter culture. The starter culture is then diluted 1:100 into a larger volume of LB broth (250 mL) with 100 mg/L kanamycin and grown overnight at 28° C. with shaking at 200 rpm. The next day, the liquid culture is centrifuged at 4000 g for 30 min at room temperature. After discarding the supernatant, the pellet is resuspended in 5% sucrose to achieve an optical density of 0.8 at 600 nm. Silwet L-77 is added to the *Agrobacterium* to a concentration of ~0.05% (0.5 mL added to a liter of *Agrobacterium* suspension).

*Arabidopsis* flowers are dipped into the *Agrobacterium* suspension for 2 seconds. The plants are then placed under a clear plastic dome to keep them at high relative humidity until the next day. The plants are grown at 22° C. with 18 hours light (100 ρE/m2/s) and daily watering until siliques start to become yellow. Seeds (T1 generation) are harvested once siliques turn brown. T1 Seeds are sterilized with isopropanol (30 seconds) and then 50% bleach with 0.05% Tween-20 for 5 minutes, and placed on selection medium containing 0.5× Murashige and Skoog (MS) macro- and micronutrients in 0.8% plant tissue culture agar with 25 mg/L hygromycin. Hygromycin-resistant seedlings are transferred to moist soil after one week, which are then sprayed with 100 mg/L phosphinothricin once every 3 days until flowering. The plants are allowed to self-fertilize to generate the second generation (T2). T2 seeds are subjected to the same antibiotic selection and treatment as the T1 seeds to yield hygromycin and phosphinothricin double resistant plants.

Example 11: TSA2 Linked to Beta-Glucosidase and ItB Expression in *Arabidopsis*

The following example describes the transgenic expression of TSA2 (SEQ ID NO: 2) linked to beta-glucosidase, and ItB genes, ItB4 (SEQ ID NO: 3) and ItB24 (SEQ ID NO: 4), converting indole into indoxyl, which spontaneously form indigo (or indirubin in the presence of isatin). However, plants convert indoxyl into indoxyl glucosides (mainly indican), thus preventing the formation of blue (indigo) and pink (indirubin) pigments. Indican can be hydrolyzed by beta-glucosidases to release indoxyl, which can then form indigo. Thus, it can be useful to coexpress a beta-glucosidase together with TSA2 (SEQ ID NO: 2) and ItB genes. A beta-glucosidase from *Polygonum tinctorium* (PtBG) (SEQ ID NO: 53) can be used for this purpose (Minami et al. 1999). This gene can be linked to woad (*Isatis tinctoria*) TSA2 (SEQ ID NO: 2) via a 2A peptide (SEQ ID NO: 44) to enable bicistronic expression (Donnelly et al. 2001), and cotransformed into a plant with ItB24 (SEQ ID NO: 4) or ItB4 (SEQ ID NO: 3). Synthetic constructs of pAP3:TSA2-2A-PtBG (SEQ ID NO: 52) can be cloned into pCAMBIA1300, while synthetic pAP3:ItB24 (SEQ ID NO: 51) can be cloned into pCAMBIA3300, and then both introduced into *Arabidopsis* via *Agrobacterium*-mediated transformation as described in Example 10.

Example 12: TSA2 and P450 (ItB) Expression in Roses

The following example describes the transgenic expression of woad (*Isatis tinctoria*) TSA2 (SEQ ID NO: 2) and ItB genes in roses.

Because it has been shown that using an enhanced 35S promoter (E35S) (SEQ ID NO: 55) (Mitsuhara et al. 1996) to drive the expression of the viola flavonoid-3',5'-hydroxylase gene (F3'5'H) to produce the purple pigment delphinidin in petals (Katsumoto et al. 2007), it is presently thought the flower-specific promoters that work in *Arabidopsis* (AP3, PI, CHS and CmCCD4a-5 promoters) would also drive expression of genes in the petals of roses. More delphinidin can be made when the iris dihydroflavonol-4-reductase gene (DFR) is coexpressed with F3'5'H using the E35S promoter (SEQ ID NO: 55), with the two genes cloned together in the same vector (pBIN19). In the same manner, TSA2-2A-PtBG and ItB24 (SEQ ID NO: 4) (or ItB4 (SEQ ID NO: 3)) preceded by the enhanced 35S promoter (SEQ ID NO: 55) (E35S:TSA2-2A-PtBG, and E35S:ItB24 or E35S:ItB4) can be cloned into the pBIN19 vector or its derivative pBINPLUS (Engelen et al. 1995) and pBINPLUS/ARS (Belknap et al. 2008). These plasmids can then be transformed into roses by biolistic gene delivery (Marchant 1998) or *Agrobacterium* mediated transformation, which has been done successfully for different rose cultivars (Korban et al. 2006; Firoozabady et al. 1994; Borissova et al. 2005; Zakizadeh et al. 2013). The *Agrobacterium* strains that can be used include (but not limited to) AGL0, AGL1, EHA101, GV3101, GV3850 and LBA4404. The rose cultivars that can be used include Royalty, Carefree Beauty, Anny, Saltze Gold, Glad Tidings and Only Love, among others.

Example 13: TSA2-2A-PtBG and P450 (ItB) Expression in Cotton

The following example describes the transgenic expression of woad (*Isatis tinctoria*) TSA2-2A-PtBG and ItB genes in cotton.

A cotton fiber-specific promoter (LTP3) (SEQ ID NO: 54) (Liu et al. 2000) has been used to drive the coexpression of two melanin biosynthetic genes to produce brown cotton fibers (Xu et al. 2007). In the same manner, TSA2-2A-PtBG and ItB24 (SEQ ID NO: 4) (or ItB4 (SEQ ID NO: 3)) can be transformed into cotton and coexpressed under the control of the LTP3 promoter (SEQ ID NO: 54) to produce blue cotton fibers. Synthetic LTP3:TSA2-2A-PtBG and LTP3:ItB24 can be cloned together in a single vector pBIN19 (or its derivatives, pBINPLUS and pBINPLUS/ARS) and transformed into cotton via either *Agrobacterium*-mediated transformation (Umbeck et al. 1987; Firoozabady et al. 1994), particle bombardment (Finer & McMullen 1990), or the pollen tube pathway (Zhou et al. 1983).

Example 14: ItB Overexpression in Woad

The following example describes the overexpression of ItB genes in woad (*Isatis tinctoria*).

ItB genes can be overexpressed in woad (*Isatis tinctoria*) to increase the amounts of indigo that the plant can produce. Synthetic E35S:ItB4 or E35S:ItB4 cloned into pCAMBIA3300 can be transformed into woad by *Agrobacterium*-mediated transformation using a published method (Xiao et al. 2011). *Agrobacterium tumefaciens* strain EHA105 transformed with pCAMBIA-E35S:ItB4 or pCAMBIA-E35S:ItB4 are grown at 28° C. in LB broth supplemented with 100 mg/mL kanamycin. Overnight grown cultures are centrifuged and the bacterial pellet resuspended in 0.5× hormone-free MS liquid medium to obtain a bacterial suspension with a density of $1\times10^9$ cells/mL.

Seeds of *Isatis tinctoria* are sterilized and germinated on 0.5× MS medium to generate bacteria-free seedlings, from which cotyledons and hypocotyls are obtained and cut into 1 cm segments as explants. The explants are immersed in the bacterial suspension for 15 minutes and transferred to 0.5× hormone-free MS agar medium with 0.1 mg/L acetosyringone. After incubation at 25° C. in the dark for three days, the explants are placed on selection medium (MS basal medium supplemented with 2.0 mg/mL benzyl adenine, 0.5 mg/mL 1-naphthaleneacetic acid (NAA), 5 mg/mL phosphinothricin and 500 mg/mL cephapirin) and grown at 25° C. under 12 h light/12 hour dark photoperiod. Regenerated green shoots are separated from the explants and transferred to 0.5× MS medium containing 0.2 mg/mL NAA and 500 mg/mL cephapirin for rooting.

Example 15: Coexpression of ItB24 and Isatin Hydrolase (IsH) in Bacteria

The following example describes coexpression of ItB24 and isatin hydrolase (IsH) in bacteria.

Isatin hydrolase (IsH) gene from *Pseudomonas putida* strain WW2 (U.S. Pat. No. 6,190,892) with a ribosome binding site (rbs) at the 5' end was artificially synthesized and cloned into a pUC57 vector by BioBasic Inc. to generate a pUC57-rbs:IsH plasmid. pCWb-OmpA:ItB24-ATR2mod plasmid was linearized using FastDigest XbaI restriction enzyme (Thermo Scientific) at 37° C. for 30 min. The digested vector was purified using Wizard® SV gel and PCR cleanup system (Promega, Wis.). IsH was amplified using IsH_XbaI_rbsFI (SEQ ID NO: 57) (5'-TCA TGG TTA ATC TAG AGA TTA AAG AGG AGA AAT ACT AGA TGA CCA G-3') and IsH_XbaI_R1stp (SEQ ID NO: 58) (5'-CAA AAT TAT TTC TAG TTA TTC TCG ATC AAA AAT AGC CAG TAC CCG-3') as forward and reverse primers, respectively, and inserted into the linearized pCWb-OmpA:ItB24-ATR2mod plasmid using In-Fusion® HD Cloning Plus kit (Clontech), to generate pCWb-OmpA:ItB24-rbs:IsH-ATR2mod plasmid. The pCWb-OmpA:ItB24-rbs:IsH-ATR2mod plasmid was transformed into Stellar™ competent cells (Clontech) and plated onto LB agar plates containing ampicillin.

pCWb-OmpA:ItB24-rbs:IsH-ATR2mod plasmid isolated from Stellar cells was transformed into DH5a competent *E. coli* cells. A single colony grown on LB agar plate containing 100 μg/mL ampicillin was used to inoculate 5 mL LB broth containing 100 μg/mL ampicillin and was grown overnight at 37° C. at 225 rpm. 200 μL of overnight grown culture was added to 50 mL half-strength Terrific Broth (1.25 g TB in 50 mL water) containing 100 μg/mL ampicillin. When the optical density of the culture reached 0.5 (as measured by a Cary 50 spectrophotometer at 600 nm), isopropyl β-D-1-thiogalactopyranoside, 5-aminolevulenic acid hydrochloride and thiamine hydrochloride were added to a final concentration of 1, 0.5, and 1 mM, respectively. The culture was further incubated at 30° C. with shaking at 200 rpm for 48 hrs. After 48 hrs water-insoluble blue precipitates were seen in the broth.

Experimental Protocol: Four 50-mL induced cultures were combined and extracted two times with 200 mL chloroform and the chloroform layer was pooled and concentrated by evaporation with a rotovap, until a blue paste was left behind. This paste was reconstituted in 1.5 mL chloroform, which was loaded onto a silica column eluted with chloroform. 5-mL fractions were collected in glass vials and similarly colored fractions were pooled and dried by centrifugal evaporation using a centrivap. 1 mL of DMF was added to dried fractions and a UV-visible spectra was obtained using a Cary 50 spectrophotometer (Agilent, USA).

Figure 14A:
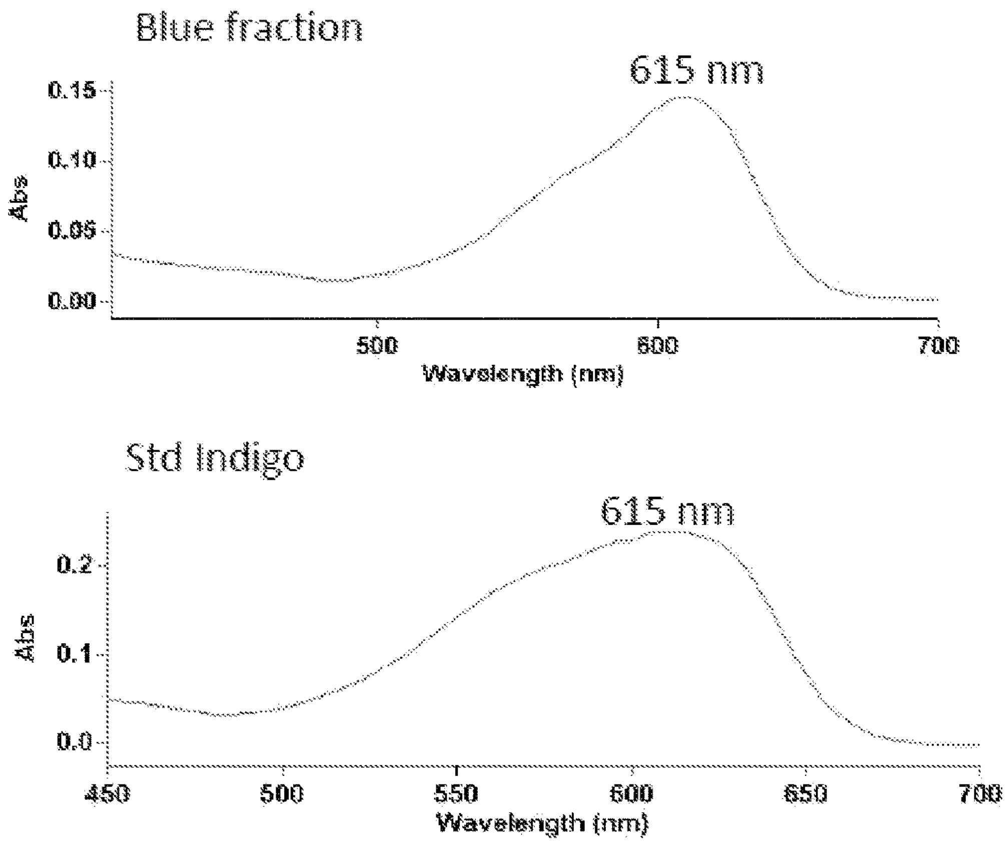
FIG. 14A is a series of graphs showing the absorbance of the collected blue fraction and the indigo standard sample.
Figure 15A:
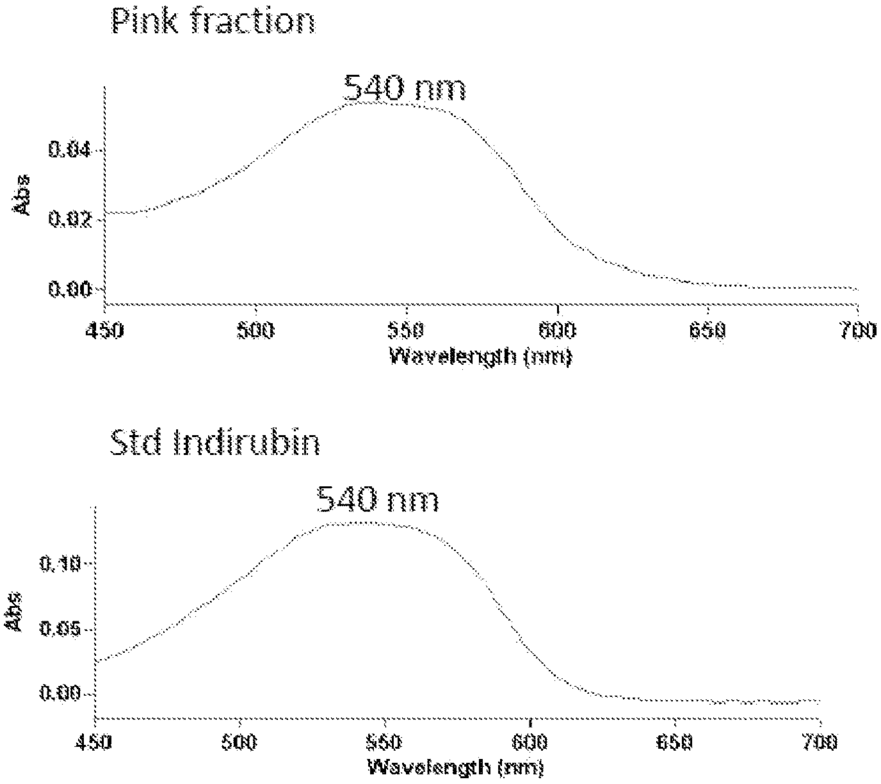
FIG. 15A is a series of graphs showing the absorbance of the collected pink fraction and the indirubin standard sample.
Figure 21:
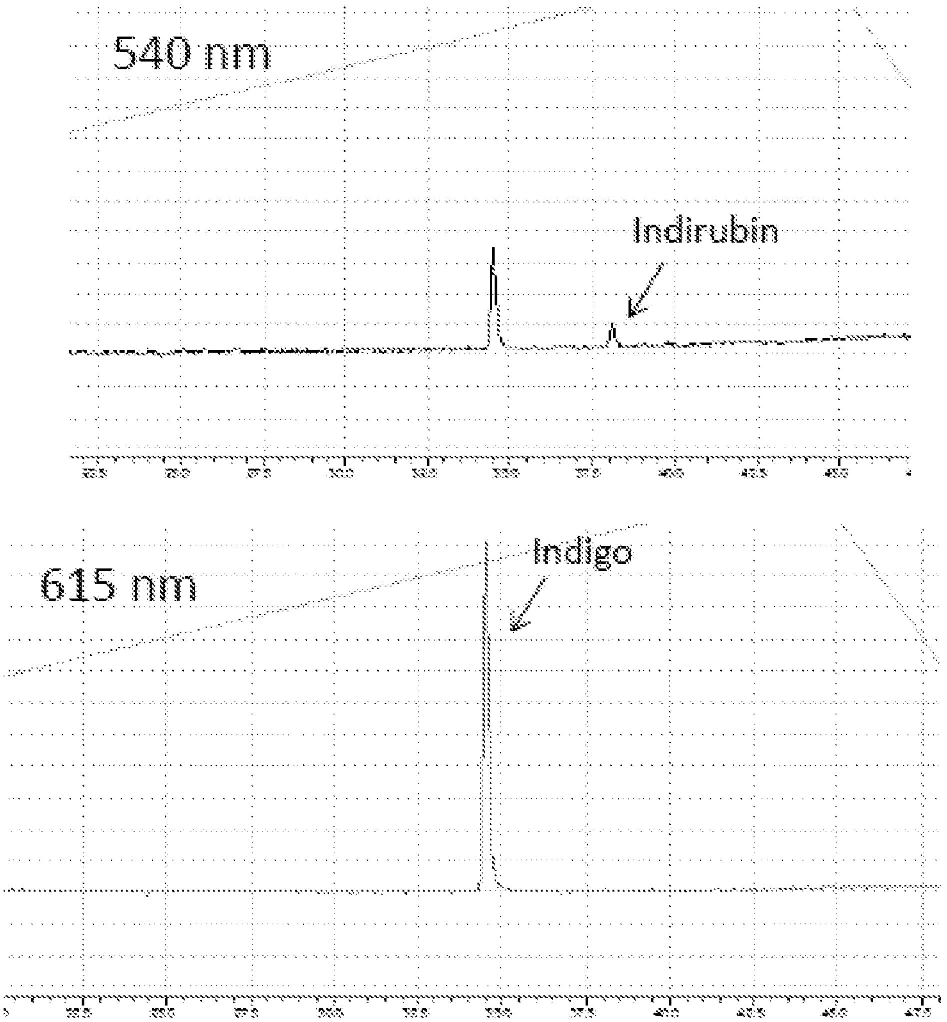
FIG. 21 is a series of HPLC chromatograms. Indigo-Rt-34.51 min. Indirubin-Rt-38.14 min. C18 column, 5 μm, 4.6 mm×250 mm. Solvent A—water.

For HPLC analysis, pigments were extracted from a 50-mL culture with 75 mL chloroform using a separatory funnel. The chloroform layer was collected and concentrated to dryness in a rotary evaporator. The blue paste obtained after evaporation was redissolved in 1 mL of dimethylformamide (DMF) and transferred to a glass vial. The remaining aqueous layer in the separatory funnel was transferred to a 50 mL centrifuge tube and centrifuged at 4000 g for 5 min. The supernatant was discarded and the blue colored pellet was resuspended in 2 mL DMF by sonication for 5 min. The suspended pellet was further centrifuged at 4000 g for 3 min and the supernatant collected in a glass vial. The pellet was again resuspended with another 2 mL DMF, which apparently dissolved all the blue precipitates. This DMF solution was combined with the previous DMF supernatant, which was then used for HPLC analysis, as follows: 5 μL of the combined DMF extract was injected onto a 5 μm C18 Sunfire column (4.6 mm×250 mm) (see e.g., FIG. 21). The column was eluted with a gradient of methanol and water, starting with 50% methanol for 10 min, then increasing to 100 methanol at 30 min, at a flow rate of 0.5 mL/min. The elution of pigments were monitored with a UV-visible detector set at 615 nm for indigo, 540 nm for indirubin, and 245 nm for indole, isatin and 3-oxindole (see e.g., FIG. 14A, FIG. 15A).

Figure 14B:
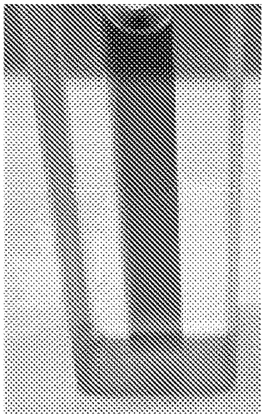
FIG. 14B is an image of the collected blue fraction.

Four 50-mL *E. coli* cultures (DH5alpha transformed with pCWb-OmpA:ItB24-rbs:IsH-ATR2mod plasmid) were combined and extracted two times with 200 mL chloroform and the chloroform layer was pooled and concentrated by evaporation with a rotovap, until a blue paste was left behind. This paste was reconstituted in 1.5 mL chloroform, which was loaded onto a silica column eluted with chloroform. 5-mL fractions were collected in glass vials and blue colored fractions were pooled and dried by centrifugal evaporation. 1 mL of DMF was added to dried fractions and a UV-visible spectra was obtained using a Cary 50 spectrophotometer (see e.g., FIG. 14A-FIG. 14B).

Figure 15B:
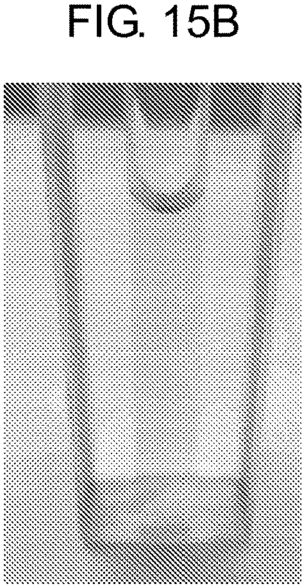
FIG. 15B is an image of the collected pink fraction.

Four 50-mL *E. coli* cultures (DH5alpha transformed with pCWb-OmpA:ItB24-rbs:IsH-ATR2mod plasmid) were combined and extracted two times with 200 ml chloroform and the chloroform layer was pooled and concentrated by evaporation with a rotovap, until a blue paste was left behind. This paste was reconstituted in 1.5 mL chloroform, which was loaded onto a silica column eluted with chloroform. 5-mL fractions were collected in glass vials and pink fractions were pooled and dried by centrifugal evaporation. 1 mL of DMF was added to dried fractions and a UV-visible spectra was obtained using a Cary 50 spectrophotometer (see e.g., FIG. 15A-FIG. 15B).

Figure 11:
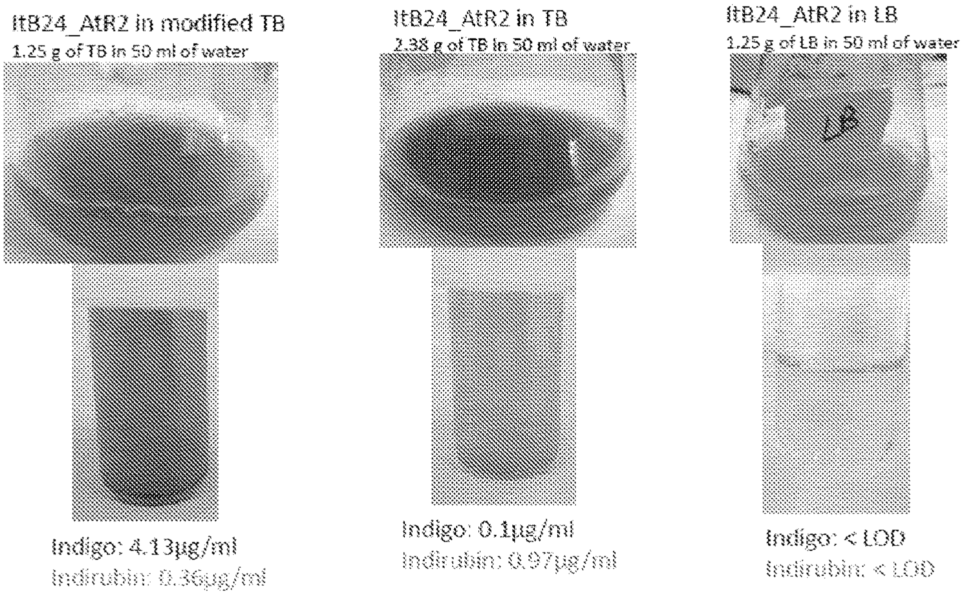
FIG. 11 is a series of images showing heterologous expression of ItB24 in different media (blue, yellow, yellow).

*E. coli* DH5alpha transformed with pCWb-OmpA:ItB24-rbs:IsH-ATR2mod plasmid were grown in different media and found that half-strength TB produces the most indigo (see e.g., FIG. 11). Indigo and indirubin were quantified by HPLC as described above.

Figure 12:
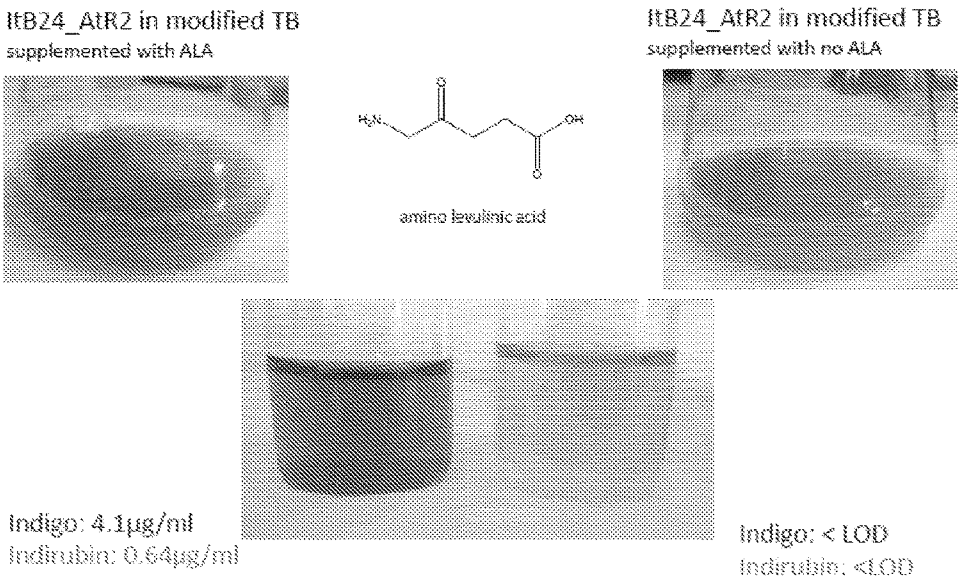
FIG. 12 is a series of images showing the effect of amino levulinic acid (ALA) supplementation and a chemical structure of ALA (blue and green).
Figure 13:
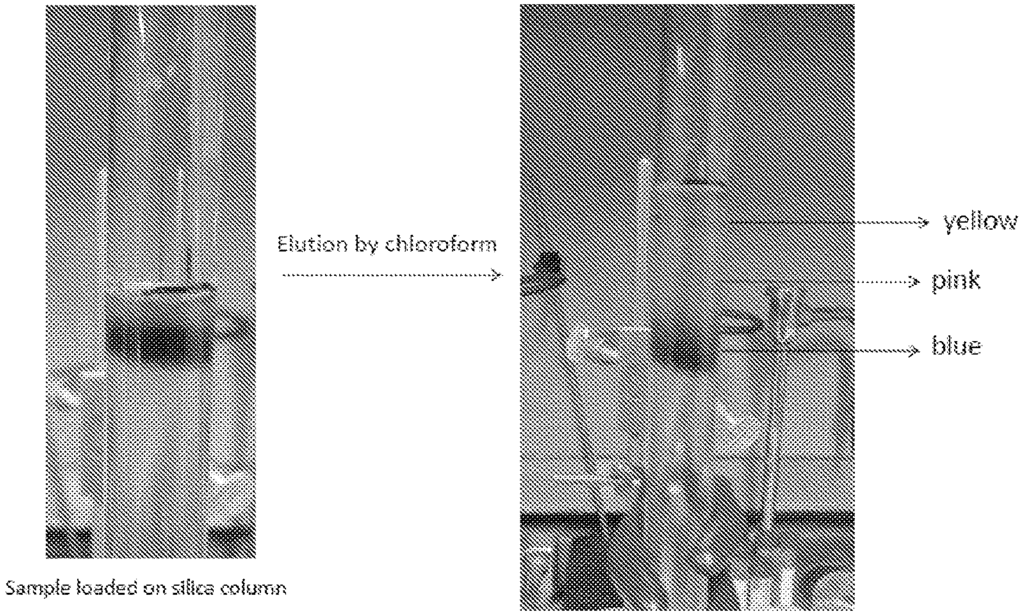
FIG. 13 is a series of images showing the purification of pigments (blue, yellow, pink).

*E. coli* DH5alpha transformed with pCWb-OmpA:ItB24-ATR2mod plasmid produces decreased indigo and increased indirubin, while *E. coli* DH5alpha transformed with pCWb-OmpA:ItB24-rbs:IsH-ATR2mod produces increased indigo compared to indirubin (see e.g., FIG. 12). This suggests that isatin may have an inhibitory effect on indigo formation.

Figure 17:
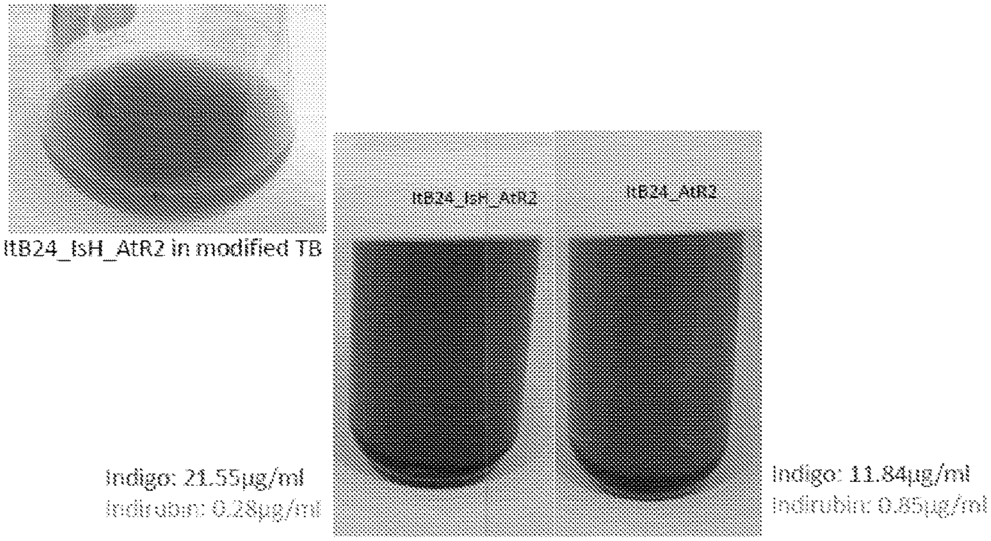
FIG. 17 is a series of images showing the effect of isatin hydroxylase (IsH) on indigo and indirubin concentration (blue, blue).

Coexpression of isatin hydrolase with ItB24 increases indigo while decreasing indirubin formation (see e.g., FIG. 17). It is presently thought that this is because isatin hydrolase converts isatin to isatic acid (see e.g., FIG. 16, FIG. 36). This pathway (see e.g., FIG. 16) shows how isatin hydrolase increases indigo while decreasing indirubin. Isatin is converted to isatic acid so it is no longer available to couple with 3-oxindole to form indirubin. Thus all the remaining 3-oxindole forms only indigo, instead of forming both indigo and indirubin.

In summary, the above example showed the identification of indole hydroxylase in woad and was cloned into *E. coli*. Indigo and indirubin was confirmed by UV-Vis spectroscopy (see e.g., FIG. 14A, FIG. 15A) and HPLC.

Figure 18:
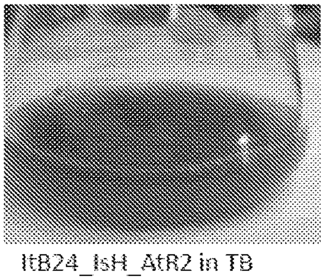
FIG. 18 is a series of images showing the effect of isatin hydroxylase (IsH) on indigo and indirubin concentration (green, yellow).
Figure 18:
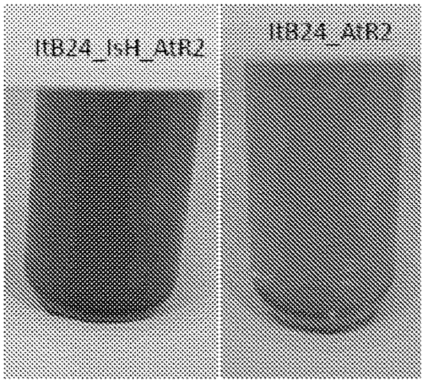

With the help of isatin hydrolase, indigo production was increased and that of indirubin was decreased (see e.g., FIG. 17, FIG. 18).

Example 16: Biosynthetic Pathway

The following example describes the biosynthetic pathway proposed based on the results from isatin hydrolase experiments (see e.g., Example 15) which shows that indirubin formation is dependent on the presence of isatin.

Figure 19:
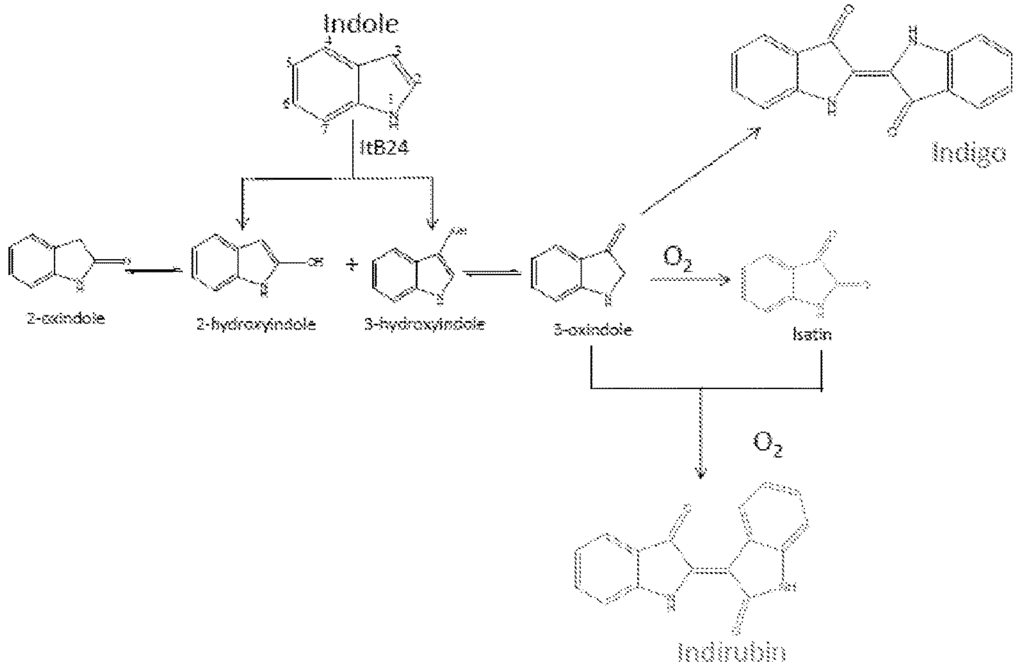
FIG. 19 is a scheme showing the pathway that is presently thought to be catalyzed by ItB24.
Figure 20:
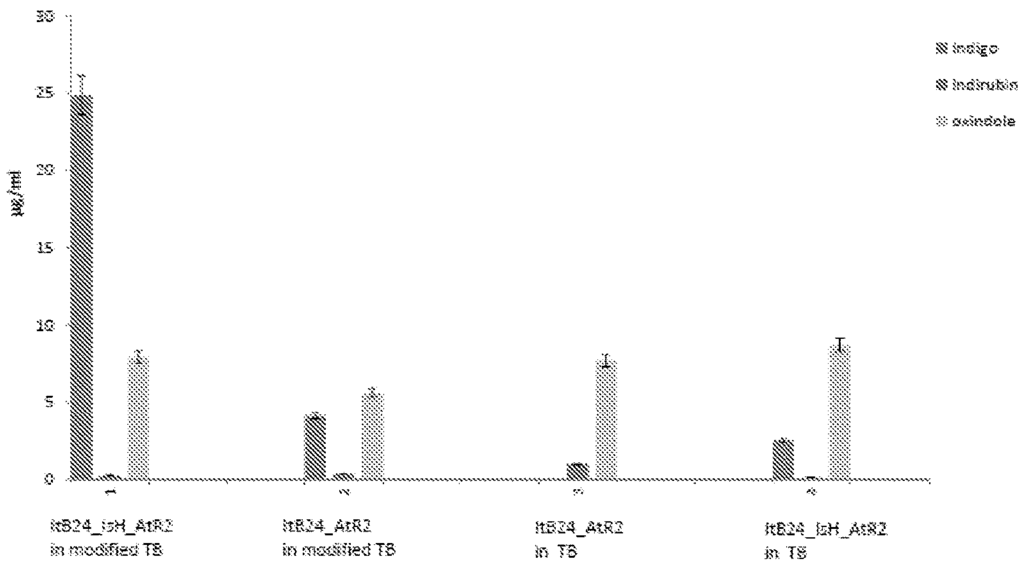
FIG. 20 is a bar graph showing the role of oxindole in indigo and indirubin production.

It is presently thought that indigo is derived from indoxyl (a.k.a. 3-hydroxyindole) by oxidative coupling of its tautomer 3-oxindole, while indirubin is derived from the coupling of 3-oxindole with isatin (see e.g., FIG. 19, FIG. 36).

Example 17: Gene Constructs in Onion and Rose

The following example shows the gene construct expressed in an onion cell culture line and rose (results of rose not shown). Similar results were obtained in Rose, but the cells were denser in Rose which resulted in an insufficient image.

The following Example describes the experimental scope of work for indigo gene transformation performed in onion and rose.

Starting point-cDNA in a cloning vector for the following genes:

a. Gene A, the tryptophan synthase A2 (TSA2) gene isolated from woad and capable of making indole when expressed in *E. coli.* b. Gene B, a woad gene (named ItB24) encoding a P450 enzyme capable of hydroxylating indole and producing indigo and indirubin when expressed in *E. coli.* c. Gene C, the PtBG gene from *Polygonum tinctorium* (another indigo-producing plant) that encodes a beta-glucosidase that can hydrolyze indican to indoxyl, which is involved in turning colorless indigo precursors to the blue indigo dye.

d. Gene D, the isatin hydrolase (IsH) gene from *Pseudomonas putida*, which is also known as the "isatin-removing enzyme." Removal of isatin prevents formation of indirubin, which is a red pigment that can make the indigo dye look purple instead of blue.

Experimental Protocol:

1. Designed and assembled four sequence-verified transcriptional units corresponding to genes A-D including a strong constitutive promoter and suitable terminator sequence
2. Provided transcriptional unit for GFP (control to validate gene insertion and expression)
3. Assembled two sequence-verified gene cassettes containing the following
 a. TU A, TU B, TU GFP
 b. TU A, TU B, TU GFP, TU C, TU D
4. Transient gene gun bombardment of both cassettes into generic rose petal and onion cell lines. 5 petal bombardments per gene cassette (total of 10 bombardments)
5. Experimental results were documented though imaging of petals and onion cells under fluorescent light and white light.

The experiment showed cells were transformed, which was shown by the successful expression of GFP (see e.g., FIG. 37A-FIG. 37D). No toxicity of the genetic construct was observed within the timeframe of the experiment (16 hours).

It was observed that there was accumulation of blue color between the cells, in the cell walls.

SEQUENCE LISTING

| Name | Sequence |
|---|---|
| TSA1 (SEQ ID NO: 1) | ATGGCGATTGCTTTCAAATCCGGCGTCTGCTTCCT<br>CCAATCCGCAAAACCCCAAATCGGAATCCGCCATT<br>CATCCCCTGATTCTTCGCTTTCATTCAAGAGATTG<br>ACTCCCATAGCTGCCCTCTCCACCTCTTCTCCTAC<br>TCTCGGTCTCGCCGATACTTTCAAAGAGCTCAAAA<br>AACAAGGCAAAGTAGCATTCATACCGTACATCACA<br>GCTGGTGATCCAGATCTCTCTACTACTGCAGAAGC<br>ATTGAAAGTTCTTGCCGCTTCTGGGTCAGACATTA<br>TTGAATTGGGTGTTCCTTACTCTGACCCTTTAGCT<br>GATGGACCTGTTATTCAGGCTGCGGCGACAAGGGC<br>TTTGGAGAATGGGACCAACCTTGATAACATCCTTG<br>ACATGTTAGATAAGGTTCTTCCACAAGTATCTTGT<br>GCCAGTTTCGCTGTTCACGTATTACAACCCATTCT<br>TAAACGTGGGTTGGGGAAGTTCATGTCCAGCATCA<br>GAGATGTTGGTGTACAGGGACTTGTGGTTCCAGAT<br>GTTCCTCTTGAGGAAACCGAGATGCTGAGAAAAGA<br>CAGCCCTTAACAACAACATTGAACTGGTCCTACTC<br>ACTAACCAACCACACCAACAGAGCGAATGAAGCGA<br>ATTGTTGATGCATCAGAGGGATTTATTTACCTTGT<br>GAGTTCAATCGGAGTGACTGGTGCACGAGCATCTG<br>TAAGCGGAAAGGTTCAGTCGCTCTTGAAGGATATC<br>AAAGAGGCAACAGACAAGCCAGTGGCGGTCGGTTT<br>TGGAATATCACAGCCCGAGCATGTGAAACAGATAG<br>CTGGTTGGGGAGCTGATGGAGTGATTGTAGGCAGT<br>GCAATGGTGAGGCTTTTGGGAGATGCCAAGTCGCC<br>AACGGAAGGGCTTAAGGAGCTTGAGCGTCTCACAA<br>AGTCTCTCAAATCTGCTCTTCTTTGA |
| TSA2 (SEQ ID NO: 2) | ATGGATCTTCTCAAGAACCCTCCCACAACGGTGGGTC<br>TATCAGAGACTTTCGCTAGGTTGAAGTCTAAAGGCAA<br>AGTGGCTCTGATTCCATATATCACAGCTGGTGATCCA<br>GATCTTTCCACAACAGCTAAAGCTCTCAAAGTGCTCG<br>ACTCTTGTGGCTCTGACATTATCGAACTCGGTGTTCC<br>ATACTCTGATCCATTAGCTGATGGTCCAGCAATCCAG<br>CGTGCTGCGAGACGTTCTTTGCTTAAAGGAACTAACT<br>TTAACTCCATTATCACTATGCTTAAAGAGGTTATTCC<br>TCAGTTATCTTGTCCGATTGCATTGTTTACGTATTAC<br>AACCCGATCCTGCGGAGAGGAATCGAGAACTACATGA<br>CTATTATAAAGAATGCTGGAGTTCATGGGCTTCTTGT<br>TCCTGATGTTCCACTCGAAGAGACTGAGACTCTGCGG<br>AAAGGAGCTCAAAAGCATCAGATTGAACTTGTACTGC<br>TGACGACACCCACAACCCCGAAAGAACGGATGAATGC<br>CATTGTTGAAGCATCCCAAGGATTCATCTATCTCGTA<br>AGCTCAGTGGGAGTTACTGGCACGAGAGAGTCTGTTA<br>ACGAACACGTTCAATCCCTTCTACAACAAATCAAAGA<br>GGCTACAAACAAGCCAGTCGCGGTTGGATTTGGCATA<br>TCGAAACCTGAGCATGTGAAACAGGTGGCTGAATGGG<br>GAGCAGACGGAGTCATTGTAGGAAGCGCTATGGTTAA<br>GATATTGGGAGAGGCTGAATCACCTGAGCAAGGACTC<br>AAGGAGCTGGAAGTCTTCACTAAATCTTTAAAGTCTG<br>CTCTTATCTCTTGA |
| ItB4 (SEQ ID NO: 3) | ATGGTGATTCTTCTGTCTTTTCTCTTGCTTCTATTCA<br>TTCCCCTACTCTTCTCGTTCATATACACCAACAAGAA<br>CAAAACCTCAAGTAATCTTCCTTCGGGCCCAGCACAA<br>ATTCCGATAATCGGAAACCTACACCAGATCCAGGGAT<br>TGCTTCACAGATGTTTTCACTATCTCTCCAAGAAACA<br>CGGACCTGTGATGCTTCTCCGTCTAGGGTTTGTTCGC<br>GTGGTCGTGATCTCATCAAGTGAAGCGGCTGAAGACG<br>TTCTTAAAATCCATGACCTTGTGTGTTGTACACGACC<br>TGCCACTAAGGCCTCAAGGGTTTTCTCGCGTAATGGT<br>AAAGGCATCGGCTTTGGGGAGTCATGGAGAGACCTGC<br>GTAAGCTTGCGGTTCGTGAGTTTTTCAGCGTGAAAAA<br>GGTTCGATCTTTCAGGTATGTCAGAGAGGAAGAGAAT<br>GAGTCGATGGTCAAGAACCTGAGAGAATCGGCTTTGA<br>AGCAATCTCCGGTGGATTTGAGCAAAACACTTTTCTG<br>CTTAGCTGCGAGTATCATCTTCAGAACCGCCTTCGGA |

SEQUENCE LISTING

| Name | Sequence |
| --- | --- |
| | CAGAGTTTCTTCGAGAACAAGCATATCGATAAGGAAA<br>GGATCGAAGGACTCATGTTAGAAGCTCACAGTAACAT<br>GTCTTTCAACTTCACTGATATCTTCCCCGCTGCTGGT<br>TTTGGATCGTTTATGGACTTTGTGTCAGGGAAACATA<br>AGAGACTTCACGATGTCTTCACTGAGGTTGATACTTT<br>TATTAGTCATATCATTGATGATCATCAATTGAAGAGT<br>TTCACACAAGATCGTCCTGATTTCATCGATTCCATAT<br>TAGAAATGATACGTAAACAAGAACAAAATGAATCTTT<br>CAAGCTCACCATTGATAATCTCAAAGGGATCAGCCAA<br>GATATATATCTTGCTGGAGTAGACACAAGCGCCATCA<br>CCATGATTTGGACGATGGCAGAGCTTGTTAGAAACCC<br>TAGAGTGATGAAAACTGTCCAAGACGAGATCAGAAAT<br>TGCATTGGAACCAAACACAAAGAGAGAATCGAGGAAG<br>AAGATCTCAATAAGCTTCAATACTTGAAGCTTGTGGT<br>GAAAGAAAGCTTAAGACTACACCCACCAGCTCCTCTG<br>CTACTCCCCAGAGAAACAATGAGCCAGATCAAGATTC<br>AAGGCTACGACATACCACCAAAAACCGTTGTAATGGT<br>TAATGCTTGGTCGATAGGTCGGGATCCTAAACACTGG<br>GAAGATCCAGAAGAGTTTATCCCGGAGAGGTTTATCA<br>ATTGTCCTGTAGATTACAAAGGACATAGCTTTGAGAT<br>GTTACCATTTGGTTCTGGACGGAGGATCTGCCCAGGA<br>ATGGCTTCAGGGATTGCTACCATTGAATTGGGACTCT<br>TGAATTTGCTTTACTACTTCGATTGGAGATTGCCTGA<br>GGAGAAGAAAGATATGGACATGGAAGAAGCTGGTGGT<br>CTTACTGTTGTTAAGAAAGTTCCTCTTGAGCTTATCC<br>CCATTCTTCGTCAGTGA |
| ItB24 (SEQ ID NO: 4) | ATGTCGATTATTCTGTATTTCTTTTCGTTTTTGCTTCTC<br>CCCGCTCTTTTCTCGTTAATTTTAGTGAAGAAAATCAA<br>AGACACGAAACAAAACCTTCCTCCGAGCCCACCAAAG<br>CTTCCGATCATCGGTAACCTACACCAGCTTCGAGGAT<br>TGTTTCACAGATGTCTTCATGATTTGTCCAAGAAACAT<br>GGACCCGTGTTGCTTCTCCGTCTAGGTTTTCTCGAAA<br>TGGTTGTTATCTCCTCAAGCGAAGCAGCTGAAGAAGT<br>TCTCAAAACACATGACCTTGAGTGTTGTACCAGACCG<br>AACACTCACGCCTCATCCATATTCTGGCGTAATGGTAA<br>AGACATTGGCTTTGCCCCATATGGTGAGGGGTGGAAA<br>GAGGTTCGCAAGCTTGCTGTTCTCAATTTTTTCAGCGC<br>GACAAAGGTTCGATCTTTCAGGTACATCAGAGAGGAA<br>GAGAATGATTTGATGGTCAAGCAACTGAAGGAATTAG<br>CTCAAAAGAAGTCTCCAGTGGATTTGAGCCAAACGTT<br>TTTCTGTCTAGCCGGAAGTATCATATTCAGATCTGCCT<br>TTGGACAGCGTTTCTACGAGAACGTTCATGTCGACAA<br>GGAAAGGATCAAAGACCTCATGTTCGAGGCCCAGAGA<br>ATTGGATCTGTAAGTAGCTCTGATATTTTCCCTGGTTT<br>GGGATGGTTTATGGACTTTTTTTCAGGACGACATAGG<br>AGACTTCACCAAGTTTTCGACGAGGTTGATACTTTGCT<br>GAGTCATATAATTGATGATCACTTGAAGAATCCTGACG<br>AAAAAACAAATCAAGATCGCCCTGATATCGTCGACTC<br>CATCTTAAAAACTATGCAAAGTCAAGAAGAAGATGAAT<br>CTTTCAAGTTCACCATTGATCATCTCAAAGGAATCATC<br>CAAGATATATATCTTGCTGGAATAGACACAAGTGCCAT<br>CACCATGATCTGGGCAATGGCAGAGCTCGTTAGAAAC<br>CCTAGAGTGATGAAAAAAGTCCAAGACGAGATCAGAA<br>CTTGCATTGGAATCAAACAAAAGGAGAGAATCGAGGA<br>AGAAGATATCGACAAGCTTCAGTACTTTAAGCTTGTGA<br>TCAAAGAAACCTTAAGACTACACCCAGCATCTCCTATG<br>TTACTCCCAAGAGAAACAATGAGTCAAATCAAGATTCA<br>AGGCTACGACATTCCGCCAAAAACCATTCTACTGGTT<br>AACAGTTGGTCGATAGGTCGAGATCCTAAACACTGGA<br>AAGATCCAGAAGAGTTTATCCCTGAGAGGTTCATCGA<br>TTGTCCTGTAGATTACAAAGGACAGAGCTTTGAGATGT<br>TACCATTTGGTTCTGGACGGAGGGTGTGCCCAGGAAT<br>GGCTTCAGGGCTTGCGACCGTTGAATTGGGACTCTTG<br>AATTTACTTTACTACTTCGATTGGAGTTTGCCTGAGGG<br>GAAGAAAGTTATGGACATGGAAGAAGCTGGTGATGCT<br>ACCATTATTAAGAAATTTCCTCTTGAGCTTCTTCCAAC<br>TCTTCATGGTTAA |
| coltB4: His (SEQ ID NO: 5) | CCTAGGAGGTACCATATGCTGGTTGTAATTCTGCTGT<br>CTTTCCTGCTGCTGCTGTTCATTCCACTGCTGTTCTCT<br>TTCATCTATACGAACAAAAACAAAACTTCCTCTAACCT<br>GCCGTCTGGCCCTGCGCAGATCCCGATTATCGGCAA<br>CCTGCACCAGATTCAGGGCCTGCTGCATCGCTGCTTC<br>CACTATCTGAGCAAAAAGCACGGCCCGGTGATGCTGC |

SEQUENCE LISTING

| Name | Sequence |
| --- | --- |
| | TGCGTCTGGGCTTCGTTCGTGTTGTTGTGATCTCTTCT<br>TCTGAAGCTGCTGAGGACGTGCTGAAGATTCACGATC<br>TGGTGTGTTGCACCCGTCCGGCGACCAAAGCGTCCC<br>GCGTCTTCAGCCGTAACGGCAAAGGCATCGGTTTCG<br>GCGAATCCTGGCGCGAACTGCGTAAACTGGCGGTGC<br>GTGAATTCTTTAGCGTGAAAAAGTTTCGTTCTTTCCGT<br>TACGTTCGTGAGGAAGAATCTGATTTCATGGTTAAGAA<br>CCTGCGCGAGTCCGCTCTGAAACAGTCTCCGGTTGAT<br>CTGTCCAAAACTCTGTTCTGTCTGAGCGCCTCTATCGT<br>CTTTCGTACCGCCTTCGGCCAGAGCTTCTTTGAAAAC<br>AAACACATCGACAAAGAACGTATCGACGGCCTGATGC<br>TGGAAGCACACTCTAATATGTCCTTTACCTTTACGGAC<br>ATTTTCCCGGCGGCGGGTTTTGGCTCTTTCATGGACT<br>TCGTTTCTGGCAAACATAAACGTCTGCACGACGTGTT<br>CACGGAAGTAGACACTTTCATCTCTCACATCATCGAC<br>GACCACCAGCTGAAGTCCTTCACTAAAGATCGTCCAG<br>ACTTCATCGATTCTATTCTGGAAATGATTCGCAAACAA<br>GAGCAAAACGAGTCCTTCAAACTGACTATCGATAACC<br>TGAAAGGTATTAGCCAGGACATCTACCTGGCCGGTGT<br>TGACACCAGCGCAATCACCATGATCTGGACTATGGCA<br>GAACTGGTTCGCAATCCGCGCGTAATGAAAACGGTTC<br>AGGACGAAATTCGCAACTGCATCGGTACCAAACACAA<br>AGAACGCATTGAAGAAGAAGATCTGAACAAACTGCAA<br>TACCTGAAACTGGTGGTCAAAGAATCCCTGCGTCTGC<br>ACCCTCCGGCTCCTCTGCTGCTGCCACGTGAAACCAT<br>GTCCCAGATCAAAATCCAGGGTTATGACATCCCGCCG<br>AAAACCGTCGTTATGGTTAATGCTTGGAGCATCGGTC<br>GCGATCCAAAACATTGGGAGGACCCGGAGGAGTTCA<br>TCCCGGAGCGTTTTATGAACTGCCCGGTGGATTACAA<br>AGGTCACAGCTTTGAAATGCTGCCGTTTGGTTCTGGT<br>CGTCGTATCTGTCCGGGTATGGCATCTGGTATTGCAA<br>CCATCGAACTGGGTCTGCTGAACCTGCTGTACTACTT<br>CGATTGGCGTCTGCCGGAAGAAAAGAAGGATATGGAT<br>ATGGAAGAAGCTGGTGGCCTGACCGTAGTAAAAAAGG<br>TACCGCTGGAACTGATTCCGATCCTGCGTCAGCACCA<br>CCACCATCACCACTAGT |
| coltB24: His (SEQ ID NO: 6) | ATGTCTATTATCCTGTACTTTTTCTCTTTCCTGCTGCT<br>GCCGGCTCTGTTCTCTCTGATCCTGGTAAAAAAGATTA<br>AAGACACCAAACAGAACCTGCCGCCGAGCCCGCCGAA<br>ACTGCCTATCATCGGCAACCTGCACCAACTGCGTGGT<br>CTGTTTCACCGCTGTCTGCACGACCTGTCTAAGAAAC<br>ATGGCCCGGTTCTGCTGCTGCGCCTGGGTTTTCTGGA<br>AATGGTTGTCATCTCTAGCTCCGAAGCTGCCGAAGAG<br>GTTCTGAAAACCCATGATCTGGAATGCTGCACTCGTC<br>CGAACACCCACGCGAGCAGCATTTTTTGGCGTAACGG<br>CAAGGATATTGGCTTCGCTCCGTACGGCGAAGGCTG<br>GAAAGAAGTGCGCAAACTGGCGGTGCTGAACTTCTTT<br>TCTGCTACCAAAGTGCGTTCTTTCCGCTACATCCGTG<br>AGGAAGAAAACGACCTGATGGTTAAACAGCTGAAAGA<br>ACTGGCACAGAAGAAATCTCCGGTCGATCTGAGCCAA<br>ACGTTCTTCTGCCTGGCGGGCAGCATTATTTTCCGTA<br>GCGCATTTGGTCAGCGTTTCTACGAGAACGTTCACGT<br>GGACAAAGAGCGTATCAAAGACCTGATGTTTGAAGCT<br>CAACGTATTGGCTCCGTAAGCTCTTCCGATATCTTCCC<br>TGGCCTGGGTTGGTTCATGGACTTCTTCAGCGGTCGC<br>CACCGTCGTCTGCACCAGGTTTTTGACGAAGTAGATA<br>CTCTGCTGTCCCACATCATTGATGATCACCTGAAAAAC<br>CCGGACGAGAAAACTAACCAGGATCGCCCGGATATC<br>GTAGACTCCATCCTGAAAACTATGCAGTCCCAGGAAG<br>AAGATGAGTCCTTCAAATTCACCATCGACCACCTGAAA<br>GGTATTATCCAGGACATTTATCTGGCAGGTATCGACA<br>CCTCCGCAATTACCATGATTTGGGCAATGGCCGAACT<br>GGTTCGCAATCCACGTGTCATGAAAAAGGTTCAGGAC<br>GAAATCCGTACTTGTATCGGCATCAAACAGAAAGAAC<br>GTATCGAAGAGGAAGACATCGATAAACTGCAGTATTT<br>CAAACTGGTGATCAAAGAAACCCTGCGCCTGCACCCT<br>GCGTCCCCGATGCTGCTGCCACGTGAAACGATGTCTC<br>AGATTAAAATCCAGGGTTACGACATCCCGCCGAAGAC<br>CATCCTGCTGGTGAATAGCTGGTCCATTGGTCGTGAC<br>CCGAAACACTGGAAAGATCCGGAAGAGTTCATCCCGG<br>AACGTTTTATCGATTGTCCGGTTGATTATAAAGGTCAG<br>AGCTTCGAGATGCTGCCATTCGGTTCTGGTCGTCGCG<br>TTTGCCCAGGTATGGCCTCTGGTCTGGCGACTGTAGA<br>ACTGGGCCTGCTGAACCTGCTGTATTACTTCGATTGG |

-continued

SEQUENCE LISTING

| Name | Sequence |
|---|---|
| | TCCCTGCCGGAAGGTAAAAAGGTGATGGACATGGAA<br>GAAGCTGGCGACGCGACCATCATCAAGAAATTCCCGC<br>TGGAACTGCTGCCAACGCTCCATGGTCACCACCACCA<br>TCACCACTAGT |
| ompA: T13H: His (SEQ ID NO: 7) | CATATGAAAAAGACAGCTATCGCGATTGCAGTGGCAC<br>TGGCTGGTTTCGCTACCGTAGCGCAGGCCGCTCCGA<br>TGCTAGCGGTGATGGCCGGTATTATTCTGTTCTTCCG<br>TTCCAAACGTCATTCCTCTGTTAAACTGCCGCCGGGT<br>AACCTGGGTTTCCCACTGGTAGGTGAAACGCTGCAGT<br>TCGTACGCAGCCTGGGTTCCTCCACTCCGCAGCAGTT<br>CATCGAGGAACGCATGTCCAAATTCGGCGACGTATTC<br>AAAACTAGCATCATTGGTCACCCGACCGTTGTTCTGT<br>GTGGCCCGGCAGGCAACCGTCTGGTGCTGAGCAATG<br>AAAACAAACTGGTACAGATGTCTTGGCCGTCTTCCAT<br>GATGAAGCTGATCGGCGAGGATTGCCTGGGCGGCAA<br>AACGGGTGAACAACACCGTATTGTTCGTGCTGCACTG<br>ACTCGCTTCCTGGGTCCTCAGGCACTGCAAAATCACT<br>TCGCAAAGATGTCCTCTGGCATTCAACGTCACATCAA<br>CGAGAAATGGAAGGGTAAAGACGAAGCCACCGTGCT<br>GCCGCTGGTTAAAGACCTGGTGTTCTCTGTTGCATCT<br>CGTCTGTTCTTTGGTATCACCGAAGAACACCTGCAGG<br>AGCAACTGCATAACCTGCTGGAGGTGATCCTGGTTGG<br>TTCTTTCTCTGTGCCGCTGAACATTCCGGGTTTCTCCT<br>ATCACAAAGCTATCCAGGCGCGTGCTACCCTGGCCGA<br>CATTATGACCCACCTGATCGAAAAACGTCGTAACGAA<br>CTGCGTGCGGGCACCGCCTCTGAAAACCAGGACCTG<br>CTGTCCGTTCTGCTGACTTTTACGGATGAACGTGGCA<br>ATTCTCTGGCGGATAAAGAAATTCTGGACAACTTCTCT<br>ATGCTGCTGCATGGTAGCTATGATAGCACCAACTCCC<br>CGCTGACTATGCTGATCAAAGTGCTGGCGAGCCACCC<br>GGAATCTTACGAAAAAGTGGCTCAGGAACAGTTCGGT<br>ATCCTGAGCACCAAGATGGAAGGCGAAGAGATCGCG<br>TGGAAAGATCTGAAGGAAATGAAATACAGCTGGCAGG<br>TTGTCCAGGAAACCCTGCGCATGTACCCACCGATTTT<br>TGGTACCTTCCGTAAAGCTATCACCGACATCCACTATA<br>ACGGCTACACGATCCCGAAAGGCTGGAAACTGCTGT<br>GGACTACTTATTCTACCCAGACCAAGGAAGAGTACTT<br>CAAAGATGCGGATCAGTTTAAACCGTCCCGCTTCGAA<br>GAAGAAGGCAAACATGTCACCCCGTACACCTACCTGC<br>CGTTTGGCGGTGGTATGCGCGTTTGCCCAGGTTGGG<br>AGTTTGCGAAAATGGAAACTCTGCTGTTCCTGCACCA<br>TTTCGTAAAAGCGTTTTCTGGTCTGAAAGCGATCGAC<br>CCTAACGAAAAACTGTCCGGCAAACCGCTGCCTCCGC<br>TGCCGGTTAACGGTCTGCCGATCAAACTGTACAGCCG<br>CTCTCACCACCACCATCACCACTAGT |
| Oligo_dT24 (SEQ ID NO: 8) | GCT GTC AAC GAT ACG CTA CGT AAC GGC<br>ATG ACA GTG TTT TTT TTT TTT TTT TTT<br>TTT TTT |
| GR_3' primer (SEQ ID NO: 9) | GCT GTC AAC GAT ACG CTA CGT AAC G |
| ItB4_ 5utr_F1 (SEQ ID NO: 10) | CAG TAT CTC CAA GAA AAC GGA GCA |
| ItB24_ 5utr_F1 (SEQ ID NO: 11) | GGT ACA GAG GCC TTT AAG TAT CTC T |
| ItB4_ F1cacc (SEQ ID NO: 12) | CAC CAT GGT GAT TCT TCT GTC TTT TCT<br>CTT GC |
| ItB24_ F1cacc (SEQ ID NO: 13) | CAC CAT GTC GAT TAT TCT GTA TTT CTT<br>TTC GTT T |

-continued

SEQUENCE LISTING

| Name | Sequence |
|---|---|
| ItB4_ R1stp (SEQ ID NO: 14) | TCA CTG ACG AAG AAT GGG GAT AAG CTC |
| ItB24_ R1stp (SEQ ID NO: 15) | TAA CCA TGA AGA GTT GGA AGA AGC TCA |
| OmpA_ItB4_ NheI_F1 (SEQ ID NO: 16) | CCG CTC CGA TGC TAG TGG TGA TTC TTC<br>TGT CTT TTC TCT TGC T |
| pCWB_ItB4_ XbaI_R1stp (SEQ ID NO: 17) | AAA ATT ATT TCT AGA TCA CTG ACG AAG<br>AAT GGG GAT AAG C |
| OmpA_ ItB24_ NheI_F1 (SEQ ID NO: 18) | CCG CTC CGA TGC TAG TGT CGA TTA TTC<br>TGT ATT TCT TTT CGT TT |
| pCWB_ ItB24_ XbaI_R1st p (SEQ ID NO: 19) | AAA ATT ATT TCT AGA TTA ACC ATG AAG<br>AGT TGG AAG AAG CTC A |
| pCWb_AtR2_ F1coR (SEQ ID NO: 20) | GGA GAT ATA ACC ATG CGT CGC TCC GGT<br>TCT GGG AAT |
| pCWb_AtR2_ R1stp (SEQ ID NO: 21) | TAT CAT CGA TAA GCT TTA CCA TAC ATC<br>TCT AAG ATA TCT TCC ACT G |
| pCWb_OmpA_ Nde_F1 (SEQ ID NO: 22) | GCT TAG GAG GTC ATC ATA TGA AAA AGA<br>CAG CTA TCG CGA TTG C |
| pCWb_His_ XbaI_R1 (SEQ ID NO: 23) | AAA ATT ATT TCT AGA CTA GTG GTG ATG<br>GTG GTG GT |
| pCWb_ vector_F1 (SEQ ID NO: 24) | AGC TTA TCG ATG ATA AGC TGT CAA ACA |
| pCWb_ vector_R1 (SEQ ID NO: 25) | AGC CAT ATT TAT ATC TCC TTC TTA AAG<br>TTA AAC AA |
| TSA1_5utr_ F1 (SEQ ID NO: 26) | GCA GTC TCC ATA GCT TCT TAC AAT |
| TSA1_cacc_ F1 (SEQ ID NO: 27) | CAC CAT GGC GAT TGC TTT CAA ATC C |

-continued

SEQUENCE LISTING

| Name | Sequence |
| --- | --- |
| TSA1_stp_<br>R1<br>(SEQ ID<br>NO: 28) | TCA AAG AAG AGC AGA TTT GAG AGA C |
| TSA2_5utr_<br>F1<br>(SEQ ID<br>NO: 29) | CGC TAG TGA CCA ACA TTC ATT TTC T |
| TSA2_cacc_<br>F1<br>(SEQ ID<br>NO: 30) | CAC CAT GGA TCT TCT CAA GAA CCC TCC C |
| TSA2_stp_<br>R1<br>(SEQ ID<br>NO: 31) | TCA AGA GAT AAG AGC AGA CTT TAA AGA |
| OmpA_<br>coltB4_<br>NheI_F1<br>(SEQ ID<br>NO: 32) | CCG CTC CGA TGC TAG TGC TGG TTG TAA<br>TTC TGC TGT CTT TC |
| OmpA_<br>coltB24_<br>NheI_F1<br>(SEQ ID<br>NO: 33) | CCG CTC CGA TGC TAG TGT CTA TTA TCC<br>TGT ACT TTT TCT CTT TCC TG |
| pUC18_<br>TSA1_<br>EcoRI_F1<br>(SEQ ID<br>NO: 34) | CCA TGA TTA CGA ATT CCA TGG CGA TTG<br>CTT TCA AAT CC |
| pUC18_<br>TSA1_<br>HindIII_<br>R1stp<br>(SEQ ID<br>NO: 35) | GGC CAG TGC CAA GCT TTC AAA GAA GAG<br>CAG ATT TGA GAG AC |
| pUC18_<br>TSA2_<br>EcoRI_F1<br>(SEQ ID<br>NO: 36) | CCA TGA TTA CGA ATT CCA TGG ATC TTC<br>TCA AGA ACC CTC CC |
| pUC18_<br>TSA2_<br>HindIII_<br>R1stp<br>(SEQ ID<br>NO: 37)<br>(Barnes,<br>1996) | GGC CAG TGC CAA GCT TTC AAG AGA TAA<br>GAG CAG ACT TTA AAG A |
| CYP2A6<br>(SEQ ID<br>NO: 38)<br>(NCBI<br>Reference<br>Sequence:<br>NM_<br>000762.5) | ATGCTGGCCTCAGGGATGCTTCTGGTGGCCTTGCTG<br>GTCTGCCTGACTGTAATGGTCTTGATGTCTGTTT<br>GGCAGCAGAGGAAGAGCAAGGGGAAGCTGCCTCCG<br>GGACCCACCCCATTGCCCTTCATTGGAAACTACCT<br>GCAGCTGAACACAGAGCAGATGTACAACTCCCTCATG<br>AAGATCAGTGAGCGCTATGGCCCCGTGTTCACC<br>ATTCACTTGGGGCCCCGGCGGGTCGTGGTGCTGTGT<br>GGACATGATGCCGTCAGGGAGGCTCTGGTGGACC<br>AGGCTGAGGAGTTCAGCGGGCGAGGCGAGCAAGCCA<br>CCTTCGACTGGGTCTTCAAAGGCTATGGCGTGGT<br>ATTCAGCAACGGGGAGCGCGCCAAGCAGCTCCGGCG<br>CTTCTCCATCGCCACCCTGCGGGACTTCGGGGTG<br>GGCAAGCGAGGCATCGAGGAGCGCATCCAGGAGGA<br>GGCGGGCTTCCTCATCGACGCCCTCCGGGGCACTG<br>GCGGCGCCAATATCGATCCCACCTTCTTCCTGAGCCG<br>CACAGTCTCCAATGTCATCAGCTCCATTGTCTT |
| | TGGGGACCGCTTTGACTATAAGGACAAAGAGTTCCTG<br>TCACTGTTGCGCATGATGCTAGGAATCTTCCAG<br>TTCACGTCAACCTCCACGGGGCAGCTCTATGAGATGT<br>TCTCTTCGGTGATGAAACACCTGCCAGGACCAC<br>AGCAACAGGCCTTTCAGTTGCTGCAAGGGCTGGAGG<br>ACTTCATAGCCAAGAAGGTGGAGCACAACCAGCG<br>CACGCTGGATCCCAATTCCCCACGGGACTTCATTGAC<br>TCCTTTCTCATCCGCATGCAGGAGGAGGAGAAG<br>AACCCCAACACGGAGTTCTACTTGAAAAACCTGGTGA<br>TGACCACGTTGAACCTCTTCATTGGGGGCACCG<br>AGACCGTCAGCACCACCCTGCGCTATGGCTTCTTGCT<br>GCTCATGAAGCACCCAGAGGTGGAGGCCAAGGT<br>CCATGAGGAGATTGACAGAGTGATCGGCAAGAACCG<br>GCAGCCCAAGTTTGAGGACCGGGCCAAGATGCCC<br>TACATGGAGGCAGTGATCCACGAGATCCAAAGATTTG<br>GAGACGTGATCCCCATGAGTTTGGCCCGCAGAG<br>TCAAAAAGGACACCAAGTTTCGGGATTTCTTCCTCCCT<br>AAGGGCACCGAAGTGTACCCTATGCTGGGCTC<br>TGTGCTGAGAGACCCCAGTTTCTTCTCCAACCCCCAG<br>GACTTCAATCCCCAGCACTTCCTGAATGAGAAG<br>GGGCAGTTTAAGAAGAGTGATGCTTTTGTGCCCTTTT<br>CCATCGGAAAGCGGAACTGTTTCGGAGAAGGCC<br>TGGCCAGAATGGAGCTCTTTCTCTTCTTCACCACCGT<br>CATGCAGAACTTCCGCCTCAAGTCCTCCCAGTC<br>ACCTAAGGACATTGACGTGTCCCCCAAACACGTGGGC<br>TTTGCCACGATCCCACGAAACTACACCATGAGC<br>TTCCTGCCCCGCTGA |
| hNPR<br>(SEQ ID<br>NO: 39)<br>(NCBI<br>Reference<br>Sequence:<br>NM_<br>000941.2) | ATGATCAACATGGGAGACTCCCACGTGGACACCAGCT<br>CCACCGTGTCCGAGGCGGTGGCCGAAGAAGTAT<br>CTCTTTTCAGCATGACGGACATGATTCTGTTTTCGCTC<br>ATCGTGGGTCTCCTAACCTACTGGTTCCTCTT<br>CAGAAAGAAAAAAGAAGAAGTCCCCGAGTTCACCAAA<br>ATTCAGACATTGACCTCCTCTGTCAGAGAGAGC<br>AGCTTTGTGGAAAAGATGAAGAAAACGGGGAGGAACA<br>TCATCGTGTTCTACGGCTCCCAGACGGGGACTG<br>CAGAGGAGTTTGCCAACCGCCTGTCCAAGGACGCCC<br>ACCGCTACGGGATGCGAGGCATGTCAGCGGACCC<br>TGAGGAGTATGACCTGGCCGACCTGAGCAGCCTGCC<br>AGAGATCGACAACGCCCTGGTGGTTTTCTGCATG<br>GCCACCTACGGTGAGGGAGACCCCACCGACAATGCC<br>CAGGACTTCTACGACTGGCTGCAGGAGACAGACG<br>TGGATCTCTCTGGGGTCAAGTTCGCGGTGTTTGGTCT<br>TGGGAACAAGACCTACGAGCACTTCAATGCCAT<br>GGGCAAGTACGTGGACAAGCGGCTGGAGCAGCTCGG<br>CGCCCAGCGCATCTTTGAGCTGGGGTTGGGCGAC<br>GACGATGGGAACTTGGAGGAGGACTTCATCACCTGG<br>CGAGAGCAGTTCTGGCCGGCCGTGTGTGAACACT<br>TTGGGGTGGAAGCCACTGGCGAGGAGTCCAGCATTC<br>GCCAGTACGAGCTTGTGGTCCACACCGACATAGA<br>TGCGGCCAAGGTGTACATGGGGGAGATGGGCCGGCT<br>GAAGAGCTACGAGAACCAGAAGCCCCCCTTTGAT<br>GCCAAGAATCCGTTCCTGGCTGCAGTCACCACCAACC<br>GGAAGCTGAACCAGGGAACCGAGCGCCACCTCA<br>TGCACCTGGAATTGGACATCTCGGACTCCAAAATCAG<br>GTATGAATCTGGGGACCACGTGGCTGTGTACCC<br>AGCCAACGACTCTGCTCTCGTCAACCAGCTGGGCAAA<br>ATCCTGGGTGCCGACCTGGACGTCGTCATGTCC<br>CTGAACAACCTGGATGAGGAGTCCAACAAGAAGCACC<br>CATTCCCGTGCCCTACGTCCTACCGCACGGCCC<br>TCACCTACTACCTGGACATCACCAACCCGCCGCGTAC<br>CAACGTGCTGTACGAGCTGGCGCAGTACGCCTC<br>GGAGCCCTCGGAGCAGGAGCTGCTGCGCAAGATGGC<br>CTCCTCCTCCGGCGAGGGCAAGGAGCTGTACCTG<br>AGCTGGGTGGTGGAGGCCCGGAGGCACATCCTGGCC<br>ATCCTGCAGGACTGCCCGTCCCTGCGGCCCCCCA<br>TCGACCACCTGTGTGAGCTGCTGCCGCGCCTGCAGG<br>CCCGCTACTACTCCATCGCCTCATCCTCCAAGGT<br>CCACCCCAACTCTGTGCACATCTGTGCGGTGGTTGTG<br>GAGTACGAGACCAAGGCTGGCCGCATCAACAAG<br>GGCGTGGCCACCAACTGGCTGCGGGCCAAGGAGCCT<br>GCCGGGGAGAACGGCGGCCGTGCGCTGGTGCCCA<br>TGTTCGTGCGCAAGTCCCAGTTCCGCCTGCCCTTCAA<br>GGCCACCACGCCTGTCATCATGGTGGGCCCCGG<br>CACCGGGGTGGCACCCTTCATAGGCTTCATCCAGGA |

-continued

SEQUENCE LISTING

| Name | Sequence |
| --- | --- |
| | GCGGGCCTGGCTGCGACAGCAGGGCAAGGAGGTG<br>GGGGAGACGCTGCTGTACTACGGCTGCCGCCGCTCG<br>GATGAGGACTACCTGTACCGGGAGGAGCTGGCGC<br>AGTTCCACAGGGACGGTGCGCTCACCCAGCTCAACG<br>TGGCCTTCTCCCGGGAGCAGTCCCACAAGGTCTA<br>CGTCCAGCACCTGCTAAAGCAAGACCGAGAGCACCT<br>GTGGAAGTTGATCGAAGGCGGTGCCCACATCTAC<br>GTCTGTGGGGATGCACGGAACATGGCCAGGGATGTG<br>CAGAACACCTTCTACGACATCGTGGCTGAGCTCG<br>GGGCCATGGAGCACGCGCAGGCGGTGGACTACATCA<br>AGAAACTGATGACCAAGGGCCGCTACTCCCTGGA<br>CGTGTGGAGCTAG |
| pAP3:ItB4 (SEQ ID NO: 40) | GTCCCCCTCTTTTACCAAGTGACAATTGATTTAAGCAG<br>TGTCTTGTAATTATACAACCATCGATGTCCGT<br>TGATTTAAACAGTGTCTTGTAATTAAAAAAATCAGTTTA<br>CATAAATGGAAAATTTATCACTTAGTTTTCA<br>TCAACTTCTGAACTTACCTTTCATGGATTAGGCAATAC<br>TTTCCATTTTTAGTAACTCAAGTGGACCCTTT<br>ACTTCTTCAACTCCATCTCTCTCTTTCTATTTCACTTCT<br>TTCTTCTCATTATATCTCTTGTCCTCTCCAC<br>CAAATCTCTTCAACAAAAAGATTAAACAAAGAGAGAAG<br>AATATGGTGATTCTTCTGTCTTTTCTCTTGCT<br>TCTATTCATTCCCCTACTCTTCTCGTTCATATACACCAA<br>CAAGAACAAAACCTCAAGTAATCTTCCTTCG<br>GGCCCAGCACAAATTCCGATAATCGGAAACCTACACC<br>AGATCCAGGGATTGCTTCACAGATGTTTTCACT<br>ATCTCTCCAAGAAACACGGACCTGTGATGCTTCTCCG<br>TCTAGGGTTTGTTCGCGTGGTCGTGATCTCATC<br>AAGTGAAGCGGCTGAAGACGTTCTTAAAATCCATGAC<br>CTTGTGTGTTGTACACGACCTGCCACTAAGGCC<br>TCAAGGGTTTTCTCGCGTAATGGTAAAGGCATCGGCT<br>TTGGGGAGTCATGGAGAGACCTGCGTAAGCTTG<br>CGGTTCGTGAGTTTTTCAGCGTGAAAAAGGTTCGATC<br>TTTCAGGTATGTCAGAGAGGAAGAGAATGAGTC<br>GATGGTCAAGAACCTGAGAGAATCGGCTTTGAAGCAA<br>TCTCCGGTGGATTTGAGCAAAACACTTTTCTGC<br>TTAGCTGCGAGTATCATCTTCAGAACCGCCTTCGGAC<br>AGAGTTTCTTCGAGAACAAGCATATCGATAAGG<br>AAAGGATCGAAGGACTCATGTTAGAAGCTCACAGTAA<br>CATGTCTTTCAACTTCACTGATATCTTCCCCGC<br>TGCTGGTTTTGGATCGTTTATGGACTTTGTGTCAGGG<br>AAACATAAGAGACTTCACGATGTCTTCACTGAG<br>GTTGATACTTTTATTAGTCATATCATTGATGATCATCAA<br>TTGAAGAGTTTCACACAAGATCGTCCTGATT<br>TCATCGATTCCATATTAGAAATGATACGTAAACAAGAA<br>CAAAATGAATCTTTCAAGCTCACCATTGATAA<br>TCTCAAAGGGATCAGCCAAGATATATATCTTGCTGGA<br>GTAGACACAAGCGCCATCACCATGATTTGGACG<br>ATGGCAGAGCTTGTTAGAAACCCTAGAGTGATGAAAA<br>CTGTCCAAGACGAGATCAGAAATTGCATTGGAA<br>CCAAACACAAAGAGAGAATCGAGGAAGAAGATCTCAA<br>TAAGCTTCAATACTTGAAGCTTGTGGTGAAAGA<br>AAGCTTAAGACTACACCCACCAGCTCCTCTGCTACTC<br>CCCAGAGAAACAATGAGCCAGATCAAGATTCAA<br>GGCTACGACATACCACCAAAAACCGTTGTAATGGTTA<br>ATGCTTGGTCGATAGGTCGGGATCCTAAACACT<br>GGGAAGATCCAGAAGAGTTTATCCCGGAGAGGTTTAT<br>CAATTGTCCTGTAGATTACAAAGGACATAGCTT<br>TGAGATGTTACCATTTGGTTCTGGACGGAGGATCTGC<br>CCAGGAATGGCTTCAGGGATTGCTACCATTGAA<br>TTGGGACTCTTGAATTTGCTTTACTACTTCGATTGGAG<br>ATTGCCTGAGGAGAAGAAAGATATGGACATGG<br>AAGAAGCTGGTGGTCTTACTGTTGTTAAGAAAGTTCCT<br>CTTGAGCTTATCCCCATTCTTCGTCAGTGA |
| pAP3:TSA2 (SEQ ID NO: 41) | GTCCCCCTCTTTTACCAAGTGACAATTGATTTAAGCAG<br>TGTCTTGTAATTATACAACCATCGATGTCCGT<br>TGATTTAAACAGTGTCTTGTAATTAAAAAAATCAGTTTA<br>CATAAATGGAAAATTTATCACTTAGTTTTCA<br>TCAACTTCTGAACTTACCTTTCATGGATTAGGCAATAC<br>TTTCCATTTTTAGTAACTCAAGTGGACCCTTT<br>ACTTCTTCAACTCCATCTCTCTCTTTCTATTTCACTTCT<br>TTCTTCTCATTATATCTCTTGTCCTCTCCAC<br>CAAATCTCTTCAACAAAAAGATTAAACAAAGAGAGAAG |

-continued

SEQUENCE LISTING

| Name | Sequence |
| --- | --- |
| | AATATGGATCTTCTCAAGAACCCTCCCACAAC<br>GGTGGGTCTATCAGAGACTTTCGCTAGGTTGAAGTCT<br>AAAGGCAAAGTGGCTCTGATTCCATATATCACA<br>GCTGGTGATCCAGATCTTTCCACAACAGCTAAAGCTC<br>TCAAAGTGCTCGACTCTTGTGGCTCTGACATTA<br>TCGAACTCGGTGTTCCATACTCTGATCCATTAGCTGAT<br>GGTCCAGCAATCCAGGCTGCTGCGAGACGTTC<br>TTTGCTTAAAGGAACTAACTTTAACTCCATTATCACTAT<br>GCTTAAAGAGGTTATTCCTCAGTTATCTTGT<br>CCGATTGCATTGTTTACGTATTACAACCCGATCCTGCG<br>GAGAGGAATCGAGAACTACATGACTATTATAA<br>AGAATGCTGGAGTTCATGGGCTTCTTGTTCCTGATGTT<br>CCACTCGAAGAGACTGAGACTCTGCGGAAGGA<br>AGCTCAAAAGCATCAGATTGAACTTGTACTGCTGACG<br>ACACCCACAACCCCGAAAGAACGGATGAATGCC<br>ATTGTTGAAGCATCCCAAGGATTCATCTATCTCGTAAG<br>CTCAGTGGGAGTTACTGGCACGAGAGAGTCTG<br>TTAACGAACACGTTCAATCCCTTCTACAACAAATCAAA<br>GAGGCTACAAACAAGCCAGTCGCGGTTGGATT<br>TGGCATATCGAAACCTGAGCATGTGAAACAGGTGGCT<br>GAATGGGGAGCAGACGGAGTCATTGTAGGAAGC<br>GCTATGGTTAAGATATTGGGAGAGGCTGAATCACCTG<br>AGCAAGGACTCAAGGAGCTGGAAGTCTTCACTA<br>AATCTTTAAAGTCTGCTCTTATCTCTTGA |
| ompA leader sequence (SEQ ID NO: 42) | MKKTAIAIAVALAGFATVAQAAP |
| CYP17 modified N-terminal leader sequence (SEQ ID NO: 43) | MALLLAVF |
| 2A peptide (SEQ ID NO: 44) | LLNFDLLKLAGDVESNPGP |
| CYP17A (SEQ ID NO: 45) (GenBank: S75277.1) | ATGTGGGAATTGGTGACCTTGCTGGGGCTCATCCTAG<br>CTTATCTCTTTTGGCCCAGACAAGGGTCTTCTG<br>GTACCAAGTACCCAAAGAGCCTCCCCTCTCTGCCCGT<br>CGTGGGCAGCCTGCCATTCCTTCCCAAAAGCGG<br>CCACATGCACGTGAACTTTTTCAAACTGCAGAAGAAAT<br>ATGGGTCCATCTATTCCTTTCGTCTGGGCTCC<br>ACAACTACAGTGGTCATTGGCCACCACCAGCTGGCCA<br>GGGAGTTGCTTATCAAGAAGGGAAAGGAATTCT<br>CTGGACGGCCCCTGACGACCACTGTGGCCCTCCTGT<br>CAGACAATGGGAAGGGCATTGCTTTTGCTGACTC<br>CAGTGCCACTTGGCAGCTGCACCGGAGGCTGGTCCT<br>GAGCTCCTTTTCCCTGTTCAGGGATGGTGAGCAG<br>AAGCTGGAGAACATCATCTGTCAAGAACTCAGTGCCC<br>TGTGTGATTTTCTGGCCACCTGTGATGGACAGG<br>TCAAGGATTTATCTTCGTCAATCTTCATGACGGTAGTC<br>AACATCATCTGCATGATCTGCTTCAGTGTCTC<br>ATACAAGGAGGGGGACATGGAGTTGGTGACCATAAG<br>GCGCTTCACAACAGGCTTCGTGAATAGCCTGAGT<br>GATGACAATCTCGTGGACATATTCCCCTGGCTGAAGA<br>TCTTCCCCAATAAAACCCTGGAAATGATAAGGA<br>AGTATACTGAAATCCGAGGAGCCATGCTGAGTAAGAT<br>CCTGAAAGAGTGCAAGGAGAAGTTCAGAAGTGA<br>CTCTGTCTCCAACCTAATAGACCTGCTCATCCAAGCC<br>AAGGTGAATGAAAACAACAACAATTCCAGCTTG<br>GACCAGGACTCCAATCTGTTTTCAGATAAGCACATTCT<br>CACCACCTTAGGAGACATCTTTGGGGCTGGTG<br>TGGAGACCTCCAGCTCCGTGGTGCTCTGGGTCATAG<br>CCTTCCTGCTGCACAACCCACAGGTGAAGAAGAA<br>GATCCAGGAGGAGATTGACCACAATGTGGGTTTCAGC<br>CGCACGCCCACCTTCAGTGACCGGAACCACCTG |

-continued

SEQUENCE LISTING

| Name | Sequence |
|---|---|
| | CTCATGCTGGAGGCCACCATCCGAGAGGTCCTCCGC<br>ATCAGGCCGGTGGCCCCCATCCTCATCCCTCACA<br>AGGCTAACACTGACTCCAGCATTGGAGAGTTTGCCAT<br>TGACAAGGACACCAATGTGCTTGTCAACTTGTG<br>GGCCTTGCATCACAATGAGCAGGAGTGGGACCGGCC<br>GGACCAGTTCATGCCTGAGCGCTTCCTGGACCCA<br>ACAGGGAGCCAAATCATCGTCCCCTCCTCGAGCTACT<br>TGCCCTTTGGAGCTGGGCCCCGCTCCTGTGTAG<br>GTGAGGCACTGGCGCGCCAGGAGATCTTCCTCATCA<br>CAGCCTGGTTGCTGCAGAAGTTTGACCTAGAGGT<br>GCCAGAGGGTGGGCAGCTTCCGTCCCTGGAGGGCAT<br>CCCCAAGATAGTTTTCCTCATCGATCCTTTCAAA<br>GTGAAGATCACAGTGCGCCCGGCCTGGAAGGAAGCT<br>CAGGCCGAGGGCAGCGCCTAG |
| AP3 promoter (SEQ ID NO: 46) | AAGCTTCTTAAGAATTATAGTAGCACTTGTTGATATCG<br>GGGTTCTTTTTTCTTAACATAGGTTTTGGTGG<br>GTAGATCAACAGAAGACCTCGCTGTGGACATTGATTT<br>GGGAAGAGAAAAGCGGGGTAGCAAAATATCTCG<br>ACGACAGGTCGGTCAATAGTAGATACTTCTATTTGTAT<br>TTTAGGTCTTTAAGTTGTATGAGAAGCAGCAG<br>CCCAGGATCTGTAATGGTTGTTGTGTATGTTTTTTTCC<br>TTTTTGGGTTACTGAATGCAGGCGATCATACG<br>GCTGGGTGATGACGGTTCGTTTCATATAAAAAACCCT<br>GGGGAAGTATTCAATCTCAGTAAATGAGAAGGA<br>AGTAGATCCTGGACAGAGTTTAATCCTCAAATCCGATT<br>GTCTAGTTGAGGTTTGATCCGGGATACTCTTT<br>TATGACTCATTACTTACGTTCTAGGTCCGTACTTAAAC<br>CCGATATATCGTGCGCGCAGATACGGGGAATG<br>CCTTTTATATTTGAAACAAACCAAAGTTGCATGCAAGA<br>GTACCTGAAGAGAAGAGGGAAAGTGAACTGAG<br>ACCAGATCAAGAGTGCGTGTTGTTTGTGTAGATGAAT<br>GATGCATCTCTTGTGTAATGTACCTTAGCCATA<br>GGAACACGTCTTGTAGATCTTTTAATACATCTTTAGTT<br>CCGCATCATGCATAGTTGACCCTGTTTTAAGG<br>CGTTGAAATGAAAATACAAGTCTCTTGTATCTGAATTT<br>GTGTTTTAAGCGAAGAATGATTGTTCTTGTGA<br>AGTTGATACACAAGTTCTTTGGATATCCTATCAGTATA<br>AAGGATAGGTTTCCATTTTCGTGACTCACTCA<br>CTGATTTCCATTGCTGAAAATTGATGATGAACTAAGAT<br>CAATCCATGTAGTTCAAACAACAGTAACTGTG<br>CCACTAGTTTGAACAACACTAACTGGTCGAGCAAAAG<br>AAAAAGAGTTCATCATATATCTGATTTGATGGA<br>CTGTTTGGAGTTAGGACCAAACATTATCTACAAACAAA<br>GACTTTTCTCCTAACTTGTGATTCCTTCTTAA<br>ACCCTAGGGGTAATATTCTATTTTCCAAGGATCTTTAG<br>TTAAAGGCAAATCCGGGAAATTATTGTAATCA<br>TTTGGGGCCACATATAAAAGATTTGAGTTAGATGGAA<br>GTGACGATTAATCCAAACATATATATCTCTTTC<br>TTCTTATTTCCCAAATTAACAGACAAAAGTAGAATATTG<br>GCTTTTAACACCAATATAAAAACTTGCTTCA<br>CACCTAAACACTTTTGTTTACTTTAGGGTAAGTGCAAA<br>AAGCCAACCAAATCCACCTGCACTGATTTGAC<br>GTTTACAAACGCCGTTAAGTTTGTCACCGTCTAAACAA<br>AAACAAAGTAGAAGCTAACGGAGCTCCGTTAA<br>TAAATTGACGAAAAGCAAACCAAGTTTTTAGCTTTGGT<br>CCCCCTCTTTTACCAAGTGACAATTGATTTAA<br>GCAGTGTCTTGTAATTATACAACCATCGATGTCCGTTG<br>ATTTAAACAGTGTCTTGTAATTAAAAAAATCA<br>GTTTACATAAATGGAAAATTTATCACTTAGTTTTCATCA<br>ACTTCTGAACTTACCTTTCATGGATTAGGCA<br>ATACTTTCCATTTTAGTAACTCAAGTGGACCCTTTACT<br>TCTTCAACTCCATCTCTCTCTTTCTATTTCA<br>CTTCTTTCTTCTCATTATATCTCTTGTCCTCTCCACCAA<br>ATCTCTTCAACAAAAAGATTAAACAAAGAGA<br>GAAGAATATG |
| PI promoter (SEQ ID NO: 47) (GenBank: AFI 98055.1) | TCACACTCGAAACCTAGTTATGTGTTTGTTTTACCTTA<br>CTCTCCTTATTTAAATAGTCATGTATTTGATT<br>CTTTGTGAGAATAAGGACTTGTTTTCAAGTCATTATAA<br>ACGTCTTATACTTGTGATTAGTATGAGTTTCA<br>ATATATGATTATTCGGTTGCAAAATAAAGAGTGGGTTC<br>CAATATCATTGATATTACTACTATATATTACC<br>ATATTTCATGGAAATTAGTCATCTTCGTGATCCAATTT<br>GTCTCGTTTTCATGTATAATTAGACAAAATTT |

-continued

SEQUENCE LISTING

| Name | Sequence |
|---|---|
| | GCCTTCTCAATATTTTCGATCAAAGAATGCTAAACAAG<br>TAAACATGACCTGATAGTGATCCGAAGTTAGA<br>ATAATATTAAAAAGACATAGGTTATTTACTAATTCAATA<br>TACCAACAATATCCTATTTTTTTTTTGTCAA<br>TCAAACTCCATATATTAATTCACGGAAAACGACTCTTT<br>TCTAGAGAAAGCAAATTAGATACCGTCGAACT<br>TACATGAGAAAAACAGAATCCGCGAACTCTTGCACAT<br>ATGGTATTTTTGTTTCAGTGGATACGTTTCTCA<br>CCTGAATTCACGACTTTTTTTGTGGAGATTTGTAATCT<br>CTGGCTTTATAGTTAATAATCGAGAAAATGCC<br>AAAAAGTATGCCCGTACTAAGTACAAAACATAAGACCA<br>CAAAATTCCACAATAAATTGACACGTGTCTGA<br>TCGACGTGAATCAAGAAAACCATAAACTTGTTTTGTTT<br>TCAACAACCAAAGACATTTTCCCCATAAAAAT<br>GTAAGCATGATAAAGTCTAATGGTTATACCAAGGTCTT<br>TGGTAATTACACTGCTCCTTTTTCTTTTTTTT<br>TNTCTTTTTTTTTTCTTTTTTCTAAACCATCTGAATTT<br>AACTTTATTTTATTTACTTCATTTGTCAATGT<br>GATATCTTCAACTTTCAATAATTTAATATGTTTGATTT<br>TTTAGTGTAGCTACGATATTCGATAAGACCTA<br>TATATGACATAGAGTTCTTGAAATAGCAAGTCTTGGTT<br>TTGCCAAAGTAATAACCTGTAAAAATAAAAGC<br>AATTCTTTACAGAGATTTTTGGTTTTAAATCTACAAAGT<br>TGCAAAACTCGTTGCTTTCATTTGATTTAAT<br>GGTTAGTTTTCGAGATAGACAAAATGGGAAATTTATTT<br>GCAAAATGATTTAGTTGCAAAATCATTGGACA<br>CTATCTTATTTCACGTTTTATATAATTGATGACATAATA<br>AGATAGTTTCCCAAAGTAATTAATTGATGAT<br>ATATGTGGTTGGATAAGAAATTATGGTATTATCATGTT<br>TGCCTCTCAAATTTAAATCTAATTAATTATAT<br>ACATACACGAGTAAGCTAAATAAAAGTTTGACCACATT<br>TCATATGAAGAATTTTATCTTTCCAGATATCT<br>AGAATTTGTTTTCTCTACACAGTTCATTGAAGAAAACA<br>TAGTACGGAAGAGACCAGAGGTTAATTAAACG<br>ACACTTTAACCTATCACGAGAGAGACTGAGATGATCA<br>AATCAAATGAAAGAAAATAAACATCAATCACAT<br>GCAAAGAGTGTTCATTAAGCAAAATCACTAAGTTTGTT<br>TTTACTTTATTTTATTACGTTACTTCAAGTTT<br>TTTTTTATCTTCTTGGTACTGTAAAAAAAGGAGAGAAA<br>ATAGAGTTGGCTATGTGTAATAAGCGAACCAA<br>AAGCAAGCCTTCCATGACTGTGCCCTCAAGAAAGTAG<br>CTTTGTTTTCAATCCCAAACTGTCAAAGTCTCT<br>CTTCACCTCAAGATTAATCAAACATTTCTCTCTCTATC<br>TCATCAATGTTACTTTAAAACCAATGCTCCT<br>CTTCTTGTTCTTCATATAAACCACATATCCTCTCCTCCA<br>TATCTTAACAATTTCATAGCAAACCCTAAAA<br>TTGAGAAAGAGATAGAGAGAGAAAG |
| CHS promoter (SEQ ID NO: 48) (GenBank: AF 248988.1) | GAGTTAAGTATGCACGTGTAAGAACTGGGAAGTGAAA<br>CCTCCTGTATGGTGAAGAAACTATACAACAAAG<br>CCCTTTGTTGGTGTATACGTATTAATTTTTATTCTTTTA<br>TCACAAGCGATACGTATCTTAAGACATAATA<br>AATATATATCTTACTCATAATAAATATCTTAAGATATAT<br>ATACAGTATACACCTGTATATATATAATAAA<br>TAGGCATATAGTAGAAATTAATATGAGTTGTTGTTGTT<br>GCAAATATATAAATCAATCAAAAGATTTAAAA<br>CCCACCATTCAATCTTGGTAAGTAACGAAAAAAAGG<br>GAAGCAAGAAGAACCACAGAAAAGGGGGCTAAC<br>AACTAGACACGTAGATCTTCATCTGCCCGTCCATCTAA<br>CCTACCACACTCTCATCTTCTTTTTCCCGTGT<br>CAGTTTGTTATATAAGCTCTCACTCTCCGGTATATTTC<br>CAAATACACCTAACTTGTTTAGTACACAACAG<br>CAACATCAAACTCTAATAAACCCAAGTTGGTGTATACT<br>ATA |
| CmCCD4a-5 (SEQ ID NO: 49) (GenBank: AB 763911.1) | TACAATATTTGGATTATGTTGAAGGTAATGTTGAACTA<br>CTTAAAATAGAAGAACGAGACACATATGAAAC<br>TAAATCACTTTTGCTTTTTAGAATTATGAGTTGTATCTT<br>AAATAAGTTTAATTTTAGGTTTGTTACTCGC<br>AATATTGTTAGGTATACCTTAAACTCGATGCATTTAAC<br>CATAAAGCATCAGTGTGTGGCATACTGGCATT<br>TAGGTCAGCTTCGTTTTGAGTATATTTAGTACAACGGA<br>TATATGTGAAACCATTGTTACATTTCATTACT<br>TGTTTGATTTGTTCTTATTGAGTAAAATTGGGTTCTCGT<br>ACCTAAGGAATTATCTCATGCCCGCGACCAA |

-continued

SEQUENCE LISTING

| Name | Sequence |
|---|---|
| | CGAGCATGAACACAACTTCGAAACTCCGCTCATGCAC<br>GACACTTTTTTTTTTTTTTTTTTTTTTTTTTTT<br>TTTTTTTAATTCAGAACCTAGTTTTTGTTCAAGATTCAT<br>ATGGTTTGTTTCAAAACTGATTGAACATTTT<br>TCCAAAATGTTTGTAAGATAATATCCACTTCAGTTTATC<br>ATTTGAATACTGTAAACGGCTAAACGGAGCA<br>GGATCCCTTGTTCAGG CTACCGTGGTAAACAGATAAA<br>TTAATTGAAACACGTCATTTCTGGAATTTTCCC<br>TCGTTATCTCAAGATATGCACCCAACGAGGTTTGAAC<br>CCTGTTATCTTATGATACCTTCTGTCCGCCACA<br>TTGGAGATGATTCGATTTGCAAATTGGGTCCTTAATAT<br>ATAATTATGATTCTAAAATAGTATCGTTGTGA<br>TTTAGAATATATGAACTCTGATAAGACTAAAATACTTAA<br>TTATGATTCTAAAATAGTATCATTTTTTTTT<br>TTTAATTAAGAAAAACAAGGTTGAGTATTTAAAATTCAA<br>ATTAACCTTAAGTGTGATACCTTTCGGGTTA<br>TGTAAATTTGCTATGTAGCTTATTTCCGTACTTTAAGA<br>GTTTAAGATAAAAATAGAAATAATAGCTGTAA<br>TAATATAGGAATAATCCAAAAGTACGTGAAGGAACATA<br>CATACCTTTCTCAATGTTTTGCTATAAAAGCA<br>TGAGTCTTCTTCACTA |
| pAP3<br>(SEQ ID<br>NO: 50) | GTCCCCCTCTTTTACCAAGTGACAATTGATTTAAGCAG<br>TGTCTTGTAATTATACAACCATCGATGTCCGT<br>TGATTTAAACAGTGTCTTGTAATTAAAAAAATCAGTTTA<br>CATAAATGGAAAATTTATCACTTAGTTTTCA<br>TCAACTTCTGAACTTACCTTTCATGGATTAGGCAATAC<br>TTTCCATTTTTAGTAACTCAAGTGGACCCTTT<br>ACTTCTTCAACTCCATCTCTCTCTTTCTATTTCACTTCT<br>TTCTTCTCATTATATCTCTTGTCCTCTCCAC<br>CAAATCTCTTCAACAAAAAGATTAAACAAAGAGAGAAG<br>AAT |
| pAP3:<br>ItB24<br>(SEQ ID<br>NO: 51) | GTCCCCCTCTTTTACCAAGTGACAATTGATTTAAGCAG<br>TGTCTTGTAATTATACAACCATCGATGTCCGTTGATTT<br>AAAC<br>AGTGTCTTGTAATTAAAAAAATCAGTTTACATAAATGG<br>AAAATTTATCACTTAGTTTTCATCAACTTCTGAACTTAC<br>CTT<br>TCATGGATTAGGCAATACTTTCCATTTTTAGTAACTCA<br>AGTGGACCCTTTACTTCTTCAACTCCATCTCTCTCTTT<br>CTAT<br>TTCACTTCTTTCTTCTCATTATATCTCTTGTCCTCTCCA<br>CCAAATCTCTTCAACAAAAAGATTAAACAAAGAGAGAA<br>GAA<br>TATGTCGATTATTCTGTATTTCTTTTCGTTTTTGCTTCT<br>CCCCGCTCTTTTCTCGTTAATTTAGTGAAGAAAATCA<br>AAG<br>ACACGAAACAAAACCTTCCTCCGAGCCCACCAAAGCT<br>TCCGATCATCGGTAACCTACACCAGCTTCGAGGATTG<br>TTTCAC<br>AGATGTCTTCATGATTTGTCCAAGAAACATGGACCCGT<br>GTTGCTTCTCCGTCTAGGTTTTCTCGAAATGGTTGTTA<br>TCTC<br>CTCAAGCGAAGCAGCTGAAGAAGTTCTCAAAACACAT<br>GACCTTGAGTGTTGTACCAGACCGAACACTCACGCCT<br>CATCCA<br>TATTCTGGCGTAATGGTAAAGACATTGGCTTTGCCCC<br>ATATGGTGAGGGGTGGAAAGAGGTTCGCAAGCTTGCT<br>GTTCTC<br>AATTTTTTCAGCGCGACAAAGGTTCGATCTTTCAGGTA<br>CATCAGAGAGGAAGAGAATGATTTGATGGTCAAGCAA<br>CTGAA<br>GGAATTAGCTCAAAAGAAGTCTCCAGTGGATTTGAGC<br>CAAACGTTTTTCTGTCTAGCCGGAAGTATCATATTCAG<br>ATCTG<br>CCTTTGGACAGCGTTTCTACGAGAACGTTCATGTCGA<br>CAAGGAAAGGATCAAAGACCTCATGTTCGAGGCCCAG<br>AGAATT<br>GGATCTGTAAGTAGCTCTGATATTTTCCCTGGTTTGGG<br>ATGGTTTATGGACTTTTTTTCAGGACGACATAGGAGAC<br>TTCA<br>CCAAGTTTTCGACGAGGTTGATACTTTGCTGAGTCATA<br>TAATTGATGATCACTTGAAGAATCCTGACGAAAAAACA<br>AATC |

-continued

SEQUENCE LISTING

| Name | Sequence |
|---|---|
| | AAGATCGCCCTGATATCGTCGACTCCATCTTAAAAACT<br>ATGCAAAGTCAAGAAGAAGATGAATCTTTCAAGTTCAC<br>CATT<br>GATCATCTCAAAGGAATCATCCAAGATATATATCTTGC<br>TGGAATAGACACAAGTGCCATCACCATGATCTGGGCA<br>ATGGC<br>AGAGCTCGTTAGAAACCCTAGAGTGATGAAAAAAGTC<br>CAAGACGAGATCAGAACTTGCATTGGAATCAAACAAA<br>AGGAGA<br>GAATCGAGGAAGAAGATATCGACAAGCTTCAGTACTT<br>TAAGCTTGTGATCAAAGAAACCTTAAGACTACACCCAG<br>CATCT<br>CCTATGTTACTCCCAAGAGAAACAATGAGTCAAATCAA<br>GATTCAAGGCTACGACATTCCGCCAAAAACCATTCTA<br>CTGGT<br>TAACAGTTGGTCGATAGGTCGAGATCCTAAACACTGG<br>AAAGATCCAGAAGAGTTTATCCCTGAGAGGTTCATCG<br>ATTGTC<br>CTGTAGATTACAAAGGACAGAGCTTTGAGATGTTACC<br>ATTTGGTTCTGGACGGAGGGTGTGCCCAGGAATGGC<br>TTCAGGG<br>CTTGCGACCGTTGAATTGGGACTCTTGAATTTACTTTA<br>CTACTTCGATTGGAGTTTGCCTGAGGGGAAGAAAGTT<br>ATGGA<br>CATGGAAGAAGCTGGTGATGCTACCATTATTAAGAAAT<br>TTCCTCTTGAGCTTCTTCCAACTCTTCATGGTTAA |
| pAP3:<br>TSA2-2A-<br>PtBG<br>(SEQ ID<br>NO: 52) | GTCCCCCTCTTTTACCAAGTGACAATTGATTTAAGCAG<br>TGTCTTGTAATTATACAACCATCGATGTCCGTTGATTT<br>AAAC<br>AGTGTCTTGTAATTAAAAAAATCAGTTTACATAAATGG<br>AAAATTTATCACTTAGTTTTCATCAACTTCTGAACTTA<br>CCTT<br>TCATGGATTAGGCAATACTTTCCATTTTTAGTAACTCA<br>AGTGGACCCTTTACTTCTTCAACTCCATCTCTCTCTTT<br>CTAT<br>TTCACTTCTTTCTTCTCATTATATCTCTTGTCCTCTCCA<br>CCAAATCTCTTCAACAAAAAGATTAAACAAAGAGAGAA<br>GAA<br>TATGGATCTTCTCAAGAACCCTCCCACAACGGTGGGT<br>CTATCAGAGACTTTCGCTAGGTTGAAGTCTAAAGGCA<br>AAGTGG<br>CTCTGATTCCATATATCACAGCTGGTGATCCAGATCTT<br>TCCACAACAGCTAAAGCTCTCAAAGTGCTCGACTCTT<br>GTGGC<br>TCTGACATTATCGAACTCGGTGTTCCATACTCTGATCC<br>ATTAGCTGATGGTCCAGCAATCCAGGCTGCTGCGAGA<br>CGTTC<br>TTTGCTTAAAGGAACTAACTTTAACTCCATTATCACTAT<br>GCTTAAAGAGGTTATTCCTCAGTTATCTTGTCCGATTG<br>CAT<br>TGTTTACGTATTACAACCCGATCCTGCGGAGAGGAAT<br>CGAGAACTACATGACTATTATAAAGAATGCTGGAGTTC<br>ATGGG<br>CTTCTTGTTCCTGATGTTCCACTCGAAGAGACTGAGA<br>CTCTGCGGAAGGAAGCTCAAAAGCATCAGATTGAACT<br>TGTACT<br>GCTGACGACACCCACAACCCCGAAAGAACGGATGAAT<br>GCCATTGTTGAAGCATCCCAAGGATTCATCTATCTCGT<br>AAGCT<br>CAGTGGGAGTTACTGGCACGAGAGAGTCTGTTAACGA<br>ACACGTTCAATCCCTTCTACAACAAATCAAAGAGGCTA<br>CAAAC<br>AAGCCAGTCGCGGTTGGATTTGGCATATCGAAACCTG<br>AGCATGTGAAACAGGTGGCTGAATGGGGAGCAGACG<br>GAGTCAT<br>TGTAGGAAGCGCTATGGTTAAGATATTGGGAGAGGCT<br>GAATCACCTGAGCAAGGACTCAAGGAGCTGGAAGTCT<br>TCACTA<br>AATCTTTAAAGTCTGCTCTTATCTCTctgctgaacttcg<br>acctccttaagcttgcgggagacgtcgagtccaacccag<br>gtcccATGGCGATCACCTCCATAGCTCATCTCCGTGTCG<br>TCAATGCGAACATGAGCATTCCGCTAGCTCGTCTTCGT<br>GTCGT<br>CAATGCAAACATAAGCATTCCGCTTAAGCGGACTAGT |

-continued

SEQUENCE LISTING

| Name | Sequence |
|---|---|
| | TTCCCCAAGAAATTCCTGTTTGGGGCTGGCTCTGCTT<br>CTTACC<br>AATATGAAGGAGCAGCACATATAGATGGGCGAGGACT<br>TAGCGTCTGGGATGTCTTCACTAAGGAACACCCTGAA<br>AAGATC<br>GCAGATCAGTCGAATGGAGATGTTGCTCAAGACTTTT<br>ATCACCGATACAAGGAAGATATAAAGTCGATGAAGGA<br>AATGGG<br>TTTGGAGTCATTCAGGTTCTCCATTTCATGGTCAAGAA<br>TATTACCTAATGGGAAAATCAGTGGAGGAATCAACAA<br>GCTTG<br>GGATCAAGTTCTACAATAATCTCATTGACGAACTGCTA<br>GCCAATGGAATCAAGCCACTTGTCACTATCTACCATTG<br>GGAC<br>CTTCCACAAGCACTTCAAGACGAATATGGAGGGTTCT<br>TGAGCCCCAAAATCGTGGATGACTTTCTGGAATATGC<br>AAACCT<br>AGTTTTTAAGGAGTTCGGGGATAGGGTTAAGCATTGG<br>GCGACACTGAATGAACCCAATATAATGACCCAACAAG<br>GGTACG<br>TATTTGGGGCACATGCACCCGGACGATGTTCTCACTT<br>CGAATGGAACTGCCCGGCTGGAAACTCCGGCACCGA<br>GCCTTAT<br>ATAGTTGGTCACCACCTCCTCCTATGTCATGCTGCAG<br>CTTTTCAACTATACAAACAAAAGTATAAGGATGATCAA<br>AAGGG<br>TATAATCGGAATAACAACCGCGACACAGATGGCCATA<br>CCGTTAAACGACAACGTTGCCAACCTCTTGGCAGCGT<br>CACGAG<br>CCATCGATTTCAACATTGGATGGTTTTTGCATCCGGTT<br>GTTTACGGCGAGTATCCACAGACGATGAGGGAGCGG<br>TTGGGA<br>AGTCGACTGCCAAAATTCACAGAAAAAGAGTCGGAGA<br>TGTTGAAACAATCGTTCGACTTTATAGGGTTGAATTAC<br>TACTC<br>AACTGATTATGCAGCCGCATCATCTTTTTCAGTTGATC<br>CAGTGAATGTCAGTTACACAACTGATTCCCGAGCAAC<br>ATTAT<br>CAGCGATAAAAGATGGGGTTCCTATCGGCGACCCGA<br>CATTTATGAGCTGGTTGCATATATATCCAGAGGGCATC<br>CTAACT<br>CTGTTGCGATACGTAAAGGAAAGGTACAACAATCCAT<br>TTGTCATGATCACTGAGAATGGGATGGCCGATGAAAA<br>CAAGGG<br>ATCATTAGCGGAAGATCCGATGGCTTTAAAAGACAAC<br>GTCAGAATTCGATATCACCGCGAACATCTATACTATGT<br>TCTTG<br>AAGCTATAAAGGAGGGTGTGAACGTGGGAGGATACTA<br>CGCATGGACATGGATGGATGATTTCGAGTGGGGTTCT<br>GGATAT<br>ACTCCTCGATTCGGTCTCAACTTTGTGGATTTCGACAA<br>TGATTTGAAGAGAACCCCCAAGGATTCTTACTTCTGGT<br>TCAA<br>GGACTTCCTTGCAAATTAA |
| PtBG<br>(SEQ ID<br>NO: 53)<br>(GenBank:<br>AB<br>003089.1) | ATGGCGATCACCTCCATAGCTCATCTCCGTGTCGTCA<br>ATGCGAACATGAGCATTCCGCTAGCTCGTCTTC<br>GTGTCGTCAATGCAAACATAAGCATTCCGCTTAAGCG<br>GACTAGTTTCCCCAAGAAATTCCTGTTTGGGGC<br>TGGCTCTGCTTCTTACCAATATGAAGGAGCAGCACAT<br>ATAGATGGGCGAGGACTTAGCGTCTGGGATGTC<br>TTCACTAAGGAACACCCTGAAAAGATCGCAGATCAGT<br>CGAATGGAGATGTTGCTCAAGACTTTTATCACC<br>GATACAAGGAAGATATAAAGTCGATGAAGGAAATGGG<br>TTTGGAGTCATTCAGGTTCTCCATTTCATGGTC<br>AAGAATATTACCTAATGGGAAAATCAGTGGAGGAATC<br>AACAAGCTTGGGATCAAGTTCTACAATAATCTC<br>ATTGACGAACTGCTAGCCAATGGAATCAAGCCACTTG<br>TCACTATCTACCATTGGGACCTTCCACAAGCAC<br>TTCAAGACGAATATGGAGGGTTCTTGAGCCCCAAAAT<br>CGTGGATGACTTTCTGGAATATGCAAACCTAGT<br>TTTTAAGGAGTTCGGGGATAGGGTTAAGCATTGGGCG<br>ACACTGAATGAACCCAATATAATGACCCAACAA<br>GGGTACGTATTTGGGGCACATGCACCCGGACGATGTT<br>CTCACTTCGAATGGAACTGCCCGGCTGGAAACT |

-continued

SEQUENCE LISTING

| Name | Sequence |
|---|---|
| | CCGGCACCGAGCCTTATATAGTTGGTCACCACCTCCT<br>CCTATGTCATGCTGCAGCTTTTCAACTATACAA<br>ACAAAAGTATAAGGATGATCAAAAGGGTATAATCGGA<br>ATAACAACCGCGACACAGATGGCCATACCGTTA<br>AACGACAACGTTGCCAACCTCTTGGCAGCGTCACGAG<br>CCATCGATTTCAACATTGGATGGTTTTTGCATC<br>CGGTTGTTTACGGCGAGTATCCACAGACGATGAGGGA<br>GCGGTTGGGAAGTCGACTGCCAAAATTCACAGA<br>AAAAGAGTCGGAGATGTTGAAACAATCGTTCGACTTTA<br>TAGGGTTGAATTACTACTCAACTGATTATGCA<br>GCCGCATCATCTTTTTCAGTTGATCCAGTGAATGTCAG<br>TTACACAACTGATTCCCGAGCAACATTATCAG<br>CGATAAAAGATGGGGTTCCTATCGGCGACCCGACATT<br>TATGAGCTGGTTGCATATATATCCAGAGGGCAT<br>CCTAACTCTGTTGCGATACGTAAAGGAAAGGTACAAC<br>AATCCATTTGTCATGATCACTGAGAATGGGATG<br>GCCGATGAAAACAAGGGATCATTAGCGGAAGATCCGA<br>TGGCTTTAAAAGACAACGTCAGAATTCGATATC<br>ACCGCGAACATCTATACTATGTTCTTGAAGCTATAAAG<br>GAGGGTGTGAACGTGGGAGGATACTACGCATG<br>GACATGGATGGATGATTTCGAGTGGGGTTCTGGATAT<br>ACTCCTCGATTCGGTCTCAACTTTGTGGATTTC<br>GACAATGATTTGAAGAGAACCCCCAAGGATTCTTACTT<br>CTGGTTCAAGGACTTCCTTGCAAATTAA |
| LTP3<br>promoter<br>(SEQ ID<br>NO: 54)<br>(GenBank:<br>AF<br>228333.1) | TTTAAATCCTATTGTAGTGTTATTTATAAAAAAAATGAG<br>AAAAGATAAAAAATACCTTTATATTAATATTTGTTATATT<br>GT<br>AAAATAAGGATATTTTTAACAAATTTTCAATTGAATAGA<br>TGTTTGGGTGAATCCTAATACCAATTAAAGTATATATA<br>CAC<br>AAACAATTATAAATCAAATTACTTTTAATAAAATGGTAT<br>CATTCAATTCAATGACAATAAATGCATTTATAAATACAT<br>CA<br>AATGTAAATCTCATGTTTATAAGAAAACACGTAGAAAA<br>AAGTTAAACCAATATTTGAGTCCTAGCTGTGGAGGCAT<br>GATT<br>GAGTGAAATCAAATGGACGCTGGTTTTAATTGTATTGA<br>AAGAAACCAATAATCACGTAGGTTGGCAGTTGAACAT<br>AATTG<br>AATGGTCTCAACTTTTAATGTGGTGTTAATGTTTGGAT<br>CGGATAATCTCAACTTACCTAATAGCTAGGAAAGTAAA<br>ATTC<br>AAACATCACCCGCTACTACTTTTGGCTATAAAAACCCT<br>CCTACCCTCAAGCCCTAACGACGACAATCACCAATAG<br>TACTA<br>CTACTCCAAGCAAGTATTTTCCTTACACGTTTGTTTTT<br>CTTGTGATTAATCGAT |
| 35S<br>promoter<br>(SEQ ID<br>NO: 55)<br>(GenBank:<br>S51061.1) | TCCACTGACGTAAGGGATGACGCACAATCCCACTATC<br>CTTCGCAAGACCCTTCCTCTATATAAGGAAGTT<br>CATTTCATTTGGAGAGGACACGCTGAAATCACCAGTC<br>TCTCTCTACAAATCTATCTCTCTCTATTTTCTC<br>CATAATAATGTGTGAGTAGTTCCCAGATAAGGGAATTA<br>GGGTTCTTATAGGGTTTCGCTCACGTGTTGAG |
| ATR2<br>(SEQ ID<br>NO: 56)<br>(GenBank:<br>NC_<br>003075) | AAAAGGAGTCTCTCTCTCACCTACACCACACCTAACC<br>AAACCCCCTACGATTCACACAGAGAGAGATCTT<br>CTTCTTCCTTCTTCTTCCTTCTTCTTTCTTCTTCTTTC<br>TTCTTCTAGCTACAACATCTACAACGCCATGT<br>CCTCTTCTTCTTCTTCGTCAACCTCCATGATCGATCTC<br>ATGGCAGCAATCATCAAAGGAGAGCCTGTAAT<br>TGTCTCCGACCCAGCTAATGCCTCCGCTTACGAGTCC<br>GTAGCTGCTGAATTATCCTCTATGCTTATAGAG<br>AATCGTCAATTCGCCATGATTGTTACCACTTCCATTGC<br>TGTTCTTATTGGTTGCATCGTTATGCTCGTTT<br>GGAGGAGATCCGGTTCTGGGAATTCAAAACGTGTCGA<br>GCCTCTTAAGCCTTTGGTTATTAAGCCTCGTGA<br>GGAAGAGATTGATGATGGGCGTAAGAAAGTTACCATC<br>TTTTTCGGTACACAAACTGGTACTGCTGAAGGT<br>TTTGCAAAGGTGAGGACTTTGTGTTTTGGTTTGTTCTG<br>ATTTCGAATGATGAAGTTGAATTTGAATCAGT<br>TTGATGTTTTTGAAATTTGCAGGCTTTAGGAGAAGAAG<br>CTAAAGCAAGATATGAAAAGACCAGATTCAAA<br>ATCGTTGATTTGGTATTTATTTTGTTCCATCAACTTTT |

-continued

SEQUENCE LISTING

| Name | Sequence |
|---|---|
| | TAGATAAAGTTTGATGCTTTAAGTATAATCTG<br>ATTCTGAGTTTATTAACAGGATGATTACGCGGCTGATG<br>ATGATGAGTATGAGGAGAAATTGAAGAAAGAG<br>GATGTGGCTTTCTTCTTCTTAGCCACGTTAGTTTTCTT<br>AGCTGATCTTTTGTTTGGGATCGGTATAAGTA<br>TTAAATTTGATTTGTTCTTGTGGCTGACTTGGTTTTAC<br>TATCTGGAATCTGGATGTAGATATGGAGATGG<br>TGAGCCTACCGACAATGCAGCGAGATTCTACAAATGG<br>TTCACCGAGGTTAGTCTTTTTTTTTGGCTTGGC<br>TCAACTAGTTGTTGTAACGTGTGTTGTTTTTGTTTTCT<br>TGTTTCTGAAGTTGTAAACATGTGTTTACAGG<br>GGAATGACAGAGGAGAATGGCTTAAGAACTTGAAGTA<br>TGGAGTGTTTGGATTAGGAAACAGACAATATGA<br>GCATTTTAATAAGGTTTATAAATGAAATCTTTATTCCC<br>CTTTTCTTAATGGTTTTGCTCTTGTCACTATT<br>ATGGTCTCCTTCCAATTACTTTGGACCGAGCTAATATG<br>CAGATTTGTTTTGTAAATTTTGGGTTGCAGGT<br>TGCCAAAGTTGTAGATGACATTCTTGTCGAACAAGGTT<br>TGTTTTGTTTCTTTCTTTCTTTCTTTCTTTCA<br>TCATCCGTTTTGGATCGCTCTGATCCGGTCTTAATGTG<br>TTGTATTTTGGTTTCTAACTTCATTGAGTGGG<br>TTGTTCAGGTGCACAGCGTCTTGTACAAGTTGGTCTT<br>GGAGATGATGACCAGTGTATTGAAGATGACTTT<br>ACCGCTTGGTATTTTACATTTCCACTTCTCGTGGCTTA<br>TCGTGTACAATGCTGTTTTGGTCATTTGTTTT<br>TTGGGGGGCTAAATTTGCTACCTCTTGCAGGCGAGAA<br>GCATTGTGGCCCGAGCTTGATACAATACTGAGG<br>GAAGAAGGGGATACAGCTGTTGCCACACCATACACTG<br>CAGCTGTGTTAGAATACAGAGTTTCTATTCACG<br>ACTCTGAAGATGCCAAATTCAATGATATAAACATGGCA<br>AATGGGAATGGTTACACTGTGTTTGATGCTCA<br>ACATCCTTACAAGTACAAAATCCAGCCGCTTCTTTTCT<br>TTTTCCTTATAATCTTGTCTTGTTACTTGATC<br>TAATCTTGCTTTTTTTGGCTTTTAAAGAGCAAATGTCG<br>CTGTTAAAAGGGAGCTTCATACTCCCGAGTCT<br>GATCGTTCTTGTATCCATTTGGAATTTGACATTGCTGG<br>AAGTGGACTTACGTGAGTTCTACTGCTATATG<br>AATATTTACTTAATCAGAGGGAAATATTATTGGAGAAT<br>AACATGAATGTATTTTTTGTATCTTGTCTGTC<br>AGGTATGAAACTGGAGATCATGTTGGTGTACTTTGTG<br>ATAACTTAAGTGAAACTGTAGATGAAGCTCTTA<br>GATTGCTGGATATGTCACCTGATACTTATTTCTCACTT<br>CACGCTGAAAAAGAAGACGGCACACCAATCAG<br>CAGCTCACTGCCTCCTCCCTTCCCACCTTGCAACTTG<br>AGAACAGCGCTTACACGATATGCATGTCTTTTG<br>AGTTCTCCAAAGAAGGTTGGTTGGATTCATTTACCATT<br>AGACTGGTTATAATCAGTTTTGTTTCTCTTCA<br>TAGAGATTCAAACTCAATTATTTTCATGTTTATTTTCT<br>TGCAGTCTGCTTTAGTTGCGTTGGCTGCTCAT<br>GCATCTGATCCTACCGAAGCAGAACGATTAAAACACC<br>TTGCTTCACCTGCTGGAAAGGTTGTGGCTGAAC<br>CTTTTGTTGGTTTCTACTCTTCATTTTCCATTTCTTTA<br>AAATGGAATCTGACAATGTATATTTTGTGTCC<br>TTTCAACAACAGGATGAATATTCAAAGTGGGTAGTAGA<br>GAGTCAAAGAAGTCTACTTGAGGTGATGGCCG<br>AGTTTCCTTCAGCCAAGCCACCACTTGGTGTCTTCTTC<br>GCTGGAGTTGCTCCAAGGTTGCAGCCTAGGTT<br>CTATTCGATATCATCATCGCCCAAGTGAGTACCTTCAT<br>TGTCTTGGTCTTTTTGTCTTCAAGTTGTTCGC<br>TTGAGACTTATATTGTGTTTTTAGTGTATTGAGCATTG<br>TCCCGTTTACTTGTATAGGATTGCTGAAACTA<br>GAATTCACGTCACATGTGCACTGGTTTATGAGAAAATG<br>CCAACTGGCAGGATTCATAAGGGAGTGTGTTC<br>CACTTGGATGAAGGTAAATATAAAAAACTTAAATCTGA<br>TAGCTTCTTGCAAACATATTGCTTTGGAATCT<br>TTTTACTGTTTGTGTCATTTCTTATCCATTGTCTTGGT<br>GTTTTTGCTGGGTACTGATTTTTTGCATCGTA<br>ATCACAGAATGCTGTGCCTTACGAGAAGAGTGAAAAC<br>TGTTCCTCGGCGCCGATATTTGTTAGGCAATCC<br>AACTTCAAGCTTCCTTCTGATTCTAAGGTACCGATCAT<br>CATGATCGGTCCAGGGACTGGATTAGCTCCAT<br>TCAGAGGATTCCTTCAGGAAAGACTAGCGTTGGTAGA<br>ATCTGGTGTTGAACTTGGGCCATCAGTTTTGTT<br>CTTTGGATGCAGAAACCGTAGAATGGTAATAAAGCCA<br>TTACTCAAAACTCAAACCTTTCATTGGTTTTGT |

-continued

SEQUENCE LISTING

| Name | Sequence |
|---|---|
| | CCAGTTTCTAATCATATCTTCTCATATATGTAGGATTT<br>CATCTACGAGGAAGAGCTCCAGCGATTTGTTG<br>AGAGTGGTGCTCTCGCAGAGCTAAGTGTCGCCTTCTC<br>TCGTGAAGGACCCACCAAAGAATACGTACAGCA<br>CAAGATGATGGACAAGGTATGAGCTTATAGAAACCCA<br>AAACTCAGATCTTCATATAGATTCAAATTCAGA<br>TTCTTGAGCTGACAATCTTTCTGCAATGCAGGCTTCTG<br>ATATCTGGAATATGATCTCTCAAGGAGCTTAT<br>TTATATGTTTGTGGTGACGCCAAAGGCATGGCAAGAG<br>ATGTTCACAGATCTCTCCACACAATAGCTCAAG<br>AACAGGTATGTCTTGTTGAGATCAATCTAGCATTATCA<br>TTGTCCGTATCACAAACCGACTCTAATGAGTT<br>TATTTCTGTCTGTCTTGTTTTCAGGGGTCAATGGATTC<br>AACTAAAGCAGAGGGCTTCGTGAAGAATCTGC<br>AAACGAGTGGAAGATATCTTAGAGATGTATGGTAACG<br>AAACTATTGAAGCCACACACTCACTGTGTACTT<br>ATATTTATATATATACGGCACAGAAATTGCCACATTAT<br>GATGATCATTAAGTTTGTGATCGCAAGAAGAA<br>AGGAACTCCTTTTTTTTTCCATTTTTAATTTCTTTTCA<br>TATATTTTGACAACTCTATTTTTTTAACTCTT<br>GTTATATATCCCCCACCCAATAGTAAGAAAAAATGCAT<br>AAGATGTTATGGGGTATTTGTGAACAATTATG<br>TTATATACAAAGTCAGTACCTTTAGTATGAATTCTTTA<br>TGTAGCACTTTCACCAAAGTCCCCATTTTGGG<br>ACAAATACAAATTCTTTGTTTATGCCTCA |
| IsH_XbaI_ rbsF1 (SEQ ID NO: 57) | TCA TGG TTA ATC TAG AGA TTA AAG AGG<br>AGA AAT ACT AGA TGA CCA |
| IsH_XbaI_ R1stp (SEQ ID NO: 58) | CAA AAT TAT TTC TAG TTA TTC TCG ATC<br>AAA AAT AGC CAG TAC CCG |
| IsH (SEQ ID NO: 59) | ATGACCAGCATTAAACTCCTTGCAGAGAGTCTGCTCA<br>AAGACAAAATAAAGATCGTCGATCTATCGCACACCTTG<br>AGATCCGAATTTCCGACACTGACATTACCTCCTCAGTT<br>TGGGCAAACCTGGGCGTTCAAGAAGGAGGAAATATC<br>GCGCTACGACGACCGTGGGCCCGCTTGGTACTGGAA<br>CAACTTTTCCTGCGGCGAACACACTGGTACTCACTTT<br>GATGCCCCAGTCCATTGGGTCACAGGCGAATCCGTG<br>CCTGAGAACTCAGTAGATCGTATTGACCCACAGCGCT<br>TTATGGCACCGGCAGTAGTGATTGATGCCTCTAAAGA<br>GGTACTAGAAAATCCGGACTGGGTTCTAGAGCCAGAA<br>TTTATCCAGGAGTGGGAGAAACTGCATGGCCGGATCG<br>AAGCCGGTTCCTGGTTTCTACTCCGGACAGATTGGTC<br>GAAGAAAATCAATAACCCGCTTGAGTTTGCTAACCTGA<br>TAGACGGCGCACCTCACACGCCAGGCCCAAGCCAGC<br>GTACAGTTGAATGGCTTATCGCCGAACGTGATGTCGT<br>GGGCTT<br>TGGGGTTGAGACGATCAATATTGATGCGGGCCTTTCA<br>GGCCGCTGGGAAGTTCCATACCCTTGCCACAACAAGA<br>TGCTGGGAGCAGGACGATTCGGGCTGCAGTGCTTGA<br>ACAATCTTGACCTGTTACCACCAACAGGAGCAGTAAT<br>CATCTCCGCTCCACTGAAGATCGAAGATGGCTCAGGC<br>AGCCCGCTGCGGGTACTGGCTATTTTTGATCGAGAAT<br>AA |
| PtBG (His-tag) (SEQ ID NO: 60 | ATGGCGATCACCTCCATAGCTCATCTCCGTGTCGTCA<br>ATGCGAACATGAGCATTCCGCTAGCTCGTCTTC<br>GTGTCGTCAATGCAAACATAAGCATTCCGCTcAAGCG<br>GACaAGTTTCCCCAAGAAATTCCTGTTTGGGGC<br>TGGCTCTGCTTCTTACCAATATGAAGGAGCAGCACAT<br>ATAGATGGGCGAGGACTTAGCGTCTGGGATGTC<br>TTCACTAAGGAACACCCTGAAAAGATCGCAGATCAGT<br>CGAATGGAGATGTTGCTCAAGACTTTTATCACC<br>GATACAAGGAAGATATAAAGTCGATGAAGGAAATGGG<br>TTTGGAGTCATTCAGGTTCTCCATTTCATGGTC<br>AAGAATATTACCTAATGGGAAAATCAGTGGAGGAATC<br>AACAAGCTaGGGATCAAGTTCTACAATAATCTC<br>ATTGACGAACTGCTAGCCAATGGAATCAAGCCACTTG<br>TCACTATCTACCATTGGGACCTTCCACAAGCAC<br>TTCAAGACGAATATGGAGGGTTCTTGAGCCCCAAAAT |

-continued

SEQUENCE LISTING

| Name | Sequence |
| --- | --- |
| | CGTGGATGACTTTCTGGAATATGCAAACCTAGT<br>TTTTAAGGAGTTCGGGGATAGGGTTAAGCATTGGGCG<br>ACACTGAATGAACCCAATATAATGACCCAACAA<br>GGGTACGTATTTGGGGCACATGCACCCGGACGATGTT<br>CTCACTTCGAATGGAACTGCCCGGCTGGAAACT<br>CCGGCACCGAGCCTTATATAGTTGGTCACCACCTCCT<br>CCTATGTCATGCTGCAGCTTTTCAACTATACAA<br>ACAAAAGTATAAGGATGATCAAAAGGGTATAATCGGA<br>ATAACAACCGCGACACAGATGGCCATACCGTTA<br>AACGACAACGTTGCCAACCTCTTGGCAGCGTCACGAG<br>CCATCGATTTCAACATTGGATGGTTTTTGCATC<br>CGGTTGTTTACGGCGAGTATCCACAGACGATGAGGGA<br>GCGGTTGGGAAGTCGACTGCCAAAATTCACAGA<br>AAAAGAGTCGGAGATGTTGAAACAATCGTTCGACTTTA<br>TAGGGTTGAATTACTACTCAACTGATTATGCA<br>GCCGCATCATCTTTTTCAGTTGATCCAGTGAATGTCAG<br>TTACACAACTGATTCCCGAGCAACATTATCAG<br>CGATAAAAGATGGGGTTCCTATCGGCGACCCGACATT<br>TATGAGCTGGTTGCATATATATCCAGAGGGCAT<br>CCTAACTCTGTTGCGATACGTAAAGGAAAGGTACAAC<br>AATCCATTTGTCATGATCACTGAGAATGGGATG<br>GCCGATGAAAACAAGGGATCATTAGCGGAAGATCCGA<br>TGGCTTTAAAAGACAACGTCAGgATTCGATATC<br>ACCGCGAACATCTATACTATGTTCTTGAAGCTATAAAG<br>GAGGGTGTGAACGTGGGAGGATACTACGCATG<br>GACATGGATGGATGATTTCGAGTGGGGTTCTGGATAT<br>ACTCCTCGATTCGGTCTCAACTTTGTGGATTTC<br>GACAATGATTTGAAGAGAACCCCCAAGGATTCTTACTT<br>CTGGTTCAAGGACTTCCTTGCAAATcaccaccaccacc<br>accactagTAA |
| Indole hydroxy-lase (SEQ ID NO: 61) | CCTTGAATTC GGTTTTCAGC ACTTGGCACA<br>GCTGTTGCAC TTTGTCCTGC GCAATCCGCC<br>AACCTGGAGA TGGCCGTGAC CAATACCCCC<br>ACACCGACTT TCGATCAGTT<br>CACTCGTTACATCCGTGTGC GCAGCGAACC<br>AGAAGCCAAG TTCGTCGAGT TCGATTTTGC<br>CCTTGGCCACCCTGAGTTGT TCGTCGAGTT<br>GGTGCTGCCG CAAGACGCCT TCGTGAAGTT<br>TTGCCAGCACAACCGCGTGG TGGCAATGGA<br>CGAAGCGATG GCCAAGGCGG TGGACGACGA<br>CATGGTCAAGTGGCGCTTCG GCGATGTCGG<br>TCGCCGCCTG CTGAAAGACC CGGGCTGAGA<br>ACCCTGCCGACAGGCAGATG GGCATCCAAC<br>AACAAGAGGG TACGGTTGAT ATGAGCGTAG<br>AGATAAAGACCAATACGGTG GATCCGATCC<br>GCCAGACCTA CGGCAACCTG CAACGGCGCT<br>TCGGGGACAAGCCGGCTAGC CGTTATCAGG<br>AAGCCAGCTA CGACATCGAA GCGGTCACCA<br>ACTTTCACTATCGCCCGCTG TGGGACCCGC<br>AGCACGAGCT GCACGATCCG ACCCGCACGG<br>CGATCCGCATGACCGATTGG CACAAGGTCA<br>CCGACCCCCG CCAGTTCTAC TACGGCGCCT<br>ATGTGCAGGGCCGCGCGCGG ATGCAGGAAG<br>CCACCGAACA CGCCTATGGC TTCTGCGAAA<br>AGCGTGAGCTGCTGAGCCGT CTGCCGGCCG<br>AGTTGCAGGC CAAGCTGCTG CGCTGCTTGG<br>TGCCGCTGCGGCATGCCGAG CTGGGCGCCA<br>ACATGAATAA CAGCAGCATC GCCGGCGACA<br>GCATCGCCGCCACCGTGACC CAGATGCACA<br>TCTACCAGGC GATGGACCGC CTGGGCATGG<br>GCCAGTACCTCTCGCGCATC GGCCTGCTGC<br>TCGATGGCGG CACCGGCGAG GCGTTGGATC<br>AAGCCAAGGCCTATTGGCTC GACGACCCGA<br>TCTGGCAGGG CCTGCGTCGC TACGTCGAAG<br>ACAGCTTCGTGATCCGCGAC TGGTTCGAGT<br>TGGGCCTGGC GCAGAACCTG GTGCTCGACG<br>GCTTGCTGCAGCCGCTGATG TACCAGCGCT<br>TCGACCAATG GCTCACAGAG AACGGTGGCA<br>GCGATGTGGCCATGCTCACC GAGTTCATGC<br>GCGACTGGTA CGGCGAAAGC ACGCGCTGGG<br>TCGACGCCATGTTCAAGACC GTGCTTGCCG<br>AAAATGACGC TAACCGTGAG CAGGTGCAGG<br>CCTGGCTGGAGGTCTGGGAG CCGCGTGCCT<br>ACGAGGCATT GTTGCCCCTG GCCGAGGAAG |

-continued

SEQUENCE LISTING

| Name | Sequence |
| --- | --- |
| | CCACCGGTATCGCCGCGCTG GATGAAGTCC<br>GCAGCGCCTT CGCTACTCGC CTGCAGAAAA<br>TCGGCCTGAAAAGCCGCGAG GAATAAAGCA<br>TGTCATCACT CGTCTACATC GCCTTCCAGG<br>ATAACGACAACGCGCGTTAC CTGGTGGAAG<br>CGATCATCCA GGACAACCCC CACGCCGTCG<br>TCCAGCACCACCCGGCGATG ATCCGTATCG<br>AGGCCGAGAA GCGCCTGGAG ATCCGCAGGG<br>AAACCGTGGAAGAGAACCTC GGCCGCGCCT<br>GGGACGTCCA GGCAATGCTG GTGGACGTAA<br>TCACCATCGGCGGCAACGTC GACGAGGACG<br>ATGACCGCTT CGTCCTCGAG TGGAAGAACT<br>AGGAGACAAGCTCATGGCTA CCCACAACAA<br>GAAACGCCTC AACCTGAAAG ACAAATACCG<br>CTACCTGACCCGCGATCTGG CCTGGGAAAC<br>GACCTACCAG AAGAAAGAAG ACGTGTTCCC<br>GCTGGAGCACTTCGAGGGCA TCAAGATCAC<br>CGACTGGGAC AAGTGGGAAG ACCCCTTCCG<br>CCTGACCATGGACAGCTACT GGAAATACCA<br>GGCGGAGAAA GAGAAGAAGC TCTACGCGAT<br>CTTCGACGCCTTTGCCCAGA ACAATGGTCA<br>TCAGAACATT TCCGATGCGC GCTACGTCAA<br>CGCCCTGAAGCTGTTCCTCA CCGGCGTTTC<br>ACCGCTGGAA TACCAGGCCT TCCAGGGCTT<br>CTCGCGGGTTGGCCGGCAGT TCAGTGGCGC<br>CGGTGCGCGG GTCGCCTGTC AGATGCAGGC<br>GATCGACGAGCTGCGCCATG TGCAGACGCA<br>AGTCCACGCC ATGAGCCATT ACAACAAGCA<br>CTTCGATGGTTTGCATGACT TCGCCCACAT<br>GTACGACCGG GTCTGGTTCC TCTCGGTACC<br>CAAGTCCTTTATGGACGATG CGCGGACCGC<br>CGGTCCGTTC GAGTTCCTCA CCGCCGTCTC<br>GTTCTCCTTCGAGTACGTGC TGACCAACCT<br>GTTGTTCGTA CCCTTCATGT CCGGTGCCGC<br>CTACAACGGCGATATGGCCA CGGTCACCTT<br>CGGTTTCTCC GCGCAGTCGG ACGAGGCGCG<br>GCACATGACCCTGGGTCTGG AAGTGATCAA<br>GTTCATGCTC GAACAGCATG AAGACAACGT<br>GCCCATCATCCAGCGCTGGA TCGATAAGTG<br>GTTCTGGCGC GGTTACCGCC TGCTGACCCT<br>GATCGGCATGATGATGGACT ACATGCTGCC<br>GAACAAAGTG ATGTCCTGGT CTGAGGCCTG<br>GGGGGTCTACTTCGAGCAGG CCGGTGGCGC<br>GCTGTTCAAG GATCTTGAGC GCTATGGCAT<br>CCGGCCGCCGAAATACGTCG AGCAGACCAC<br>CATCGGCAAG GAGCACATCA CCCACCAGGT<br>GTGGGGGGCCGTCTATCAAT ACAGCAAGGC<br>CACCAACTTC CATACCTGGA TACCCGGTGA<br>CGAGGAACTGAACTGGCTGT CGGAGAAATA<br>CCCGGACACC TTCGACAAAT ACTACCG CCC<br>GCGCTTCGAGTTCTGGCGTG AGCAGCAGGC<br>CAAGGGTGAG CGCTTCTACA ACGACACCCT<br>GCCGCACCTCTGCCAGGTGT GCCAGCTACC<br>GGCGATTTTC ACCGAGCCGG ACGATCCGAC<br>CAAGCTCAGCCTGCGCAGCC TGGTGCACGA<br>GGGGGAGCGC TATCACTTCT GCTCGGATGG<br>CTGCTGCGACATCTTCAAGA ACGAGCCGGT<br>GAAGTACATC CAGGCCTGGC TGCCGGTGCA<br>CCAGATCTACCAGGGCAACT GCGAAGGCGG<br>GGATGTCGAG ACGGTGGTGC AGAAGTACTA<br>CCACATCAAAAGCGGCGTGG ACAATTTGGA<br>GTACCTGGGC TCGCCCGAGC ACCAGCGCTG<br>GCTGGCCCTGAAAGGTCAGA CCCCACCAAC<br>TGCCGCCCCG GCGGACAAGA ACCTGGACGC<br>CGCCTGAGGCAGCGCCAGCC GCTCAGGGGT<br>GAAGCACCGC CCCTGAGCCA TTCCAAGAAC<br>AAGAGGGTTCGATCATGACT GTCAACTCAA<br>TCGGCGAATA CACTGCCACG CCACGGGATG<br>TGCAGGCCAACTTCAACGGC ATGCAACTGC<br>TCTACCTCTA CTGGGAAGAG CACCTGATGT<br>ACTGCTCCGCGCTCGCGTTC TTGGTAGCCC<br>CCGGCATGCC CTTTGCCGAG TTCCTCGAGC<br>AGGTGCTCAAGCCCGCGATC CACGCCCATC<br>CGGACAGCGC GAAGATCGAT TTCAGCCAGG<br>CGCTCTGGCAGCTGAACGAC CAGCCGTTCA |

-continued

SEQUENCE LISTING

| Name | Sequence |
|---|---|
| | CCCCGGACTA CGCCGCCAGC CTGGAAGCCA<br>ACGGCATCGACCACAAAAGC ATGCTGCGTC<br>TGAACACCCC GGGCCTGAAC GGCATCCAGG<br>GTTCCTGCAGCTGAGAGGTG TGTCATGACT<br>TACAACGTCA CCATCGAGCC TACCGGTGAA<br>ATCATCGAGGTCGAGGAGGG CCAGACCATC<br>CTGCAAGCGG CCTTGCGCCA GGGCGTCTGG<br>CTGCCATTCGCCTGCGGCCA TGGTACCTGC<br>GCGACCTGCA AGGTGCAGGT AGTCGAAGGC<br>GAGGCCGACCACGGCGCCGC CTCACCCTTT<br>GCCCTGATGG ACATGGAGCG TGACGAGGGC<br>AAGGTCCTGGCCTGCTGCGC CATGCCCATG<br>AGCGATATGG TGATAGAGGC GGATATCGAC<br>GTCGATCCGGATTTCGCCGG CCATCAAGTC<br>GAGGACTACC GCGGGGTGGT CAGCGCCCTG<br>GTCGACCTGTCGCCGACCAT CAAGGGTGTG<br>CACATCAAGC TCGATCGGCC GATGACCTTC<br>CAGGCCGGGCAATACATCAA CCTGACCCTG<br>CCGGGCGTTG AAGGATCACG CGCCTTCTCG<br>CTGGCCAACCCGCCGAGCCG GAATGACGAA<br>GTCGAGTTGC ACGTGCGCCT GGTCGAGGGC<br>GGTGCGGCCACCGGCTTTAT CCACAAGCAA<br>CTGAAAGTCG GCGACGCGGT GGAGCTGTCC<br>GGGCCTTATGGGCAGTTCTT CGTGCGCGAT<br>TCGCAGGCCG GCGACCTGAT CTTCATCGCC<br>GGCGGCTCGGGCTTATCGAG CCCGCAGTCG<br>ATGATCCTCG ATCTGCTTGA ACGCGGCGAT<br>ACGCGGCGGATCACCCTGTT CCAGGGCGCG<br>CGCAACCGCG CCGAGCTGTA CAACTGCGAA<br>CTGTTCGAGGAACTGGCCGC GCGCCACCCC<br>AACTTCAGTT ACGTGCCGGC ACTCAACCAG<br>GCCAACGACGATCCCGAATG GCAGGGTTTC<br>AAGGGCTTCG TCCACGACGC CGCCAAGGCC<br>CACTTCGACGGCCGCTTCGG CGGGCACAAG<br>GCCTACTTGT GCGGCCCGCC GCCAATGATC<br>AACGCGGCCATCACCACCCT GAGGCAGGGC<br>CGGCTGTTCG AGCGCGACAT CTTTATGGAG<br>CGCTTCTACACCGCCGCCGA TGGGGCCGGC<br>GAGAGCAGCC GTTCGGCCCT GTTCAAGCGC<br>ATCTGAGGTG AACCATGAAC CGTGCCGGTT<br>ATGAGATTCG CGA |
| AtR1 (SEQ ID NO: 62) | ATGACTTCTGCTTTGTATGCTTCCGATTTGTTTAAGCA<br>GCTCAAGTCAATTATGGGGACAGATTCGTTAT<br>CCGACGATGTTGTACTTGTGATTGCAACGACGTCTTT<br>GGCACTAGTAGCTGGATTTGTGGTGTTGTTATG<br>GAAGAAAACGACGGCGGATCGGAGCGGGGAGCTGAA<br>GCCTTTGATGATCCCTAAGTCTCTTATGGCTAAG<br>GACGAGGATGATGATTTGGATTTGGGATCCGGGAAGA<br>CTAGAGTCTCTATCTTCTTCGGTACGCAGACTG<br>GAACAGCTGAGGGATTTGCTAAGGCATTATCCGAAGA<br>AATCAAAGCGAGATATGAAAAAGCAGCAGTCAA<br>AGTCATTGACTTGGATGACTATGCTGCCGATGATGAC<br>CAGTATGAAGAGAAATTGAAGAAGGAAACTTTG<br>GCATTTTTCTGTGTTGCTACTTATGGAGATGGAGAGC<br>CTACTGACAATGCTGCCAGATTTTACAAATGGT<br>TTACGGAGGAAAATGAACGGGATATAAAGCTTCAACA<br>ACTAGCATATGGTGTGTTTGCTCTTGGTAATCG<br>CCAATATGAACATTTTAATAAGATCGGGATAGTTCTTG<br>ATGAAGAGTTATGTAAGAAAGGTGCAAAGCGT<br>CTTATTGAAGTCGGTCTAGGAGATGATGATCAGAGCA<br>TTGAGGATGATTTTAATGCCTGGAAAGAATCAC<br>TATGGTCTGAGCTAGACAAGCTCCTCAAAGACGAGGA<br>TGATAAAAGTGTGGCAACTCCTTATACAGCTGT<br>TATTCCTGAATACCGGGTGGTGACTCATGATCCTCGG<br>TTTACAACTCAAAAATCAATGGAATCAAATGTG<br>GCCAATGGAAATACTACTATTGACATTCATCATCCCTG<br>CAGAGTTGATGTTGCTGTGCAGAAGGAGCTTC<br>ACACACATGAATCTGATCGGTCTTGCATTCATCTCGAG<br>TTCGACATATCCAGGACGGGTATTACATATGA<br>AACAGGTGACCATGTAGGTGTATATGCTGAAAATCAT<br>GTTGAAATAGTTGAAGAAGCTGGAAAATTGCTT<br>GGCCACTCTTTAGATTTAGTATTTTCCATACATGCTGA<br>CAAGGAAGATGGCTCCCCATTGGAAAGCGCAG<br>TGCCGCCTCCTTTCCCTGGTCCATGCACACTTGGGAC |

-continued

SEQUENCE LISTING

| Name | Sequence |
|---|---|
| | TGGTTTGGCAAGATACGCAGACCTTTTGAACCC<br>TCCTCGAAAGTCTGCGTTAGTTGCCTTGGCGGCCTAT<br>GCCACTGAACCAAGTGAAGCCGAGAAACTTAAG<br>CACCTGACATCACCTGATGGAAAGGATGAGTACTCAC<br>AATGGATTGTTGCAAGTCAGAGAAGTCTTTTAG<br>AGGTGATGGCTGCTTTTCCATCTGCAAAACCCCCACT<br>AGGTGTATTTTTTGCTGCAATAGCTCCTCGTCT<br>ACAACCTCGTTACTACTCCATCTCATCCTCGCCAAGAT<br>TGGCGCCAAGTAGAGTTCATGTTACATCCGCA<br>CTAGTATATGGTCCAACTCCTACTGGTAGAATCCACAA<br>GGGTGTGTGTTCTACGTGGATGAAGAATGCAG<br>TTCCTGCGGAGAAAAGTCATGAATGTAGTGGAGCCCC<br>AATCTTTATTCGAGCATCTAATTTCAAGTTACC<br>ATCCAACCCTTCAACTCCAATCGTTATGGTGGGACCT<br>GGGACTGGGCTGGCACCTTTTAGAGGTTTTCTG<br>CAGGAAAGGATGGCACTAAAAGAAGATGGAGAAGAAC<br>TAGGTTCATCTTTGCTCTTCTTTGGGTGTAGAA<br>ATCGACAGATGGACTTTATATACGAGGATGAGCTCAA<br>TAATTTTGTTGATCAAGGCGTAATATCTGAGCT<br>CATCATGGCATTCTCCCGTGAAGGAGCTCAGAAGGAG<br>TATGTTCAACATAAGATGATGGAGAAGGCAGCA<br>CAAGTTTGGGATCTAATAAAGGAAGAAGGATATCTCTA<br>TGTATGCGGTGATGCTAAGGGCATGGCGAGGG<br>ACGTCCACCGAACTCTACACACCATTGTTCAGGAGCA<br>GGAAGGTGTGAGTTCGTCAGAGGCAGAGGCTAT<br>AGTTAAGAAACTTCAAACCGAAGGAAGATACCTCAGA<br>GATGTCTGGTGA |

REFERENCES

Baeyer, A. & Drewsen, V., 1882. Darstellung von Indigblau aus Orthonitrobenzaldehyd. Berichte der deutschen chemischen Gesellschaft, 15(2), pp. 2856-2864. Available at: http://doi.wiley.com/10.1002/cber.188201502274 [Accessed Feb. 12, 2014].

Berry, A. et al., 2002. Application of metabolic engineering to improve both the production and use of biotech indigo. Journal of industrial microbiology & biotechnology, 28, pp. 127-133.

Burd, V., Bantleon, R. & Pee, K. Van, 2001. Oxidation of indole and indole derivatives catalyzed by nonheme chloroperoxidases. Applied Biochemistry and . . . , 37(3), pp. 248-250. Available at: http://link.springer.com/article/10.1023/A:1010220916145 [Accessed Feb. 10, 2014].

Choi, H. S. et al., 2003. A novel flavin-containing monooxygenase from Methylophaga sp strain SK1 and its indigo synthesis in *Escherichia coli. Biochemical and biophysical research communications,* 306, pp. 930-936.

Edwards, H. G. M. et al., 2004. Nondestructive analysis of ancient Egyptian funerary relics by Raman spectroscopic techniques. Analytica Chimica Acta, 503, pp. 223-233.

Ensley, B. D. et al., 1983. Expression of naphthalene oxidation genes in *Escherichia coli* results in the biosynthesis of indigo. Science (New York, N.Y.), 222, pp. 167-169.

Frey, M. et al., 1997. Analysis of a chemical plant defense mechanism in grasses. Science (New York, N.Y.), 277 (5326), pp. 696-9. Available at: http://www.ncbi.nlm.nih.gov/pubmed/9235894 [Accessed Jun. 24, 2014].

Fukui, Y. et al., 2003. A rationale for the shift in colour towards blue in transgenic carnation flowers expressing the flavonoid 3',5'-hydroxylase gene. Phytochemistry, 63(1), pp. 15-23. Available at: http://www.sciencedirect.com/science/article/pii/S0031942202006842 [Accessed Feb. 12, 2014].

Gillam, E. M. et al., 2000. Oxidation of indole by cytochrome P450 enzymes. Biochemistry, 39(45), pp. 13817-24. Available at: http://www.ncbi.nlm.nih.gov/pubmed/11076521.

Gillam, E. M. J. et al., 1999. Formation of Indigo by Recombinant Mammalian. Biochemical and biophysical research communications, 265(2), pp. 469-472.

Hart, S. et al., 1992. Identification of indigo-related pigments produced by *Escherichia coli* containing a cloned *Rhodococcus* gene. Journal of general microbiology, 138 (1992), pp. 211-216.

Hoessel, R. et al., 1999. Indirubin, the active constituent of a Chinese antileukaemia medicine, inhibits cyclin-dependent kinases. Nature cell biology, 1(1), pp. 60-7. Available at: http://www.ncbi.nlm.nih.gov/pubmed/10559866.

Kim J Y, Kim J K, Lee S O, Kim C K, Lee K (2005). Multicomponent phenol hydroxylase-catalysed formation of hydroxyindoles and dyestuffs from indole and its derivatives. Lett Appl Microbiol 41: 163-168.

Kim J Y, Lee K, Kim Y, Kim C K, Lee K (2003). Production of dyestuffs from indole derivatives by naphthalene dioxygenase and toluene dioxygenase. Lett Appl Microbiol 36: 343-348.

Kuo, H. H. & Mauk, A. G., 2012. Indole peroxygenase activity of indoleamine 2,3-dioxygenase. Proceedings of the National Academy of Sciences, 109, pp. 13966-13971.

Li, Q. S. et al., 2000. Directed evolution of the fatty-acid hydroxylase P450 BM-3 into an indole-hydroxylating catalyst. Chemistry (Weinheim an der Bergstrasse, Germany), 6, pp. 1531-1536.

Manna, S. K. & Mazumdar, S., 2010. Tuning the substrate specificity by engineering the active site of cytochrome P450cam: a rational approach. Dalton transactions (Cambridge, England: 2003), 39, pp. 3115-3123.

Marcinek, H. et al., 2000. Indoxyl-UDPG-glucosyltransferase from *Baphicacanthus cusia*. Phytochemistry, 53(2), pp. 201-207. Available at: http://linkinghub.elsevier.com/retrieve/pii/S0031942299004306.

Maugard, T. et al., 2001. Identification of an indigo precursor from leaves of *Isatis tinctoria* (Woad). Phytochemistry, 58(6), pp. 897-904. Available at: http://www.ncbi.nlm.nih.gov/pubmed/17191785.

McBride, K. et al., 1996. Cotton fiber transcriptional factors. Available at: https://www.google.com/patents/WO1996040924A2?dq=cotton+genetically+modified+indigo+indole&ei=PZr7UriZBcekrQH164CgAQ&cl=en [Accessed Feb. 12, 2014].

McClay, K. et al., 2005. Mutations of toluene-4-monooxygenase that alter regiospecificity of indole oxidation and lead to production of novel indigoid pigments. Applied and environmental microbiology, 71(9), pp. 5476-83. Available at: http://www.pubmedcentral.nih.gov/articlerenderfcgi?artid=1214665&tool=pmcentrez&rendertype=abstract [Accessed Feb. 12, 2014].

Melanson, D. et al., 1997. A deletion in an indole synthase gene is responsible for the DIMBOA-deficient phenotype of bxbx maize. Proceedings of the National Academy of Sciences, 94(24), pp. 13345-13350. Available at: http://www.pnas.org/content/94/24/13345.long [Accessed Jun. 24, 2014].

Mermod, N., Harayama, S. & Timmis, K. N., 1986. New Route to Bacterial Production of Indigo. Nature Biotechnology, 4(4), pp. 321-324. Available at: http://dx.doi.org/10.1038/nbt0486-321 [Accessed Feb. 12, 2014].

Meyer, A. et al., 2002. Hydroxylation of indole by laboratory-evolved 2-hydroxybiphenyl 3-monooxygenase. The Journal of biological chemistry, 277, pp. 34161-34167.

Minami, Y. et al., 1999. Cloning, sequencing, characterization, and expression of a beta-glucosidase cDNA from the indigo plant. Plant Science, 142, pp. 219-226.

Minami, Y. et al., 2000. Tissue and intracellular localization of indican and the purification and characterization of indican synthase from indigo plants. Plant & cell physiology, 41(2), pp. 218-25. Available at: http://www.ncbi.nlm.nih.gov/pubmed/10795317.

Moreno-Ruiz, E. et al., 2003. Identification and functional characterization of *Sphingomonas macrogolitabida* strain TFA genes involved in the first two steps of the tetralin catabolic pathway. Journal of bacteriology, 185, pp. 2026-2030.

O'Connor, K. E., Dobson, A. D. & Hartmans, S., 1997. Indigo formation by microorganisms expressing styrene monooxygenase activity. Applied and environmental microbiology, 63, pp. 4287-4291.

Russell, G. A. & Kaupp, G., 1969. Oxidation of Carbanions. IV. Oxidation of indoxyl to indigo in basic solution. Journal of the American Chemical Society, 228(2), pp. 3851-3859.

Stephens, G. M. et al., 1989. Cloning and expression in *Escherichia coli* of the toluene dioxygenase gene from *Pseudomonas putida* NCIB11767. FEMS microbiology letters, 48, pp. 295-300.

Xia, Z.-Q. & Zenk, M. H., 1992. Biosynthesis of indigo precursors in higher plants. Phytochemistry, 31(8), pp. 2695-2697. Available at: http://www.sciencedirect.com/science/article/pii/0031942292836134 [Accessed Feb. 14, 2014].

Zhang, R. et al., 2008. *Arabidopsis* Indole Synthase, a Homolog of Tryptophan Synthase Alpha, is an Enzyme Involved in the Trp-independent Indole-containing Metabolite Biosynthesis. Journal of Integrative Plant Biology, 50(9), pp. 1070-1077.

Barnes, H. J., 1996. Maximizing expression of eukaryotic cytochrome P450s in *Escherichia coli*. Methods in enzymology, 272, pp. 3-14. Available at: http://www.ncbi.nlm.nih.gov/pubmed/8791757 [Accessed Jun. 21, 2014].

Belknap, W., Rockhold, D. & McCue, K., 2008. pBINPLUS/ARS: an improved plant transformation vector based on pBINPLUS. BioTechniques, 44(6), pp. 753-6. Available at: http://www.ncbi.nlm.nih.gov/pubmed/18476828 [Accessed Jun. 23, 2014].

Bent, A., 2006. *Arabidopsis thaliana* floral dip transformation method. Methods in molecular biology (Clifton, N.J.), 343, pp. 87-103. Available at: http://www.ncbi.nlm.nih.gov/pubmed/16988336 [Accessed Jun. 11, 2014].

Borissova, A. et al., 2005. *Agrobacterium*-Mediated Transformation of Secondary Somatic Embryos from *Rosa Hybrida* L. and Recovery of Transgenic Plants. Biotechnology & Biotechnological Equipment, 19(1), pp. 70-74. Available at: http://www.tandfonline.com/doi/abs/10.1080/13102818.2005. Ser. No. 10/817,156 [Accessed Jun. 24, 2014].

Clough, S. J. & Bent, A. F., 1998. Floral dip: a simplified method for *Agrobacterium*-mediated transformation of *Arabidopsis thaliana*. The Plant Journal, 16(6), pp. 735-743. Available at: http://doi.wiley.com/10.1046/j.1365-313x.1998.00343.x [Accessed Jun. 4, 2014].

Davis, A. M. et al., 2009. Protocol: Streamlined sub-protocols for floral-dip transformation and selection of transformants in *Arabidopsis thaliana*. Plant methods, 5(1), p.

3. Available at: http://www.plantmethods.com/content/5/1/3 [Accessed May 29, 2014].

Donnelly, M. L. L. et al., 2001. Analysis of the aphthovirus 2A/2B polyprotein "cleavage" mechanism indicates not a proteolytic reaction, but a novel translational effect: a putative ribosomal "skip." J. Gen. Virol., 82(5), pp. 1013-1025. Available at: http://vir.sgmjournals.org/content/82/5/1013.long [Accessed Jun. 23, 2014].

Engelen, F. A. et al., 1995. pBINPLUS: An improved plant transformation vector based on pBIN19. Transgenic Research, 4(4), pp. 288-290. Available at: http://link.springer.com/10.1007/BF01969123 [Accessed Jun. 23, 2014].

Finer, J. J. & McMullen, M. D., 1990. Transformation of cotton (*Gossypium hirsutum* L.) via particle bombardment. Plant cell reports, 8(10), pp. 586-9. Available at: http://www.ncbi.nlm.nih.gov/pubmed/24232677 [Accessed Jun. 24, 2014].

Firoozabady, E. et al., 1994. Regeneration of Transgenic Rose (*Rosa hybrida*) Plants from Embryogenic Tissue. Bio/Technology, 12(6), pp. 609-613. Available at: http://dx.doi.org/10.1038/nbt0694-609 [Accessed Jun. 24, 2014].

Fisher, C. W. et al., 1992. High-level expression in *Escherichia coli* of enzymatically active fusion proteins containing the domains of mammalian cytochromes P450 and NADPH-P450 reductase flavoprotein. Proceedings of the National Academy of Sciences of the United States of America, 89(22), pp. 10817-21. Available at: http://www.pubmedcentral.nih.gov/articlerenderfcgi?artid=50433&tool=pmcentrez&rendertype=abstract [Accessed Jun. 21, 2014].

Gillam, E. M. J. et al., 1999. Formation of Indigo by Recombinant Mammalian. Biochemical and biophysical research communications, 265(2), pp. 469-472.

Harada, H. et al., 2011. Efficient functional analysis system for cyanobacterial or plant cytochromes P450 involved in sesquiterpene biosynthesis. Applied microbiology and biotechnology, 90(2), pp. 467-76. Available at: http://www.ncbi.nlm.nih.gov/pubmed/21229242 [Accessed Sep. 3, 2011].

Hull, a K. & Celenza, J. L., 2000. Bacterial expression and purification of the *Arabidopsis* NADPH-cytochrome P450 reductase ATR2. Protein expression and purification, 18(3), pp. 310-5. Available at: http://www.ncbi.nlm.nih.gov/pubmed/10733884 [Accessed Nov. 3, 2011].

Katsumoto, Y. et al., 2007. Engineering of the rose flavonoid biosynthetic pathway successfully generated blue-hued flowers accumulating delphinidin. Plant & cell physiology, 48(11), pp. 1589-600. Available at: http://pcp.oxfordjournals.org/content/48/11/1589.full [Accessed May 28, 2014].

Korban, S. S., Gasic, K. & Li, X., 2006. Rose (*Rosa hybrida* L.). Methods in molecular biology (Clifton, N.J.), 344, pp. 351-8. Available at: http://www.ncbi.nlm.nih.gov/pubmed/17033077 [Accessed Jun. 9, 2014].

Liu, H.-C. et al., 2000. Cloning and promoter analysis of the cotton lipid transfer protein gene Ltp311 The nucleotide sequence data reported will appear in the GenBank Nucleotide Sequence Databases under the accession number AF228333. Biochimica et Biophysica Acta (BBA)—Molecular and Cell Biology of Lipids, 1487(1), pp. 106-111. Available at: http://www.sciencedirect.com/science/article/pii/S138819810000072X [Accessed Jun. 24, 2014].

Logemann, E. et al., 2006. An improved method for preparing *Agrobacterium* cells that simplifies the *Arabidopsis* transformation protocol. Plant methods, 2(1), p. 16. Available at: http://www.plantmethods.com/content/2/1/16 [Accessed May 25, 2014].

Marchant, R., 1998. Biolistic Transformation of Rose (*Rosa hybrida* L.). Annals of Botany, 81(1), pp. 109-114. Available at: http://aob.oxfordjournals.org/content/81/1/109 [Accessed Jun. 23, 2014].

Minami, Y. et al., 1999. Cloning, sequencing, characterization, and expression of a β-glucosidase cDNA from the indigo plant. Plant Science, 142(2), pp. 219-226. Available at: http://www.sciencedirect.com/science/article/pii/S0168945299000151 [Accessed Jun. 21, 2014].

Mitsuhara, I. et al., 1996. Efficient Promoter Cassettes for Enhanced Expression of Foregin Genes in Dicotyledonous and Monocotyledonous Plants. Plant and Cell Physiology, 37(1), pp. 49-59. Available at: http://pcp.oxfordjournals.org/content/37/1/49.abstract?ijkey=35dfa8fbf87d4a4cbb11cc05ba53cc206654bbcc&keytype2=tf_ipsecsha [Accessed Jun. 23, 2014].

Pritchard, M. P. et al., 1997. A general strategy for the expression of recombinant human cytochrome P450s in *Escherichia coli* using bacterial signal peptides: expression of CYP3A4, CYP2A6, and CYP2E1. Archives of biochemistry and biophysics, 345(2), pp. 342-54. Available at: http://www.sciencedirect.com/science/article/pii/S0003986197902654 [Accessed Jun. 21, 2014].

Umbeck, P. et al., 1987. Genetically Transformed Cotton (*Gossypium Hirsutum* L.) Plants. Bio/Technology, 5(3), pp. 263-266. Available at: http://dx.doi.org/10.1038/nbt0387-263 [Accessed Jun. 24, 2014].

Xiao, Y. et al., 2011. Transgenic tetraploid *Isatis indigotica* expressing Bt Cry1Ac and Pinellia ternata agglutinin showed enhanced resistance to moths and aphids. Molecular biology reports, 39(1), pp. 485-91. Available at: http://www.ncbi.nlm.nih.gov/pubmed/21559837 [Accessed Nov. 15, 2011].

Xu, X. et al., 2007. Designing and transgenic expression of melanin gene in tobacco trichome and cotton fiber. Plant biology (Stuttgart, Germany), 9(1), pp. 41-8. Available at: http://www.ncbi.nlm.nih.gov/pubmed/17006798 [Accessed Jun. 24, 2014].

Zakizadeh, H. et al., 2013. Transformation of miniature potted rose (*Rosa hybrida* cv. Linda) with P(SAG12)-ipt gene delays leaf senescence and enhances resistance to exogenous ethylene. Plant cell reports, 32(2), pp. 195-205. Available at: http://www.ncbi.nlm.nih.gov/pubmed/23207761 [Accessed Jun. 24, 2014].

Zhang, X. et al., 2006. *Agrobacterium*-mediated transformation of *Arabidopsis thaliana* using the floral dip method. Nature protocols, 1(2), pp. 641-6. Available at: http://dx.doi.org/10.1038/nprot.2006.97 [Accessed May 30, 2014].

Zhou, G. et al., 1983. Introduction of exogenous DNA into cotton embryos. Methods in enzymology, 101, pp. 433-81. Available at: http://www.ncbi.nlm.nih.gov/pubmed/6577258 [Accessed Jun. 24, 2014].

What is claimed is:

1. A transgenic organism engineered to accumulate an indole-derived compound, the organism transformed with an artificial DNA construct comprising, as operably associated components in the 5' to 3' direction of transcription:

(i) a promoter that functions in the organism;

(ii) a first transcribable nucleic acid sequence encoding a cytochrome P450 polypeptide, comprising:

(1) SEQ ID NO 3 (ItB4), or a nucleotide sequence at least 95% identical thereto and encoding a polypeptide catalyzing formation of 2-hydroxyindole from indole; or (2) SEQ ID NO: 4 (ItB24), or a nucleotide sequence at least 95% identical thereto and encoding a polypeptide catalyzing formation of 3-hydroxyindole from indole; and (iii) a transcriptional termination sequence;

wherein the organism produces increased levels of indole-derived compounds, or precursors thereof, compared to an organism without the artificial DNA construct.

2. The transgenic organism of claim 1, wherein the artificial DNA construct further comprises a transcribable nucleic acid sequence comprising:

(a) SEQ ID NO: 61 (indole hydroxylase), or a nucleotide sequence at least 95% identical thereto and encoding a polypeptide having indole hydroxylase activity;

(b) SEQ ID NO: 59 (isatin hydrolase, IsH), or a nucleotide sequence at least 95% identical thereto and encoding a polypeptide having IsH activity;

(c) SEQ ID NO: 60 (PtBG), or a nucleotide sequence at least 95% identical thereto and encoding a polypeptide having PtBG activity;

(d) SEQ ID NO: 56 (AtR2), or a nucleotide sequence at least 95% identical thereto and encoding a polypeptide having AtR2 activity or P450 reductase activity; or (e) SEQ ID NO: 62 (AtR1), or a nucleotide sequence at least 95% identical thereto and encoding a polypeptide having AtR1 activity or P450 reductase activity.

3. A method for producing a transgenic organism comprising: transforming an organism with an artificial DNA construct, the artificial construct comprising, as operably associated components in the 5' to 3' direction of transcription, (i) a promoter that functions in the organism;

(ii) a first transcribable nucleic acid sequence encoding a cytochrome P450 polypeptide, comprising:

(1) SEQ ID NO 3 (ItB4), or a nucleotide sequence at least 95% identical thereto and encoding a polypeptide catalyzing formation of 2-hydroxyindole from indole; or (2) SEQ ID NO: 4 (ItB24), or a nucleotide sequence at least 95% identical thereto and encoding a polypeptide catalyzing formation of 3-hydroxyindole from indole; and (iii) a transcriptional termination sequence;

wherein the organism produces increased levels of indole-derived compounds, or precursors thereof, compared to an organism without the artificial DNA construct.

4. The method of claim 3, wherein the artificial DNA construct further comprises a transcribable nucleic acid sequence comprising:

(a) SEQ ID NO: 61 (indole hydroxylase), or a nucleotide sequence at least 95% identical thereto and encoding a polypeptide having indole hydroxylase activity;

(b) SEQ ID NO: 59 (isatin hydrolase, IsH), or a nucleotide sequence at least 95% identical thereto and encoding a polypeptide having IsH activity;

(c) SEQ ID NO: 60 (PtBG), or a nucleotide sequence at least 95% identical thereto and encoding a polypeptide having PtBG activity;

(d) SEQ ID NO: 56 (AtR2), or a nucleotide sequence at least 95% identical thereto and encoding a polypeptide having AtR2 activity or P450 reductase activity; or (e) SEQ ID NO: 62 (AtR1), or a nucleotide sequence at least 95% identical thereto and encoding a polypeptide having AtR1 activity or P450 reductase activity.

5. The method of claim 3, further comprising a growth medium comprising amino levulinic acid (ALA).

6. The transgenic organism of claim 1, wherein the organism comprises a bacteria or plant.

7. The transgenic organism of claim 1, wherein the organism comprises *E. coli* or *Agrobacterium tumefaciens.*

8. The transgenic organism of claim 1, wherein the organism comprises *Indigofera tinctoria* (Fabaceae); *Indigofera suffruticosa* (Fabaceae); *Indigofera micheliana; Indigofera arrecta; Inidgofera coerulea; Baptisia leucantha* (Fabaceae); *Isatis tinctoria* (Brassicacea); *Polygonum tinctorium* (Polygonaceae) aka *Persicaria tinctoria; Calanthe discolor* (Orchidaceae); *Strobilanthes cusia* (Acanthaceae) aka *Baphicacanthus cusia; Justicia spicegera* (Acanthaceae) aka *Jacobinia mohintli; Justicia colorifera* (Acanthaceae) aka *Jacobinia tinctoria; Couroupita guaianensis* (Lecythidaceae); *Wrightia tinctoria* (Apocyanceae); *Marsdenia tinctoria* (Apocynaceae); *Lonchocarpus cyanescence* (Fabaceae) syn *Philenoptera cyanescens; Isatis indigotica* (Brassicaceae); *Isatis candoleana; Isatis buschiana; Isatis tinctoria* subsp. *Corymbosa; Koaophyllon tinctorium* (Compositae, Eupatorieae) syn *Eupatorium indigofera; Cybistax antisyphilitica* (Bignoniacea) aka *Yangua tinctoria, Isatis tinctoria; Arabidopsis thaliana; Indigofera tinctoria; Polygonum tinctorium; Baphicacanthus cusia*; rose; onion; carnation; or cotton.

9. The transgenic organism of claim 1, wherein the artificial DNA construct further comprises beta-glucosidase or P450 reductase.

10. The transgenic organism of claim 1, wherein the transgenic organism, or a portion thereof, comprises a colored phenotype.

11. The transgenic organism of claim 10, wherein the colored phenotype comprises a visible color selected from the group consisting of magenta, violet, blue, pink, green, yellow, red, yellow, orange, or purple.

12. The transgenic organism of claim 1, wherein accumulation of an indole derived compound imparts a visible color to the transgenic organism or a portion of the transgenic organism.

13. The transgenic organism of claim 1, wherein accumulation of an indole derived compound imparts a magenta, violet, blue, pink, green, yellow, red, yellow, orange, or purple color to the transgenic organism or a portion of the transgenic organism.

14. An artificial DNA construct comprising:

(i) a promoter that functions in the organism;

(ii) a first transcribable nucleic acid sequence encoding a cytochrome P450 polypeptide, comprising (1) SEQ ID NO 3 (ItB4), or a nucleotide sequence at least 95% identical thereto and encoding a polypeptide catalyzing formation of 2-hydroxyindole from indole; or (2) SEQ ID NO: 4 (ItB24), or a nucleotide sequence at least 95% identical thereto and encoding a polypeptide catalyzing formation of 3-hydroxyindole from indole; and (iii) a transcriptional termination sequence.

15. The artificial DNA construct of claim 14, further comprising a transcribable nucleic acid sequence comprising:

(a) SEQ ID NO: 61 (indole hydroxylase), or a nucleotide sequence at least 95% identical thereto and encoding a polypeptide having indole hydroxylase activity;

(b) SEQ ID NO: 59 (isatin hydrolase, IsH), or a nucleotide sequence at least 95% identical thereto and encoding a polypeptide having IsH activity;

(c) SEQ ID NO: 60 (PtBG), or a nucleotide sequence at least 95% identical thereto and encoding a polypeptide having PtBG activity;

(d) SEQ ID NO: 56 (AtR2), or a nucleotide sequence at least 9095% identical thereto and encoding a polypeptide having AtR2 activity or P450 reductase activity; or (e) SEQ ID NO: 62 (AtR1), or a nucleotide sequence at least 95% identical thereto and encoding a polypeptide having AtR1 activity or P450 reductase activity.

16. The artificial DNA construct of claim 14 further comprising beta-glucosidase or P450 reductase.

17. The transgenic organism of claim 1, wherein the artificial DNA construct further comprises a transcribable nucleic acid sequence comprising:

(a) SEQ ID NO: 1 (TSA1), or a nucleotide sequence at least 95% identical thereto and encoding a polypeptide catalyzing cleavage of indole-3-glycerol phosphate (I3GP) into indole and D-glyceraldehyde-3-phosphate (G3P); or (b) SEQ ID NO: 2 (TSA2), or a nucleotide sequence at least 95% identical thereto and encoding a polypeptide catalyzing cleavage of indole-3-glycerol phosphate (I3GP) into indole and D-glyceraldehyde-3-phosphate (G3P).

18. The method of claim 3, wherein the artificial DNA construct further comprises a transcribable nucleic acid sequence comprising:

(a) SEQ ID NO: 1 (TSA1), or a nucleotide sequence at least 95% identical thereto and encoding a polypeptide catalyzing cleavage of indole-3-glycerol phosphate (I3GP) into indole and D-glyceraldehyde-3-phosphate (G3P); or (b) SEQ ID NO: 2 (TSA2), or a nucleotide sequence at least 95% identical thereto and encoding a polypeptide catalyzing cleavage of indole-3-glycerol phosphate (I3GP) into indole and D-glyceraldehyde-3-phosphate (G3P).

19. The artificial DNA construct of claim 14, further comprising a transcribable nucleic acid sequence comprising:

(a) SEQ ID NO: 1 (TSA1), or a nucleotide sequence at least 95% identical thereto and encoding a polypeptide catalyzing cleavage of indole-3-glycerol phosphate (I3GP) into indole and D-glyceraldehyde-3-phosphate (G3P); or (b) SEQ ID NO: 2 (TSA2), or a nucleotide sequence at least 95% identical thereto and encoding a polypeptide catalyzing cleavage of indole-3-glycerol phosphate (I3GP) into indole and D-glyceraldehyde-3-phosphate (G3P).

* * * * *

SEQUENCE LISTING

<160> NUMBER OF SEQ ID NOS: 62

<210> SEQ ID NO 1
<211> LENGTH: 936
<212> TYPE: DNA
<213> ORGANISM: artificial sequence
<220> FEATURE:
<223> OTHER INFORMATION: Synthetic Construct

<400> SEQUENCE: 1
atggcgattg ctttcaaatc cggcgtctgc ttcctccaat ccgcaaaacc ccaaatcgga 60
atccgccatt catcccctga ttcttcgctt tcattcaaga gattgactcc catagctgcc 120
ctctccacct cttctcctac tctcggtctc gccgatactt tcaaagagct caaaaaacaa 180
ggcaaagtag cattcatacc gtacatcaca gctggtgatc cagatctctc tactactgca 240
gaagcattga aagttcttgc cgcttctggg tcagacatta ttgaattggg tgttccttac 300
tctgaccctt tagctgatgg acctgttatt caggctgcgg cgacaagggc tttggagaat 360
gggaccaacc ttgataacat ccttgacatg ttagataagg ttcttccaca agtatcttgt 420
ccagtttcgc tgttcacgta ttacaacccg attcttaaac gtgggttggg gaagttcatg 480
tccagcatca gagatgttgg tgtacaggga cttgtggttc cagatgttcc tcttgaggaa 540
accgagatgc tgagaaaaga agcccttaac aacaacattg aactggtcct actcactaca 600
ccaaccacac caacagagcg aatgaagcga attgttgatg catcagaggg atttatttac 660
cttgtgagtt caatcggagt gactggtgca cgagcatctg taagcggaaa ggttcagtcg 720
ctcttgaagg atatcaaaga ggcaacagac aagccagtgg cggtcggttt tggaatatca 780
cagcccgagc atgtgaaaca gatagctggt tggggagctg atggagtgat tgtaggcagt 840
gcaatggtga ggcttttggg agatgccaag tcgccaacgg aagggcttaa ggagcttgag 900
cgtctcacaa agtctctcaa atctgctctt ctttga 936

<210> SEQ ID NO 2
<211> LENGTH: 828
<212> TYPE: DNA
<213> ORGANISM: artificial sequence
<220> FEATURE:
<223> OTHER INFORMATION: Synthetic Construct

<400> SEQUENCE: 2
atggatcttc tcaagaaccc tcccacaacg gtgggtctat cagagacttt cgctaggttg 60
aagtctaaag gcaaagtggc tctgattcca tatatcacag ctggtgatcc agatctttcc 120
acaacagcta aagctctcaa agtgctcgac tcttgtggct ctgacattat cgaactcggt 180
gttccatact ctgatccatt agctgatggt ccagcaatcc aggctgctgc gagacgttct 240
ttgcttaaag gaactaactt taactccatt atcactatgc ttaaagaggt tattcctcag 300
ttatcttgtc cgattgcatt gtttacgtat tacaacccga tcctgcggag aggaatcgag 360
aactacatga ctattataaa gaatgctgga gttcatgggc ttcttgttcc tgatgttcca 420
ctcgaagaga ctgagactct gcggaaggaa gctcaaaagc atcagattga acttgtactg 480
ctgacgacac ccacaacccc gaaagaacgg atgaatgcca ttgttgaagc atcccaagga 540
ttcatctatc tcgtaagctc agtgggagtt actggcacga gagagtctgt taacgaacac 600
gttcaatccc ttctacaaca aatcaaagag gctacaaaca agccagtcgc ggttggattt 660
ggcatatcga aacctgagca tgtgaaacag gtggctgaat ggggagcaga cggagtcatt 720
gtaggaagcg ctatggttaa gatattggga gaggctgaat cacctgagca aggactcaag 780
gagctggaag tcttcactaa atctttaaag tctgctctta tctcttga 828

<210> SEQ ID NO 3
<211> LENGTH: 1497
<212> TYPE: DNA
<213> ORGANISM: artificial sequence
<220> FEATURE:
<223> OTHER INFORMATION: Synthetic Construct

<400> SEQUENCE: 3
atggtgattc ttctgtcttt tctcttgctt ctattcattc ccctactctt ctcgttcata 60
tacaccaaca agaacaaaac ctcaagtaat cttccttcgg gcccagcaca aattccgata 120
atcggaaacc tacaccagat ccagggattg cttcacagat gttttcacta tctctccaag 180
aaacacggac ctgtgatgct tctccgtcta gggtttgttc gcgtggtcgt gatctcatca 240
agtgaagcgg ctgaagacgt tcttaaaatc catgaccttg tgtgttgtac acgacctgcc 300
actaaggcct caagggtttt ctcgcgtaat ggtaaaggca tcggctttgg ggagtcatgg 360
agagacctgc gtaagcttgc ggttcgtgag tttttcagcg tgaaaaaggt tcgatctttc 420
aggtatgtca gagaggaaga gaatgagtcg atggtcaaga acctgagaga atcggctttg 480
aagcaatctc cggtggattt gagcaaaaca cttttctgct tagctgcgag tatcatcttc 540
agaaccgcct tcggacagag tttcttcgag aacaagcata tcgataagga aaggatcgaa 600
ggactcatgt tagaagctca cagtaacatg tctttcaact tcactgatat cttccccgct 660
gctggttttg gatcgtttat ggactttgtg tcagggaaac ataagagact tcacgatgtc 720
ttcactgagg ttgatacttt tattagtcat atcattgatg atcatcaatt gaagagtttc 780
acacaagatc gtcctgattt catcgattcc atattagaaa tgatacgtaa acaagaacaa 840
aatgaatctt tcaagctcac cattgataat ctcaaaggga tcagccaaga tatatatctt 900
gctggagtag acacaagcgc catcaccatg atttggacga tggcagagct tgttagaaac 960
cctagagtga tgaaaactgt ccaagacgag atcagaaatt gcattggaac caaacacaaa 1020
gagagaatcg aggaagaaga tctcaataag cttcaatact tgaagcttgt ggtgaaagaa 1080
agcttaagac tacacccacc agctcctctg ctactcccca gagaaacaat gagccagatc 1140
aagattcaag gctacgacat accaccaaaa accgttgtaa tggttaatgc ttggtcgata 1200
ggtcgggatc ctaaacactg ggaagatcca gaagagttta tcccggagag gtttatcaat 1260
tgtcctgtag attacaaagg acatagcttt gagatgttac catttggttc tggacggagg 1320
atctgcccag gaatggcttc agggattgct accattgaat tgggactctt gaatttgctt 1380
tactacttcg attggagatt gcctgaggag aagaaagata tggacatgga agaagctggt 1440
ggtcttactg ttgttaagaa agttcctctt gagcttatcc ccattcttcg tcagtga 1497

<210> SEQ ID NO 4
<211> LENGTH: 1512
<212> TYPE: DNA
<213> ORGANISM: artificial sequence
<220> FEATURE:
<223> OTHER INFORMATION: Synthetic Construct

<400> SEQUENCE: 4
atgtcgatta ttctgtattt cttttcgttt ttgcttctcc ccgctctttt ctcgttaatt 60
ttagtgaaga aaatcaaaga cacgaaacaa aaccttcctc cgagcccacc aaagcttccg 120
atcatcggta acctacacca gcttcgagga ttgtttcaca gatgtcttca tgatttgtcc 180

-continued

```
aagaaacatg gacccgtgtt gcttctccgt ctaggttttc tcgaaatggt tgttatctcc    240

tcaagcgaag cagctgaaga agttctcaaa acacatgacc ttgagtgttg taccagaccg    300

aacactcacg cctcatccat attctggcgt aatggtaaag acattggctt tgccccatat    360

ggtgaggggt ggaaagaggt tcgcaagctt gctgttctca attttttcag cgcgacaaag    420

gttcgatctt tcaggtacat cagagaggaa gagaatgatt tgatggtcaa gcaactgaag    480

gaattagctc aaaagaagtc tccagtggat ttgagccaaa cgtttttctg tctagccgga    540

agtatcatat tcagatctgc ctttggacag cgtttctacg agaacgttca tgtcgacaag    600

gaaaggatca aagacctcat gttcgaggcc cagagaattg gatctgtaag tagctctgat    660

attttccctg gtttgggatg gtttatggac ttttttttcag gacgacatag gagacttcac    720

caagttttcg acgaggttga tactttgctg agtcatataa ttgatgatca cttgaagaat    780

cctgacgaaa aaacaaatca agatcgccct gatatcgtcg actccatctt aaaaactatg    840

caaagtcaag aagaagatga atctttcaag ttcaccattg atcatctcaa aggaatcatc    900

caagatatat atcttgctgg aatagacaca agtgccatca ccatgatctg ggcaatggca    960

gagctcgtta gaaaccctag agtgatgaaa aaagtccaag acgagatcag aacttgcatt   1020

ggaatcaaac aaaaggagag aatcgaggaa gaagatatcg acaagcttca gtactttaag   1080

cttgtgatca aagaaacctt aagactacac ccagcatctc ctatgttact cccaagagaa   1140

acaatgagtc aaatcaagat tcaaggctac gacattccgc caaaaaccat tctactggtt   1200

aacagttggt cgataggtcg agatcctaaa cactggaaag atccagaaga gtttatccct   1260

gagaggttca tcgattgtcc tgtagattac aaaggacaga gctttgagat gttaccattt   1320

ggttctggac ggagggtgtg cccaggaatg gcttcagggc ttgcgaccgt tgaattggga   1380

ctcttgaatt tactttacta cttcgattgg agtttgcctg aggggaagaa agttatggac   1440

atggaagaag ctggtgatgc taccattatt aagaaatttc ctcttgagct tcttccaact   1500

cttcatggtt aa                                                       1512


<210> SEQ ID NO 5
<211> LENGTH: 1537
<212> TYPE: DNA
<213> ORGANISM: artificial sequence
<220> FEATURE:
<223> OTHER INFORMATION: Synthetic Construct

<400> SEQUENCE: 5

cctaggaggt accatatgct ggttgtaatt ctgctgtctt tcctgctgct gctgttcatt     60

ccactgctgt tctctttcat ctatacgaac aaaaacaaaa cttcctctaa cctgccgtct    120

ggccctgcgc agatcccgat tatcggcaac ctgcaccaga ttcagggcct gctgcatcgc    180

tgcttccact atctgagcaa aaagcacggc ccggtgatgc tgctgcgtct gggcttcgtt    240

cgtgttgttg tgatctcttc ttctgaagct gctgaggacg tgctgaagat tcacgatctg    300

gtgtgttgca cccgtccggc gaccaaagcg tcccgcgtct tcagccgtaa cggcaaaggc    360

atcggtttcg gcgaatcctg gcgcgaactg cgtaaactgg cggtgcgtga attctttagc    420

gtgaaaaagt ttcgttcttt ccgttacgtt cgtgaggaag aatctgattt catggttaag    480

aacctgcgcg agtccgctct gaaacagtct ccggttgatc tgtccaaaac tctgttctgt    540

ctgagcgcct ctatcgtctt tcgtaccgcc ttcggccaga gcttctttga aaacaaacac    600

atcgacaaag aacgtatcga cggcctgatg ctggaagcac actctaatat gtcctttacc    660

tttacggaca ttttcccggc ggcgggtttt ggctctttca tggacttcgt ttctggcaaa    720
```

-continued

```
cataaacgtc tgcacgacgt gttcacggaa gtagacactt tcatctctca catcatcgac    780

gaccaccagc tgaagtcctt cactaaagat cgtccagact tcatcgattc tattctggaa    840

atgattcgca aacaagagca aaacgagtcc ttcaaactga ctatcgataa cctgaaaggt    900

attagccagg acatctacct ggccggtgtt gacaccagcg caatcaccat gatctggact    960

atggcagaac tggttcgcaa tccgcgcgta atgaaaacgg ttcaggacga aattcgcaac   1020

tgcatcggta ccaaacacaa agaacgcatt gaagaagaag atctgaacaa actgcaatac   1080

ctgaaactgg tggtcaaaga atccctgcgt ctgcaccctc cggctcctct gctgctgcca   1140

cgtgaaacca tgtcccagat caaaatccag ggttatgaca tcccgccgaa aaccgtcgtt   1200

atggttaatg cttggagcat cggtcgcgat ccaaaacatt gggaggaccc ggaggagttc   1260

atcccggagc gttttatgaa ctgcccggtg gattacaaag gtcacagctt tgaaatgctg   1320

ccgtttggtt ctggtcgtcg tatctgtccg ggtatggcat ctggtattgc aaccatcgaa   1380

ctgggtctgc tgaacctgct gtactacttc gattggcgtc tgccggaaga aaagaaggat   1440

atggatatgg aagaagctgg tggcctgacc gtagtaaaaa aggtaccgct ggaactgatt   1500

ccgatcctgc gtcagcacca ccaccatcac cactagt                            1537
```

<210> SEQ ID NO 6
<211> LENGTH: 1531
<212> TYPE: DNA
<213> ORGANISM: artificial sequence
<220> FEATURE:
<223> OTHER INFORMATION: Synthetic Construct

<400> SEQUENCE: 6

```
atgtctatta tcctgtactt tttctctttc ctgctgctgc cggctctgtt ctctctgatc     60

ctggtaaaaa agattaaaga caccaaacag aacctgccgc cgagcccgcc gaaactgcct    120

atcatcggca acctgcacca actgcgtggt ctgtttcacc gctgtctgca cgacctgtct    180

aagaaacatg gcccggttct gctgctgcgc ctgggttttc tggaaatggt tgtcatctct    240

agctccgaag ctgccgaaga ggttctgaaa acccatgatc tggaatgctg cactcgtccg    300

aacacccacg cgagcagcat tttttggcgt aacggcaagg atattggctt cgctccgtac    360

ggcgaaggct ggaaagaagt gcgcaaactg gcggtgctga acttcttttc tgctaccaaa    420

gtgcgttctt tccgctacat ccgtgaggaa gaaaacgacc tgatggttaa acagctgaaa    480

gaactggcac agaagaaatc tccggtcgat ctgagccaaa cgttcttctg cctggcgggc    540

agcattattt tccgtagcgc atttggtcag cgtttctacg agaacgttca cgtggacaaa    600

gagcgtatca aagacctgat gtttgaagct caacgtattg gctccgtaag ctcttccgat    660

atcttccctg gcctgggttg gttcatggac ttcttcagcg gtcgccaccg tcgtctgcac    720

caggtttttg acgaagtaga tactctgctg tcccacatca ttgatgatca cctgaaaaac    780

ccggacgaga aaactaacca ggatcgcccg gatatcgtag actccatcct gaaaactatg    840

cagtcccagg aagaagatga gtccttcaaa ttcaccatcg accacctgaa aggtattatc    900

caggacattt atctggcagg tatcgacacc tccgcaatta ccatgatttg ggcaatggcc    960

gaactggttc gcaatccacg tgtcatgaaa aaggttcagg acgaaatccg tacttgtatc   1020

ggcatcaaac agaaagaacg tatcgaagag gaagacatcg ataaactgca gtatttcaaa   1080

ctggtgatca aagaaaccct gcgcctgcac cctgcgtccc cgatgctgct gccacgtgaa   1140

acgatgtctc agattaaaat ccagggttac gacatcccgc cgaagaccat cctgctggtg   1200
```

-continued

```
aatagctggt ccattggtcg tgacccgaaa cactggaaag atccggaaga gttcatcccg   1260

gaacgtttta tcgattgtcc ggttgattat aaaggtcaga gcttcgagat gctgccattc   1320

ggttctggtc gtcgcgtttg cccaggtatg gcctctggtc tggcgactgt agaactgggc   1380

ctgctgaacc tgctgtatta cttcgattgg tccctgccgg aaggtaaaaa ggtgatggac   1440

atggaagaag ctggcgacgc gaccatcatc aagaaattcc cgctggaact gctgccaacg   1500

ctccatggtc accaccacca tcaccactag t                                  1531
```

<210> SEQ ID NO 7
<211> LENGTH: 1501
<212> TYPE: DNA
<213> ORGANISM: artificial sequence
<220> FEATURE:
<223> OTHER INFORMATION: Synthetic Construct

<400> SEQUENCE: 7

```
catatgaaaa agacagctat cgcgattgca gtggcactgg ctggtttcgc taccgtagcg     60

caggccgctc cgatgctagc ggtgatggcc ggtattattc tgttcttccg ttccaaacgt    120

cattcctctg ttaaactgcc gccgggtaac ctgggtttcc cactggtagg tgaaacgctg    180

cagttcgtac gcagcctggg ttcctccact ccgcagcagt tcatcgagga acgcatgtcc    240

aaattcggcg acgtattcaa aactagcatc attggtcacc cgaccgttgt tctgtgtggc    300

ccggcaggca accgtctggt gctgagcaat gaaaacaaac tggtacagat gtcttggccg    360

tcttccatga tgaagctgat cggcgaggat tgcctgggcg gcaaaacggg tgaacaacac    420

cgtattgttc gtgctgcact gactcgcttc ctgggtcctc aggcactgca aaatcacttc    480

gcaaagatgt cctctggcat tcaacgtcac atcaacgaga aatggaaggg taaagacgaa    540

gccaccgtgc tgccgctggt taaagacctg gtgttctctg ttgcatctcg tctgttcttt    600

ggtatcaccg aagaacacct gcaggagcaa ctgcataacc tgctggaggt gatcctggtt    660

ggttctttct ctgtgccgct gaacattccg ggtttctcct atcacaaagc tatccaggcg    720

cgtgctaccc tggccgacat tatgacccac ctgatcgaaa aacgtcgtaa cgaactgcgt    780

gcgggcaccg cctctgaaaa ccaggacctg ctgtccgttc tgctgacttt tacggatgaa    840

cgtggcaatt ctctggcgga taaagaaatt ctggacaact tctctatgct gctgcatggt    900

agctatgata gcaccaactc cccgctgact atgctgatca aagtgctggc gagccacccg    960

gaatcttacg aaaaagtggc tcaggaacag ttcggtatcc tgagcaccaa gatggaaggc   1020

gaagagatcg cgtggaaaga tctgaaggaa atgaaataca gctggcaggt tgtccaggaa   1080

accctgcgca tgtacccacc gatttttggt accttccgta aagctatcac cgacatccac   1140

tataacggct acacgatccc gaaaggctgg aaactgctgt ggactactta ttctacccag   1200

accaaggaag agtacttcaa agatgcggat cagtttaaac cgtcccgctt cgaagaagaa   1260

ggcaaacatg tcaccccgta cacctacctg ccgtttggcg gtggtatgcg cgtttgccca   1320

ggttgggagt ttgcgaaaat ggaaactctg ctgttcctgc accatttcgt aaaagcgttt   1380

tctggtctga aagcgatcga ccctaacgaa aaactgtccg gcaaaccgct gcctccgctg   1440

ccggttaacg gtctgccgat caaactgtac agccgctctc accaccacca tcaccactag   1500

t                                                                   1501
```

<210> SEQ ID NO 8
<211> LENGTH: 60
<212> TYPE: DNA
<213> ORGANISM: artificial sequence
<220> FEATURE:
<223> OTHER INFORMATION: Synthetic Construct

<400> SEQUENCE: 8
gctgtcaacg atacgctacg taacggcatg acagtgtttt tttttttttt tttttttttt 60

<210> SEQ ID NO 9
<211> LENGTH: 25
<212> TYPE: DNA
<213> ORGANISM: artificial sequence
<220> FEATURE:
<223> OTHER INFORMATION: Synthetic Construct

<400> SEQUENCE: 9
gctgtcaacg atacgctacg taacg 25

<210> SEQ ID NO 10
<211> LENGTH: 24
<212> TYPE: DNA
<213> ORGANISM: artificial sequence
<220> FEATURE:
<223> OTHER INFORMATION: Synthetic Construct

<400> SEQUENCE: 10
cagtatctcc aagaaaacgg agca 24

<210> SEQ ID NO 11
<211> LENGTH: 25
<212> TYPE: DNA
<213> ORGANISM: artificial sequence
<220> FEATURE:
<223> OTHER INFORMATION: Synthetic Construct

<400> SEQUENCE: 11
ggtacagagg cctttaagta tctct 25

<210> SEQ ID NO 12
<211> LENGTH: 32
<212> TYPE: DNA
<213> ORGANISM: artificial sequence
<220> FEATURE:
<223> OTHER INFORMATION: Synthetic Construct

<400> SEQUENCE: 12
caccatggtg attcttctgt cttttctctt gc 32

<210> SEQ ID NO 13
<211> LENGTH: 34
<212> TYPE: DNA
<213> ORGANISM: artificial sequence
<220> FEATURE:
<223> OTHER INFORMATION: Synthetic Construct

<400> SEQUENCE: 13
caccatgtcg attattctgt atttcttttc gttt 34

<210> SEQ ID NO 14
<211> LENGTH: 27
<212> TYPE: DNA
<213> ORGANISM: artificial sequence
<220> FEATURE:
<223> OTHER INFORMATION: Synthetic Construct

<400> SEQUENCE: 14
tcactgacga agaatgggga taagctc 27

<210> SEQ ID NO 15
<211> LENGTH: 27
<212> TYPE: DNA
<213> ORGANISM: artificial sequence
<220> FEATURE:
<223> OTHER INFORMATION: Synthetic Construct

<400> SEQUENCE: 15
taaccatgaa gagttggaag aagctca 27

<210> SEQ ID NO 16
<211> LENGTH: 43
<212> TYPE: DNA
<213> ORGANISM: artificial sequence
<220> FEATURE:
<223> OTHER INFORMATION: Synthetic Construct

<400> SEQUENCE: 16
ccgctccgat gctagtggtg attcttctgt cttttctctt gct 43

<210> SEQ ID NO 17
<211> LENGTH: 40
<212> TYPE: DNA
<213> ORGANISM: artificial sequence
<220> FEATURE:
<223> OTHER INFORMATION: Synthetic Construct

<400> SEQUENCE: 17
aaaattattt ctagatcact gacgaagaat ggggataagc 40

<210> SEQ ID NO 18
<211> LENGTH: 44
<212> TYPE: DNA
<213> ORGANISM: artificial sequence
<220> FEATURE:
<223> OTHER INFORMATION: Synthetic Construct

<400> SEQUENCE: 18
ccgctccgat gctagtgtcg attattctgt atttcttttc gttt 44

<210> SEQ ID NO 19
<211> LENGTH: 43
<212> TYPE: DNA
<213> ORGANISM: artificial sequence
<220> FEATURE:
<223> OTHER INFORMATION: Synthetic Construct

<400> SEQUENCE: 19
aaaattattt ctagattaac catgaagagt tggaagaagc tca 43

<210> SEQ ID NO 20
<211> LENGTH: 36
<212> TYPE: DNA
<213> ORGANISM: artificial sequence
<220> FEATURE:
<223> OTHER INFORMATION: Synthetic Construct

<400> SEQUENCE: 20
ggagatataa ccatgcgtcg ctccggttct gggaat 36

<210> SEQ ID NO 21
<211> LENGTH: 46
<212> TYPE: DNA
<213> ORGANISM: artificial sequence
<220> FEATURE:
<223> OTHER INFORMATION: Synthetic Construct

<400> SEQUENCE: 21
tatcatcgat aagctttacc atacatctct aagatatctt ccactg 46

<210> SEQ ID NO 22
<211> LENGTH: 43
<212> TYPE: DNA
<213> ORGANISM: artificial sequence
<220> FEATURE:
<223> OTHER INFORMATION: Synthetic Construct

<400> SEQUENCE: 22
gcttaggagg tcatcatatg aaaaagacag ctatcgcgat tgc 43

<210> SEQ ID NO 23
<211> LENGTH: 35
<212> TYPE: DNA
<213> ORGANISM: artificial sequence
<220> FEATURE:
<223> OTHER INFORMATION: Synthetic Construct

<400> SEQUENCE: 23
aaaattattt ctagactagt ggtgatggtg gtggt 35

<210> SEQ ID NO 24
<211> LENGTH: 27
<212> TYPE: DNA
<213> ORGANISM: artificial sequence
<220> FEATURE:
<223> OTHER INFORMATION: Synthetic Construct

<400> SEQUENCE: 24
agcttatcga tgataagctg tcaaaca 27

<210> SEQ ID NO 25
<211> LENGTH: 35
<212> TYPE: DNA
<213> ORGANISM: artificial sequence
<220> FEATURE:
<223> OTHER INFORMATION: Synthetic Construct

<400> SEQUENCE: 25
agccatattt atatctcctt cttaaagtta aacaa 35

<210> SEQ ID NO 26
<211> LENGTH: 24
<212> TYPE: DNA
<213> ORGANISM: artificial sequence
<220> FEATURE:
<223> OTHER INFORMATION: Synthetic Construct

<400> SEQUENCE: 26
gcagtctcca tagcttctta caat 24

<210> SEQ ID NO 27
<211> LENGTH: 25
<212> TYPE: DNA
<213> ORGANISM: artificial sequence
<220> FEATURE:
<223> OTHER INFORMATION: Synthetic Construct

<400> SEQUENCE: 27
caccatggcg attgctttca aatcc 25

<210> SEQ ID NO 28

<211> LENGTH: 25
<212> TYPE: DNA
<213> ORGANISM: artificial sequence
<220> FEATURE:
<223> OTHER INFORMATION: Synthetic Construct

<400> SEQUENCE: 28
tcaaagaaga gcagatttga gagac 25

<210> SEQ ID NO 29
<211> LENGTH: 25
<212> TYPE: DNA
<213> ORGANISM: artificial sequence
<220> FEATURE:
<223> OTHER INFORMATION: Synthetic Construct

<400> SEQUENCE: 29
cgctagtgac caacattcat tttct 25

<210> SEQ ID NO 30
<211> LENGTH: 28
<212> TYPE: DNA
<213> ORGANISM: artificial sequence
<220> FEATURE:
<223> OTHER INFORMATION: Synthetic Construct

<400> SEQUENCE: 30
caccatggat cttctcaaga accctccc 28

<210> SEQ ID NO 31
<211> LENGTH: 27
<212> TYPE: DNA
<213> ORGANISM: artificial sequence
<220> FEATURE:
<223> OTHER INFORMATION: Synthetic Construct

<400> SEQUENCE: 31
tcaagagata agagcagact ttaaaga 27

<210> SEQ ID NO 32
<211> LENGTH: 41
<212> TYPE: DNA
<213> ORGANISM: artificial sequence
<220> FEATURE:
<223> OTHER INFORMATION: Synthetic Construct

<400> SEQUENCE: 32
ccgctccgat gctagtgctg gttgtaattc tgctgtcttt c 41

<210> SEQ ID NO 33
<211> LENGTH: 47
<212> TYPE: DNA
<213> ORGANISM: artificial sequence
<220> FEATURE:
<223> OTHER INFORMATION: Synthetic Construct

<400> SEQUENCE: 33
ccgctccgat gctagtgtct attatcctgt actttttctc tttcctg 47

<210> SEQ ID NO 34
<211> LENGTH: 38
<212> TYPE: DNA
<213> ORGANISM: artificial sequence
<220> FEATURE:
<223> OTHER INFORMATION: Synthetic Construct

<400> SEQUENCE: 34
ccatgattac gaattccatg gcgattgctt tcaaatcc 38

<210> SEQ ID NO 35
<211> LENGTH: 41
<212> TYPE: DNA
<213> ORGANISM: artificial sequence
<220> FEATURE:
<223> OTHER INFORMATION: Synthetic Construct

<400> SEQUENCE: 35
ggccagtgcc aagctttcaa agaagagcag atttgagaga c 41

<210> SEQ ID NO 36
<211> LENGTH: 41
<212> TYPE: DNA
<213> ORGANISM: artificial sequence
<220> FEATURE:
<223> OTHER INFORMATION: Synthetic Construct

<400> SEQUENCE: 36
ccatgattac gaattccatg gatcttctca agaaccctcc c 41

<210> SEQ ID NO 37
<211> LENGTH: 43
<212> TYPE: DNA
<213> ORGANISM: artificial sequence
<220> FEATURE:
<223> OTHER INFORMATION: Synthetic Construct

<400> SEQUENCE: 37
ggccagtgcc aagctttcaa gagataagag cagactttaa aga 43

<210> SEQ ID NO 38
<211> LENGTH: 1485
<212> TYPE: DNA
<213> ORGANISM: artificial sequence
<220> FEATURE:
<223> OTHER INFORMATION: Synthetic Construct

<400> SEQUENCE: 38
atgctggcct cagggatgct tctggtggcc ttgctggtct gcctgactgt aatggtcttg 60
atgtctgttt ggcagcagag gaagagcaag gggaagctgc ctccgggacc caccccattg 120
cccttcattg gaaactacct gcagctgaac acagagcaga tgtacaactc cctcatgaag 180
atcagtgagc gctatggccc cgtgttcacc attcacttgg ggccccggcg ggtcgtggtg 240
ctgtgtggac atgatgccgt cagggaggct ctggtggacc aggctgagga gttcagcggg 300
cgaggcgagc aagccacctt cgactgggtc ttcaaaggct atggcgtggt attcagcaac 360
ggggagcgcg ccaagcagct ccggcgcttc tccatcgcca ccctgcggga cttcggggtg 420
ggcaagcgag gcatcgagga gcgcatccag gaggaggcgg gcttcctcat cgacgccctc 480
cggggcactg gcggcgccaa tatcgatccc accttcttcc tgagccgcac agtctccaat 540
gtcatcagct ccattgtctt tggggaccgc tttgactata aggacaaaga gttcctgtca 600
ctgttgcgca tgatgctagg aatcttccag ttcacgtcaa cctccacggg gcagctctat 660
gagatgttct cttcggtgat gaaacacctg ccaggaccac agcaacaggc ctttcagttg 720
ctgcaagggc tggaggactt catagccaag aaggtggagc acaaccagcg cacgctggat 780
cccaattccc cacgggactt cattgactcc tttctcatcc gcatgcagga ggaggagaag 840
aaccccaaca cggagttcta cttgaaaaac ctggtgatga ccacgttgaa cctcttcatt 900

```
gggggcaccg agaccgtcag caccaccctg cgctatggct tcttgctgct catgaagcac     960
ccagaggtgg aggccaaggt ccatgaggag attgacagag tgatcggcaa gaaccggcag    1020
cccaagtttg aggaccgggc caagatgccc tacatggagg cagtgatcca cgagatccaa    1080
agatttggag acgtgatccc catgagtttg gcccgcagag tcaaaaagga caccaagttt    1140
cgggatttct tcctccctaa gggcaccgaa gtgtacccta tgctgggctc tgtgctgaga    1200
gaccccagtt tcttctccaa cccccaggac ttcaatcccc agcacttcct gaatgagaag    1260
gggcagttta agaagagtga tgcttttgtg cccttttcca tcggaaagcg gaactgtttc    1320
ggagaaggcc tggccagaat ggagctcttt ctcttcttca ccaccgtcat gcagaacttc    1380
cgcctcaagt cctcccagtc acctaaggac attgacgtgt cccccaaaca cgtgggcttt    1440
gccacgatcc cacgaaacta caccatgagc ttcctgcccc gctga                    1485
```

<210> SEQ ID NO 39
<211> LENGTH: 2043
<212> TYPE: DNA
<213> ORGANISM: artificial sequence
<220> FEATURE:
<223> OTHER INFORMATION: Synthetic Construct

<400> SEQUENCE: 39

```
atgatcaaca tgggagactc ccacgtggac accagctcca ccgtgtccga ggcggtggcc      60
gaagaagtat ctcttttcag catgacggac atgattctgt tttcgctcat cgtgggtctc     120
ctaacctact ggttcctctt cagaaagaaa aaagaagaag tccccgagtt caccaaaatt     180
cagacattga cctcctctgt cagagagagc agctttgtgg aaaagatgaa gaaaacgggg     240
aggaacatca tcgtgttcta cggctcccag acggggactg cagaggagtt tgccaaccgc     300
ctgtccaagg acgcccaccg ctacgggatg cgaggcatgt cagcggaccc tgaggagtat     360
gacctggccg acctgagcag cctgccagag atcgacaacg ccctggtggt tttctgcatg     420
gccacctacg gtgagggaga ccccaccgac aatgcccagg acttctacga ctggctgcag     480
gagacagacg tggatctctc tggggtcaag ttcgcggtgt ttggtcttgg gaacaagacc     540
tacgagcact tcaatgccat gggcaagtac gtggacaagc ggctggagca gctcggcgcc     600
cagcgcatct ttgagctggg gttgggcgac gacgatggga acttggagga ggacttcatc     660
acctggcgag agcagttctg gccggccgtg tgtgaacact ttggggtgga agccactggc     720
gaggagtcca gcattcgcca gtacgagctt gtggtccaca ccgacataga tgcggccaag     780
gtgtacatgg gggagatggg ccggctgaag agctacgaga accagaagcc ccccttgat      840
gccaagaatc cgttcctggc tgcagtcacc accaaccgga agctgaacca gggaaccgag     900
cgccacctca tgcacctgga attggacatc tcggactcca aaatcaggta tgaatctggg     960
gaccacgtgg ctgtgtaccc agccaacgac tctgctctcg tcaaccagct gggcaaaatc    1020
ctgggtgccg acctggacgt cgtcatgtcc ctgaacaacc tggatgagga gtccaacaag    1080
aagcacccat tcccgtgccc tacgtcctac cgcacggccc tcacctacta cctggacatc    1140
accaacccgc cgcgtaccaa cgtgctgtac gagctggcgc agtacgcctc ggagccctcg    1200
gagcaggagc tgctgcgcaa gatggcctcc tcctccggcg agggcaagga gctgtacctg    1260
agctgggtgg tggaggcccg gaggcacatc ctggccatcc tgcaggactg cccgtccctg    1320
cggcccccca tcgaccacct gtgtgagctg ctgccgcgcc tgcaggcccg ctactactcc    1380
atcgcctcat cctccaaggt ccaccccaac tctgtgcaca tctgtgcggt ggttgtggag    1440
tacgagacca aggctggccg catcaacaag ggcgtggcca ccaactggct gcgggccaag    1500
```

```
gagcctgccg gggagaacgg cggccgtgcg ctggtgccca tgttcgtgcg caagtcccag   1560
ttccgcctgc ccttcaaggc caccacgcct gtcatcatgg tgggccccgg caccggggtg   1620
gcacccttca taggcttcat ccaggagcgg gcctggctgc gacagcaggg caaggaggtg   1680
ggggagacgc tgctgtacta cggctgccgc cgctcggatg aggactacct gtaccgggag   1740
gagctggcgc agttccacag ggacggtgcg ctcacccagc tcaacgtggc cttctcccgg   1800
gagcagtccc acaaggtcta cgtccagcac ctgctaaagc aagaccgaga gcacctgtgg   1860
aagttgatcg aaggcggtgc ccacatctac gtctgtgggg atgcacggaa catggccagg   1920
gatgtgcaga acaccttcta cgacatcgtg gctgagctcg ggccatgga gcacgcgcag    1980
gcggtggact acatcaagaa actgatgacc aagggccgct actccctgga cgtgtggagc   2040
tag                                                                 2043
```

```
<210> SEQ ID NO 40
<211> LENGTH: 1818
<212> TYPE: DNA
<213> ORGANISM: artificial sequence
<220> FEATURE:
<223> OTHER INFORMATION: Synthetic Construct

<400> SEQUENCE: 40
```

```
gtccccctct tttaccaagt gacaattgat ttaagcagtg tcttgtaatt atacaaccat     60
cgatgtccgt tgatttaaac agtgtcttgt aattaaaaaa atcagtttac ataaatggaa    120
aatttatcac ttagttttca tcaacttctg aacttacctt tcatggatta ggcaatactt    180
tccattttta gtaactcaag tggacccttt acttcttcaa ctccatctct ctctttctat    240
ttcacttctt tcttctcatt atatctcttg tcctctccac caaatctctt caacaaaaag    300
attaaacaaa gagagaagaa tatggtgatt cttctgtctt ttctcttgct tctattcatt    360
cccctactct tctcgttcat atacaccaac aagaacaaaa cctcaagtaa tcttccttcg    420
ggcccagcac aaattccgat aatcggaaac ctacaccaga tccagggatt gcttcacaga    480
tgttttcact atctctccaa gaaacacgga cctgtgatgc ttctccgtct agggtttgtt    540
cgcgtggtcg tgatctcatc aagtgaagcg gctgaagacg ttcttaaaat ccatgacctt    600
gtgtgttgta cacgacctgc cactaaggcc tcaagggttt tctcgcgtaa tggtaaaggc    660
atcggctttg gggagtcatg gagagacctg cgtaagcttg cggttcgtga gtttttcagc    720
gtgaaaaagg ttcgatcttt caggtatgtc agagaggaag agaatgagtc gatggtcaag    780
aacctgagag aatcggcttt gaagcaatct ccggtggatt tgagcaaaac acttttctgc    840
ttagctgcga gtatcatctt cagaaccgcc ttcggacaga gtttcttcga gaacaagcat    900
atcgataagg aaaggatcga aggactcatg ttagaagctc acagtaacat gtctttcaac    960
ttcactgata tcttccccgc tgctggtttt ggatcgttta tggactttgt gtcagggaaa   1020
cataagagac ttcacgatgt cttcactgag gttgatactt ttattagtca tatcattgat   1080
gatcatcaat tgaagagttt cacacaagat cgtcctgatt tcatcgattc catattagaa   1140
atgatacgta aacaagaaca aaatgaatct ttcaagctca ccattgataa tctcaaaggg   1200
atcagccaag atatatatct tgctggagta gacacaagcg ccatcaccat gatttggacg   1260
atggcagagc ttgttagaaa ccctagagtg atgaaaactg tccaagacga gatcagaaat   1320
tgcattggaa ccaaacacaa agagagaatc gaggaagaag atctcaataa gcttcaatac   1380
ttgaagcttg tggtgaaaga aagcttaaga ctacacccac cagctcctct gctactcccc   1440
```

agagaaacaa tgagccagat caagattcaa ggctacgaca taccaccaaa aaccgttgta 1500
atggttaatg cttggtcgat aggtcgggat cctaaacact gggaagatcc agaagagttt 1560
atcccggaga ggtttatcaa ttgtcctgta gattacaaag gacatagctt tgagatgtta 1620
ccatttggtt ctggacggag gatctgccca ggaatggctt cagggattgc taccattgaa 1680
ttgggactct tgaatttgct ttactacttc gattggagat tgcctgagga gaagaaagat 1740
atggacatgg aagaagctgg tggtcttact gttgttaaga aagttcctct tgagcttatc 1800
cccattcttc gtcagtga 1818

<210> SEQ ID NO 41
<211> LENGTH: 1149
<212> TYPE: DNA
<213> ORGANISM: artificial sequence
<220> FEATURE:
<223> OTHER INFORMATION: Synthetic Construct

<400> SEQUENCE: 41
gtccccctct tttaccaagt gacaattgat ttaagcagtg tcttgtaatt atacaaccat 60
cgatgtccgt tgatttaaac agtgtcttgt aattaaaaaa atcagtttac ataaatggaa 120
aatttatcac ttagttttca tcaacttctg aacttacctt tcatggatta ggcaatactt 180
tccattttta gtaactcaag tggacccttt acttcttcaa ctccatctct ctctttctat 240
ttcacttctt tcttctcatt atatctcttg tcctctccac caaatctctt caacaaaaag 300
attaaacaaa gagagaagaa tatggatctt ctcaagaacc ctcccacaac ggtgggtcta 360
tcagagactt tcgctaggtt gaagtctaaa ggcaaagtgg ctctgattcc atatatcaca 420
gctggtgatc cagatctttc cacaacagct aaagctctca aagtgctcga ctcttgtggc 480
tctgacatta tcgaactcgg tgttccatac tctgatccat tagctgatgg tccagcaatc 540
caggctgctg cgagacgttc tttgcttaaa ggaactaact ttaactccat tatcactatg 600
cttaaagagg ttattcctca gttatcttgt ccgattgcat tgtttacgta ttacaacccg 660
atcctgcgga gaggaatcga gaactacatg actattataa agaatgctgg agttcatggg 720
cttcttgttc ctgatgttcc actcgaagag actgagactc tgcggaagga agctcaaaag 780
catcagattg aacttgtact gctgacgaca cccacaaccc cgaaagaacg gatgaatgcc 840
attgttgaag catcccaagg attcatctat ctcgtaagct cagtgggagt tactggcacg 900
agagagtctg ttaacgaaca cgttcaatcc cttctacaac aaatcaaaga ggctacaaac 960
aagccagtcg cggttggatt tggcatatcg aaacctgagc atgtgaaaca ggtggctgaa 1020
tggggagcag acggagtcat tgtaggaagc gctatggtta agatattggg agaggctgaa 1080
tcacctgagc aaggactcaa ggagctggaa gtcttcacta aatctttaaa gtctgctctt 1140
atctcttga 1149

<210> SEQ ID NO 42
<211> LENGTH: 23
<212> TYPE: PRT
<213> ORGANISM: Artificial Sequence
<220> FEATURE:
<223> OTHER INFORMATION: Synthetic Construct

<400> SEQUENCE: 42

Met Lys Lys Thr Ala Ile Ala Ile Ala Val Ala Leu Ala Gly Phe Ala
1 5 10 15

Thr Val Ala Gln Ala Ala Pro
20

<210> SEQ ID NO 43
<211> LENGTH: 4
<212> TYPE: PRT
<213> ORGANISM: Artificial Sequence
<220> FEATURE:
<223> OTHER INFORMATION: Synthetic construct

<400> SEQUENCE: 43

Met Ala Ala Val
1

<210> SEQ ID NO 44
<211> LENGTH: 10
<212> TYPE: PRT
<213> ORGANISM: Artificial Sequence
<220> FEATURE:
<223> OTHER INFORMATION: Synthetic construct

<400> SEQUENCE: 44

Asn Asp Lys Ala Gly Asp Val Ser Asn Gly
1 5 10

<210> SEQ ID NO 45
<211> LENGTH: 1527
<212> TYPE: DNA
<213> ORGANISM: artificial sequence
<220> FEATURE:
<223> OTHER INFORMATION: Synthetic Construct

<400> SEQUENCE: 45
atgtgggaat tggtgacctt gctggggctc atcctagctt atctcttttg gcccagacaa 60
gggtcttctg gtaccaagta cccaaagagc ctcccctctc tgcccgtcgt gggcagcctg 120
ccattccttc ccaaaagcgg ccacatgcac gtgaactttt tcaaactgca gaagaaatat 180
gggtccatct attcctttcg tctgggctcc acaactacag tggtcattgg ccaccaccag 240
ctggccaggg agttgcttat caagaaggga aaggaattct ctggacggcc cctgacgacc 300
actgtggccc tcctgtcaga caatgggaag ggcattgctt ttgctgactc cagtgccact 360
tggcagctgc accggaggct ggtcctgagc tccttttccc tgttcaggga tggtgagcag 420
aagctggaga acatcatctg tcaagaactc agtgccctgt gtgattttct ggccacctgt 480
gatggacagg tcaaggattt atcttcgtca atcttcatga cggtagtcaa catcatctgc 540
atgatctgct tcagtgtctc atacaaggag ggggacatgg agttggtgac cataaggcgc 600
ttcacaacag gcttcgtgaa tagcctgagt gatgacaatc tcgtggacat attcccctgg 660
ctgaagatct tccccaataa aaccctggaa atgataagga agtatactga aatccgagga 720
gccatgctga gtaagatcct gaaagagtgc aaggagaagt tcagaagtga ctctgtctcc 780
aacctaatag acctgctcat ccaagccaag gtgaatgaaa acaacaacaa ttccagcttg 840
gaccaggact ccaatctgtt ttcagataag cacattctca ccaccttagg agacatcttt 900
ggggctggtg tggagacctc cagctccgtg gtgctctggg tcatagcctt cctgctgcac 960
aacccacagg tgaagaagaa gatccaggag gagattgacc acaatgtggg tttcagccgc 1020
acgcccacct tcagtgaccg gaaccacctg ctcatgctgg aggccaccat ccgagaggtc 1080
ctccgcatca ggccggtggc ccccatcctc atccctcaca aggctaacac tgactccagc 1140
attggagagt ttgccattga caaggacacc aatgtgcttg tcaacttgtg ggccttgcat 1200
cacaatgagc aggagtggga ccggccggac cagttcatgc ctgagcgctt cctggaccca 1260

-continued

```
acagggagcc aaatcatcgt cccctcctcg agctacttgc cctttggagc tgggccccgc   1320

tcctgtgtag gtgaggcact ggcgcgccag gagatcttcc tcatcacagc ctggttgctg   1380

cagaagtttg acctagaggt gccagagggt gggcagcttc cgtccctgga gggcatcccc   1440

aagatagttt tcctcatcga tcctttcaaa gtgaagatca cagtgcgccc ggcctggaag   1500

gaagctcagg ccgagggcag cgcctag                                         1527
```

<210> SEQ ID NO 46
<211> LENGTH: 1760
<212> TYPE: DNA
<213> ORGANISM: artificial sequence
<220> FEATURE:
<223> OTHER INFORMATION: Synthetic Construct

<400> SEQUENCE: 46

```
aagcttctta agaattatag tagcacttgt tgatatcggg gttctttttt cttaacatag     60

gttttggtgg gtagatcaac agaagacctc gctgtggaca ttgatttggg aagagaaaag    120

cggggtagca aaatatctcg acgacaggtc ggtcaatagt agatacttct atttgtattt    180

taggtcttta agttgtatga gaagcagcag cccaggatct gtaatggttg ttgtgtatgt    240

ttttttcctt tttgggttac tgaatgcagg cgatcatacg gctgggtgat gacggttcgt    300

ttcatataaa aaaccctggg gaagtattca atctcagtaa atgagaagga agtagatcct    360

ggacagagtt taatcctcaa atccgattgt ctagttgagg tttgatccgg gatactcttt    420

tatgactcat tacttacgtt ctaggtccgt acttaaaccc gatatatcgt gcgcgcagat    480

acggggaatg ccttttatat ttgaaacaaa ccaaagttgc atgcaagagt acctgaagag    540

aagagggaaa gtgaactgag accagatcaa gagtgcgtgt tgtttgtgta gatgaatgat    600

gcatctcttg tgtaatgtac cttagccata ggaacacgtc ttgtagatct tttaatacat    660

ctttagttcc gcatcatgca tagttgaccc tgttttaagg cgttgaaatg aaaatacaag    720

tctcttgtat ctgaatttgt gttttaagcg aagaatgatt gttcttgtga agttgataca    780

caagttcttt ggatatccta tcagtataaa ggataggttt ccattttcgt gactcactca    840

ctgatttcca ttgctgaaaa ttgatgatga actaagatca atccatgtag ttcaaacaac    900

agtaactgtg ccactagttt gaacaacact aactggtcga gcaaaagaaa aagagttcat    960

catatatctg atttgatgga ctgtttggag ttaggaccaa acattatcta caaacaaaga   1020

cttttctcct aacttgtgat tccttcttaa accctagggg taatattcta ttttccaagg   1080

atctttagtt aaaggcaaat ccgggaaatt attgtaatca tttggggcca catataaaag   1140

atttgagtta gatggaagtg acgattaatc caaacatata tatctctttc ttcttatttc   1200

ccaaattaac agacaaaagt agaatattgg cttttaacac caatataaaa acttgcttca   1260

cacctaaaca cttttgttta ctttagggta agtgcaaaaa gccaaccaaa tccacctgca   1320

ctgatttgac gtttacaaac gccgttaagt ttgtcaccgt ctaaacaaaa acaaagtaga   1380

agctaacgga gctccgttaa taaattgacg aaaagcaaac caagttttta gctttggtcc   1440

ccctctttta ccaagtgaca attgatttaa gcagtgtctt gtaattatac aaccatcgat   1500

gtccgttgat ttaaacagtg tcttgtaatt aaaaaaatca gtttacataa atggaaaatt   1560

tatcacttag ttttcatcaa cttctgaact tacctttcat ggattaggca atactttcca   1620

tttttagtaa ctcaagtgga ccctttactt cttcaactcc atctctctct ttctatttca   1680

cttctttctt ctcattatat ctcttgtcct ctccaccaaa tctcttcaac aaaaagatta   1740

aacaaagaga gaagaatatg                                                1760
```

```
<210> SEQ ID NO 47
<211> LENGTH: 1915
<212> TYPE: DNA
<213> ORGANISM: artificial sequence
<220> FEATURE:
<223> OTHER INFORMATION: Synthetic Construct
<220> FEATURE:
<221> NAME/KEY: misc_feature
<222> LOCATION: (842)..(842)
<223> OTHER INFORMATION: n is a, c, g, or t

<400> SEQUENCE: 47

tcacactcga aacctagtta tgtgtttgtt ttaccttact ctccttattt aaatagtcat     60

gtatttgatt ctttgtgaga ataaggactt gttttcaagt cattataaac gtcttatact    120

tgtgattagt atgagtttca atatatgatt attcggttgc aaaataaaga gtgggttcca    180

atatcattga tattactact atatattacc atatttcatg gaaattagtc atcttcgtga    240

tccaatttgt ctcgttttca tgtataatta gacaaaattt gccttctcaa tattttcgat    300

caaagaatgc taaacaagta aacatgacct gatagtgatc cgaagttaga ataatattaa    360

aaagacatag gttatttact aattcaatat accaacaata tcctattttt tttttgtcaa    420

tcaaactcca tatattaatt cacggaaaac gactcttttc tagagaaagc aaattagata    480

ccgtcgaact tacatgagaa aaacagaatc cgcgaactct tgcacatatg gtatttttgt    540

ttcagtggat acgtttctca cctgaattca cgactttttt tgtggagatt tgtaatctct    600

ggctttatag ttaataatcg agaaaatgcc aaaaagtatg cccgtactaa gtacaaaaca    660

taagaccaca aaattccaca ataaattgac acgtgtctga tcgacgtgaa tcaagaaaac    720

cataaacttg ttttgtttc aacaaccaaa gacattttcc ccataaaaat gtaagcatga    780

taaagtctaa tggttatacc aaggtctttg gtaattacac tgctcctttt tcttttttt     840

tntcttttt ttttctttt tctaaaccat ctgaatttaa ctttatttta tttacttcat    900

ttgtcaatgt gatatcttca actttcaata atttaatatg tttgattttt tagtgtagct    960

acgatattcg ataagaccta tatatgacat agagttcttg aaatagcaag tcttggtttt   1020

gccaaagtaa taacctgtaa aaataaaagc aattctttac agagattttt ggttttaaat   1080

ctacaaagtt gcaaaactcg ttgctttcat ttgatttaat ggttagtttt cgagatagac   1140

aaaatgggaa atttatttgc aaaatgattt agttgcaaaa tcattggaca ctatcttatt   1200

tcacgtttta tataattgat gacataataa gatagtttcc caaagtaatt aattgatgat   1260

atatgtggtt ggataagaaa ttatggtatt atcatgtttg cctctcaaat ttaaatctaa   1320

ttaattatat acatacacga gtaagctaaa taaaagtttg accacatttc atatgaagaa   1380

ttttatcttt ccagatatct agaatttgtt ttctctacac agttcattga agaaaacata   1440

gtacggaaga gaccagaggt taattaaacg acactttaac ctatcacgag agagactgag   1500

atgatcaaat caaatgaaag aaaataaaca tcaatcacat gcaaagagtg ttcattaagc   1560

aaaatcacta agtttgtttt tactttattt tattacgtta cttcaagttt ttttttatct   1620

tcttggtact gtaaaaaaag gagagaaaat agagttggct atgtgtaata agcgaaccaa   1680

aagcaagcct tccatgactg tgccctcaag aaagtagctt tgttttcaat cccaaactgt   1740

caaagtctct cttcacctca agattaatca aaacatttct ctctctatct catcaatgtt   1800

actttaaaac caatgctcct cttcttgttc ttcatataaa ccacatatcc tctcctccat   1860

atcttaacaa tttcatagca aaccctaaaa ttgagaaaga gatagagaga gaaag        1915
```

<210> SEQ ID NO 48
<211> LENGTH: 531
<212> TYPE: DNA
<213> ORGANISM: artificial sequence
<220> FEATURE:
<223> OTHER INFORMATION: Synthetic Construct

<400> SEQUENCE: 48
gagttaagta tgcacgtgta agaactggga agtgaaacct cctgtatggt gaagaaacta 60
tacaacaaag ccctttgttg gtgtatacgt attaattttt attcttttat cacaagcgat 120
acgtatctta agacataata aatatatatc ttactcataa taaatatctt aagatatata 180
tacagtatac acctgtatat atataataaa taggcatata gtagaaatta atatgagttg 240
ttgttgttgc aaatatataa atcaatcaaa agatttaaaa cccaccattc aatcttggta 300
agtaacgaaa aaaaagggaa gcaagaagaa ccacagaaaa gggggctaac aactagacac 360
gtagatcttc atctgcccgt ccatctaacc taccacactc tcatcttctt tttcccgtgt 420
cagtttgtta tataagctct cactctccgg tatatttcca aatacaccta acttgtttag 480
tacacaacag caacatcaaa ctctaataaa cccaagttgg tgtatactat a 531

<210> SEQ ID NO 49
<211> LENGTH: 1066
<212> TYPE: DNA
<213> ORGANISM: artificial sequence
<220> FEATURE:
<223> OTHER INFORMATION: Synthetic Construct

<400> SEQUENCE: 49
tacaatattt ggattatgtt gaaggtaatg ttgaactact taaaatagaa gaacgagaca 60
catatgaaac taaatcactt ttgcttttta gaattatgag ttgtatctta aataagttta 120
attttaggtt tgttactcgc aatattgtta ggtatacctt aaactcgatg catttaacca 180
taaagcatca gtgtgtggca tactggcatt taggtcagct tcgttttgag tatatttagt 240
acaacggata tatgtgaaac cattgttaca tttcattact tgtttgattt gttcttattg 300
agtaaaattg ggttctcgta cctaaggaat tatctcatgc ccgcgaccaa cgagcatgaa 360
cacaacttcg aaactccgct catgcacgac acttttttttt ttttttttt ttttttttt 420 ttttttaat tcagaaccta gtttttgttc aagattcata tggtttgttt caaaactgat 480
tgaacatttt tccaaaatgt ttgtaagata atatccactt cagtttatca tttgaatact 540
gtaaacggct aaacggagca ggatcccttg ttcaggctac cgtggtaaac agataaatta 600
attgaaacac gtcatttctg gaattttccc tcgttatctc aagatatgca cccaacgagg 660
tttgaaccct gttatcttat gataccttct gtccgccaca ttggagatga ttcgatttgc 720
aaattgggtc cttaatatat aattatgatt ctaaaatagt atcgttgtga tttagaatat 780
atgaactctg ataagactaa aatacttaat tatgattcta aaatagtatc atttttttt 840 tttaattaag aaaaacaagg ttgagtattt aaaattcaaa ttaaccttaa gtgtgatacc 900
tttcgggtta tgtaaatttg ctatgtagct tatttccgta ctttaagagt ttaagataaa 960
aatagaaata atagctgtaa taatatagga ataatccaaa agtacgtgaa ggaacataca 1020
tacctttctc aatgttttgc tataaaagca tgagtcttct tcacta 1066

<210> SEQ ID NO 50
<211> LENGTH: 321
<212> TYPE: DNA
<213> ORGANISM: artificial sequence
<220> FEATURE:
<223> OTHER INFORMATION: Synthetic Construct

<400> SEQUENCE: 50
gtccccctct tttaccaagt gacaattgat ttaagcagtg tcttgtaatt atacaaccat 60
cgatgtccgt tgatttaaac agtgtcttgt aattaaaaaa atcagtttac ataaatggaa 120
aatttatcac ttagttttca tcaacttctg aacttacctt tcatggatta ggcaatactt 180
tccattttta gtaactcaag tggacccttt acttcttcaa ctccatctct ctctttctat 240
ttcacttctt tcttctcatt atatctcttg tcctctccac caaatctctt caacaaaaag 300
attaaacaaa gagagaagaa t 321

<210> SEQ ID NO 51
<211> LENGTH: 1833
<212> TYPE: DNA
<213> ORGANISM: artificial sequence
<220> FEATURE:
<223> OTHER INFORMATION: Synthetic Construct

<400> SEQUENCE: 51
gtccccctct tttaccaagt gacaattgat ttaagcagtg tcttgtaatt atacaaccat 60
cgatgtccgt tgatttaaac agtgtcttgt aattaaaaaa atcagtttac ataaatggaa 120
aatttatcac ttagttttca tcaacttctg aacttacctt tcatggatta ggcaatactt 180
tccattttta gtaactcaag tggacccttt acttcttcaa ctccatctct ctctttctat 240
ttcacttctt tcttctcatt atatctcttg tcctctccac caaatctctt caacaaaaag 300
attaaacaaa gagagaagaa tatgtcgatt attctgtatt tcttttcgtt tttgcttctc 360
cccgctcttt tctcgttaat tttagtgaag aaaatcaaag acacgaaaca aaaccttcct 420
ccgagcccac caaagcttcc gatcatcggt aacctacacc agcttcgagg attgtttcac 480
agatgtcttc atgatttgtc caagaaacat ggacccgtgt tgcttctccg tctaggtttt 540
ctcgaaatgg ttgttatctc ctcaagcgaa gcagctgaag aagttctcaa aacacatgac 600
cttgagtgtt gtaccagacc gaacactcac gcctcatcca tattctggcg taatggtaaa 660
gacattggct ttgccccata tggtgagggg tggaaagagg ttcgcaagct tgctgttctc 720 aatttttca gcgcgacaaa ggttcgatct ttcaggtaca tcagagagga agagaatgat 780
ttgatggtca agcaactgaa ggaattagct caaaagaagt ctccagtgga tttgagccaa 840
acgtttttct gtctagccgg aagtatcata ttcagatctg cctttggaca gcgtttctac 900
gagaacgttc atgtcgacaa ggaaaggatc aaagacctca tgttcgaggc ccagagaatt 960
ggatctgtaa gtagctctga tattttccct ggtttgggat ggtttatgga ctttttttca 1020
ggacgacata ggagacttca ccaagttttc gacgaggttg atactttgct gagtcatata 1080
attgatgatc acttgaagaa tcctgacgaa aaaacaaatc aagatcgccc tgatatcgtc 1140
gactccatct taaaaactat gcaaagtcaa gaagaagatg aatctttcaa gttcaccatt 1200
gatcatctca aaggaatcat ccaagatata tatcttgctg gaatagacac aagtgccatc 1260
accatgatct gggcaatggc agagctcgtt agaaacccta gagtgatgaa aaaagtccaa 1320
gacgagatca gaacttgcat tggaatcaaa caaaaggaga gaatcgagga agaagatatc 1380
gacaagcttc agtactttaa gcttgtgatc aaagaaacct taagactaca cccagcatct 1440
cctatgttac tcccaagaga aacaatgagt caaatcaaga ttcaaggcta cgacattccg 1500
ccaaaaacca ttctactggt taacagttgg tcgataggtc gagatcctaa acactggaaa 1560

-continued

```
gatccagaag agtttatccc tgagaggttc atcgattgtc ctgtagatta caaaggacag   1620

agctttgaga tgttaccatt tggttctgga cggagggtgt gcccaggaat ggcttcaggg   1680

cttgcgaccg ttgaattggg actcttgaat ttactttact acttcgattg gagtttgcct   1740

gaggggaaga aagttatgga catggaagaa gctggtgatg ctaccattat taagaaattt   1800

cctcttgagc ttcttccaac tcttcatggt taa                                1833
```

<210> SEQ ID NO 52
<211> LENGTH: 2739
<212> TYPE: DNA
<213> ORGANISM: artificial sequence
<220> FEATURE:
<223> OTHER INFORMATION: Synthetic Construct

<400> SEQUENCE: 52

```
gtccccctct tttaccaagt gacaattgat ttaagcagtg tcttgtaatt atacaaccat     60

cgatgtccgt tgatttaaac agtgtcttgt aattaaaaaa atcagtttac ataaatggaa    120

aatttatcac ttagttttca tcaacttctg aacttacctt tcatggatta ggcaatactt    180

tccattttta gtaactcaag tggacccttt acttcttcaa ctccatctct ctctttctat    240

ttcacttctt tcttctcatt atatctcttg tcctctccac caaatctctt caacaaaaag    300

attaaacaaa gagagaagaa tatggatctt ctcaagaacc ctcccacaac ggtgggtcta    360

tcagagactt tcgctaggtt gaagtctaaa ggcaaagtgg ctctgattcc atatatcaca    420

gctggtgatc cagatctttc cacaacagct aaagctctca aagtgctcga ctcttgtggc    480

tctgacatta tcgaactcgg tgttccatac tctgatccat tagctgatgg tccagcaatc    540

caggctgctg cgagacgttc tttgcttaaa ggaactaact ttaactccat tatcactatg    600

cttaaagagg ttattcctca gttatcttgt ccgattgcat tgtttacgta ttacaacccg    660

atcctgcgga gaggaatcga gaactacatg actattataa agaatgctgg agttcatggg    720

cttcttgttc ctgatgttcc actcgaagag actgagactc tgcggaagga agctcaaaag    780

catcagattg aacttgtact gctgacgaca cccacaaccc cgaaagaacg gatgaatgcc    840

attgttgaag catcccaagg attcatctat ctcgtaagct cagtgggagt tactggcacg    900

agagagtctg ttaacgaaca cgttcaatcc cttctacaac aaatcaaaga ggctacaaac    960

aagccagtcg cggttggatt tggcatatcg aaacctgagc atgtgaaaca ggtggctgaa   1020

tggggagcag acggagtcat tgtaggaagc gctatggtta agatattggg agaggctgaa   1080

tcacctgagc aaggactcaa ggagctggaa gtcttcacta aatctttaaa gtctgctctt   1140

atctctctgc tgaacttcga cctccttaag cttgcgggag acgtcgagtc caacccaggt   1200

cccatggcga tcacctccat agctcatctc cgtgtcgtca atgcgaacat gagcattccg   1260

ctagctcgtc ttcgtgtcgt caatgcaaac ataagcattc cgcttaagcg gactagtttc   1320

cccaagaaat tcctgtttgg ggctggctct gcttcttacc aatatgaagg agcagcacat   1380

atagatgggc gaggacttag cgtctgggat gtcttcacta aggaacaccc tgaaaagatc   1440

gcagatcagt cgaatggaga tgttgctcaa gacttttatc accgatacaa ggaagatata   1500

aagtcgatga aggaaatggg tttggagtca ttcaggttct ccatttcatg gtcaagaata   1560

ttacctaatg ggaaaatcag tggaggaatc aacaagcttg ggatcaagtt ctacaataat   1620

ctcattgacg aactgctagc caatggaatc aagccacttg tcactatcta ccattgggac   1680

cttccacaag cacttcaaga cgaatatgga gggttcttga gccccaaaat cgtggatgac   1740

tttctggaat atgcaaacct agtttttaag gagttcgggg atagggttaa gcattgggcg   1800
```

acactgaatg aacccaatat aatgacccaa caagggtacg tatttggggc acatgcaccc 1860
ggacgatgtt ctcacttcga atggaactgc ccggctggaa actccggcac cgagccttat 1920
atagttggtc accacctcct cctatgtcat gctgcagctt ttcaactata caaacaaaag 1980
tataaggatg atcaaaaggg tataatcgga ataacaaccg cgacacagat ggccataccg 2040
ttaaacgaca acgttgccaa cctcttggca gcgtcacgag ccatcgattt caacattgga 2100
tggtttttgc atccggttgt ttacggcgag tatccacaga cgatgaggga gcggttggga 2160
agtcgactgc caaaattcac agaaaaagag tcggagatgt tgaaacaatc gttcgacttt 2220
atagggttga attactactc aactgattat gcagccgcat catctttttc agttgatcca 2280
gtgaatgtca gttacacaac tgattcccga gcaacattat cagcgataaa agatggggtt 2340
cctatcggcg acccgacatt tatgagctgg ttgcatatat atccagaggg catcctaact 2400
ctgttgcgat acgtaaagga aaggtacaac aatccatttg tcatgatcac tgagaatggg 2460
atggccgatg aaaacaaggg atcattagcg gaagatccga tggctttaaa agacaacgtc 2520
agaattcgat atcaccgcga acatctatac tatgttcttg aagctataaa ggagggtgtg 2580
aacgtgggag gatactacgc atggacatgg atggatgatt tcgagtgggg ttctggatat 2640
actcctcgat tcggtctcaa ctttgtggat ttcgacaatg atttgaagag aacccccaag 2700
gattcttact tctggttcaa ggacttcctt gcaaattaa 2739

<210> SEQ ID NO 53
<211> LENGTH: 1536
<212> TYPE: DNA
<213> ORGANISM: artificial sequence
<220> FEATURE:
<223> OTHER INFORMATION: Synthetic Construct

<400> SEQUENCE: 53
atggcgatca cctccatagc tcatctccgt gtcgtcaatg cgaacatgag cattccgcta 60
gctcgtcttc gtgtcgtcaa tgcaaacata agcattccgc ttaagcggac tagtttcccc 120
aagaaattcc tgtttggggc tggctctgct tcttaccaat atgaaggagc agcacatata 180
gatgggcgag gacttagcgt ctgggatgtc ttcactaagg aacaccctga aaagatcgca 240
gatcagtcga atggagatgt tgctcaagac ttttatcacc gatacaagga agatataaag 300
tcgatgaagg aaatgggttt ggagtcattc aggttctcca tttcatggtc aagaatatta 360
cctaatggga aaatcagtgg aggaatcaac aagcttggga tcaagttcta caataatctc 420
attgacgaac tgctagccaa tggaatcaag ccacttgtca ctatctacca ttgggacctt 480
ccacaagcac ttcaagacga atatggaggg ttcttgagcc ccaaaatcgt ggatgacttt 540
ctggaatatg caaacctagt ttttaaggag ttcgggggata gggttaagca ttgggcgaca 600
ctgaatgaac ccaatataat gacccaacaa gggtacgtat ttggggcaca tgcacccgga 660
cgatgttctc acttcgaatg gaactgcccg gctggaaact ccggcaccga gccttatata 720
gttggtcacc acctcctcct atgtcatgct gcagcttttc aactatacaa acaaaagtat 780
aaggatgatc aaaagggtat aatcggaata acaaccgcga cacagatggc cataccgtta 840
aacgacaacg ttgccaacct cttggcagcg tcacgagcca tcgatttcaa cattggatgg 900
tttttgcatc cggttgttta cggcgagtat ccacagacga tgagggagcg gttgggaagt 960
cgactgccaa aattcacaga aaaagagtcg gagatgttga aacaatcgtt cgactttata 1020
gggttgaatt actactcaac tgattatgca gccgcatcat ctttttcagt tgatccagtg 1080

```
aatgtcagtt acacaactga ttcccgagca acattatcag cgataaaaga tggggttcct   1140

atcggcgacc cgacatttat gagctggttg catatatatc cagagggcat cctaactctg   1200

ttgcgatacg taaaggaaag gtacaacaat ccatttgtca tgatcactga gaatgggatg   1260

gccgatgaaa acaagggatc attagcggaa gatccgatgg ctttaaaaga caacgtcaga   1320

attcgatatc accgcgaaca tctatactat gttcttgaag ctataaagga gggtgtgaac   1380

gtgggaggat actacgcatg gacatggatg gatgatttcg agtggggttc tggatatact   1440

cctcgattcg gtctcaactt tgtggatttc gacaatgatt tgaagagaac cccaaggat    1500

tcttacttct ggttcaagga cttccttgca aattaa                             1536
```

<210> SEQ ID NO 54
<211> LENGTH: 614
<212> TYPE: DNA
<213> ORGANISM: artificial sequence
<220> FEATURE:
<223> OTHER INFORMATION: Synthetic Construct

<400> SEQUENCE: 54

```
tttaaatcct attgtagtgt tatttataaa aaaaatgaga aaagataaaa atacctttat     60

attaatattt gttatattgt aaaataagga tatttttaac aaattttcaa ttgaatagat    120

gtttgggtga atcctaatac caattaaagt atatatacac aaacaattat aaatcaaatt    180

acttttaata aaatggtatc attcaattca atgacaataa atgcatttat aaatacatca    240

aatgtaaatc tcatgtttat aagaaaacac gtagaaaaaa gttaaaccaa tatttgagtc    300

ctagctgtgg aggcatgatt gagtgaaatc aaatggacgc tggttttaat tgtattgaaa    360

gaaaccaata atcacgtagg ttggcagttg aacataattg aatggtctca acttttaatg    420

tggtgttaat gtttggatcg gataatctca acttacctaa tagctaggaa agtaaaattc    480

aaacatcacc cgctactact tttggctata aaaaccctcc taccctcaag ccctaacgac    540

gacaatcacc aatagtacta ctactccaag caagtatttt ccttacacgt ttgtttttct    600

tgtgattaat cgat                                                      614
```

<210> SEQ ID NO 55
<211> LENGTH: 210
<212> TYPE: DNA
<213> ORGANISM: artificial sequence
<220> FEATURE:
<223> OTHER INFORMATION: Synthetic Construct

<400> SEQUENCE: 55

```
tccactgacg taagggatga cgcacaatcc cactatcctt cgcaagaccc ttcctctata     60

taaggaagtt catttcattt ggagaggaca cgctgaaatc accagtctct ctctacaaat    120

ctatctctct ctattttctc cataataatg tgtgagtagt tcccagataa gggaattagg    180

gttcttatag ggtttcgctc acgtgttgag                                     210
```

<210> SEQ ID NO 56
<211> LENGTH: 4159
<212> TYPE: DNA
<213> ORGANISM: artificial sequence
<220> FEATURE:
<223> OTHER INFORMATION: Synthetic Construct

<400> SEQUENCE: 56

```
aaaaggagtc tctctctcac ctacaccaca cctaaccaaa ccccctacga ttcacacaga     60

gagagatctt cttcttcctt cttcttcctt cttctttctt cttctttctt cttctagcta    120
```

```
caacatctac aacgccatgt cctcttcttc ttcttcgtca acctccatga tcgatctcat    180
ggcagcaatc atcaaaggag agcctgtaat tgtctccgac ccagctaatg cctccgctta    240
cgagtccgta gctgctgaat tatcctctat gcttatagag aatcgtcaat tcgccatgat    300
tgttaccact tccattgctg ttcttattgg ttgcatcgtt atgctcgttt ggaggagatc    360
cggttctggg aattcaaaac gtgtcgagcc tcttaagcct ttggttatta agcctcgtga    420
ggaagagatt gatgatgggc gtaagaaagt taccatcttt ttcggtacac aaactggtac    480
tgctgaaggt tttgcaaagg tgaggacttt gtgttttggt ttgttctgat ttcgaatgat    540
gaagttgaat ttgaatcagt ttgatgtttt tgaaatttgc aggctttagg agaagaagct    600
aaagcaagat atgaaaagac cagattcaaa atcgttgatt tggtatttat tttgttccat    660
caacttttta gataaagttt gatgctttaa gtataatctg attctgagtt tattaacagg    720
atgattacgc ggctgatgat gatgagtatg aggagaaatt gaagaaagag gatgtggctt    780
tcttcttctt agccacgtta gtttcttag ctgatctttt gtttgggatc ggtataagta    840
ttaaatttga tttgttcttg tggctgactt ggttttacta tctggaatct ggatgtagat    900
atggagatgg tgagcctacc gacaatgcag cgagattcta caaatggttc accgaggtta    960
gtcttttttt ttggcttggc tcaactagtt gttgtaacgt gtgttgtttt tgttttcttg   1020
tttctgaagt tgtaaacatg tgtttacagg ggaatgacag aggagaatgg cttaagaact   1080
tgaagtatgg agtgtttgga ttaggaaaca gacaatatga gcattttaat aaggtttata   1140
aatgaaatct ttattcccct tttcttaatg gttttgctct tgtcactatt atggtctcct   1200
tccaattact ttggaccgag ctaatatgca gatttgtttt gtaaattttg ggttgcaggt   1260
tgccaaagtt gtagatgaca ttcttgtcga acaaggtttg ttttgtttct ttctttcttt   1320
ctttctttca tcatccgttt tggatcgctc tgatccggtc ttaatgtgtt gtattttggt   1380
ttctaacttc attgagtggg ttgttcaggt gcacagcgtc ttgtacaagt tggtcttgga   1440
gatgatgacc agtgtattga agatgacttt accgcttggt attttacatt tccacttctc   1500
gtggcttatc gtgtacaatg ctgttttggt catttgtttt ttgggggggct aaatttgcta   1560
cctcttgcag gcgagaagca ttgtggcccg agcttgatac aatactgagg gaagaagggg   1620
atacagctgt tgccacacca tacactgcag ctgtgttaga atacagagtt tctattcacg   1680
actctgaaga tgccaaattc aatgatataa acatggcaaa tgggaatggt tacactgtgt   1740
ttgatgctca acatccttac aagtacaaaa tccagccgct tcttttcttt ttccttataa   1800
tcttgtcttg ttacttgatc taatcttgct ttttttggct tttaaagagc aaatgtcgct   1860
gttaaaaggg agcttcatac tcccgagtct gatcgttctt gtatccattt ggaatttgac   1920
attgctggaa gtggacttac gtgagttcta ctgctatatg aatatttact taatcagagg   1980
gaaatattat tggagaataa catgaatgta tttttgtat cttgtctgtc aggtatgaaa   2040
ctggagatca tgttggtgta ctttgtgata acttaagtga aactgtagat gaagctctta   2100
gattgctgga tatgtcacct gatacttatt tctcacttca cgctgaaaaa gaagacggca   2160
caccaatcag cagctcactg cctcctccct tcccaccttg caacttgaga acagcgctta   2220
cacgatatgc atgtcttttg agttctccaa agaaggttgg ttggattcat ttaccattag   2280
actggttata atcagttttg tttctcttca tagagattca aactcaatta ttttcatgtt   2340
tattttcttg cagtctgctt tagttgcgtt ggctgctcat gcatctgatc ctaccgaagc   2400
agaacgatta aaacaccttg cttcacctgc tggaaaggtt gtggctgaac cttttgttgg   2460
```

-continued

```
tttctactct tcattttcca tttctttaaa atggaatctg acaatgtata ttttgtgtcc   2520

tttcaacaac aggatgaata ttcaaagtgg gtagtagaga gtcaaagaag tctacttgag   2580

gtgatggccg agtttccttc agccaagcca ccacttggtg tcttcttcgc tggagttgct   2640

ccaaggttgc agcctaggtt ctattcgata tcatcatcgc ccaagtgagt accttcattg   2700

tcttggtctt tttgtcttca agttgttcgc ttgagactta tattgtgttt ttagtgtatt   2760

gagcattgtc ccgtttactt gtataggatt gctgaaacta gaattcacgt cacatgtgca   2820

ctggtttatg agaaaatgcc aactggcagg attcataagg gagtgtgttc cacttggatg   2880

aaggtaaata taaaaaactt aaatctgata gcttcttgca aacatattgc tttggaatct   2940

ttttactgtt tgtgtcattt cttatccatt gtcttggtgt ttttgctggg tactgatttt   3000

ttgcatcgta atcacagaat gctgtgcctt acgagaagag tgaaaactgt tcctcggcgc   3060

cgatatttgt taggcaatcc aacttcaagc ttccttctga ttctaaggta ccgatcatca   3120

tgatcggtcc agggactgga ttagctccat tcagaggatt ccttcaggaa agactagcgt   3180

tggtagaatc tggtgttgaa cttgggccat cagttttgtt ctttggatgc agaaaccgta   3240

gaatggtaat aaagccatta ctcaaaactc aaacctttca ttggttttgt ccagtttcta   3300

atcatatctt ctcatatatg taggatttca tctacgagga agagctccag cgatttgttg   3360

agagtggtgc tctcgcagag ctaagtgtcg ccttctctcg tgaaggaccc accaaagaat   3420

acgtacagca caagatgatg gacaaggtat gagcttatag aaacccaaaa ctcagatctt   3480

catatagatt caaattcaga ttcttgagct gacaatcttt ctgcaatgca ggcttctgat   3540

atctggaata tgatctctca aggagcttat ttatatgttt gtggtgacgc caaaggcatg   3600

gcaagagatg ttcacagatc tctccacaca atagctcaag aacaggtatg tcttgttgag   3660

atcaatctag cattatcatt gtccgtatca caaaccgact ctaatgagtt tatttctgtc   3720

tgtcttgttt tcaggggtca atggattcaa ctaaagcaga gggcttcgtg aagaatctgc   3780

aaacgagtgg aagatatctt agagatgtat ggtaacgaaa ctattgaagc cacacactca   3840

ctgtgtactt atatttatat atatacggca cagaaattgc cacattatga tgatcattaa   3900

gtttgtgatc gcaagaagaa aggaactcct tttttttcc attttaatt tcttttcata   3960

tattttgaca actctatttt tttaactctt gttatatatc ccccacccaa tagtaagaaa   4020

aaatgcataa gatgttatgg ggtatttgtg aacaattatg ttatatacaa agtcagtacc   4080

tttagtatga attctttatg tagcactttc accaaagtcc ccattttggg acaaatacaa   4140

attctttgtt tatgcctca                                                4159
```

<210> SEQ ID NO 57
<211> LENGTH: 45
<212> TYPE: DNA
<213> ORGANISM: artificial sequence
<220> FEATURE:
<223> OTHER INFORMATION: Synthetic Construct

<400> SEQUENCE: 57

```
tcatggttaa tctagagatt aaagaggaga aatactagat gacca                  45
```

<210> SEQ ID NO 58
<211> LENGTH: 45
<212> TYPE: DNA
<213> ORGANISM: artificial sequence
<220> FEATURE:
<223> OTHER INFORMATION: Synthetic Construct

<400> SEQUENCE: 58

```
caaaattatt tctagttatt ctcgatcaaa aatagccagt acccg                45


<210> SEQ ID NO 59
<211> LENGTH: 783
<212> TYPE: DNA
<213> ORGANISM: artificial sequence
<220> FEATURE:
<223> OTHER INFORMATION: Synthetic Construct

<400> SEQUENCE: 59

atgaccagca ttaaactcct tgcagagagt ctgctcaaag acaaaaataaa gatcgtcgat    60

ctatcgcaca ccttgagatc cgaatttccg acactgacat tacctcctca gtttgggcaa   120

acctgggcgt tcaagaagga ggaaatatcg cgctacgacg accgtgggcc cgcttggtac   180

tggaacaact tttcctgcgg cgaacacact ggtactcact ttgatgcccc agtccattgg   240

gtcacaggcg aatccgtgcc tgagaactca gtagatcgta ttgacccaca gcgctttatg   300

gcaccggcag tagtgattga tgcctctaaa gaggtactag aaaatccgga ctgggttcta   360

gagccagaat ttatccagga gtgggagaaa ctgcatggcc ggatcgaagc cggttcctgg   420

tttctactcc ggacagattg gtcgaagaaa atcaataacc cgcttgagtt tgctaacctg   480

atagacggcg cacctcacac gccaggccca agccagcgta cagttgaatg gcttatcgcc   540

gaacgtgatg tcgtgggctt tggggttgag acgatcaata ttgatgcggg cctttcaggc   600

cgctgggaag ttccataccc ttgccacaac aagatgctgg gagcaggacg attcgggctg   660

cagtgcttga acaatcttga cctgttacca ccaacaggag cagtaatcat ctccgctcca   720

ctgaagatcg aagatggctc aggcagcccg ctgcgggtac tggctatttt tgatcgagaa   780

taa                                                                 783


<210> SEQ ID NO 60
<211> LENGTH: 1557
<212> TYPE: DNA
<213> ORGANISM: artificial sequence
<220> FEATURE:
<223> OTHER INFORMATION: Synthetic Construct

<400> SEQUENCE: 60

atggcgatca cctccatagc tcatctccgt gtcgtcaatg cgaacatgag cattccgcta    60

gctcgtcttc gtgtcgtcaa tgcaaacata agcattccgc tcaagcggac aagtttcccc   120

aagaaattcc tgtttggggc tggctctgct tcttaccaat atgaaggagc agcacatata   180

gatgggcgag gacttagcgt ctgggatgtc ttcactaagg aacaccctga aaagatcgca   240

gatcagtcga atggagatgt tgctcaagac ttttatcacc gatacaagga agatataaag   300

tcgatgaagg aaatgggttt ggagtcattc aggttctcca tttcatggtc aagaatatta   360

cctaatggga aaatcagtgg aggaatcaac aagctaggga tcaagttcta caataatctc   420

attgacgaac tgctagccaa tggaatcaag ccacttgtca ctatctacca ttgggacctt   480

ccacaagcac ttcaagacga atatggaggg ttcttgagcc ccaaaatcgt ggatgacttt   540

ctggaatatg caaacctagt ttttaaggag ttcggggata gggttaagca ttgggcgaca   600

ctgaatgaac ccaatataat gacccaacaa gggtacgtat ttggggcaca tgcacccgga   660

cgatgttctc acttcgaatg gaactgcccg gctggaaact ccggcaccga gccttatata   720

gttggtcacc acctcctcct atgtcatgct gcagcttttc aactatacaa acaaaagtat   780

aaggatgatc aaaagggtat aatcggaata acaaccgcga cacagatggc cataccgtta   840
```

-continued

```
aacgacaacg ttgccaacct cttggcagcg tcacgagcca tcgatttcaa cattggatgg    900

tttttgcatc cggttgttta cggcgagtat ccacagacga tgagggagcg gttgggaagt    960

cgactgccaa aattcacaga aaaagagtcg gagatgttga aacaatcgtt cgactttata   1020

gggttgaatt actactcaac tgattatgca gccgcatcat ctttttcagt tgatccagtg   1080

aatgtcagtt acacaactga ttcccgagca acattatcag cgataaaaga tggggttcct   1140

atcggcgacc cgacatttat gagctggttg catatatatc cagagggcat cctaactctg   1200

ttgcgatacg taaaggaaag gtacaacaat ccatttgtca tgatcactga gaatgggatg   1260

gccgatgaaa acaagggatc attagcggaa gatccgatgg ctttaaaaga caacgtcagg   1320

attcgatatc accgcgaaca tctatactat gttcttgaag ctataaagga gggtgtgaac   1380

gtgggaggat actacgcatg gacatggatg gatgatttcg agtggggttc tggatatact   1440

cctcgattcg gtctcaactt tgtggatttc gacaatgatt tgaagagaac cccccaaggat  1500

tcttacttct ggttcaagga cttccttgca aatcaccacc accaccacca ctagtaa      1557
```

```
<210> SEQ ID NO 61
<211> LENGTH: 4773
<212> TYPE: DNA
<213> ORGANISM: Pseudomonas putida

<400> SEQUENCE: 61

ccttgaattc ggttttcagc acttggcaca gctgttgcac tttgtcctgc gcaatccgcc     60

aacctggaga tggccgtgac caataccccc acaccgactt tcgatcagtt cactcgttac    120

atccgtgtgc gcagcgaacc agaagccaag ttcgtcgagt tcgattttgc ccttggccac    180

cctgagttgt tcgtcgagtt ggtgctgccg caagacgcct tcgtgaagtt ttgccagcac    240

aaccgcgtgg tggcaatgga cgaagcgatg gccaaggcgg tggacgacga catggtcaag    300

tggcgcttcg gcgatgtcgg tcgccgcctg ctgaaagacc cgggctgaga accctgccga    360

caggcagatg ggcatccaac aacaagaggg tacggttgat atgagcgtag agataaagac    420

caatacggtg gatccgatcc gccagaccta cggcaacctg caacggcgct tcggggacaa    480

gccggctagc cgttatcagg aagccagcta cgacatcgaa gcggtcacca actttcacta    540

tcgcccgctg tgggacccgc agcacgagct gcacgatccg acccgcacgg cgatccgcat    600

gaccgattgg cacaaggtca ccgacccccg ccagttctac tacggcgcct atgtgcaggg    660

ccgcgcgcgg atgcaggaag ccaccgaaca cgcctatggc ttctgcgaaa agcgtgagct    720

gctgagccgt ctgccggccg agttgcaggc caagctgctg cgctgcttgg tgccgctgcg    780

gcatgccgag ctgggcgcca acatgaataa cagcagcatc gccggcgaca gcatcgccgc    840

caccgtgacc cagatgcaca tctaccaggc gatggaccgc ctgggcatgg gccagtacct    900

ctcgcgcatc ggcctgctgc tcgatggcgg caccggcgag gcgttggatc aagccaaggc    960

ctattggctc gacgacccga tctggcaggg cctgcgtcgc tacgtcgaag acagcttcgt   1020

gatccgcgac tggttcgagt tgggcctggc gcagaacctg gtgctcgacg gcttgctgca   1080

gccgctgatg taccagcgct tcgaccaatg gctcacagag aacggtggca gcgatgtggc   1140

catgctcacc gagttcatgc gcgactggta cggcgaaagc acgcgctggg tcgacgccat   1200

gttcaagacc gtgcttgccg aaaatgacgc taaccgtgag caggtgcagg cctggctgga   1260

ggtctgggag ccgcgtgcct acgaggcatt gttgcccctg gccgaggaag ccaccggtat   1320

cgccgcgctg gatgaagtcc gcagcgcctt cgctactcgc ctgcagaaaa tcggcctgaa   1380

aagccgcgag gaataaagca tgtcatcact cgtctacatc gccttccagg ataacgacaa   1440
```

-continued

```
cgcgcgttac ctggtggaag cgatcatcca ggacaacccc cacgccgtcg tccagcacca   1500
cccggcgatg atccgtatcg aggccgagaa gcgcctggag atccgcaggg aaaccgtgga   1560
agagaacctc ggccgcgcct gggacgtcca ggcaatgctg gtggacgtaa tcaccatcgg   1620
cggcaacgtc gacgaggacg atgaccgctt cgtcctcgag tggaagaact aggagacaag   1680
ctcatggcta cccacaacaa gaaacgcctc aacctgaaag acaaataccg ctacctgacc   1740
cgcgatctgg cctgggaaac gacctaccag aagaaagaag acgtgttccc gctggagcac   1800
ttcgagggca tcaagatcac cgactgggac aagtgggaag accccttccg cctgaccatg   1860
gacagctact ggaaatacca ggcggagaaa gagaagaagc tctacgcgat cttcgacgcc   1920
tttgcccaga acaatggtca tcagaacatt tccgatgcgc gctacgtcaa cgccctgaag   1980
ctgttcctca ccggcgtttc accgctggaa taccaggcct tccagggctt ctcgcgggtt   2040
ggccggcagt tcagtggcgc cggtgcgcgg gtcgcctgtc agatgcaggc gatcgacgag   2100
ctgcgccatg tgcagacgca agtccacgcc atgagccatt acaacaagca cttcgatggt   2160
ttgcatgact tcgcccacat gtacgaccgg gtctggttcc tctcggtacc caagtccttt   2220
atggacgatg cgcggaccgc cggtccgttc gagttcctca ccgccgtctc gttctccttc   2280
gagtacgtgc tgaccaacct gttgttcgta cccttcatgt ccggtgccgc ctacaacggc   2340
gatatggcca cggtcacctt cggtttctcc gcgcagtcgg acgaggcgcg gcacatgacc   2400
ctgggtctgg aagtgatcaa gttcatgctc gaacagcatg aagacaacgt gcccatcatc   2460
cagcgctgga tcgataagtg gttctggcgc ggttaccgcc tgctgaccct gatcggcatg   2520
atgatggact acatgctgcc gaacaaagtg atgtcctggt ctgaggcctg gggggtctac   2580
ttcgagcagg ccggtggcgc gctgttcaag gatcttgagc gctatggcat ccggccgccg   2640
aaatacgtcg agcagaccac catcggcaag gagcacatca cccaccaggt gtgggggcc    2700
gtctatcaat acagcaaggc caccaacttc catacctgga tacccggtga cgaggaactg   2760
aactggctgt cggagaaata cccggacacc ttcgacaaat actaccgccc gcgcttcgag   2820
ttctggcgtg agcagcaggc caagggtgag cgcttctaca acgacaccct gccgcacctc   2880
tgccaggtgt gccagctacc ggcgattttc accgagccgg acgatccgac caagctcagc   2940
ctgcgcagcc tggtgcacga gggggagcgc tatcacttct gctcggatgg ctgctgcgac   3000
atcttcaaga acgagccggt gaagtacatc caggcctggc tgccggtgca ccagatctac   3060
cagggcaact gcgaaggcgg ggatgtcgag acggtggtgc agaagtacta ccacatcaaa   3120
agcggcgtgg acaatttgga gtacctgggc tcgcccgagc accagcgctg gctggccctg   3180
aaaggtcaga ccccaccaac tgccgccccg gcggacaaga acctggacgc cgcctgaggc   3240
agcgccagcc gctcaggggt gaagcaccgc ccctgagcca ttccaagaac aagagggttc   3300
gatcatgact gtcaactcaa tcggcgaata cactgccacg ccacgggatg tgcaggccaa   3360
cttcaacggc atgcaactgc tctacctcta ctgggaagag cacctgatgt actgctccgc   3420
gctcgcgttc ttggtagccc ccggcatgcc ctttgccgag ttcctcgagc aggtgctcaa   3480
gcccgcgatc cacgcccatc cggacagcgc gaagatcgat ttcagccagg cgctctggca   3540
gctgaacgac cagccgttca ccccggacta cgccgccagc ctggaagcca acggcatcga   3600
ccacaaaagc atgctgcgtc tgaacacccc gggcctgaac ggcatccagg gttcctgcag   3660
ctgagaggtg tgtcatgact tacaacgtca ccatcgagcc taccggtgaa atcatcgagg   3720
tcgaggaggg ccagaccatc ctgcaagcgg ccttgcgcca gggcgtctgg ctgccattcg   3780
```

-continued

```
cctgcggcca tggtacctgc gcgacctgca aggtgcaggt agtcgaaggc gaggccgacc   3840

acggcgccgc ctcacccttt gccctgatgg acatggagcg tgacgagggc aaggtcctgg   3900

cctgctgcgc catgcccatg agcgatatgg tgatagaggc ggatatcgac gtcgatccgg   3960

atttcgccgg ccatcaagtc gaggactacc gcggggtggt cagcgccctg gtcgacctgt   4020

cgccgaccat caagggtgtg cacatcaagc tcgatcggcc gatgaccttc caggccgggc   4080

aatacatcaa cctgaccctg ccgggcgttg aaggatcacg cgccttctcg ctggccaacc   4140

cgccgagccg gaatgacgaa gtcgagttgc acgtgcgcct ggtcgagggc ggtgcggcca   4200

ccggctttat ccacaagcaa ctgaaagtcg gcgacgcggt ggagctgtcc gggccttatg   4260

ggcagttctt cgtgcgcgat tcgcaggccg gcgacctgat cttcatcgcc ggcggctcgg   4320

gcttatcgag cccgcagtcg atgatcctcg atctgcttga acgcggcgat acgcggcgga   4380

tcaccctgtt ccagggcgcg cgcaaccgcg ccgagctgta caactgcgaa ctgttcgagg   4440

aactggccgc gcgccacccc aacttcagtt acgtgccggc actcaaccag gccaacgacg   4500

atcccgaatg gcagggtttc aagggcttcg tccacgacgc cgccaaggcc cacttcgacg   4560

gccgcttcgg cgggcacaag gcctacttgt gcggcccgcc gccaatgatc aacgcggcca   4620

tcaccaccct gaggcagggc cggctgttcg agcgcgacat ctttatggag cgcttctaca   4680

ccgccgccga tggggccggc gagagcagcc gttcggccct gttcaagcgc atctgaggtg   4740

aaccatgaac cgtgccggtt atgagattcg cga                                4773
```

```
<210> SEQ ID NO 62
<211> LENGTH: 2079
<212> TYPE: DNA
<213> ORGANISM: Arabidopsis thaliana

<400> SEQUENCE: 62

atgacttctg ctttgtatgc ttccgatttg tttaagcagc tcaagtcaat tatggggaca     60

gattcgttat ccgacgatgt tgtacttgtg attgcaacga cgtctttggc actagtagct    120

ggatttgtgg tgttgttatg gaagaaaacg acggcggatc ggagcgggga gctgaagcct    180

ttgatgatcc ctaagtctct tatggctaag gacgaggatg atgatttgga tttgggatcc    240

gggaagacta gagtctctat cttcttcggt acgcagactg gaacagctga gggatttgct    300

aaggcattat ccgaagaaat caaagcgaga tatgaaaaag cagcagtcaa agtcattgac    360

ttggatgact atgctgccga tgatgaccag tatgaagaga aattgaagaa ggaaactttg    420

gcatttttct gtgttgctac ttatggagat ggagagccta ctgacaatgc tgccagattt    480

tacaaatggt ttacggagga aaatgaacgg gatataaagc ttcaacaact agcatatggt    540

gtgtttgctc ttggtaatcg ccaatatgaa cattttaata agatcgggat agttcttgat    600

gaagagttat gtaagaaagg tgcaaagcgt cttattgaag tcggtctagg agatgatgat    660

cagagcattg aggatgattt taatgcctgg aaagaatcac tatggtctga gctagacaag    720

ctcctcaaag acgaggatga taaaagtgtg gcaactcctt atacagctgt tattcctgaa    780

taccgggtgg tgactcatga tcctcggttt acaactcaaa aatcaatgga atcaaatgtg    840

gccaatggaa atactactat tgacattcat catccctgca gagttgatgt tgctgtgcag    900

aaggagcttc acacacatga atctgatcgg tcttgcattc atctcgagtt cgacatatcc    960

aggacgggta ttacatatga aacaggtgac catgtaggtg tatatgctga aaatcatgtt   1020

gaaatagttg aagaagctgg aaaattgctt ggccactctt tagatttagt attttccata   1080

catgctgaca aggaagatgg ctccccattg gaaagcgcag tgccgcctcc tttccctggt   1140
```

-continued

```
ccatgcacac ttgggactgg tttggcaaga tacgcagacc ttttgaaccc tcctcgaaag   1200

tctgcgttag ttgccttggc ggcctatgcc actgaaccaa gtgaagccga gaaacttaag   1260

cacctgacat cacctgatgg aaaggatgag tactcacaat ggattgttgc aagtcagaga   1320

agtcttttag aggtgatggc tgcttttcca tctgcaaaac ccccactagg tgtatttttt   1380

gctgcaatag ctcctcgtct acaacctcgt tactactcca tctcatcctc gccaagattg   1440

gcgccaagta gagttcatgt tacatccgca ctagtatatg gtccaactcc tactggtaga   1500

atccacaagg gtgtgtgttc tacgtggatg aagaatgcag ttcctgcgga gaaaagtcat   1560

gaatgtagtg gagccccaat ctttattcga gcatctaatt tcaagttacc atccaaccct   1620

tcaactccaa tcgttatggt gggacctggg actgggctgg caccttttag aggttttctg   1680

caggaaagga tggcactaaa agaagatgga gaagaactag gttcatcttt gctcttcttt   1740

gggtgtagaa atcgacagat ggactttata tacgaggatg agctcaataa ttttgttgat   1800

caaggcgtaa tatctgagct catcatggca ttctcccgtg aaggagctca gaaggagtat   1860

gttcaacata agatgatgga gaaggcagca caagtttggg atctaataaa ggaagaagga   1920

tatctctatg tatgcggtga tgctaagggc atggcgaggg acgtccaccg aactctacac   1980

accattgttc aggagcagga aggtgtgagt tcgtcagagg cagaggctat agttaagaaa   2040

cttcaaaccg aaggaagata cctcagagat gtctggtga                          2079
```